US008759046B2

(12) United States Patent
Ohto et al.

(10) Patent No.: US 8,759,046 B2
(45) Date of Patent: Jun. 24, 2014

(54) PROCESS FOR PRODUCING PRENYL ALCOHOLS

(75) Inventors: Chikara Ohto, Toyota (JP); Shusei Obata, Nagoya (JP)

(73) Assignee: Toyota Jidosha Kabushiki Kaisha, Toyota-Shi (JP)

( * ) Notice: Subject to any disclaimer, the term of this patent is extended or adjusted under 35 U.S.C. 154(b) by 604 days.

(21) Appl. No.: 12/060,434

(22) Filed: Apr. 1, 2008

(65) Prior Publication Data

US 2008/0213847 A1 Sep. 4, 2008

Related U.S. Application Data

(63) Continuation of application No. 10/450,941, filed as application No. PCT/JP01/11215 on Dec. 20, 2001, now abandoned.

(30) Foreign Application Priority Data

Dec. 28, 2000 (JP) .................. 2000-401701
Dec. 28, 2000 (JP) .................. 2000-403067
Sep. 18, 2001 (JP) .................. 2001-282978

(51) Int. Cl.
*C12P 7/02* (2006.01)
*C12N 1/00* (2006.01)
*C12N 15/00* (2006.01)
*C07H 21/04* (2006.01)

(52) U.S. Cl.
USPC ...... 435/155; 435/193; 435/254.21; 536/23.2

(58) Field of Classification Search
CPC ...... C07P 7/04; C12N 15/81; C07K 2319/003
USPC ...................... 435/157, 193, 255.2
See application file for complete search history.

(56) References Cited

U.S. PATENT DOCUMENTS

| | | | |
|---|---|---|---|
| 5,460,949 A | 10/1995 | Saunders et al. | |
| 5,578,466 A | 11/1996 | Hayano et al. | |
| 5,663,461 A | 9/1997 | Mori et al. | |
| 5,773,273 A | 6/1998 | Nishino et al. | |
| 6,040,165 A | 3/2000 | Narita et al. | |
| 6,156,913 A | 12/2000 | Hyatt | |
| 6,225,096 B1 | 5/2001 | Narita et al. | |
| 6,242,227 B1 | 6/2001 | Millis et al. | |
| 6,262,279 B1 | 7/2001 | Hyatt | |
| 6,689,593 B2 | 2/2004 | Millis et al. | |
| 7,501,268 B2 | 3/2009 | Ohto et al. | |

FOREIGN PATENT DOCUMENTS

| | | |
|---|---|---|
| EP | 0 123 811 A2 | 11/1984 |
| EP | 0 509 841 A2 | 10/1992 |
| EP | 1219704 A2 | 7/2002 |
| JP | 05-317037 | 3/1993 |
| JP | 5115298 A | 5/1993 |
| JP | 05-192184 A | 8/1993 |
| JP | 8242861 A | 9/1996 |
| WO | WO 00/01649 | 1/2000 |
| WO | WO 00/01650 | 1/2000 |
| WO | WO 00/01685 | 1/2000 |
| WO | WO 00/01686 | 1/2000 |

OTHER PUBLICATIONS

Baker et al. Science 2001, 294, 93-96.*
Linbladh et al., (Biochemistry 1994, vol. 33:11684-11691.*
Anderson, Matt S., et al., "Farnesyl Diphosphate Synthetase," *The Journal of Biological Chemistry*, vol. 261, No. 32, Nov. 15, 1989, pp. 19176-19184.
Fujisaki, Shingo, et al., "Cloning and Nucleotide Sequence of the *ispA* Gene Responsible for Farnesyl Diphosphate Synthase Activity in *Escherichia coli*," *J Biochem*, vol. 108, 1990, pp. 995-1000.
Office Action issued Mar. 14, 2006 in Japanese Application No. 2002-555252.
H.W. Mewes, et al.: "Overview of the yeast genome", Nature, vol. 387, Supp, May 29, 1997, pp. 7-65.
Frederick M. Hahn, et al.: "*Escherichia coli* Open Reading Frame 696 Is idi, a Nonessential Gene Encoding Isopentenyl Diphosphate Isomerase", Journal of Bacteriology, vol. 181, No. 15, Aug. 1999, pp. 4499-4504.
Office Action issued May 17, 2011 in Japanese Application No. 2001-282978.
Maria-Jose Farfan, et al.: "Threonine Overproduction in Yeast Strains Carrying the HOM3-R2 Mutant Allele under the Control of Different Inducible Promotors"; Applied and Environmental Biology, Jan. 1999, vol. 65, No. 1, pp. 110-116.
Ikuku Miyajima, et al.: "GPA1, A Haploid-Specific Essential Gene, Encodes a Yeast Homolog of Mammalian G Protein Which May Be Involved in Mating Factor Signal Transduction"; Cell, vol. 50, Sep. 25, 1987, Cell Press, pp. 1011-1019.
Ung-Jin Kim, et al.: "Effects of histone H4 depletion on the cell cycle and transcription of *Saccharomyces cerevisiae*"; The EMBO Journal, vol. 7, No. 7, 1988, pp. 2211-2219.
Nahla Abushadi, et al.: "Role of Peroxisomes in Isoprenoid Biosynthesis"; The Journal of Histochemistry & Cytochemistry, 1999, vol. 47, pp. 1127-1132.
Office Action issued Jan. 10, 2006 in Japanese Application No. 2000-401701.
Chia-Wei Wang, et al.: "Engineering Isoprenoid Pathway Enhances Astaxanthin Production in *Escherichia coli*", Biotechnology and Bioengineering, vol. 62, No. 2, Jan. 20, 1999. pp. 235-241.
Office Action issued on Apr. 9, 2007, in U.S. Appl. No. 10/451,643.
Office Action issued on Jul. 20, 2007, in U.S. Appl. No. 10/451,643.
Final Office Action issued on Feb. 6, 2008, in U.S. Appl. No. 10/451,643.
Advisory Action issued on Jun. 30, 2008, in U.S. Appl. No. 10/451,643.
Notice of Allowance issued on Oct. 17, 2008, in U.S. Appl. No. 10/451,643.
J.L. Goldstein et al., "Regulation of the mevalonate pathway," Nature, vol. 343, Feb. 1, 1990, pp. 425-430.

(Continued)

*Primary Examiner* — Tekchand Saidha
*Assistant Examiner* — Younus Meah
(74) *Attorney, Agent, or Firm* — Kenyon & Kenyon LLP

(57) ABSTRACT

A method of producing a prenyl alcohol(s) by culturing a mutant cell into which a fusion gene of farnesyl diphosphate synthase gene and geranylgeranyl diphosphate synthase gene has been introduced and recovering the prenyl alcohol(s) from the resultant culture.

7 Claims, 60 Drawing Sheets

(56) References Cited

OTHER PUBLICATIONS

M. Thorsness et al., "Positive and Negative Transcriptional Control by Heme of Genes Encoding 3-Hydroxy-3 Methylglutaryl Coenzyme a Reductase in *Saccharomyces cerevisiae*," Molecular and Cellular Biology, vol. 9, No. 12, Dec. 1989, pp. 5702-5712.

C. Sengstag et al., "Genetic and Biochemical Evaluation of Eucaryotic Membrane Protein Topology: Multiple Transmembrane Domains of *Saccharomyces cerevisiae* 3-Hydroxy-3-Methylglutaryl Coenzyme A Reductase," Molecular and Cellular Biology, vol. 10, No. 2, Feb. 1990, pp. 672-680.

C. Chambon et al., "Sterol Pathway Yeast Identification and Properties of Mutant Strains Defective in Mevalonate Diphosphate Decarboxylase and Farnesyl Diphosphate Synthetase," Lipids, vol. 26, No. 8, 1991, pp. 633-636.

B. Behalova et al., "Regulation of Sterol Biosynthesis in *Saccharomyces cerevisiae*," Folia Microbiol., vol. 39, No. 4, 1994, pp. 287-290.

R.Y. Hampton et al., "Regulated Degradation of HMG-CoA Reductase, an Integral Membrane Protein of the Endoplasmic Reticulum, in Yeast," The Journal of Cell Biology, vol. 125, No. 2, Apr. 1994, pp. 299-312.

W. Yamano et al., "Metabolic Engineering for Production of Beta-Carotene and Lycopene in *Saccharomyces cerevisiae*," Biosci. Biotech Biochem., vol. 58, No. 6, 1994, pp. 1112-1114.

S. Kajiwara et al., "Expression of an exogenous isopentenyl diphosphate isomerase gene enhances isoprenoid biosynthesis in *Escherichia coli*," Biochem. J., vol. 324, 1997, pp. 421-426.

K.A.G. Donald et al., "Effects of Overproduction of the Catalytic Domain of 3-Hydroxy-3-Methylglutaryl Coenzyme A Reductase on Squalene Synthesis in *Saccharomyces cerevisiae*," Applied and Environmental Microbiology, vol. 63, No. 9, Sep. 1997, pp. 3341-3344.

N. Misawa et al., "Metabolic engineering for the production of carotenoids in non-carotenogenic bacteria and yeasts," Journal of Biotechnology, vol. 59, 1998, pp. 169-181.

R. Y. Hampton, "Genetic analysis of hydroxymethylglutaryl-coenzyme a reductase regulated degradation," Current Opinion Lipidology, 1998, pp. 9:93-97.

Y. Miura et al., "Production of the Carotenoids Lycopene Beta-Carotene, and Astaxanthin in the Food Yeast *Candida utilis*," Applied and Environmental Microbiology, vol. 64, No. 4, Apr. 1998, pp. 1226-1229.

Y. Miura et al., "Production of Lycopene by the Food Yeast, *Candida utilis* That Does Not Naturally Synthesize Carotenoid," Biotechnology and Bioengineering, vol. 58, Nos. 2 & 3, Apr. 20/May 5, 1998, pp. 306-308.

H. Hemmi et al., "Identification of Genes Affecting Lycopene Formation in *Escherichia coli* Transformed with Carotenoid Biosynthetic Genes: Candidates for Early Genes in Isoprenoid Biosynthesis," J. Biochem., vol. 123, 1998, pp. 1088-1096.

H. Shimada et al., "Increased Carotenoid Production by the Food Yeast *Candida utilis* through Metabolic Engineering of the Isoprenoid Pathway," Applied and Environmental Microbiology, vol. 64, No. 7, Jul. 1998, pp. 2676-2680.

R. Gardner et al., "Sequence Determinants for Regulated Degradation of Yeast 3-Hydroxy-3-Methylglutaryl-CoA Reductase, an Integral Endoplasmic Reticulum Membrane Protein," Molecular Biology of the Cell, vol. 9, Sep. 1998, pp. 2611-2626.

D. Dimster-Denk et al., "Comprehensive evaluation of isoprenoid biosynthesis regulation in *Saccharomyces cerevisiae* utilizing the Genome Reporter Matrix," Journal of Lipid Research, vol. 40, 1999, pp. 850-860.

D. Profant et al., "The Role of the 3-Hydroxy 3-Methylglutaryl Coenzyme A Reductase Cytosolic Domain in Karmellae Biogenesis," Molecular Biology of the Cell, vol. 10, Oct. 1999, pp. 3409-3423.

R.G. Gardner et al., "A Highly Conserved Signal Controls Degradation of 3-Hydroxy-3-methylglutaryl-coenzyme a (Hmg-CoA) Reductase in Eukaryotes*," The Journal of Biological Chemistry, vol. 274, No. 44, Oct. 29, 1999, pp. 31671-31678.

W R Farmer et al., "Improving lycopene production in *Escherichia coli* by engineering metabolic control," Nature Biotechnology, vol. 18, May 2000, pp. 533-537.

D. A. Profant et al., "Mutational analysis of the karmellae-inducing signal in Hmg1p, a yeast HMG-CoA reductase isozyme," Yeast 2000, vol. 16, 2000, pp. 811-827.

D. Plochocka et al., "The role of ERG20 gene (encoding yeast farnesyl diphosphate synthase) mutation in long dolichol formation. Molecular modeling of FPP synthase," Biochimie, vol. 82, 2000, pp. 733-738.

W R Farmer et al., "Precursor Balancing for Metabolic Engineering of Lycopene Production in *Escherichia coli*," Biotechnol. Prog., vol. 17, 2001, pp. 57-61.

A. Oulmouden et al., "Isolation of the ERG12 gene of *Saccharomyces cerevisiae* encoding . . . ," Gene, vol. 88, 1990, pp. 253-257.

Y.H. Tsay et al., "Cloning and Characterization of ERG8, an Essential Gene of *Saccharomyces cerevisiae* That Encodes Phosphomevalonate Kinase," Molecular and Cellular Biology, vol. 11, No. 2, Feb. 1991, pp. 620-631.

M.P. Mayer et al., "Disruption and Mapping of IdI 1, The Gene for Isopentenyl Diphosphate Isomerase in *Saccharomyces cerevisiae*," Yeast, vol. 8, 1992, pp. 743-748.

L. Hiser et al., "ERG10 from *Saccharomyces cerevisiae* Encodes Acetoacetyl-CoA Thiolase," The Journal of Biological Chemistry, vol. 269, No. 50, Dec. 16, 1994, pp. 31383-31389.

L. Blanchard et al., "Characterization of a lysine-to-glutamic acid mutation in a conservative sequence of farnesyl diphosphate synthase from *Saccharomyces cerevisiae*," Gene, vol. 125, 1993, pp. 185-189.

P. Broun et al., "Catalytic plasticity of fatty acid modification enzymes underlying chemical diversity of plant lipids," Science, vol. 282, Nov. 13, 1998, pp. 1315-1317.

A. Witkowski et al., "Conversion of Beta-Ketoacyl Synthase to a Malonyl Decarboxylase by Replacement of the Active-Site Cysteine with Glutamine," Biochemistry, 1999, vol. 38, pp. 11643-11650.

J. Seffernick et al., "Melamine Deaminase and Atrazine Chlorohydrolase: 98 Percent Identical but Functionally Different," J. Bacteriol., Apr. 2001, vol. 183, No. 8, pp. 2405-2410.

Anderson, Matt S., et al., "Farnesyl Diphosphate Synthetase," The Journal of Biological Chemistry, vol. 264, No. 32, Nov. 15, 1989, pp. 19176-19184.

Toth, Matthew J., et al., "Molecular Cloning and Expression of the cDNAs Encoding Human and Yeast Mevalonate Pyrophosphate Decarboxylase," The Journal of Biological Chemistry, vol. 271, No. 14, Apr. 5, 1996, pp. 7895-7898.

Fujisaki, Shingo, et al., "Cloning and Nucleotide Sequence of the *ispA* Gene Responsible for Farnesyl Diphosphate Synthase Activity in *Escherichia coli*," J. Biochem, vol. 108, 1990, pp. 995-1000.

Jiang, Yu, et al., "*BTS1* Encodes a Geranylgeranyl Diphosphate Synthase in *Saccharomyces cerevisiae*," The Journal of Biological Chemistry, vol. 270, No. 37, Sep. 15, 1995, pp. 21793-21799.

Basson, Michael E., et al., "Structural and Functional Conservation between Yeast and Human 3-Hydroxy-3-Methylglutaryl Coenzyme A Reductases, the Rate-Limiting Enzyme of Sterol Biosynthesis," Molecular and Cellular Biology, vol. 8, No. 9, Sep. 1988, pp. 3797-3808.

Bradfute, D.L., et al.: *Squalene Synthase-deficient Mutant of Chinese Hamster Ovary Cells*, J. Biol. Chem., vol. 267, No. 26, p. 18308-18314 (1992).

Chambon C., et al.: *Isolation and Properties of Yeast Mutants . . .* , Curr. Genet., vol. 18, p. 41-46 (1990).

Bergstrom J.D. et al.: *Zaragozic acids: A Family of Fungal Metabolites . . .* , Proc. Natl. Acad. Sci., USA, vol. 90, p. 80-84 (1993).

Craig, C. Correll, et al.: *Identification of Farnesol as the Non-sterol Derivative of . . .* , Journal of Biological Chemistry, vol. 269, No. 26, p. 17390-17393 (1994).

N. Kamimura, et al.: *Construction of Squalene-accumulating Saccharomyces . . .* , Appl. Microbiol. Biotechnol., vol. 42, p. 353-357 (1994).

Thomas E. Meigs, et al.: *Regulation of 3-Hydroxy-3-methylglutaryl-Coenzyme A Reductase . . .* , Journal of Biological Chemistry, vol. 271, No. 14, p. 7916-7922 (1996).

(56) References Cited

OTHER PUBLICATIONS

R. Kennedy Keller, et al.: *Farnesol is not the Nonsterol Regulator* . . . , Archives of Biochemistry and Biophysics, vol. 328, No. 2, Article No. 0180, p. 324-330 (1996).

Anna Szkopinska, et al.: *Polyprenol Formation in the Yeast Saccharomyces cerevisiae*, Journal of Lipid Research, vol. 38, p. 962-968 (1997).

Polakowski T., et al.: *Overexpression of a Cytosolic Hydroxymethylglutaryl-CoA* . . . , Appl. Microbiol. Biotechnol., vol. 49, p. 66-71 (1998).

Dorota Grabowska, et al.: *Effect of Squalene Synthase Gene Disruption on FEBS Letters*, vol. 434, p. 406-408 (1998).

Kiyotaka Machida, et al.: *Farnesol-induced Growth Inhibition in Microbiology*, vol. 145, p. 293-299 (1999).

Anna Szkopinska, et al.: *The Regulation of Activity of Main Mevalonic Acid* . . . , Biochemical and Biophysical Research Communications, vol. 267, p. 473-477 (2000).

Moss et al. Prenol nomeneclature, IUPAC_IUB JCBN 1986.

\* cited by examiner

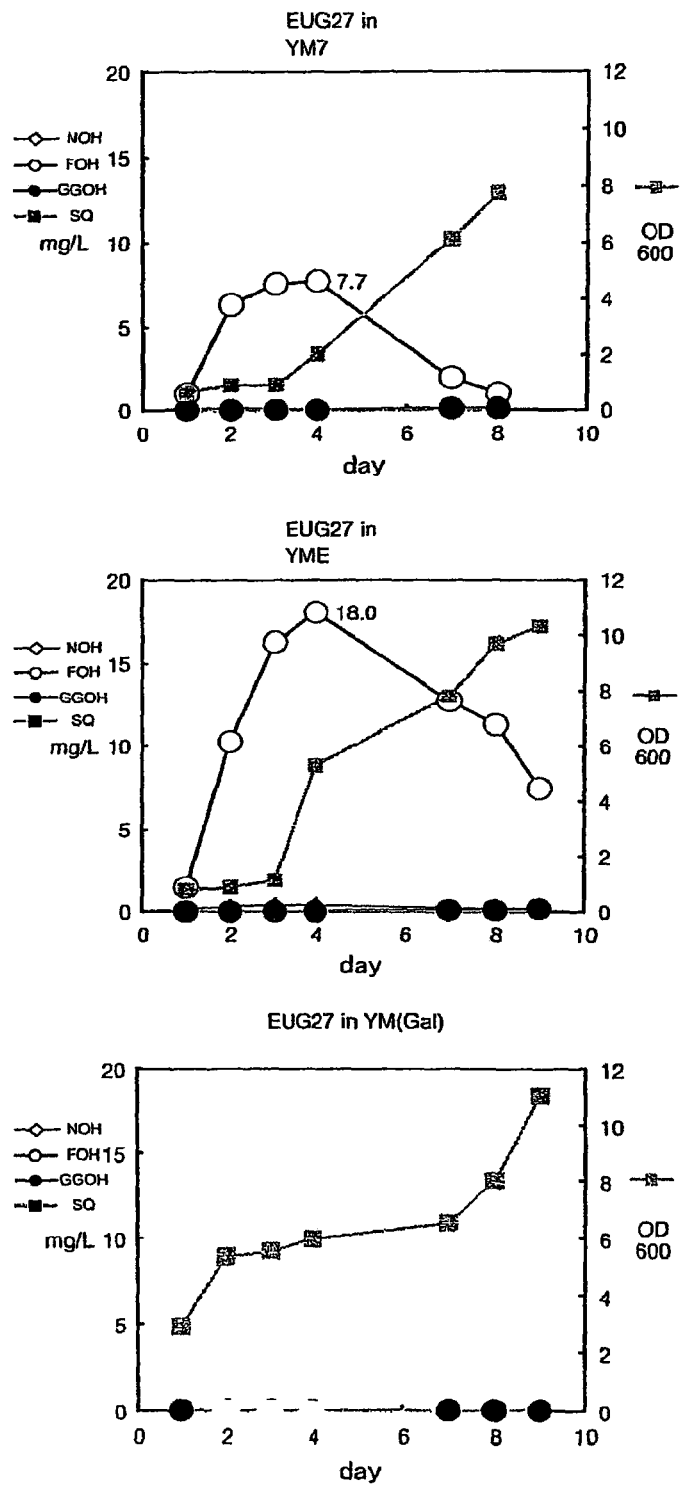

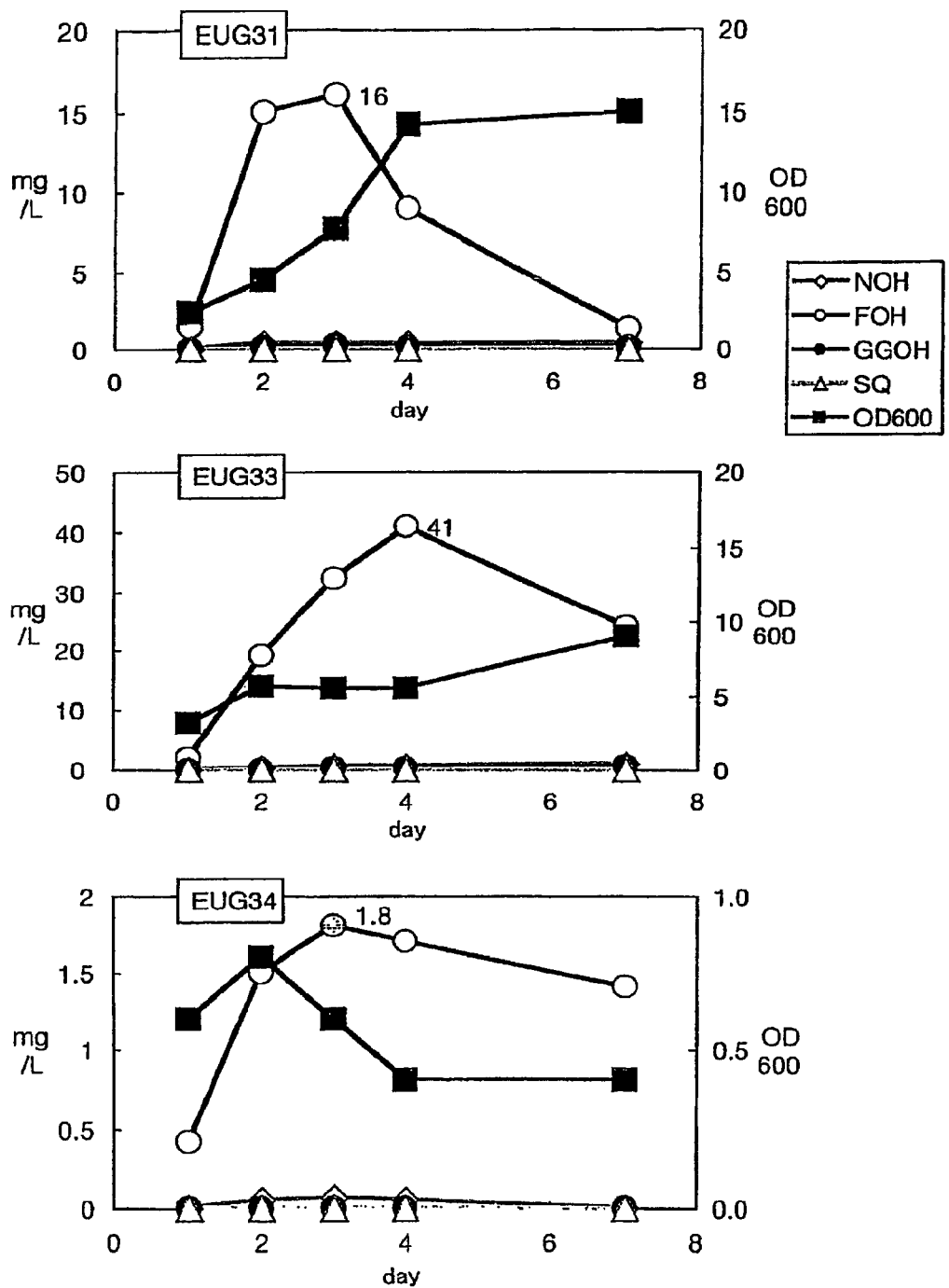

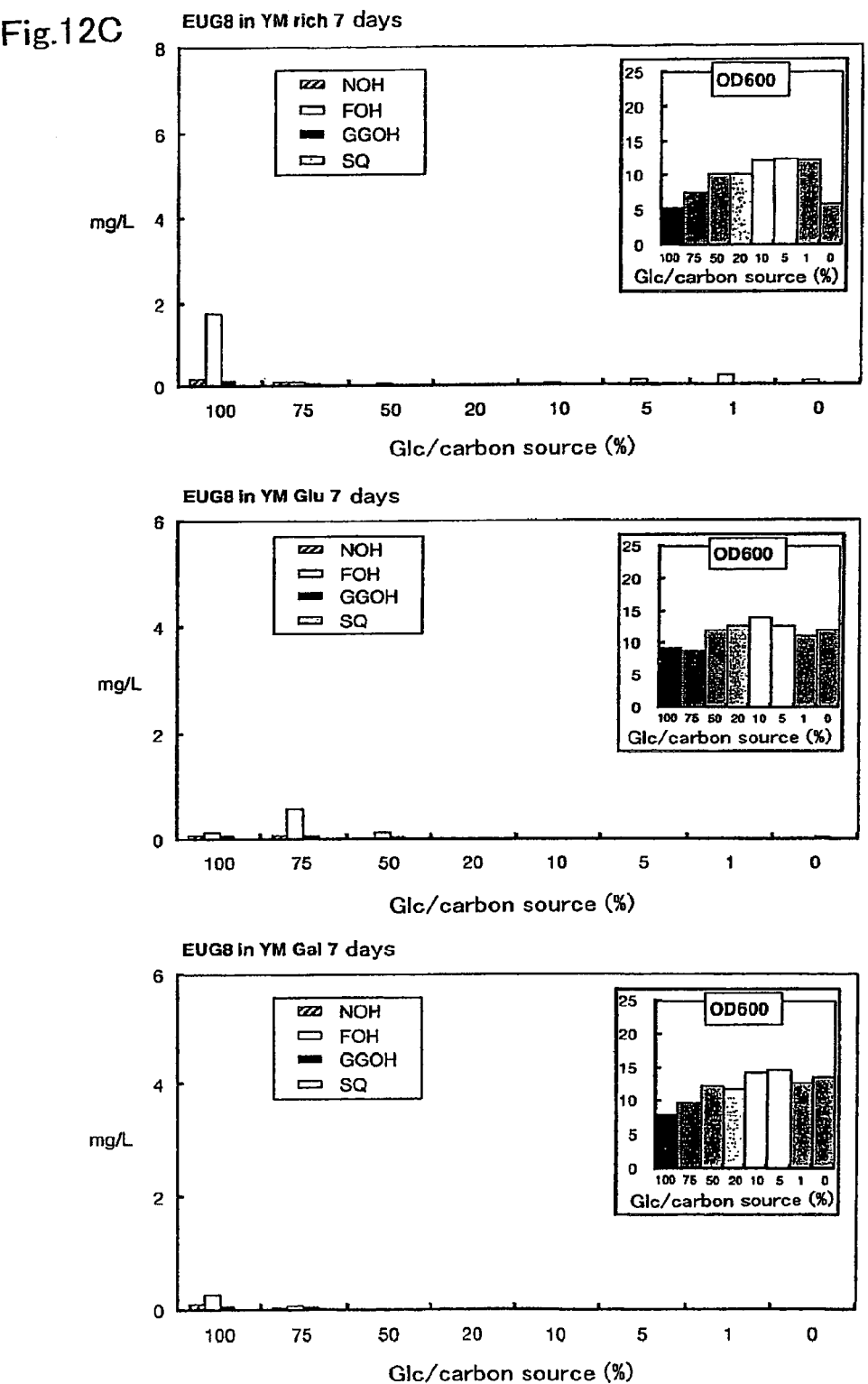

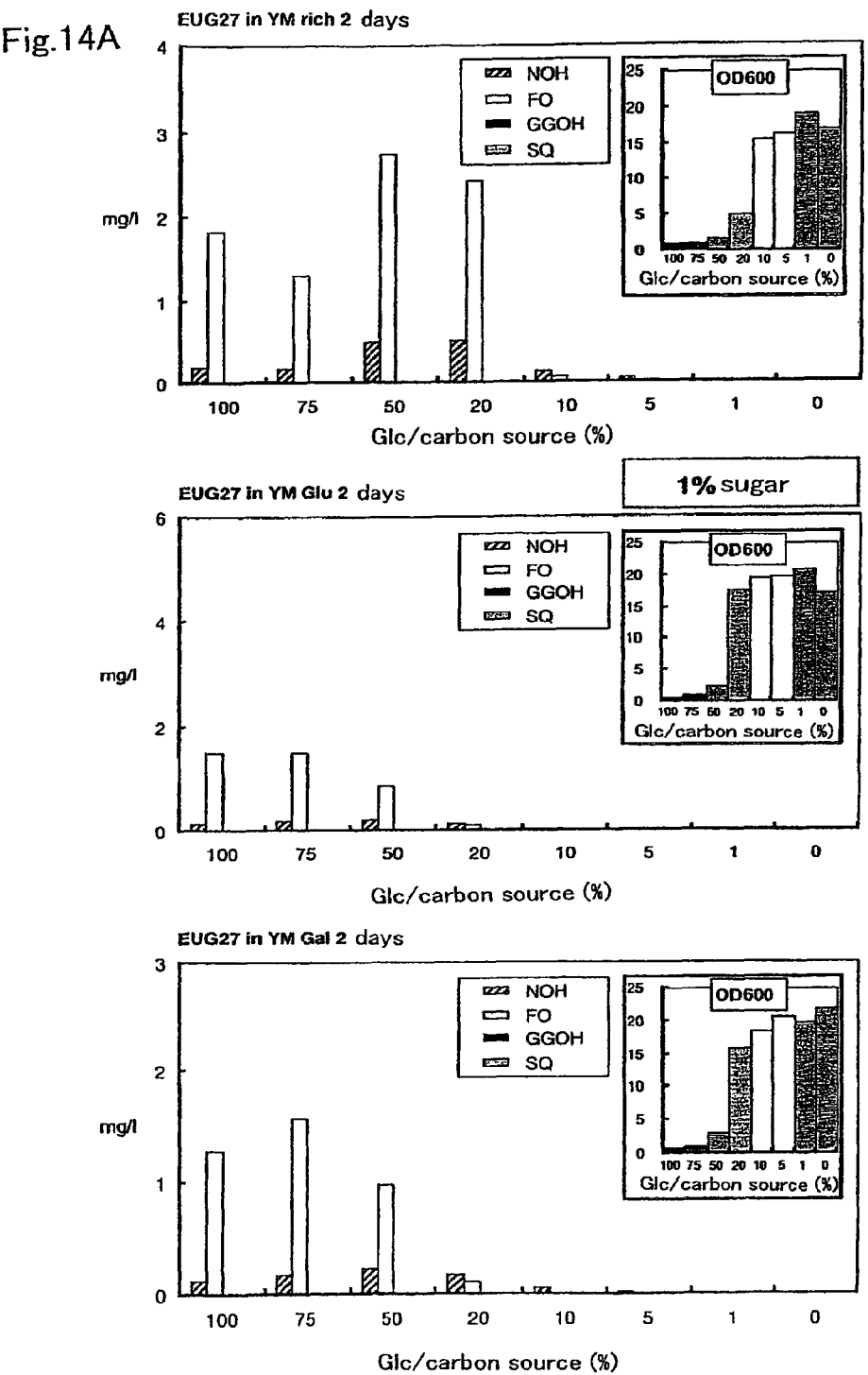

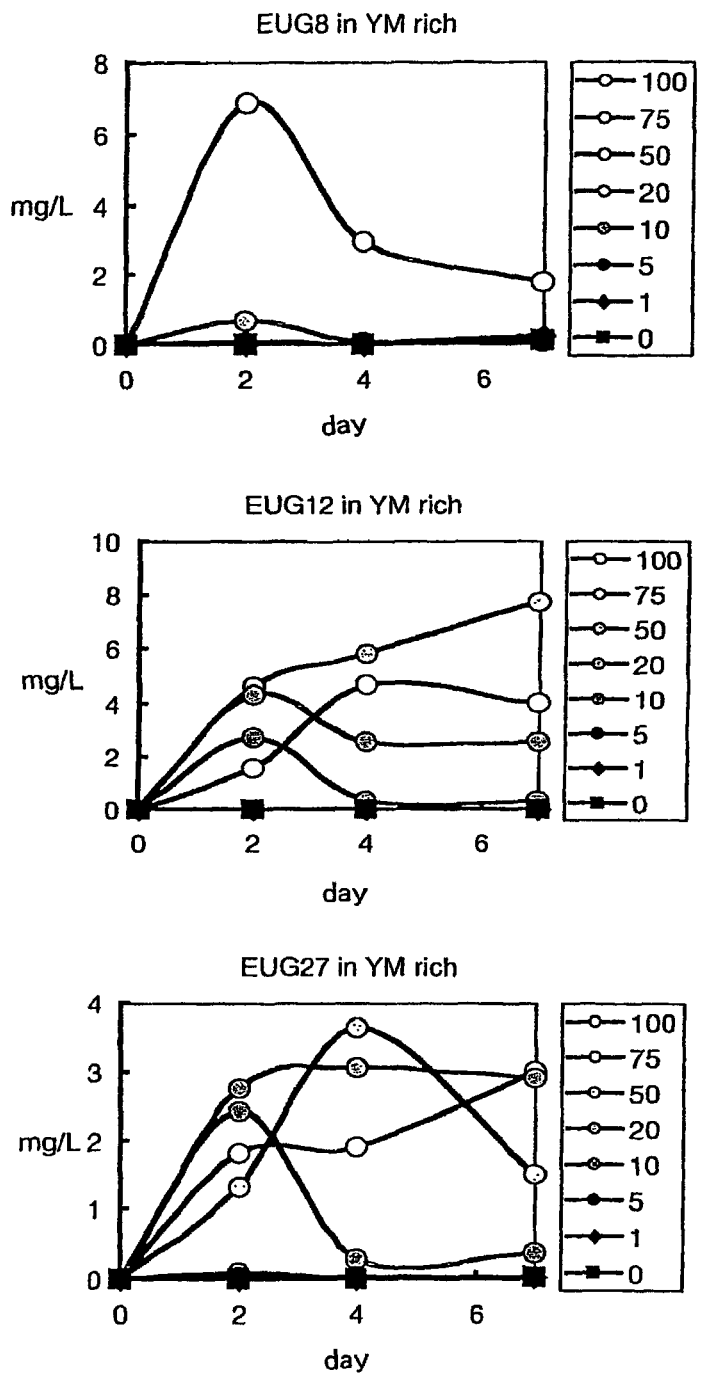

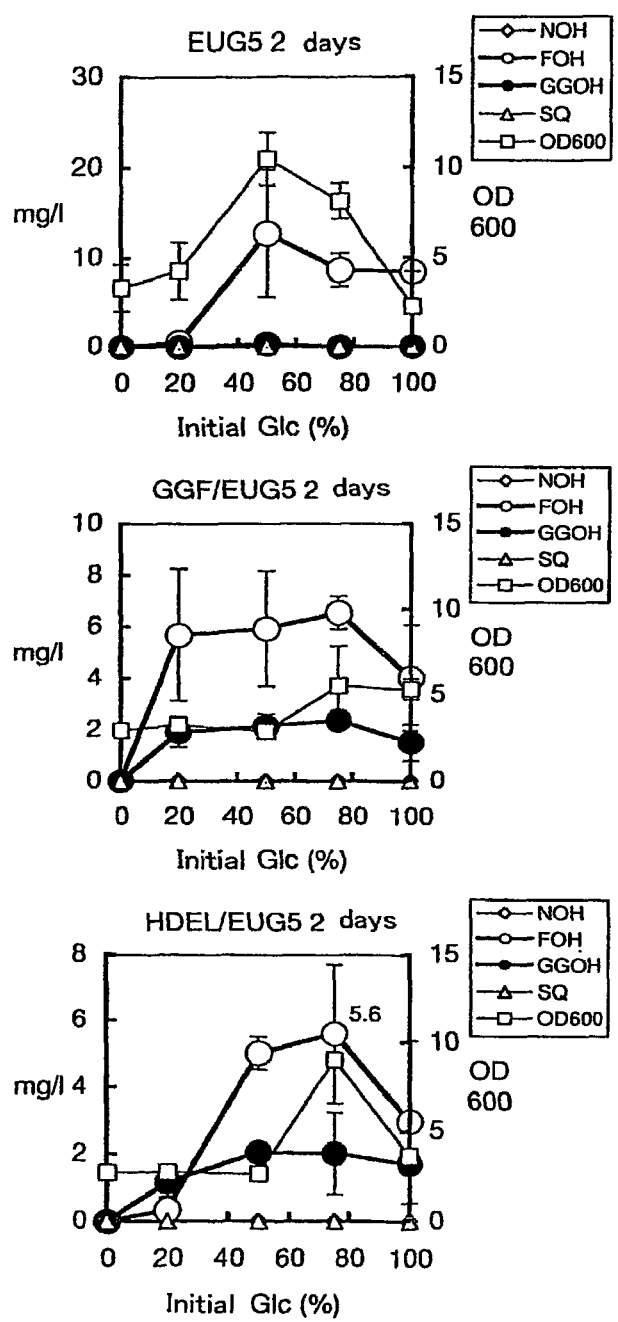

```
                              SEQUENCE LISTING

<160> NUMBER OF SEQ ID NOS: 79

<210> SEQ ID NO 1
<211> LENGTH: 1059
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 1 atg gct tca gaa aaa gaa att agg aga gag aga ttc ttg aac gtt ttc        48
Met Ala Ser Glu Lys Glu Ile Arg Arg Glu Arg Phe Leu Asn Val Phe
  1               5                  10                  15 cct aaa tta gta gag gaa ttg aac gca tcg ctt ttg gct tac ggt atg        96
Pro Lys Leu Val Glu Glu Leu Asn Ala Ser Leu Leu Ala Tyr Gly Met
             20                  25                  30 cct aag gaa gca tgt gac tgg tat gcc cac tca ttg aac tac aac act       144
Pro Lys Glu Ala Cys Asp Trp Tyr Ala His Ser Leu Asn Tyr Asn Thr
         35                  40                  45 cca ggc ggt aag cta aat aga ggt ttg tcc gtt gtg gac acg tat gct       192
Pro Gly Gly Lys Leu Asn Arg Gly Leu Ser Val Val Asp Thr Tyr Ala
     50                  55                  60 att ctc tcc aac aag acc gtt gaa caa ttg ggg caa gaa gaa tac gaa       240
Ile Leu Ser Asn Lys Thr Val Glu Gln Leu Gly Gln Glu Glu Tyr Glu
 65                  70                  75                  80 aag gtt gcc att cta ggt tgg tgc att gag ttg ttg cag gct tac ttc       288
Lys Val Ala Ile Leu Gly Trp Cys Ile Glu Leu Leu Gln Ala Tyr Phe
                 85                  90                  95 ttg gtc gcc gat gat atg atg gac aag tcc att acc aga aga ggc caa       336
Leu Val Ala Asp Asp Met Met Asp Lys Ser Ile Thr Arg Arg Gly Gln
            100                 105                 110 cca tgt tgg tac aag gtt cct gaa gtt ggg gaa att gcc atc aat gac       384
Pro Cys Trp Tyr Lys Val Pro Glu Val Gly Glu Ile Ala Ile Asn Asp
        115                 120                 125 gca ttc atg tta gag gct gct atc tac aag ctt ttg aaa tct cac ttc       432
Ala Phe Met Leu Glu Ala Ala Ile Tyr Lys Leu Leu Lys Ser His Phe
    130                 135                 140 aga aac gaa aaa tac tac ata gat atc acc gaa ttg ttc cat gag gtc       480
Arg Asn Glu Lys Tyr Tyr Ile Asp Ile Thr Glu Leu Phe His Glu Val
145                 150                 155                 160 acc ttc caa acc gaa ttg ggc caa ttg atg gac tta atc act gca cct       528
Thr Phe Gln Thr Glu Leu Gly Gln Leu Met Asp Leu Ile Thr Ala Pro
                165                 170                 175 gaa gac aaa gtc gac ttg agt aag ttc tcc cta aag aag cac tcc ttc       576
Glu Asp Lys Val Asp Leu Ser Lys Phe Ser Leu Lys Lys His Ser Phe
            180                 185                 190 ata gtt act ttc aag act gct tac tat tct ttc tac ttg cct gtc gca       624
```

```
Ile Val Thr Phe Lys Thr Ala Tyr Tyr Ser Phe Tyr Leu Pro Val Ala
        195                 200                 205 ttg gcc atg tac gtt gcc ggt atc acg gat gaa aag gat ttg aaa caa        672
Leu Ala Met Tyr Val Ala Gly Ile Thr Asp Glu Lys Asp Leu Lys Gln
210                 215                 220 gcc aga gat gtc ttg att cca ttg ggt gaa tac ttc caa att caa gat        720
Ala Arg Asp Val Leu Ile Pro Leu Gly Glu Tyr Phe Gln Ile Gln Asp
225                 230                 235                 240 gac tac tta gac tgc ttc ggt acc cca gaa cag atc ggt aag atc ggt        768
Asp Tyr Leu Asp Cys Phe Gly Thr Pro Glu Gln Ile Gly Lys Ile Gly
                245                 250                 255 aca gat atc caa gat aac aaa tgt tct tgg gta atc aac aag gca ttg        816
Thr Asp Ile Gln Asp Asn Lys Cys Ser Trp Val Ile Asn Lys Ala Leu
            260                 265                 270 gaa ctt gct tcc gca gaa caa aga aag act tta gac gaa aat tac ggt        864
Glu Leu Ala Ser Ala Glu Gln Arg Lys Thr Leu Asp Glu Asn Tyr Gly
        275                 280                 285 aag aag gac tca gtc gca gaa gcc aaa tgc aaa aag att ttc aat gac        912
Lys Lys Asp Ser Val Ala Glu Ala Lys Cys Lys Lys Ile Phe Asn Asp
290                 295                 300 ttg aaa att gaa cag cta tac cac gaa tat gaa gag tct att gcc aag        960
Leu Lys Ile Glu Gln Leu Tyr His Glu Tyr Glu Glu Ser Ile Ala Lys
305                 310                 315                 320 gat ttg aag gcc aaa att tct cag gtc gat gag tct cgt ggc ttc aaa       1008
Asp Leu Lys Ala Lys Ile Ser Gln Val Asp Glu Ser Arg Gly Phe Lys
                325                 330                 335 gct gat gtc tta act gcg ttc ttg aac aaa gtt tac aag aga agc aaa       1056
Ala Asp Val Leu Thr Ala Phe Leu Asn Lys Val Tyr Lys Arg Ser Lys
            340                 345                 350 tag                                                                    1059

<210> SEQ ID NO 2
<211> LENGTH: 352
<212> TYPE: PRT
<213> ORGANISM: Saccharomyces cerevisiae

<400> SEQUENCE: 2

Met Ala Ser Glu Lys Glu Ile Arg Arg Glu Arg Phe Leu Asn Val Phe
 1               5                  10                  15

Pro Lys Leu Val Glu Glu Leu Asn Ala Ser Leu Leu Ala Tyr Gly Met
                20                  25                  30

Pro Lys Glu Ala Cys Asp Trp Tyr Ala His Ser Leu Asn Tyr Asn Thr
            35                  40                  45

Pro Gly Gly Lys Leu Asn Arg Gly Leu Ser Val Val Asp Thr Tyr Ala
        50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160
```

```
Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350

<210> SEQ ID NO 3
<211> LENGTH: 900
<212> TYPE: DNA
<213> ORGANISM: Escherichia coli
<220> FEATURE:
<221> NAME/KEY: CDS
<222> LOCATION: (1)..(897)

<400> SEQUENCE: 3 atg gac ttt ccg cag caa ctc gaa gcc tgc gtt aag cag gcc aac cag      48
Met Asp Phe Pro Gln Gln Leu Glu Ala Cys Val Lys Gln Ala Asn Gln
1               5                   10                  15 gcg ctg agc cgt ttt atc gcc cca ctg ccc ttt cag aac act ccc gtg      96
Ala Leu Ser Arg Phe Ile Ala Pro Leu Pro Phe Gln Asn Thr Pro Val
            20                  25                  30 gtc gaa acc atg cag tat ggc gca tta tta ggt ggt aag cgc ctg cga     144
Val Glu Thr Met Gln Tyr Gly Ala Leu Leu Gly Gly Lys Arg Leu Arg
        35                  40                  45 cct ttc ctg gtt tat gcc acc ggt cat atg ttc ggc gtt agc aca aac     192
Pro Phe Leu Val Tyr Ala Thr Gly His Met Phe Gly Val Ser Thr Asn
    50                  55                  60 acg ctg gac gca ccc gct gcc gcc gtt gag tgt atc cac gct tac tca     240
Thr Leu Asp Ala Pro Ala Ala Ala Val Glu Cys Ile His Ala Tyr Ser
65                  70                  75                  80 tta att cat gat gat tta ccg gca atg gat gat gac gat ctg cgt cgc     288
Leu Ile His Asp Asp Leu Pro Ala Met Asp Asp Asp Asp Leu Arg Arg
                85                  90                  95 ggt ttg cca acc tgc cat gtg aag ttt ggc gaa gca aac gcg att ctc     336
Gly Leu Pro Thr Cys His Val Lys Phe Gly Glu Ala Asn Ala Ile Leu
            100                 105                 110 gct ggc gac gct tta caa acg ctg gcg ttc tcg att tta agc gat gcc     384
Ala Gly Asp Ala Leu Gln Thr Leu Ala Phe Ser Ile Leu Ser Asp Ala
        115                 120                 125
```

```
gat atg ccg gaa gtg tcg gac cgc gac aga att tcg atg att tct gaa      432
Asp Met Pro Glu Val Ser Asp Arg Asp Arg Ile Ser Met Ile Ser Glu
    130                 135                 140 ctg gcg agc gcc agt ggt att gcc gga atg tgc ggt ggt cag gca tta      480
Leu Ala Ser Ala Ser Gly Ile Ala Gly Met Cys Gly Gly Gln Ala Leu
145                 150                 155                 160 gat tta gac gcg gaa ggc aaa cac gta cct ctg gac gcg ctt gag cgt      528
Asp Leu Asp Ala Glu Gly Lys His Val Pro Leu Asp Ala Leu Glu Arg
                165                 170                 175 att cat cgt cat aaa acc ggc gca ttg att cgc gcc gcc gtt cgc ctt      576
Ile His Arg His Lys Thr Gly Ala Leu Ile Arg Ala Ala Val Arg Leu
            180                 185                 190 ggt gca tta agc gcc gga gat aaa gga cgt cgt gct ctg ccg gta ctc      624
Gly Ala Leu Ser Ala Gly Asp Lys Gly Arg Arg Ala Leu Pro Val Leu
        195                 200                 205 gac aag tat gca gag agc atc ggc ctt gcc ttc cag gtt cag gat gac      672
Asp Lys Tyr Ala Glu Ser Ile Gly Leu Ala Phe Gln Val Gln Asp Asp
    210                 215                 220 atc ctg gat gtg gtg gga gat act gca acg ttg gga aaa cgc cag ggt      720
Ile Leu Asp Val Val Gly Asp Thr Ala Thr Leu Gly Lys Arg Gln Gly
225                 230                 235                 240 gcc gac cag caa ctt ggt aaa agt acc tac cct gca ctt ctg ggt ctt      768
Ala Asp Gln Gln Leu Gly Lys Ser Thr Tyr Pro Ala Leu Leu Gly Leu
                245                 250                 255 gag caa gcc cgg aag aaa gcc cgg gat ctg atc gac gat gcc cgt cag      816
Glu Gln Ala Arg Lys Lys Ala Arg Asp Leu Ile Asp Asp Ala Arg Gln
            260                 265                 270 tcg ctg aaa caa ctg gct gaa cag tca ctc gat acc tcg gca ctg gaa      864
Ser Leu Lys Gln Leu Ala Glu Gln Ser Leu Asp Thr Ser Ala Leu Glu
        275                 280                 285 gcg cta gcg gac tac atc atc cag cgt aat aaa taa                      900
Ala Leu Ala Asp Tyr Ile Ile Gln Arg Asn Lys
    290                 295
```

<210> SEQ ID NO 4
<211> LENGTH: 299
<212> TYPE: PRT
<213> ORGANISM: Escherichia coli

<400> SEQUENCE: 4

```
Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Ser
65              70                  75                  80

Leu Ile His Asp Asp Leu Pro Ala Met Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140
```

```
Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
            165                 170                 175

Ile His Arg His Lys Thr Gly Ala Leu Ile Arg Ala Val Arg Leu
        180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
        210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
            245                 250                 255

Glu Gln Ala Arg Lys Lys Ala Arg Asp Leu Ile Asp Asp Ala Arg Gln
        260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
        290                 295

<210> SEQ ID NO 5
<211> LENGTH: 1008
<212> TYPE: DNA
<213> ORGANISM: Saccharomyces cerevisiae
<220> FEATURE:
<221> NAME/KEY: CDS
<222> LOCATION: (1)..(1005)

<400> SEQUENCE: 5 atg gag gcc aag ata gat gag ctg atc aat aat gat cct gtt tgg tcc      48
Met Glu Ala Lys Ile Asp Glu Leu Ile Asn Asn Asp Pro Val Trp Ser
 1               5                  10                  15 agc caa aat gaa agc ttg att tca aaa cct tat aat cac atc ctt ttg      96
Ser Gln Asn Glu Ser Leu Ile Ser Lys Pro Tyr Asn His Ile Leu Leu
            20                  25                  30 aaa cct ggc aag aac ttt aga cta aat tta ata gtt caa att aac aga     144
Lys Pro Gly Lys Asn Phe Arg Leu Asn Leu Ile Val Gln Ile Asn Arg
        35                  40                  45 gtt atg aat ttg ccc aaa gac cag ctg gcc ata gtt tcg caa att gtt     192
Val Met Asn Leu Pro Lys Asp Gln Leu Ala Ile Val Ser Gln Ile Val
    50                  55                  60 gag ctc ttg cat aat tcc agc ctt tta atc gac gat ata gaa gat aat     240
Glu Leu Leu His Asn Ser Ser Leu Leu Ile Asp Asp Ile Glu Asp Asn
 65                  70                  75                  80 gct ccc ttg aga agg gga cag acc act tct cac tta atc ttc ggt gta     288
Ala Pro Leu Arg Arg Gly Gln Thr Thr Ser His Leu Ile Phe Gly Val
                 85                  90                  95 ccc tcc act ata aac acc gca aat tat atg tat ttc aga gcc atg caa     336
Pro Ser Thr Ile Asn Thr Ala Asn Tyr Met Tyr Phe Arg Ala Met Gln
            100                 105                 110 ctt gta tcg cag cta acc aca aaa gag cct ttg tat cat aat ttg att     384
Leu Val Ser Gln Leu Thr Thr Lys Glu Pro Leu Tyr His Asn Leu Ile
        115                 120                 125 acg att ttc aac gaa gaa ttg atc aat cta cat agg gga caa ggc ttg     432
Thr Ile Phe Asn Glu Glu Leu Ile Asn Leu His Arg Gly Gln Gly Leu
    130                 135                 140 gat ata tac tgg aga gac ttt ctg cct gaa atc ata cct act cag gag     480
Asp Ile Tyr Trp Arg Asp Phe Leu Pro Glu Ile Ile Pro Thr Gln Glu
145                 150                 155                 160
```

```
                    145                 150                 155                 160
atg tat ttg aat atg gtt atg aat aaa aca ggc ggc ctt ttc aga tta        528
Met Tyr Leu Asn Met Val Met Asn Lys Thr Gly Gly Leu Phe Arg Leu
                    165                 170                 175 acg ttg aga ctc atg gaa gcg ctg tct cct tcc tca cac cac ggc cat        576
Thr Leu Arg Leu Met Glu Ala Leu Ser Pro Ser Ser His His Gly His
                180                 185                 190 tcg ttg gtt cct ttc ata aat ctt ctg ggt att att tat cag att aga        624
Ser Leu Val Pro Phe Ile Asn Leu Leu Gly Ile Ile Tyr Gln Ile Arg
            195                 200                 205 gat gat tac ttg aat ttg aaa gat ttc caa atg tcc agc gaa aaa ggc        672
Asp Asp Tyr Leu Asn Leu Lys Asp Phe Gln Met Ser Ser Glu Lys Gly
        210                 215                 220 ttt gct gag gac att aca gag ggg aag tta tct ttt ccc atc gtc cac        720
Phe Ala Glu Asp Ile Thr Glu Gly Lys Leu Ser Phe Pro Ile Val His
225                 230                 235                 240 gcc ctt aac ttc act aaa acg aaa ggt caa act gag caa cac aat gaa        768
Ala Leu Asn Phe Thr Lys Thr Lys Gly Gln Thr Glu Gln His Asn Glu
                245                 250                 255 att cta aga att ctc ctg ttg agg aca agt gat aaa gat ata aaa cta        816
Ile Leu Arg Ile Leu Leu Leu Arg Thr Ser Asp Lys Asp Ile Lys Leu
            260                 265                 270 aag ctg att caa ata ctg gaa ttc gac acc aat tca ttg gcc tac acc        864
Lys Leu Ile Gln Ile Leu Glu Phe Asp Thr Asn Ser Leu Ala Tyr Thr
        275                 280                 285 aaa aat ttt att aat caa tta gtg aat atg ata aaa aat gat aat gaa        912
Lys Asn Phe Ile Asn Gln Leu Val Asn Met Ile Lys Asn Asp Asn Glu
    290                 295                 300 aat aag tat tta cct gat ttg gct tcg cat tcc gac acc gcc acc aat        960
Asn Lys Tyr Leu Pro Asp Leu Ala Ser His Ser Asp Thr Ala Thr Asn
305                 310                 315                 320 tta cat gac gaa ttg tta tat ata ata gac cac tta tcc gaa ttg tga       1008
Leu His Asp Glu Leu Leu Tyr Ile Ile Asp His Leu Ser Glu Leu
                325                 330                 335

<210> SEQ ID NO 6
<211> LENGTH: 335
<212> TYPE: PRT
<213> ORGANISM: Saccharomyces cerevisiae

<400> SEQUENCE: 6

Met Glu Ala Lys Ile Asp Glu Leu Ile Asn Asn Asp Pro Val Trp Ser
1               5                   10                  15

Ser Gln Asn Glu Ser Leu Ile Ser Lys Pro Tyr Asn His Ile Leu Leu
            20                  25                  30

Lys Pro Gly Lys Asn Phe Arg Leu Asn Leu Ile Val Gln Ile Asn Arg
        35                  40                  45

Val Met Asn Leu Pro Lys Asp Gln Leu Ala Ile Val Ser Gln Ile Val
    50                  55                  60

Glu Leu Leu His Asn Ser Ser Leu Leu Ile Asp Asp Ile Glu Asp Asn
65                  70                  75                  80

Ala Pro Leu Arg Arg Gly Gln Thr Thr Ser His Leu Ile Phe Gly Val
                85                  90                  95

Pro Ser Thr Ile Asn Thr Ala Asn Tyr Met Tyr Phe Arg Ala Met Gln
            100                 105                 110

Leu Val Ser Gln Leu Thr Thr Lys Glu Pro Leu Tyr His Asn Leu Ile
        115                 120                 125

Thr Ile Phe Asn Glu Glu Leu Ile Asn Leu His Arg Gly Gln Gly Leu
```

```
                130                 135                 140
Asp Ile Tyr Trp Arg Asp Phe Leu Pro Glu Ile Ile Pro Thr Gln Glu
145                 150                 155                 160

Met Tyr Leu Asn Met Val Met Asn Lys Thr Gly Gly Leu Phe Arg Leu
                165                 170                 175

Thr Leu Arg Leu Met Glu Ala Leu Ser Pro Ser Ser His His Gly His
            180                 185                 190

Ser Leu Val Pro Phe Ile Asn Leu Leu Gly Ile Ile Tyr Gln Ile Arg
        195                 200                 205

Asp Asp Tyr Leu Asn Leu Lys Asp Phe Gln Met Ser Ser Glu Lys Gly
    210                 215                 220

Phe Ala Glu Asp Ile Thr Glu Gly Lys Leu Ser Phe Pro Ile Val His
225                 230                 235                 240

Ala Leu Asn Phe Thr Lys Thr Lys Gly Gln Thr Glu Gln His Asn Glu
                245                 250                 255

Ile Leu Arg Ile Leu Leu Leu Arg Thr Ser Asp Lys Asp Ile Lys Leu
            260                 265                 270

Lys Leu Ile Gln Ile Leu Glu Phe Asp Thr Asn Ser Leu Ala Tyr Thr
        275                 280                 285

Lys Asn Phe Ile Asn Gln Leu Val Asn Met Ile Lys Asn Asp Asn Glu
    290                 295                 300

Asn Lys Tyr Leu Pro Asp Leu Ala Ser His Ser Asp Thr Ala Thr Asn
305                 310                 315                 320

Leu His Asp Glu Leu Leu Tyr Ile Ile Asp His Leu Ser Glu Leu
                325                 330                 335

<210> SEQ ID NO 7
<211> LENGTH: 3165
<212> TYPE: DNA
<213> ORGANISM: Saccharomyces cerevisiae
<220> FEATURE:
<221> NAME/KEY: CDS
<222> LOCATION: (1)..(3162)

<400> SEQUENCE: 7 atg ccg ccg cta ttc aag gga ctg aaa cag atg gca aag cca att gcc      48
Met Pro Pro Leu Phe Lys Gly Leu Lys Gln Met Ala Lys Pro Ile Ala
 1               5                  10                  15 tat gtt tca aga ttt tcg gcg aaa cga cca att cat ata ata ctt ttt      96
Tyr Val Ser Arg Phe Ser Ala Lys Arg Pro Ile His Ile Ile Leu Phe
            20                  25                  30 tct cta atc ata tcc gca ttc gct tat cta tcc gtc att cag tat tac     144
Ser Leu Ile Ile Ser Ala Phe Ala Tyr Leu Ser Val Ile Gln Tyr Tyr
        35                  40                  45 ttc aat ggt tgg caa cta gat tca aat agt gtt ttt gaa act gct cca     192
Phe Asn Gly Trp Gln Leu Asp Ser Asn Ser Val Phe Glu Thr Ala Pro
    50                  55                  60 aat aaa gac tcc aac act cta ttt caa gaa tgt tcc cat tac tac aga     240
Asn Lys Asp Ser Asn Thr Leu Phe Gln Glu Cys Ser His Tyr Tyr Arg
65                  70                  75                  80 gat tcc tct cta gat ggt tgg gta tca atc acc gcg cat gaa gct agt     288
Asp Ser Ser Leu Asp Gly Trp Val Ser Ile Thr Ala His Glu Ala Ser
                85                  90                  95 gag tta cca gcc cca cac cat tac tat cta tta aac ctg aac ttc aat     336
Glu Leu Pro Ala Pro His His Tyr Tyr Leu Leu Asn Leu Asn Phe Asn
            100                 105                 110 agt cct aat gaa act gac tcc att cca gaa cta gct aac acg gtt ttt     384
Ser Pro Asn Glu Thr Asp Ser Ile Pro Glu Leu Ala Asn Thr Val Phe
```

-continued

|     | 115 |     |     |     | 120 |     |     |     | 125 |     |     |     |     |      |
|-----|-----|-----|-----|-----|-----|-----|-----|-----|-----|-----|-----|-----|-----|------|
| gag | aaa | gat | aat | aca | aaa | tat | att | ctg | caa | gaa | gat | ctc | agt | gtt | tcc | 432 |
| Glu | Lys | Asp | Asn | Thr | Lys | Tyr | Ile | Leu | Gln | Glu | Asp | Leu | Ser | Val | Ser |    |
|     | 130 |     |     |     | 135 |     |     |     | 140 |     |     |     |     |     |     |    |

```
gag aaa gat aat aca aaa tat att ctg caa gaa gat ctc agt gtt tcc       432
Glu Lys Asp Asn Thr Lys Tyr Ile Leu Gln Glu Asp Leu Ser Val Ser
    130             135             140 aaa gaa att tct tct act gat gga acg aaa tgg agg tta aga agt gac       480
Lys Glu Ile Ser Ser Thr Asp Gly Thr Lys Trp Arg Leu Arg Ser Asp
145             150             155             160 aga aaa agt ctt ttc gac gta aag acg tta gca tat tct ctc tac gat       528
Arg Lys Ser Leu Phe Asp Val Lys Thr Leu Ala Tyr Ser Leu Tyr Asp
        165             170             175 gta ttt tca gaa aat gta acc caa gca gac ccg ttt gac gtc ctt att       576
Val Phe Ser Glu Asn Val Thr Gln Ala Asp Pro Phe Asp Val Leu Ile
    180             185             190 atg gtt act gcc tac cta atg atg ttc tac acc ata ttc ggc ctc ttc       624
Met Val Thr Ala Tyr Leu Met Met Phe Tyr Thr Ile Phe Gly Leu Phe
        195             200             205 aat gac atg agg aag acc ggg tca aat ttt tgg ttg agc gcc tct aca       672
Asn Asp Met Arg Lys Thr Gly Ser Asn Phe Trp Leu Ser Ala Ser Thr
    210             215             220 gtg gtc aat tct gca tca tca ctt ttc tta gca ttg tat gtc acc caa       720
Val Val Asn Ser Ala Ser Ser Leu Phe Leu Ala Leu Tyr Val Thr Gln
225             230             235             240 tgt att cta ggc aaa gaa gtt tcc gca tta act ctt ttt gaa ggt ttg       768
Cys Ile Leu Gly Lys Glu Val Ser Ala Leu Thr Leu Phe Glu Gly Leu
        245             250             255 cct ttc att gta gtt gtt gtt ggt ttc aag cac aaa atc aag att gcc       816
Pro Phe Ile Val Val Val Val Gly Phe Lys His Lys Ile Lys Ile Ala
    260             265             270 cag tat gcc ctg gag aaa ttt gaa aga gtc ggt tta tct aaa agg att       864
Gln Tyr Ala Leu Glu Lys Phe Glu Arg Val Gly Leu Ser Lys Arg Ile
        275             280             285 act acc gat gaa atc gtt ttt gaa tcc gtg agc gaa gag ggt ggt cgt       912
Thr Thr Asp Glu Ile Val Phe Glu Ser Val Ser Glu Glu Gly Gly Arg
    290             295             300 ttg att caa gac cat ttg ctt tgt att ttt gcc ttt atc gga tgc tct       960
Leu Ile Gln Asp His Leu Leu Cys Ile Phe Ala Phe Ile Gly Cys Ser
305             310             315             320 atg tat gct cac caa ttg aag act ttg aca aac ttc tgc ata tta tca      1008
Met Tyr Ala His Gln Leu Lys Thr Leu Thr Asn Phe Cys Ile Leu Ser
        325             330             335 gca ttt atc cta att ttt gaa ttg att tta act cct aca ttt tat tct      1056
Ala Phe Ile Leu Ile Phe Glu Leu Ile Leu Thr Pro Thr Phe Tyr Ser
    340             345             350 gct atc tta gcg ctt aga ctg gaa atg aat gtt atc cac aga tct act      1104
Ala Ile Leu Ala Leu Arg Leu Glu Met Asn Val Ile His Arg Ser Thr
        355             360             365 att atc aag caa aca tta gaa gaa gac ggt gtt gtt cca tct aca gca      1152
Ile Ile Lys Gln Thr Leu Glu Glu Asp Gly Val Val Pro Ser Thr Ala
370             375             380 aga atc att tct aaa gca gaa aag aaa tcc gta tct tct ttc tta aat      1200
Arg Ile Ile Ser Lys Ala Glu Lys Lys Ser Val Ser Ser Phe Leu Asn
385             390             395             400 ctc agt gtg gtt gtc att atc atg aaa ctc tct gtc ata ctg ttg ttt      1248
Leu Ser Val Val Val Ile Ile Met Lys Leu Ser Val Ile Leu Leu Phe
        405             410             415 gtc ttc atc aac ttt tat aac ttt ggt gca aat tgg gtc aat gat gcc      1296
Val Phe Ile Asn Phe Tyr Asn Phe Gly Ala Asn Trp Val Asn Asp Ala
    420             425             430 ttc aat tca ttg tac ttc gat aag gaa cgt gtt tct cta cca gat ttt      1344
```

```
                Phe Asn Ser Leu Tyr Phe Asp Lys Glu Arg Val Ser Leu Pro Asp Phe
                        435                 440                 445 att acc tcg aat gcc tct gaa aac ttt aaa gag caa gct att gtt agt         1392
Ile Thr Ser Asn Ala Ser Glu Asn Phe Lys Glu Gln Ala Ile Val Ser
        450                 455                 460 gtc acc cca tta tta tat tac aaa ccc att aag tcc tac caa cgc att         1440
Val Thr Pro Leu Leu Tyr Tyr Lys Pro Ile Lys Ser Tyr Gln Arg Ile
465                 470                 475                 480 gag gat atg gtt ctt cta ttg ctt cgt aat gtc agt gtt gcc att cgt         1488
Glu Asp Met Val Leu Leu Leu Leu Arg Asn Val Ser Val Ala Ile Arg
                485                 490                 495 gat agg ttc gtc agt aaa tta gtt ctt tcc gcc tta gta tgc agt gct         1536
Asp Arg Phe Val Ser Lys Leu Val Leu Ser Ala Leu Val Cys Ser Ala
            500                 505                 510 gtc atc aat gtg tat tta ttg aat gct gct aga att cat acc agt tat         1584
Val Ile Asn Val Tyr Leu Leu Asn Ala Ala Arg Ile His Thr Ser Tyr
        515                 520                 525 act gca gac caa ttg gtg aaa act gaa gtc acc aag aag tct ttt act         1632
Thr Ala Asp Gln Leu Val Lys Thr Glu Val Thr Lys Lys Ser Phe Thr
530                 535                 540 gct cct gta caa aag gct tct aca cca gtt tta acc aat aaa aca gtc         1680
Ala Pro Val Gln Lys Ala Ser Thr Pro Val Leu Thr Asn Lys Thr Val
545                 550                 555                 560 att tct gga tcg aaa gtc aaa agt tta tca tct gcg caa tcg agc tca         1728
Ile Ser Gly Ser Lys Val Lys Ser Leu Ser Ser Ala Gln Ser Ser Ser
                565                 570                 575 tca gga cct tca tca tct agt gag gaa gat gat tcc cgc gat att gaa         1776
Ser Gly Pro Ser Ser Ser Ser Glu Glu Asp Asp Ser Arg Asp Ile Glu
            580                 585                 590 agc ttg gat aag aaa ata cgt cct tta gaa gaa tta gaa gca tta tta         1824
Ser Leu Asp Lys Lys Ile Arg Pro Leu Glu Glu Leu Glu Ala Leu Leu
        595                 600                 605 agt agt gga aat aca aaa caa ttg aag aac aaa gag gtc gct gcc ttg         1872
Ser Ser Gly Asn Thr Lys Gln Leu Lys Asn Lys Glu Val Ala Ala Leu
    610                 615                 620 gtt att cac ggt aag tta cct ttg tac gct ttg gag aaa aaa tta ggt         1920
Val Ile His Gly Lys Leu Pro Leu Tyr Ala Leu Glu Lys Lys Leu Gly
625                 630                 635                 640 gat act acg aga gcg gtt gcg gta cgt agg aag gct ctt tca att ttg         1968
Asp Thr Thr Arg Ala Val Ala Val Arg Arg Lys Ala Leu Ser Ile Leu
                645                 650                 655 gca gaa gct cct gta tta gca tct gat cgt tta cca tat aaa aat tat         2016
Ala Glu Ala Pro Val Leu Ala Ser Asp Arg Leu Pro Tyr Lys Asn Tyr
            660                 665                 670 gac tac gac cgc gta ttt ggc gct tgt tgt gaa aat gtt ata ggt tac         2064
Asp Tyr Asp Arg Val Phe Gly Ala Cys Cys Glu Asn Val Ile Gly Tyr
        675                 680                 685 atg cct ttg ccc gtt ggt gtt ata ggc ccc ttg gtt atc gat ggt aca         2112
Met Pro Leu Pro Val Gly Val Ile Gly Pro Leu Val Ile Asp Gly Thr
    690                 695                 700 tct tat cat ata cca atg gca act aca gag ggt tgt ttg gta gct tct         2160
Ser Tyr His Ile Pro Met Ala Thr Thr Glu Gly Cys Leu Val Ala Ser
705                 710                 715                 720 gcc atg cgt ggc tgt aag gca atc aat gct ggc ggt ggt gca aca act         2208
Ala Met Arg Gly Cys Lys Ala Ile Asn Ala Gly Gly Gly Ala Thr Thr
                725                 730                 735 gtt tta act aag gat ggt atg aca aga ggc cca gta gtc cgt ttc cca         2256
Val Leu Thr Lys Asp Gly Met Thr Arg Gly Pro Val Val Arg Phe Pro
            740                 745                 750
```

```
act ttg aaa aga tct ggt gcc tgt aag ata tgg tta gac tca gaa gag    2304
Thr Leu Lys Arg Ser Gly Ala Cys Lys Ile Trp Leu Asp Ser Glu Glu
        755                 760                 765 gga caa aac gca att aaa aaa gct ttt aac tct aca tca aga ttt gca    2352
Gly Gln Asn Ala Ile Lys Lys Ala Phe Asn Ser Thr Ser Arg Phe Ala
    770                 775                 780 cgt ctg caa cat att caa act tgt cta gca gga gat tta ctc ttc atg    2400
Arg Leu Gln His Ile Gln Thr Cys Leu Ala Gly Asp Leu Leu Phe Met
785                 790                 795                 800 aga ttt aga aca act act ggt gac gca atg ggt atg aat atg att tct    2448
Arg Phe Arg Thr Thr Thr Gly Asp Ala Met Gly Met Asn Met Ile Ser
                805                 810                 815 aaa ggt gtc gaa tac tca tta aag caa atg gta gaa gag tat ggc tgg    2496
Lys Gly Val Glu Tyr Ser Leu Lys Gln Met Val Glu Glu Tyr Gly Trp
        820                 825                 830 gaa gat atg gag gtt gtc tcc gtt tct ggt aac tac tgt acc gac aaa    2544
Glu Asp Met Glu Val Val Ser Val Ser Gly Asn Tyr Cys Thr Asp Lys
    835                 840                 845 aaa cca gct gcc atc aac tgg atc gaa ggt cgt ggt aag agt gtc gtc    2592
Lys Pro Ala Ala Ile Asn Trp Ile Glu Gly Arg Gly Lys Ser Val Val
850                 855                 860 gca gaa gct act att cct ggt gat gtt gtc aga aaa gtg tta aaa agt    2640
Ala Glu Ala Thr Ile Pro Gly Asp Val Val Arg Lys Val Leu Lys Ser
865                 870                 875                 880 gat gtt tcc gca ttg gtt gag ttg aac att gct aag aat ttg gtt gga    2688
Asp Val Ser Ala Leu Val Glu Leu Asn Ile Ala Lys Asn Leu Val Gly
                885                 890                 895 tct gca atg gct ggg tct gtt ggt gga ttt aac gca cat gca gct aat    2736
Ser Ala Met Ala Gly Ser Val Gly Gly Phe Asn Ala His Ala Ala Asn
        900                 905                 910 tta gtg aca gct gtt ttc ttg gca tta gga caa gat cct gca caa aat    2784
Leu Val Thr Ala Val Phe Leu Ala Leu Gly Gln Asp Pro Ala Gln Asn
    915                 920                 925 gtt gaa agt tcc aac tgt ata aca ttg atg aaa gaa gtg gac ggt gat    2832
Val Glu Ser Ser Asn Cys Ile Thr Leu Met Lys Glu Val Asp Gly Asp
930                 935                 940 ttg aga att tcc gta tcc atg cca tcc atc gaa gta ggt acc atc ggt    2880
Leu Arg Ile Ser Val Ser Met Pro Ser Ile Glu Val Gly Thr Ile Gly
945                 950                 955                 960 ggt ggt act gtt cta gaa cca caa ggt gcc atg ttg gac tta tta ggt    2928
Gly Gly Thr Val Leu Glu Pro Gln Gly Ala Met Leu Asp Leu Leu Gly
                965                 970                 975 gta aga ggc ccg cat gct acc gct cct ggt acc aac gca cgt caa tta    2976
Val Arg Gly Pro His Ala Thr Ala Pro Gly Thr Asn Ala Arg Gln Leu
        980                 985                 990 gca aga ata gtt gcc tgt gcc gtc ttg gca ggt gaa tta tcc tta tgt    3024
Ala Arg Ile Val Ala Cys Ala Val Leu Ala Gly Glu Leu Ser Leu Cys
    995                 1000                1005 gct gcc cta gca gcc ggc cat ttg gtt caa agt cat atg acc cac aac    3072
Ala Ala Leu Ala Ala Gly His Leu Val Gln Ser His Met Thr His Asn
1010                1015                1020 agg aaa cct gct gaa cca aca aaa cct aac aat ttg gac gcc act gat    3120
Arg Lys Pro Ala Glu Pro Thr Lys Pro Asn Asn Leu Asp Ala Thr Asp
1025                1030                1035                1040 ata aat cgt ttg aaa gat ggg tcc gtc acc tgc att aaa tcc taa       3165
Ile Asn Arg Leu Lys Asp Gly Ser Val Thr Cys Ile Lys Ser
                1045                1050

<210> SEQ ID NO 8
<211> LENGTH: 1054
```

<212> TYPE: PRT
<213> ORGANISM: Saccharomyces cerevisiae

<400> SEQUENCE: 8

```
Met Pro Pro Leu Phe Lys Gly Leu Lys Gln Met Ala Lys Pro Ile Ala
 1               5                  10                  15

Tyr Val Ser Arg Phe Ser Ala Lys Arg Pro Ile His Ile Ile Leu Phe
             20                  25                  30

Ser Leu Ile Ile Ser Ala Phe Ala Tyr Leu Ser Val Ile Gln Tyr Tyr
         35                  40                  45

Phe Asn Gly Trp Gln Leu Asp Ser Asn Ser Val Phe Glu Thr Ala Pro
     50                  55                  60

Asn Lys Asp Ser Asn Thr Leu Phe Gln Glu Cys Ser His Tyr Tyr Arg
 65                  70                  75                  80

Asp Ser Ser Leu Asp Gly Trp Val Ser Ile Thr Ala His Glu Ala Ser
                 85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
    210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
    290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
    370                 375                 380

Arg Ile Ile Ser Lys Ala Glu Lys Lys Ser Val Ser Ser Phe Leu Asn
385                 390                 395                 400
```

-continued

```
Leu Ser Val Val Ile Ile Met Lys Leu Ser Val Ile Leu Leu Phe
            405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
            435                 440                 445

Ile Thr Ser Asn Ala Ser Glu Asn Phe Lys Glu Gln Ala Ile Val Ser
            450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Arg Asn Val Ser Val Ala Ile Arg
            485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
            515                 520                 525

Thr Ala Asp Gln Leu Val Lys Thr Glu Val Thr Lys Lys Ser Phe Thr
            530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
            565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
            595                 600                 605

Ser Ser Gly Asn Thr Lys Gln Leu Lys Asn Lys Glu Val Ala Ala Leu
            610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
            645                 650                 655

Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
            675                 680                 685

Met Pro Leu Pro Val Gly Val Ile Gly Pro Leu Val Ile Asp Gly Thr
            690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
            725                 730                 735

Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
            755                 760                 765

Gly Gln Asn Ala Ile Lys Lys Ala Phe Asn Ser Thr Ser Arg Phe Ala
            770                 775                 780

Arg Leu Gln His Ile Gln Thr Cys Leu Ala Gly Asp Leu Leu Phe Met
785                 790                 795                 800

Arg Phe Arg Thr Thr Gly Asp Ala Met Gly Met Asn Met Ile Ser
            805                 810                 815
```

-continued

```
Lys Gly Val Glu Tyr Ser Leu Lys Gln Met Val Glu Tyr Gly Trp
            820                 825                 830

Glu Asp Met Glu Val Val Ser Val Ser Gly Asn Tyr Cys Thr Asp Lys
        835                 840                 845

Lys Pro Ala Ala Ile Asn Trp Ile Glu Gly Arg Gly Lys Ser Val Val
850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
        915                 920                 925

Val Glu Ser Ser Asn Cys Ile Thr Leu Met Lys Glu Val Asp Gly Asp
    930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
        995                 1000                1005

Ala Ala Leu Ala Ala Gly His Leu Val Gln Ser His Met Thr His Asn
    1010                1015                1020

Arg Lys Pro Ala Glu Pro Thr Lys Pro Asn Asn Leu Asp Ala Thr Asp
1025                1030                1035                1040

Ile Asn Arg Leu Lys Asp Gly Ser Val Thr Cys Ile Lys Ser
                1045                1050

<210> SEQ ID NO 9
<211> LENGTH: 1191
<212> TYPE: DNA
<213> ORGANISM: Saccharomyces cerevisiae
<220> FEATURE:
<221> NAME/KEY: CDS
<222> LOCATION: (1)..(1188)

<400> SEQUENCE: 9 atg acc gtt tac aca gca tcc gtt acc gca ccc gtc aac atc gca acc      48
Met Thr Val Tyr Thr Ala Ser Val Thr Ala Pro Val Asn Ile Ala Thr
1               5                   10                  15 ctt aag tat tgg ggg aaa agg gac acg aag ttg aat ctg ccc acc aat      96
Leu Lys Tyr Trp Gly Lys Arg Asp Thr Lys Leu Asn Leu Pro Thr Asn
            20                  25                  30 tcg tcc ata tca gtg act tta tcg caa gat gac ctc aga acg ttg acc     144
Ser Ser Ile Ser Val Thr Leu Ser Gln Asp Asp Leu Arg Thr Leu Thr
        35                  40                  45 tct gcg gct act gca cct gag ttt gaa cgc gac act ttg tgg tta aat     192
Ser Ala Ala Thr Ala Pro Glu Phe Glu Arg Asp Thr Leu Trp Leu Asn
    50                  55                  60 gga gaa cca cac agc atc gac aat gaa aga act caa aat tgt ctg cgc     240
Gly Glu Pro His Ser Ile Asp Asn Glu Arg Thr Gln Asn Cys Leu Arg
65                  70                  75                  80 gac cta cgc caa tta aga aag gaa atg gaa tcg aag gac gcc tca ttg     288
Asp Leu Arg Gln Leu Arg Lys Glu Met Glu Ser Lys Asp Ala Ser Leu
                85                  90                  95
```

```
ccc aca tta tct caa tgg aaa ctc cac att gtc tcc gaa aat aac ttt      336
Pro Thr Leu Ser Gln Trp Lys Leu His Ile Val Ser Glu Asn Asn Phe
            100                 105                 110 cct aca gca gct ggt tta gct tcc tcc gct gct ggc ttt gct gca ttg      384
Pro Thr Ala Ala Gly Leu Ala Ser Ser Ala Ala Gly Phe Ala Ala Leu
        115                 120                 125 gtc tct gca att gct aag tta tac caa tta cca cag tca act tca gaa     432
Val Ser Ala Ile Ala Lys Leu Tyr Gln Leu Pro Gln Ser Thr Ser Glu
130                 135                 140 ata tct aga ata gca aga aag ggg tct ggt tca gct tgt aga tcg ttg     480
Ile Ser Arg Ile Ala Arg Lys Gly Ser Gly Ser Ala Cys Arg Ser Leu
145                 150                 155                 160 ttt ggc gga tac gtg gcc tgg gaa atg gga aaa gct gaa gat ggt cat     528
Phe Gly Gly Tyr Val Ala Trp Glu Met Gly Lys Ala Glu Asp Gly His
                165                 170                 175 gat tcc atg gca gta caa atc gca gac agc tct gac tgg cct cag atg     576
Asp Ser Met Ala Val Gln Ile Ala Asp Ser Ser Asp Trp Pro Gln Met
            180                 185                 190 aaa gct tgt gtc cta gtt gtc agc gat att aaa aag gat gtg agt tcc     624
Lys Ala Cys Val Leu Val Val Ser Asp Ile Lys Lys Asp Val Ser Ser
        195                 200                 205 act cag ggt atg caa ttg acc gtg gca acc tcc gaa cta ttt aaa gaa     672
Thr Gln Gly Met Gln Leu Thr Val Ala Thr Ser Glu Leu Phe Lys Glu
210                 215                 220 aga att gaa cat gtc gta cca aag aga ttt gaa gtc atg cgt aaa gcc     720
Arg Ile Glu His Val Val Pro Lys Arg Phe Glu Val Met Arg Lys Ala
225                 230                 235                 240 att gtt gaa aaa gat ttc gcc acc ttt gca aag gaa aca atg atg gat     768
Ile Val Glu Lys Asp Phe Ala Thr Phe Ala Lys Glu Thr Met Met Asp
                245                 250                 255 tcc aac tct ttc cat gcc aca tgt ttg gac tct ttc cct cca ata ttc     816
Ser Asn Ser Phe His Ala Thr Cys Leu Asp Ser Phe Pro Pro Ile Phe
            260                 265                 270 tac atg aat gac act tcc aag cgt atc atc agt tgg tgc cac acc att     864
Tyr Met Asn Asp Thr Ser Lys Arg Ile Ile Ser Trp Cys His Thr Ile
        275                 280                 285 aat cag ttt tac gga gaa aca atc gtt gca tac acg ttt gat gca ggt     912
Asn Gln Phe Tyr Gly Glu Thr Ile Val Ala Tyr Thr Phe Asp Ala Gly
290                 295                 300 cca aat gct gtg ttg tac tac tta gct gaa aat gag tcg aaa ctc ttt     960
Pro Asn Ala Val Leu Tyr Tyr Leu Ala Glu Asn Glu Ser Lys Leu Phe
305                 310                 315                 320 gca ttt atc tat aaa ttg ttt ggc tct gtt cct gga tgg gac aag aaa    1008
Ala Phe Ile Tyr Lys Leu Phe Gly Ser Val Pro Gly Trp Asp Lys Lys
                325                 330                 335 ttt act act gag cag ctt gag gct ttc aac cat caa ttt gaa tca tct    1056
Phe Thr Thr Glu Gln Leu Glu Ala Phe Asn His Gln Phe Glu Ser Ser
            340                 345                 350 aac ttt act gca cgt gaa ttg gat ctt gag ttg caa aag gat gtt gcc    1104
Asn Phe Thr Ala Arg Glu Leu Asp Leu Glu Leu Gln Lys Asp Val Ala
        355                 360                 365 aga gtg att tta act caa gtc ggt tca ggc cca caa gaa aca aac gaa    1152
Arg Val Ile Leu Thr Gln Val Gly Ser Gly Pro Gln Glu Thr Asn Glu
370                 375                 380 tct ttg att gac gca aag act ggt cta cca aag gaa taa                1191
Ser Leu Ile Asp Ala Lys Thr Gly Leu Pro Lys Glu
385                 390                 395
```

<210> SEQ ID NO 10

<211> LENGTH: 396
<212> TYPE: PRT
<213> ORGANISM: Saccharomyces cerevisiae

<400> SEQUENCE: 10

```
Met Thr Val Tyr Thr Ala Ser Val Thr Ala Pro Val Asn Ile Ala Thr
 1               5                  10                  15

Leu Lys Tyr Trp Gly Lys Arg Asp Thr Lys Leu Asn Leu Pro Thr Asn
                20                  25                  30

Ser Ser Ile Ser Val Thr Leu Ser Gln Asp Asp Leu Arg Thr Leu Thr
            35                  40                  45

Ser Ala Ala Thr Ala Pro Glu Phe Glu Arg Asp Thr Leu Trp Leu Asn
 50                  55                  60

Gly Glu Pro His Ser Ile Asp Asn Glu Arg Thr Gln Asn Cys Leu Arg
 65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
```

```
385              390              395

<210> SEQ ID NO 11
<211> LENGTH: 3165
<212> TYPE: DNA
<213> ORGANISM: Saccharomyces cerevisiae
<220> FEATURE:
<221> NAME/KEY: CDS
<222> LOCATION: (1)..(3162)

<400> SEQUENCE: 11 atg ccg ccg cta ttc aag gga ctg aaa cag atg gca aag cca att gcc      48
Met Pro Pro Leu Phe Lys Gly Leu Lys Gln Met Ala Lys Pro Ile Ala
 1               5                  10                  15 tat gtt tca aga ttt tcg gcg aaa cga cca att cat ata ata ctt ttt      96
Tyr Val Ser Arg Phe Ser Ala Lys Arg Pro Ile His Ile Ile Leu Phe
             20                  25                  30 tct cta atc ata tcc gca ttc gct tat cta tcc gtc att cag tat tac     144
Ser Leu Ile Ile Ser Ala Phe Ala Tyr Leu Ser Val Ile Gln Tyr Tyr
         35                  40                  45 ttc aat ggt tgg caa cta gat tca aat agt gtt ttt gaa act gct cca     192
Phe Asn Gly Trp Gln Leu Asp Ser Asn Ser Val Phe Glu Thr Ala Pro
     50                  55                  60 aat aaa gac ttc aac act cta ttt caa gaa tgt tcc cat tac tac aga     240
Asn Lys Asp Phe Asn Thr Leu Phe Gln Glu Cys Ser His Tyr Tyr Arg
 65                  70                  75                  80 gat tcc tct cta gat ggt tgg gta tca atc acc gcg cat gaa gct agt     288
Asp Ser Ser Leu Asp Gly Trp Val Ser Ile Thr Ala His Glu Ala Ser
                 85                  90                  95 gag tta cca gcc cca cac cat tac tat cta tta aac ctg aac ttc aat     336
Glu Leu Pro Ala Pro His His Tyr Tyr Leu Leu Asn Leu Asn Phe Asn
            100                 105                 110 agt cct aat gaa act gac tcc att cca gaa cta gct aac acg gtt ttt     384
Ser Pro Asn Glu Thr Asp Ser Ile Pro Glu Leu Ala Asn Thr Val Phe
        115                 120                 125 gag aaa gat aat aca aaa tat att ctg caa gaa gat ctc agc gtt tcc     432
Glu Lys Asp Asn Thr Lys Tyr Ile Leu Gln Glu Asp Leu Ser Val Ser
    130                 135                 140 aaa gaa att tct tct act gat gga acg aaa tgg agg tta aga agt gac     480
Lys Glu Ile Ser Ser Thr Asp Gly Thr Lys Trp Arg Leu Arg Ser Asp
145                 150                 155                 160 aga aaa agt ctt ttc gac gta aag acg tta gca tat tct ctc tac gat     528
Arg Lys Ser Leu Phe Asp Val Lys Thr Leu Ala Tyr Ser Leu Tyr Asp
                165                 170                 175 gta ttt tca gaa aat gta acc caa gca gac ccg ttt gac gtc ctt att     576
Val Phe Ser Glu Asn Val Thr Gln Ala Asp Pro Phe Asp Val Leu Ile
            180                 185                 190 atg gtt act gcc tac cta atg atg ttc tac acc ata ttc ggc ctc ttc     624
Met Val Thr Ala Tyr Leu Met Met Phe Tyr Thr Ile Phe Gly Leu Phe
        195                 200                 205 aat gac atg agg aag acc ggg tca aat ttt tgg ttg agc gcc tct aca     672
Asn Asp Met Arg Lys Thr Gly Ser Asn Phe Trp Leu Ser Ala Ser Thr
    210                 215                 220 gtg gtc aat tct gca tca tca ctt ttc tta gca ttg tat gtc acc caa     720
Val Val Asn Ser Ala Ser Ser Leu Phe Leu Ala Leu Tyr Val Thr Gln
225                 230                 235                 240 tgt att cta ggc aaa gaa gtt tcc gca tta act ctt ttt gaa ggt ttg     768
Cys Ile Leu Gly Lys Glu Val Ser Ala Leu Thr Leu Phe Glu Gly Leu
                245                 250                 255 cct ttc att gta gtt gtt gtt ggt ttc aag cac aaa atc aag att gcc     816
Pro Phe Ile Val Val Val Val Gly Phe Lys His Lys Ile Lys Ile Ala
```

-continued

```
              260                 265                 270
cag tat gcc ctg gag aaa ttt gaa aga gtc ggt tta tct aaa agg att        864
Gln Tyr Ala Leu Glu Lys Phe Glu Arg Val Gly Leu Ser Lys Arg Ile
        275                 280                 285 act acc gat gaa atc gtt ttt gaa tcc gtg agc gaa gag ggt ggt cgt        912
Thr Thr Asp Glu Ile Val Phe Glu Ser Val Ser Glu Glu Gly Gly Arg
290                 295                 300 ttg att caa gac cat ttg ctt tgt att ttt gcc ttt atc gga tgc tct        960
Leu Ile Gln Asp His Leu Leu Cys Ile Phe Ala Phe Ile Gly Cys Ser
305                 310                 315                 320 atg tat gct cac caa ttg aag act ttg aca aac ttc tgc ata tta tca       1008
Met Tyr Ala His Gln Leu Lys Thr Leu Thr Asn Phe Cys Ile Leu Ser
            325                 330                 335 gca ttt atc cta att ttc gaa ttg att tta act cct aca ttt tat tct       1056
Ala Phe Ile Leu Ile Phe Glu Leu Ile Leu Thr Pro Thr Phe Tyr Ser
                340                 345                 350 gct atc tta gcg ctt aga ctg gaa atg aat gtt atc cac aga tct act       1104
Ala Ile Leu Ala Leu Arg Leu Glu Met Asn Val Ile His Arg Ser Thr
                    355                 360                 365 att atc aag caa aca tta gaa gaa gac ggt gtt gtt cca tct aca gca       1152
Ile Ile Lys Gln Thr Leu Glu Glu Asp Gly Val Val Pro Ser Thr Ala
370                 375                 380 aga atc att tct aag gca gaa aag aaa tcc gta tct tct ttc tta aat       1200
Arg Ile Ile Ser Lys Ala Glu Lys Lys Ser Val Ser Ser Phe Leu Asn
385                 390                 395                 400 ctc agt gtg gtt gtc att atc atg aaa ctc tct gtc ata ctg ttg ttc       1248
Leu Ser Val Val Val Ile Ile Met Lys Leu Ser Val Ile Leu Leu Phe
                405                 410                 415 gtc ttc atc aac ttt tat aac ttt ggt gca aat tgg gtc aat gat gcc       1296
Val Phe Ile Asn Phe Tyr Asn Phe Gly Ala Asn Trp Val Asn Asp Ala
                    420                 425                 430 ttc aat tca ttg tac ttc gat aag gaa cgt gtt tct cta cca gat ttt       1344
Phe Asn Ser Leu Tyr Phe Asp Lys Glu Arg Val Ser Leu Pro Asp Phe
                        435                 440                 445 att acc tcg aat gcc tct gaa aac ttt aaa gag caa gct att gtt agt       1392
Ile Thr Ser Asn Ala Ser Glu Asn Phe Lys Glu Gln Ala Ile Val Ser
450                 455                 460 gtc acc cca tta tta tat tac aaa ccc att aag tcc tac caa cgc att       1440
Val Thr Pro Leu Leu Tyr Tyr Lys Pro Ile Lys Ser Tyr Gln Arg Ile
465                 470                 475                 480 gag gat atg gtt ctt cta ttg ctt cgt aat gtc agt gtt gcc att cgt       1488
Glu Asp Met Val Leu Leu Leu Arg Asn Val Ser Val Ala Ile Arg
                485                 490                 495 gat agg ttc gtc agt aaa tta gtt ctt tcc gcc tta gta tgc agt gct       1536
Asp Arg Phe Val Ser Lys Leu Val Leu Ser Ala Leu Val Cys Ser Ala
                    500                 505                 510 gtc atc aat gtg tat tta tta aat gct gct aga att cat acc agt tat       1584
Val Ile Asn Val Tyr Leu Leu Asn Ala Ala Arg Ile His Thr Ser Tyr
            515                 520                 525 act gca gac caa ttg gtg aag act gaa gtc acc aag aag tct ttt act       1632
Thr Ala Asp Gln Leu Val Lys Thr Glu Val Thr Lys Lys Ser Phe Thr
530                 535                 540 gct cct gta caa aag gct tct aca cca gtt tta acc aat aaa aca gtc       1680
Ala Pro Val Gln Lys Ala Ser Thr Pro Val Leu Thr Asn Lys Thr Val
545                 550                 555                 560 att tct gga tcg aaa gtc aaa agt tta tca tct gcg caa tcg agc tca       1728
Ile Ser Gly Ser Lys Val Lys Ser Leu Ser Ser Ala Gln Ser Ser Ser
                565                 570                 575 tca gga cct tca tca tct agt gag gaa gat gat tcc cgc gat att gaa       1776
```

```
Ser Gly Pro Ser Ser Ser Glu Glu Asp Asp Ser Arg Asp Ile Glu
            580             585                 590 agc ttg gat aag aaa ata cgt cct tta gaa gaa tta gaa gca tca tta      1824
Ser Leu Asp Lys Lys Ile Arg Pro Leu Glu Glu Leu Glu Ala Ser Leu
            595             600             605 agt agt gga aat aca aaa caa ttg aag aac aaa gag gtc gct gcc ttg      1872
Ser Ser Gly Asn Thr Lys Gln Leu Lys Asn Lys Glu Val Ala Ala Leu
            610             615             620 gtt att cac ggt aag tta cct ttg tac gct ttg gag aaa aaa tta ggt      1920
Val Ile His Gly Lys Leu Pro Leu Tyr Ala Leu Glu Lys Lys Leu Gly
625             630             635             640 gat act acg aga gcg gtt gcg gta cgt agg aag gct ctt tca att ttg      1968
Asp Thr Thr Arg Ala Val Ala Val Arg Arg Lys Ala Leu Ser Ile Leu
            645             650             655 gca gaa gct cct gta tta gca tct gat cgt tta cca tat aaa aat tat      2016
Ala Glu Ala Pro Val Leu Ala Ser Asp Arg Leu Pro Tyr Lys Asn Tyr
            660             665             670 gac tac gac cgc gta ttt ggc gct tgt tgt gaa aat gtt ata ggt tac      2064
Asp Tyr Asp Arg Val Phe Gly Ala Cys Cys Glu Asn Val Ile Gly Tyr
            675             680             685 atg cct ttg ccc gtt ggt gtt ata ggc ccc ttg gtt atc gat ggt aca      2112
Met Pro Leu Pro Val Gly Val Ile Gly Pro Leu Val Ile Asp Gly Thr
690             695             700 tct tat cat ata cca atg gca act aca gag ggt tgt ttg gta gct tct      2160
Ser Tyr His Ile Pro Met Ala Thr Thr Glu Gly Cys Leu Val Ala Ser
705             710             715             720 gcc atg cgt ggc tgt aag gca atc aat gct ggc ggt ggt gca aca act      2208
Ala Met Arg Gly Cys Lys Ala Ile Asn Ala Gly Gly Gly Ala Thr Thr
            725             730             735 gtt tta act aag gat ggt atg aca aga ggc cca gta gtc cgt ttc cca      2256
Val Leu Thr Lys Asp Gly Met Thr Arg Gly Pro Val Val Arg Phe Pro
            740             745             750 act ttg aaa aga tct ggt gcc tgt aag ata tgg tta gac tca gaa gag      2304
Thr Leu Lys Arg Ser Gly Ala Cys Lys Ile Trp Leu Asp Ser Glu Glu
            755             760             765 gga caa aac gca att aaa aaa gct ttt aac tct aca tca aga ttt gca      2352
Gly Gln Asn Ala Ile Lys Lys Ala Phe Asn Ser Thr Ser Arg Phe Ala
770             775             780 cgt ctg caa cat att caa act tgt cta gca gga gat tta ctc ttc atg      2400
Arg Leu Gln His Ile Gln Thr Cys Leu Ala Gly Asp Leu Leu Phe Met
785             790             795             800 aga ttt aga aca act act ggt gac gca atg ggt atg aat atg att tct      2448
Arg Phe Arg Thr Thr Thr Gly Asp Ala Met Gly Met Asn Met Ile Ser
            805             810             815 aag ggt gtc gaa tac tca tta aag caa atg gta gaa gag tat ggc tgg      2496
Lys Gly Val Glu Tyr Ser Leu Lys Gln Met Val Glu Glu Tyr Gly Trp
            820             825             830 gaa gat atg gag gtt gtc tcc gtt tct ggt aac tac tgt acc gac aaa      2544
Glu Asp Met Glu Val Val Ser Val Ser Gly Asn Tyr Cys Thr Asp Lys
            835             840             845 aaa cca gct gcc atc aac tgg atc gaa ggt cgt ggt aag agt gtc gtc      2592
Lys Pro Ala Ala Ile Asn Trp Ile Glu Gly Arg Gly Lys Ser Val Val
850             855             860 gca gaa gct act att cct ggt gat gtt gtc aga aaa gtg tta aaa agt      2640
Ala Glu Ala Thr Ile Pro Gly Asp Val Val Arg Lys Val Leu Lys Ser
865             870             875             880 gat gtt tcc gca ttg gtt gag ttg aac att gct aag aat ttg gtt gga      2688
Asp Val Ser Ala Leu Val Glu Leu Asn Ile Ala Lys Asn Leu Val Gly
            885             890             895
```

```
tct gca atg gct ggg tct gtt ggt gga ttt aac gca cgt gca gct aat    2736
Ser Ala Met Ala Gly Ser Val Gly Gly Phe Asn Ala Arg Ala Ala Asn
        900                 905                 910 tta gtg aca gct gtt ttc ttg gca tta gga caa gat cct gca caa aat    2784
Leu Val Thr Ala Val Phe Leu Ala Leu Gly Gln Asp Pro Ala Gln Asn
            915                 920                 925 gtc gaa agt tcc aac tgt ata aca ttg atg aaa gaa gtg gac ggt gat    2832
Val Glu Ser Ser Asn Cys Ile Thr Leu Met Lys Glu Val Asp Gly Asp
        930                 935                 940 ttg aga att tcc gta tcc atg cca tcc atc gaa gta ggt acc atc ggt    2880
Leu Arg Ile Ser Val Ser Met Pro Ser Ile Glu Val Gly Thr Ile Gly
945                 950                 955                 960 ggt ggt act gtt cta gaa cca caa ggt gcc atg ttg gac tta tta ggt    2928
Gly Gly Thr Val Leu Glu Pro Gln Gly Ala Met Leu Asp Leu Leu Gly
            965                 970                 975 gta aga ggc cca cat gct acc gct cct ggt acc aac gca cgt caa tta    2976
Val Arg Gly Pro His Ala Thr Ala Pro Gly Thr Asn Ala Arg Gln Leu
        980                 985                 990 gca aga ata gtt gcc tgt gcc gtc ttg gca ggt gaa tta tcc tta tgt    3024
Ala Arg Ile Val Ala Cys Ala Val Leu Ala Gly Glu Leu Ser Leu Cys
        995                1000                1005 gct gcc cta gca gcc ggc cat ttg gtt caa agt cat atg acc cac aac    3072
Ala Ala Leu Ala Ala Gly His Leu Val Gln Ser His Met Thr His Asn
    1010                1015                1020 agg aaa cct gct gaa cca aca aaa cct aac aat ttg gac gcc act gat    3120
Arg Lys Pro Ala Glu Pro Thr Lys Pro Asn Asn Leu Asp Ala Thr Asp
1025                1030                1035                1040 ata aat cgt ttg aaa gat ggg tcc gtc acc tgc att aaa tcc taa        3165
Ile Asn Arg Leu Lys Asp Gly Ser Val Thr Cys Ile Lys Ser
            1045                1050

<210> SEQ ID NO 12
<211> LENGTH: 1054
<212> TYPE: PRT
<213> ORGANISM: Saccharomyces cerevisiae

<400> SEQUENCE: 12

Met Pro Pro Leu Phe Lys Gly Leu Lys Gln Met Ala Lys Pro Ile Ala
 1               5                  10                  15

Tyr Val Ser Arg Phe Ser Ala Lys Arg Pro Ile His Ile Ile Leu Phe
                20                  25                  30

Ser Leu Ile Ile Ser Ala Phe Ala Tyr Leu Ser Val Ile Gln Tyr Tyr
            35                  40                  45

Phe Asn Gly Trp Gln Leu Asp Ser Asn Ser Val Phe Glu Thr Ala Pro
        50                  55                  60

Asn Lys Asp Phe Asn Thr Leu Phe Gln Glu Cys Ser His Tyr Tyr Arg
 65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
```

```
                165                 170                 175
Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
            195                 200                 205

Asn Asp Met Arg Lys Thr Gly Ser Asn Phe Trp Leu Ser Ala Ser Thr
        210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Gly Gly Leu
                245                 250                 255

Pro Phe Ile Val Val Val Gly Phe Lys His Lys Ile Lys Ile Ala
                260                 265                 270

Gln Tyr Ala Leu Glu Lys Phe Glu Arg Val Gly Leu Ser Lys Arg Ile
            275                 280                 285

Thr Thr Asp Glu Ile Val Phe Glu Ser Val Ser Glu Glu Gly Gly Arg
        290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
                340                 345                 350

Ala Ile Leu Ala Leu Arg Leu Glu Met Asn Val Ile His Arg Ser Thr
            355                 360                 365

Ile Ile Lys Gln Thr Leu Glu Glu Asp Gly Val Val Pro Ser Thr Ala
        370                 375                 380

Arg Ile Ile Ser Lys Ala Glu Lys Lys Ser Val Ser Ser Phe Leu Asn
385                 390                 395                 400

Leu Ser Val Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
                420                 425                 430

Phe Asn Ser Leu Tyr Phe Asp Lys Glu Arg Val Ser Leu Pro Asp Phe
            435                 440                 445

Ile Thr Ser Asn Ala Ser Glu Asn Phe Lys Glu Gln Ala Ile Val Ser
        450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Arg Asn Val Ser Val Ala Ile Arg
            485                 490                 495

Asp Arg Phe Val Ser Lys Leu Val Leu Ser Ala Leu Val Cys Ser Ala
                500                 505                 510

Val Ile Asn Val Tyr Leu Leu Asn Ala Ala Arg Ile His Thr Ser Tyr
                515                 520                 525

Thr Ala Asp Gln Leu Val Lys Thr Glu Val Thr Lys Lys Ser Phe Thr
            530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
                565                 570                 575

Ser Gly Pro Ser Ser Ser Ser Glu Glu Asp Asp Ser Arg Asp Ile Glu
            580                 585                 590
```

```
Ser Leu Asp Lys Lys Ile Arg Pro Leu Glu Glu Leu Glu Ala Ser Leu
        595                 600                 605

Ser Ser Gly Asn Thr Lys Gln Leu Lys Asn Lys Glu Val Ala Ala Leu
    610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Lys Ala Leu Ser Ile Leu
                645                 650                 655

Ala Glu Ala Pro Val Leu Ala Ser Asp Arg Leu Pro Tyr Lys Asn Tyr
                660                 665                 670

Asp Tyr Asp Arg Val Phe Gly Ala Cys Cys Glu Asn Val Ile Gly Tyr
            675                 680                 685

Met Pro Leu Pro Val Gly Val Ile Gly Pro Leu Val Ile Asp Gly Thr
            690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735

Val Leu Thr Lys Asp Gly Met Thr Arg Gly Pro Val Val Arg Phe Pro
                740                 745                 750

Thr Leu Lys Arg Ser Gly Ala Cys Lys Ile Trp Leu Asp Ser Glu Glu
            755                 760                 765

Gly Gln Asn Ala Ile Lys Lys Ala Phe Asn Ser Thr Ser Arg Phe Ala
            770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
                820                 825                 830

Glu Asp Met Glu Val Val Ser Val Ser Gly Asn Tyr Cys Thr Asp Lys
            835                 840                 845

Lys Pro Ala Ala Ile Asn Trp Ile Glu Gly Arg Gly Lys Ser Val Val
            850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala Arg Ala Ala Asn
                900                 905                 910

Leu Val Thr Ala Val Phe Leu Ala Leu Gly Gln Asp Pro Ala Gln Asn
            915                 920                 925

Val Glu Ser Ser Asn Cys Ile Thr Leu Met Lys Glu Val Asp Gly Asp
            930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
            995                 1000                1005
```

| | | | | | | | | | | | | |
|---|---|---|---|---|---|---|---|---|---|---|---|---|
| Ala | Ala | Leu | Ala | Ala | Gly | His | Leu | Val | Gln | Ser | His | Met | Thr | His | Asn |
| | 1010 | | | | | 1015 | | | | | 1020 | | | | |

Arg Lys Pro Ala Glu Pro Thr Lys Pro Asn Asn Leu Asp Ala Thr Asp
1025             1030            1035            1040

Ile Asn Arg Leu Lys Asp Gly Ser Val Thr Cys Ile Lys Ser
                1045            1050

<210> SEQ ID NO 13
<211> LENGTH: 3165
<212> TYPE: DNA
<213> ORGANISM: Saccharomyces cerevisiae
<220> FEATURE:
<221> NAME/KEY: CDS
<222> LOCATION: (1)..(3162)

<400> SEQUENCE: 13

```
atg ccg ccg cta ttc aag gga ctg aaa cag atg gca aag cca att gcc      48
Met Pro Pro Leu Phe Lys Gly Leu Lys Gln Met Ala Lys Pro Ile Ala
  1               5                  10                  15 tat gtt tca aga ttt tcg gcg aaa cga cca att cat ata ata ctt ttt      96
Tyr Val Ser Arg Phe Ser Ala Lys Arg Pro Ile His Ile Ile Leu Phe
             20                  25                  30 tct cta atc ata tcc gca ttc gct tat cta tcc gtc att cag tat tac     144
Ser Leu Ile Ile Ser Ala Phe Ala Tyr Leu Ser Val Ile Gln Tyr Tyr
         35                  40                  45 ttc aat ggt tgg caa cta gat tca aat agt gtt ttt gaa act gct cca     192
Phe Asn Gly Trp Gln Leu Asp Ser Asn Ser Val Phe Glu Thr Ala Pro
     50                  55                  60 aat aaa gac tcc aac act cta ttt caa gaa tgt tcc cat tac tac aga     240
Asn Lys Asp Ser Asn Thr Leu Phe Gln Glu Cys Ser His Tyr Tyr Arg
 65                  70                  75                  80 gat tcc tct cta gat ggt tgg gta tca atc acc gcg cat gaa gct agt     288
Asp Ser Ser Leu Asp Gly Trp Val Ser Ile Thr Ala His Glu Ala Ser
                 85                  90                  95 gag tta cca gcc cca cac cat tac tat cta tta aac ctg aac ttc aat     336
Glu Leu Pro Ala Pro His His Tyr Tyr Leu Leu Asn Leu Asn Phe Asn
            100                 105                 110 agt cct aat gaa act gac tcc att cca gaa cta gct aac acg gtt ttt     384
Ser Pro Asn Glu Thr Asp Ser Ile Pro Glu Leu Ala Asn Thr Val Phe
        115                 120                 125 gag aaa gat aat aca aaa tat att ctg caa gaa gat ctc agc gtt tcc     432
Glu Lys Asp Asn Thr Lys Tyr Ile Leu Gln Glu Asp Leu Ser Val Ser
    130                 135                 140 aaa gaa att tct tct act gat gga acg aaa tgg agg tta aga agt gac     480
Lys Glu Ile Ser Ser Thr Asp Gly Thr Lys Trp Arg Leu Arg Ser Asp
145                 150                 155                 160 aga aaa agt ctt ttc gac gta aag acg tta gca tat tct ctc tac gat     528
Arg Lys Ser Leu Phe Asp Val Lys Thr Leu Ala Tyr Ser Leu Tyr Asp
                165                 170                 175 gta ttt tca gaa aat gta acc caa gca gac ccg ttt gac gtc ctt att     576
Val Phe Ser Glu Asn Val Thr Gln Ala Asp Pro Phe Asp Val Leu Ile
            180                 185                 190 atg gtt act gcc tac cta atg atg ttc tac acc ata ttc ggc ctc ttc     624
Met Val Thr Ala Tyr Leu Met Met Phe Tyr Thr Ile Phe Gly Leu Phe
        195                 200                 205 aat gac atg agg aag acc ggg tca aat ttt tgg ttg agc gcc tct aca     672
Asn Asp Met Arg Lys Thr Gly Ser Asn Phe Trp Leu Ser Ala Ser Thr
    210                 215                 220 gtg gtc aat tct gca tca tca ctt ttc tta gca ttg tat gtc acc caa     720
Val Val Asn Ser Ala Ser Ser Leu Phe Leu Ala Leu Tyr Val Thr Gln
225                 230                 235                 240
```

-continued

| | | |
|---|---|---|
| tgt att cta ggc aaa gaa gtt tcc gca tta act ctt ttt gaa ggt ttg<br>Cys Ile Leu Gly Lys Glu Val Ser Ala Leu Thr Leu Phe Glu Gly Leu<br>245 250 255 | 768 | |
| cct ttc att gta gtt gtt gtt ggt ttc aag cac aaa atc aag att gcc<br>Pro Phe Ile Val Val Val Val Gly Phe Lys His Lys Ile Lys Ile Ala<br>260 265 270 | 816 | |
| cag tat gcc ctg gag aaa ttt gaa aga gtc ggt tta tct aaa agg att<br>Gln Tyr Ala Leu Glu Lys Phe Glu Arg Val Gly Leu Ser Lys Arg Ile<br>275 280 285 | 864 | |
| act acc gat gaa atc gtt ttt gaa tcc gtg agc gaa gag ggt ggt cgt<br>Thr Thr Asp Glu Ile Val Phe Glu Ser Val Ser Glu Glu Gly Gly Arg<br>290 295 300 | 912 | |
| ttg att caa gac cat ttg ctt tgt att ttt gcc ttt atc gga tgc tct<br>Leu Ile Gln Asp His Leu Leu Cys Ile Phe Ala Phe Ile Gly Cys Ser<br>305 310 315 320 | 960 | |
| atg tat gct cac caa ttg aag act ttg aca aac ttc tgc ata tta tca<br>Met Tyr Ala His Gln Leu Lys Thr Leu Thr Asn Phe Cys Ile Leu Ser<br>325 330 335 | 1008 | |
| gca ttt atc cta att ttc gaa ttg att tta act cct aca ttt tat tct<br>Ala Phe Ile Leu Ile Phe Glu Leu Ile Leu Thr Pro Thr Phe Tyr Ser<br>340 345 350 | 1056 | |
| gct atc tta gcg ctt aga ctg gaa atg aat gtt atc cac aga tct act<br>Ala Ile Leu Ala Leu Arg Leu Glu Met Asn Val Ile His Arg Ser Thr<br>355 360 365 | 1104 | |
| att atc aag caa aca tta gaa gaa gac ggt gtt gtt cca tct aca gca<br>Ile Ile Lys Gln Thr Leu Glu Glu Asp Gly Val Val Pro Ser Thr Ala<br>370 375 380 | 1152 | |
| aga atc att tct aag gca gaa aag aaa tcc gta tct tct ttc tta aat<br>Arg Ile Ile Ser Lys Ala Glu Lys Lys Ser Val Ser Ser Phe Leu Asn<br>385 390 395 400 | 1200 | |
| ctc agt gtg gtt gtc att atc atg aaa ctc tct gtc ata ctg ttg ttc<br>Leu Ser Val Val Val Ile Ile Met Lys Leu Ser Val Ile Leu Leu Phe<br>405 410 415 | 1248 | |
| gtc ttc atc aac ttt tat aac ttt ggt gca aat tgg gtc aat gat gcc<br>Val Phe Ile Asn Phe Tyr Asn Phe Gly Ala Asn Trp Val Asn Asp Ala<br>420 425 430 | 1296 | |
| ttc aat tca ttg tac ttc gat aag gaa cgt gtt tct cta cca gat ttt<br>Phe Asn Ser Leu Tyr Phe Asp Lys Glu Arg Val Ser Leu Pro Asp Phe<br>435 440 445 | 1344 | |
| att acc tcg aat gcc tct gaa aac ttt aaa gag caa gct att gtt agt<br>Ile Thr Ser Asn Ala Ser Glu Asn Phe Lys Glu Gln Ala Ile Val Ser<br>450 455 460 | 1392 | |
| gtc acc cca tta tta tat tac aaa ccc att aag tcc tac caa cgc att<br>Val Thr Pro Leu Leu Tyr Tyr Lys Pro Ile Lys Ser Tyr Gln Arg Ile<br>465 470 475 480 | 1440 | |
| gag gat atg gtt ctt cta ttg ctt cgt aat gtc agt gtt gcc att cgt<br>Glu Asp Met Val Leu Leu Leu Arg Asn Val Ser Val Ala Ile Arg<br>485 490 495 | 1488 | |
| gat agg ttc gtc agt aaa tta gtt ctt tcc gcc tta gta tgc agt gct<br>Asp Arg Phe Val Ser Lys Leu Val Leu Ser Ala Leu Val Cys Ser Ala<br>500 505 510 | 1536 | |
| gtc atc aat gtg tat tta tta aat gct gct aga att cat acc agt tat<br>Val Ile Asn Val Tyr Leu Leu Asn Ala Ala Arg Ile His Thr Ser Tyr<br>515 520 525 | 1584 | |
| act gca gac caa ttg gtg aag act gaa gtc acc aag aag tct ttt act<br>Thr Ala Asp Gln Leu Val Lys Thr Glu Val Thr Lys Lys Ser Phe Thr<br>530 535 540 | 1632 | |
| gct cct gta caa aag gct tct aca cca gtt tta acc aat aaa aca gtc<br>Ala Pro Val Gln Lys Ala Ser Thr Pro Val Leu Thr Asn Lys Thr Val | 1680 | |

```
                545                 550                 555                 560
att tct gga tcg aaa gtc aaa agt tta tca tct gcg caa tcg agc tca         1728
Ile Ser Gly Ser Lys Val Lys Ser Leu Ser Ser Ala Gln Ser Ser Ser
                565                 570                 575 tca gga cct tca tca tct agt gag gaa gat gat tcc cgc gat att gaa         1776
Ser Gly Pro Ser Ser Ser Ser Glu Glu Asp Asp Ser Arg Asp Ile Glu
            580                 585                 590 agc ttg gat aag aaa ata cgt cct tta gaa gaa tta gaa gca tta tta         1824
Ser Leu Asp Lys Lys Ile Arg Pro Leu Glu Glu Leu Glu Ala Leu Leu
        595                 600                 605 agt agt gga aat aca aaa caa ttg aag aac aaa gag gtc gct gcc ttg         1872
Ser Ser Gly Asn Thr Lys Gln Leu Lys Asn Lys Glu Val Ala Ala Leu
    610                 615                 620 gtt att cac ggt aag tta cct ttg tac gct ttg gag aaa aaa tta ggt         1920
Val Ile His Gly Lys Leu Pro Leu Tyr Ala Leu Glu Lys Lys Leu Gly
625                 630                 635                 640 gat act acg aga gcg gtt gcg gta cgt agg aag gct ctt tca att ttg         1968
Asp Thr Thr Arg Ala Val Ala Val Arg Arg Lys Ala Leu Ser Ile Leu
                645                 650                 655 gca gaa gct cct gta tta gca tct gat cgt tta cca tat aaa aat tat         2016
Ala Glu Ala Pro Val Leu Ala Ser Asp Arg Leu Pro Tyr Lys Asn Tyr
            660                 665                 670 gac tac gac cgc gta ttt ggc gct tgt tgt gaa aat gtt ata ggt tac         2064
Asp Tyr Asp Arg Val Phe Gly Ala Cys Cys Glu Asn Val Ile Gly Tyr
        675                 680                 685 atg cct ttg ccc gtt ggt gtt ata ggc ccc ttg gtt atc gat ggt aca         2112
Met Pro Leu Pro Val Gly Val Ile Gly Pro Leu Val Ile Asp Gly Thr
    690                 695                 700 tct tat cat ata cca atg gca act aca gag ggt tgt ttg gta gct tct         2160
Ser Tyr His Ile Pro Met Ala Thr Thr Glu Gly Cys Leu Val Ala Ser
705                 710                 715                 720 gcc atg cgt ggc tgt aag gca atc aat gct ggc ggt ggt gca aca act         2208
Ala Met Arg Gly Cys Lys Ala Ile Asn Ala Gly Gly Gly Ala Thr Thr
                725                 730                 735 gtt tta act aag gat ggt atg aca aga ggc cca gta gtc cgt ttc cca         2256
Val Leu Thr Lys Asp Gly Met Thr Arg Gly Pro Val Val Arg Phe Pro
            740                 745                 750 act ttg aaa aga tct ggt gcc tgt aag ata tgg tta gac tca gaa gag         2304
Thr Leu Lys Arg Ser Gly Ala Cys Lys Ile Trp Leu Asp Ser Glu Glu
        755                 760                 765 gga caa aac gca att aaa aaa gct ttt aac tct aca tca aga ttt gca         2352
Gly Gln Asn Ala Ile Lys Lys Ala Phe Asn Ser Thr Ser Arg Phe Ala
    770                 775                 780 cgt ctg caa cat att caa act tgt cta gca gga gat tta ctc ttc atg         2400
Arg Leu Gln His Ile Gln Thr Cys Leu Ala Gly Asp Leu Leu Phe Met
785                 790                 795                 800 aga ttt aga aca act act ggt gac gca atg ggt atg aat atg att tct         2448
Arg Phe Arg Thr Thr Thr Gly Asp Ala Met Gly Met Asn Met Ile Ser
                805                 810                 815 aag ggt gtc gaa tac tca tta aag caa atg gta gaa gag tat ggc tgg         2496
Lys Gly Val Glu Tyr Ser Leu Lys Gln Met Val Glu Glu Tyr Gly Trp
            820                 825                 830 gaa gat atg gag gtt gtc tcc gtt tct ggt aac tac tgt acc gac aaa         2544
Glu Asp Met Glu Val Val Ser Val Ser Gly Asn Tyr Cys Thr Asp Lys
        835                 840                 845 aaa cca gct gcc atc aac tgg atc gaa ggt cgt ggt aag agt gtc gtc         2592
Lys Pro Ala Ala Ile Asn Trp Ile Glu Gly Arg Gly Lys Ser Val Val
    850                 855                 860 gca gaa gct act att cct ggt gat gtt gtc aga aaa gtg tta aaa agt         2640
```

-continued

```
Ala Glu Ala Thr Ile Pro Gly Asp Val Val Arg Lys Val Leu Lys Ser
865                 870                 875                 880 gat gtt tcc gca ttg gtt gag ttg aac att gct aag aat ttg gtt gga    2688
Asp Val Ser Ala Leu Val Glu Leu Asn Ile Ala Lys Asn Leu Val Gly
                885                 890                 895 tct gca atg gct ggg tct gtt ggt gga ttt aac gca cat gca gct aat    2736
Ser Ala Met Ala Gly Ser Val Gly Gly Phe Asn Ala His Ala Ala Asn
            900                 905                 910 tta gtg aca gct gtt ttc ttg gca tta gga caa gat cct gca caa aat    2784
Leu Val Thr Ala Val Phe Leu Ala Leu Gly Gln Asp Pro Ala Gln Asn
        915                 920                 925 gtc gaa agt tcc aac tgt ata aca ttg atg aaa gaa gtg gac ggt gat    2832
Val Glu Ser Ser Asn Cys Ile Thr Leu Met Lys Glu Val Asp Gly Asp
    930                 935                 940 ttg aga att tcc gta tcc atg cca tcc atc gaa gta ggt acc atc ggt    2880
Leu Arg Ile Ser Val Ser Met Pro Ser Ile Glu Val Gly Thr Ile Gly
945                 950                 955                 960 ggt ggt act gtt cta gaa cca caa ggt gcc atg ttg gac tta tta ggt    2928
Gly Gly Thr Val Leu Glu Pro Gln Gly Ala Met Leu Asp Leu Leu Gly
                965                 970                 975 gta aga ggc cca cat gct acc gct cct ggt acc aac gca cgt caa tta    2976
Val Arg Gly Pro His Ala Thr Ala Pro Gly Thr Asn Ala Arg Gln Leu
            980                 985                 990 gca aga ata gtt gcc tgt gcc gtc ttg gca ggt gaa tta tcc tta tgt    3024
Ala Arg Ile Val Ala Cys Ala Val Leu Ala Gly Glu Leu Ser Leu Cys
        995                 1000                1005 gct gcc cta gca gcc ggc cat ttg gtt caa agt cat atg acc cac aac    3072
Ala Ala Leu Ala Ala Gly His Leu Val Gln Ser His Met Thr His Asn
    1010                1015                1020 agg aaa cct gct gaa cca aca aaa cct aac aat ttg gac gcc act gat    3120
Arg Lys Pro Ala Glu Pro Thr Lys Pro Asn Asn Leu Asp Ala Thr Asp
1025                1030                1035                1040 ata aat cgt ttg aaa gat ggg tcc gtc acc tgc att aaa tcc taa        3165
Ile Asn Arg Leu Lys Asp Gly Ser Val Thr Cys Ile Lys Ser
                1045                1050

<210> SEQ ID NO 14
<211> LENGTH: 1054
<212> TYPE: PRT
<213> ORGANISM: Saccharomyces cerevisiae

<400> SEQUENCE: 14

Met Pro Pro Leu Phe Lys Gly Leu Lys Gln Met Ala Lys Pro Ile Ala
1               5                   10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125
```

Glu Lys Asp Asn Thr Lys Tyr Ile Leu Gln Glu Asp Leu Ser Val Ser
130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
        290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
370                 375                 380

Arg Ile Ile Ser Lys Ala Glu Lys Lys Ser Val Ser Ser Phe Leu Asn
385                 390                 395                 400

Leu Ser Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
        435                 440                 445

Ile Thr Ser Asn Ala Ser Glu Asn Phe Lys Glu Gln Ala Ile Val Ser
450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
530                 535                 540

Ala Pro Val Gln Lys Ala Ser Thr Pro Val Leu Thr Asn Lys Thr Val

```
             545                 550                 555                 560
        Ile Ser Gly Ser Lys Val Lys Ser Leu Ser Ser Ala Gln Ser Ser Ser
                        565                 570                 575

Ser Gly Pro Ser Ser Ser Glu Glu Asp Ser Arg Asp Ile Glu
                    580                 585                 590

Ser Leu Asp Lys Lys Ile Arg Pro Leu Glu Leu Glu Ala Leu Leu
                    595                 600                 605

Ser Ser Gly Asn Thr Lys Gln Leu Lys Asn Lys Glu Val Ala Ala Leu
                    610                 615                 620

Val Ile His Gly Lys Leu Pro Leu Tyr Ala Leu Glu Lys Lys Leu Gly
        625                 630                 635                 640

Asp Thr Thr Arg Ala Val Ala Val Arg Arg Lys Ala Leu Ser Ile Leu
                        645                 650                 655

Ala Glu Ala Pro Val Leu Ala Ser Asp Arg Leu Pro Tyr Lys Asn Tyr
                        660                 665                 670

Asp Tyr Asp Arg Val Phe Gly Ala Cys Cys Glu Asn Val Ile Gly Tyr
                        675                 680                 685

Met Pro Leu Pro Val Gly Val Ile Gly Pro Leu Val Ile Asp Gly Thr
                    690                 695                 700

Ser Tyr His Ile Pro Met Ala Thr Thr Glu Gly Cys Leu Val Ala Ser
        705                 710                 715                 720

Ala Met Arg Gly Cys Lys Ala Ile Asn Ala Gly Gly Gly Ala Thr Thr
                        725                 730                 735

Val Leu Thr Lys Asp Gly Met Thr Arg Gly Pro Val Val Arg Phe Pro
                        740                 745                 750

Thr Leu Lys Arg Ser Gly Ala Cys Lys Ile Trp Leu Asp Ser Glu Glu
                    755                 760                 765

Gly Gln Asn Ala Ile Lys Lys Ala Phe Asn Ser Thr Ser Arg Phe Ala
                    770                 775                 780

Arg Leu Gln His Ile Gln Thr Cys Leu Ala Gly Asp Leu Leu Phe Met
        785                 790                 795                 800

Arg Phe Arg Thr Thr Thr Gly Asp Ala Met Gly Met Asn Met Ile Ser
                        805                 810                 815

Lys Gly Val Glu Tyr Ser Leu Lys Gln Met Val Glu Glu Tyr Gly Trp
                        820                 825                 830

Glu Asp Met Glu Val Val Ser Val Ser Gly Asn Tyr Cys Thr Asp Lys
                    835                 840                 845

Lys Pro Ala Ala Ile Asn Trp Ile Glu Gly Arg Gly Lys Ser Val Val
        850                 855                 860

Ala Glu Ala Thr Ile Pro Gly Asp Val Val Arg Lys Val Leu Lys Ser
        865                 870                 875                 880

Asp Val Ser Ala Leu Val Glu Leu Asn Ile Ala Lys Asn Leu Val Gly
                        885                 890                 895

Ser Ala Met Ala Gly Ser Val Gly Gly Phe Asn Ala His Ala Ala Asn
                    900                 905                 910

Leu Val Thr Ala Val Phe Leu Ala Leu Gly Gln Asp Pro Ala Gln Asn
                    915                 920                 925

Val Glu Ser Ser Asn Cys Ile Thr Leu Met Lys Glu Val Asp Gly Asp
                    930                 935                 940

Leu Arg Ile Ser Val Ser Met Pro Ser Ile Glu Val Gly Thr Ile Gly
        945                 950                 955                 960

Gly Gly Thr Val Leu Glu Pro Gln Gly Ala Met Leu Asp Leu Leu Gly
                        965                 970                 975
```

```
Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
        995                1000                1005

Ala Ala Leu Ala Ala Gly His Leu Val Gln Ser His Met Thr His Asn
    1010                1015                1020

Arg Lys Pro Ala Glu Pro Thr Lys Pro Asn Asn Leu Asp Ala Thr Asp
1025                1030                1035                1040

Ile Asn Arg Leu Lys Asp Gly Ser Val Thr Cys Ile Lys Ser
                1045                1050
```

<210> SEQ ID NO 15
<211> LENGTH: 2925
<212> TYPE: DNA
<213> ORGANISM: Saccharomyces cerevisiae

<400> SEQUENCE: 15

| | | | | | |
|---|---|---|---|---|---|
| atgccgccgc | tattcaaggg | actgaaacag | atggcaaagc | caattgccta | tgtttcaaga | 60 |
| ttttcggcga | aacgaccaat | tcatataata | cttttttctc | taatcatatc | cgcattcgct | 120 |
| tatctatccg | tcattcagta | ttacttcaat | ggttggcaac | tagattcaaa | tagtgttttt | 180 |
| gaaactgctc | caaataaaga | cttcaacact | ctatttcaag | aatgttccca | ttactacaga | 240 |
| gattcctctc | tagatggttg | ggtatcaatc | accgcgcatg | aagctagtga | gttaccagcc | 300 |
| ccacaccatt | actatctatt | aaacctgaac | ttcaatagtc | ctaatgaaac | tgactccatt | 360 |
| ccagaactag | ctaacacggt | ttttgagaaa | gataatacaa | aatatattct | gcaagaagat | 420 |
| ctcagcgttt | ccaaagaaat | ttcttctact | gatggaacga | atggaggtt | aagaagtgac | 480 |
| agaaaaagtc | ttttcgacgt | aaagacgtta | gcatattctc | tctacgatgt | attttcagaa | 540 |
| aatgtaaccc | aagcagacca | caaaatcaag | attgcccagt | atgccctgga | gaaatttgaa | 600 |
| agagtcggtt | tatctaaaag | gattactacc | gatgaaatcg | ttttgaatc | cgtgagcgaa | 660 |
| gagggtggtc | gtttgattca | agaccatttg | ctttgtattt | ttgcctttat | cggatgctct | 720 |
| atgtatgctc | accaattgaa | gactttgaca | aacttctgca | tattatcagc | atttatccta | 780 |
| attttcgaat | tgattttaac | tcctacattt | tattctgcta | tcttagcgct | tagactggaa | 840 |
| atgaatgtta | tccacagatc | tactattatc | aagcaaacat | tagaagaaga | cggtgttgtt | 900 |
| ccatctacag | caagaatcat | ttctaaggca | gaaagaaat | ccgtatcttc | tttcttaaat | 960 |
| ctcagtgtgg | ttgtcattat | catgaaactc | tctgtcatac | tgttgttcgt | cttcatcaac | 1020 |
| ttttataact | tggtgcaaaa | ttgggtcaat | gatgccttca | attcattgta | cttcgataag | 1080 |
| gaacgtgttt | ctctaccaga | ttttattacc | tcgaatgcct | ctgaaaactt | taaagagcaa | 1140 |
| gctattgtta | gtgtcacccc | attattatat | tacaaaccca | ttaagtccta | ccaacgcatt | 1200 |
| gaggatatgg | ttcttctatt | gcttcgtaat | gtcagtgttg | ccattcgtga | taggttcgtc | 1260 |
| agtaaattag | ttctttccgc | cttagtatgc | agtgctgtca | tcaatgtgta | tttattaaat | 1320 |
| gctgctagaa | ttcataccag | ttatactgca | gaccaattgg | tgaagactga | agtcaccaag | 1380 |
| aagtctttta | ctgctcctgt | acaaaaggct | tctacaccag | ttttaaccaa | taaaacagtc | 1440 |
| atttctggat | cgaaagtcaa | aagtttatca | tctgcgcaat | cgagctcatc | aggaccttca | 1500 |
| tcatctagtg | aggaagatga | ttcccgcgat | attgaaagct | tggataagaa | aatacgtcct | 1560 |
| ttagaagaat | tagaagcatc | attaagtagt | ggaaatacaa | aacaattgaa | gaacaaagag | 1620 |
| gtcgctgcct | tggttattca | cggtaagtta | cctttgtacg | ctttggagaa | aaaattaggt | 1680 |

```
gatactacga gagcggttgc ggtacgtagg aaggctcttt caattttggc agaagctcct   1740
gtattagcat ctgatcgttt accatataaa aattatgact acgaccgcgt atttggcgct   1800
tgttgtgaaa atgttatagg ttacatgcct ttgcccgttg gtgttatagg cccttggtt   1860 atcgatggta catcttatca tataccaatg caactacag agggttgttt ggtagcttct   1920
gccatgcgtg gctgtaaggc aatcaatgct ggcggtggtg caacaactgt tttaactaag   1980
gatggtatga caagaggccc agtagtccgt ttcccaactt tgaaaagatc tggtgcctgt   2040
aagatatggt tagactcaga agagggacaa aacgcaatta aaaaagcttt taactctaca   2100
tcaagatttg cacgtctgca acatattcaa acttgtctag caggagattt actcttcatg   2160
agatttagaa caactactgg tgacgcaatg ggtatgaata tgatttctaa gggtgtcgaa   2220
tactcattaa agcaaatggt agaagagtat ggctgggaag atatggaggt tgtctccgtt   2280
tctggtaact actgtaccga caaaaaacca gctgccatca actggatcga aggtcgtggt   2340
aagagtgtcg tcgcagaagc tactattcct ggtgatgttg tcagaaaagt gttaaaaagt   2400
gatgtttccg cattggttga gttgaacatt gctaagaatt tggttggatc tgcaatggct   2460
gggtctgttg gtggatttaa cgcacgtgca gctaatttag tgacagctgt tttcttggca   2520
ttaggacaag atcctgcaca aaatgtcgaa agttccaact gtataacatt gatgaaagaa   2580
gtggacggtg atttgagaat ttccgtatcc atgccatcca tcgaagtagg taccatcggt   2640
ggtggtactg ttctagaacc acaaggtgcc atgttggact tattaggtgt aagaggccca   2700
catgctaccg ctcctggtac caacgcacgt caattagcaa gaatagttgc ctgtgccgtc   2760
ttggcaggtg aattatcctt atgtgctgcc ctagcagccg gccatttggt tcaaagtcat   2820
atgacccaca acaggaaacc tgctgaacca acaaaaccta acaatttgga cgccactgat   2880
ataaatcgtt tgaaagatgg gtccgtcacc tgcattaaat cctaa                   2925
```

<210> SEQ ID NO 16
<211> LENGTH: 3090
<212> TYPE: DNA
<213> ORGANISM: Saccharomyces cerevisiae

<400> SEQUENCE: 16

```
atgccgccgc tattcaaggg actgaaacag atggcaaagc caattgccta tgtttcaaga    60 tttcggcga aacgaccaat tcatataata ctttttttctc taatcatatc cgcattcgct   120
tatctatccg tcattcagta ttacttcaat ggttggcaac tagattcaaa tagtgttttt   180
gaaactgctc caaataaaga cttcaacact ctatttcaag aatgttccca ttactacaga   240
gattcctctc tagatggttg ggtatcaatc accgcgcatg aagctagtga gttaccagcc   300
ccacaccatt actatctatt aaacctgaac ttcaatagtc ctaatgaaac tgactccatt   360
ccagaactag ctaacacggt ttttgagaaa gataatacaa aatatattct gcaagaagat   420
ctcagcgttt ccaaagaaat tcttctact gatggaacga atggaggtt aagaagtgac   480 agaaaaagtc ttttcgacgt aaagacgtta gcatattctc tctacgatgt attttcagaa   540
aatgtaaccc aagcagaccc gtttgacgtc cttattatgg ttactgccta cctaatgatg   600
ttctacacca tattcggcct cttcaatgac atgaggaaga ccgggtcaaa ttttttggttg   660 agcgcctcta cagtggtcaa ttctgcatca tcacttttct tagcattgta tgtcacccaa   720
tgtattctag gcaaagaagt ttccgcatta actctttttg aaggtttgcc tttcattgta   780
gttgttgttg gtttcaagca caaatcaag attgcccagt atgccctgga gaaatttgaa   840
```

```
agagtcggtt tatctaaaag gattactacc gatgaaatcg tttttgaatc cgtgagcgaa    900
gagggtggtc gtttgattca agaccatttg ctttgtattt ttgcctttat cggatgctct    960
atgtatgctc accaattgaa gactttgaca aacttctgca tattatcagc atttatccta   1020
attttcgaat tgattttaac tcctacattt tattctgcta tcttagcgct tagactggaa   1080
atgaatgtta tccacagatc tactattatc aagcaaacat tagaagaaga cggtgttgtt   1140
ccatctacag caagaatcat ttctaaggca gaaaagaaat ccgtatcttc taactttggt   1200
gcaaattggg tcaatgatgc cttcaattca ttgtacttcg ataaggaacg tgtttctcta   1260
ccagatttta ttacctcgaa tgcctctgaa aactttaaag agcaagctat tgttagtgtc   1320
accccattat tatattacaa acccattaag tcctaccaac gcattgagga tatggttctt   1380
ctattgcttc gtaatgtcag tgttgccatt cgtgataggt tcgtcagtaa attagttctt   1440
tccgccttag tatgcagtgc tgtcatcaat gtgtatttat taaatgctgc tagaattcat   1500
accagttata ctgcagacca attggtgaag actgaagtca ccaagaagtc ttttactgct   1560
cctgtacaaa aggcttctac accagtttta accaataaaa cagtcatttc tggatcgaaa   1620
gtcaaaagtt tatcatctgc gcaatcgagc tcatcaggac cttcatcatc tagtgaggaa   1680
gatgattccc gcgatattga aagcttggat aagaaaatac gtcctttaga agaattagaa   1740
gcatcattaa gtagtggaaa tacaaaacaa ttgaagaaca aagaggtcgc tgccttggtt   1800
attcacggta agttaccttt gtacgctttg gagaaaaaat taggtgatac tacgagagcg   1860
gttgcggtac gtaggaaggc tctttcaatt ttggcagaag ctcctgtatt agcatctgat   1920
cgtttaccat ataaaaatta tgactacgac cgcgtatttg gcgcttgttg tgaaaatgtt   1980
ataggttaca tgccttttgcc cgttggtgtt ataggcccct tggttatcga tggtacatct   2040
tatcatatac caatggcaac tacagagggt tgtttggtag cttctgccat gcgtggctgt   2100
aaggcaatca atgctggcgg tggtgcaaca actgttttaa ctaaggatgg tatgacaaga   2160
ggcccagtag tccgtttccc aactttgaaa agatctggtg cctgtaagat atggttagac   2220
tcagaagagg gacaaaacgc aattaaaaaa gcttttaact ctacatcaag atttgcacgt   2280
ctgcaacata ttcaaacttg tctagcagga gatttactct tcatgagatt tagaacaact   2340
actggtgacg caatgggtat gaatatgatt tctaagggtg tcgaatactc attaaagcaa   2400
atggtagaag agtatggctg ggaagatatg gaggttgtct ccgtttctgg taactactgt   2460
accgacaaaa aaccagctgc catcaactgg atcgaaggtc gtggtaagag tgtcgtcgca   2520
gaagctacta ttcctggtga tgttgtcaga aaagtgttaa aaagtgatgt tccgcattg    2580
gttgagttga acattgctaa gaatttggtt ggatctgcaa tggctgggtc tgttggtgga   2640
tttaacgcac gtgcagctaa tttagtgaca gctgttttct tggcattagg acaagatcct   2700
gcacaaaatg tcgaaagttc caactgtata acattgatga agaagtgga cggtgatttg    2760
agaatttccg tatccatgcc atccatcgaa gtaggtacca tcggtggtgg tactgttcta   2820
gaaccacaag gtgccatgtt ggacttatta ggtgtaagag gcccacatgc taccgctcct   2880
ggtaccaacg cacgtcaatt agcaagaata gttgcctgtg ccgtcttggc aggtgaatta   2940
tccttatgtg ctgccctagc agccggccat ttggttcaaa gtcatatgac ccacaacagg   3000
aaacctgctg aaccaacaaa acctaacaat ttggacgcca ctgatataaa tcgtttgaaa   3060
gatgggtccg tcacctgcat taaatcctaa                                    3090
```

<210> SEQ ID NO 17
<211> LENGTH: 2973

<212> TYPE: DNA
<213> ORGANISM: Saccharomyces cerevisiae

<400> SEQUENCE: 17

```
atgccgccgc tattcaaggg actgaaacag atggcaaagc caattgccta tgtttcaaga    60
ttttcggcga aacgaccaat tcatataata cttttttctc taatcatatc cgcattcgct   120
tatctatccg tcattcagta ttacttcaat ggttggcaac tagattcaaa tagtgttttt   180
gaaactgctc caaataaaga cttcaacact ctatttcaag aatgttccca ttactacaga   240
gattcctctc tagatggttg ggtatcaatc accgcgcatg aagctagtga gttaccagcc   300
ccacaccatt actatctatt aaacctgaac ttcaatagtc ctaatgaaac tgactccatt   360
ccagaactag ctaacacggt ttttgagaaa gataatacaa aatatattct gcaagaagat   420
ctcagcgttt ccaaagaaat ttcttctact gatggaacga aatggaggtt aagaagtgac   480
agaaaaagtc ttttcgacgt aaagacgtta gcatattctc tctacgatgt attttcagaa   540
aatgtaaccc aagcagaccc gtttgacgtc cttattatgg ttactgccta cctaatgatg   600
ttctacacca tattcggcct cttcaatgac atgaggaaga ccgggtcaaa ttttttggttg   660
agcgcctcta cagtggtcaa ttctgcatca tcactttttct tagcattgta tgtcacccaa   720
tgtattctag caaagaagt tccgcatta actctttttg aaggtttgcc tttcattgta   780
gttgttgttg gtttcaagca caaaatcaag attgcccagt atgccctgga gaaatttgaa   840
agagtcggtt tatctaaaag gattactacc gatgaaatcg ttttttgaatc cgtgagcgaa   900
gagggtggtc gtttgattca agaccatttg ctttgtatt ttgcctttat cggatgctct   960
atgtatgctc accaattgaa gactttgaca aacttctgca tattatcagc atttatccta  1020
attttcgaat tgattttaac tcctacattt tattctgcta tcttagcgct tagactggaa  1080
atgaatgtta tccacagatc tactattatc aagcaaacat tagaagaaga cggtgttgtt  1140
ccatctacag caagaatcat ttctaaggca gaaaagaaat ccgtatcttc tttcttaaat  1200
ctcagtgtgg ttgtcattat catgaaactc tctgtcatac tgttgttcgt cttcatcaac  1260
ttttataact ttggtgcaaa ttgggtcaat gatgccttca attcattgta cttcgataag  1320
gaacgtgttt ctctaccaga tttttattacc tcgaatgcct ctgaaaactt taaagagcaa  1380
cataccagtt atactgcaga ccaattggtg aagactgaag tcaccaagaa gtcttttact  1440
gctcctgtac aaaaggcttc tacaccagtt ttaaccaata aaacagtcat ttctggatcg  1500
aaagtcaaaa gtttatcatc tgcgcaatcg agctcatcag gaccttcatc atctagtgag  1560
gaagatgatt cccgcgatat tgaaagcttg ataagaaaaa tacgtccttt agaagaatta  1620
gaagcatcat taagtagtgg aaatacaaaa caattgaaga caaagaggt cgctgccttg  1680
gttattcacg gtaagttacc tttgtacgct ttggagaaaa aattaggtga tactacgaga  1740
gcggttgcgg tacgtaggaa ggctctttca attttggcag aagctcctgt attagcatct  1800
gatcgtttac catataaaaa ttatgactac gaccgcgtat ttggcgcttg ttgtgaaaat  1860
gttataggtt acatgccttt gcccgttggt gttataggcc ccttggttat cgatggtaca  1920
tcttatcata taccaatggc aactacagag ggttgtttgg tagcttctgc catgcgtggc  1980
tgtaaggcaa tcaatgctgg cggtggtgca acaactgttt taactaagga tggtatgaca  2040
agaggcccag tagtccgttt cccaactttg aaaagatctg gtgcctgtaa gatatggtta  2100
gactcagaag agggacaaaa cgcaattaaa aaagctttta actctacatc aagatttgca  2160
cgtctgcaac atattcaaac ttgtctagca ggagatttac tcttcatgag atttagaaca  2220
```

```
actactggtg acgcaatggg tatgaatatg atttctaagg gtgtcgaata ctcattaaag    2280
caaatggtag aagagtatgg ctgggaagat atggaggttg tctccgtttc tggtaactac    2340
tgtaccgaca aaaaccagc tgccatcaac tggatcgaag gtcgtggtaa gagtgtcgtc     2400
gcagaagcta ctattcctgg tgatgttgtc agaaaagtgt taaaaagtga tgtttccgca    2460
ttggttgagt tgaacattgc taagaatttg gttggatctg caatggctgg gtctgttggt    2520
ggatttaacg cacgtgcagc taatttagtg acagctgttt tcttggcatt aggacaagat    2580
cctgcacaaa atgtcgaaag ttccaactgt ataacattga tgaaagaagt ggacggtgat    2640
ttgagaattt ccgtatccat gccatccatc gaagtaggta ccatcggtgg tggtactgtt    2700
ctagaaccac aaggtgccat gttggactta ttaggtgtaa gaggcccaca tgctaccgct    2760
cctggtacca acgcacgtca attagcaaga atagttgcct gtgccgtctt ggcaggtgaa    2820
ttatccttat gtgctgccct agcagccggc catttggttc aaagtcatat gacccacaac    2880
aggaaacctg ctgaaccaac aaaacctaac aatttggacg ccactgatat aaatcgtttg    2940
aaagatgggt ccgtcacctg cattaaatcc taa                                 2973
```

<210> SEQ ID NO 18
<211> LENGTH: 2457
<212> TYPE: DNA
<213> ORGANISM: Saccharomyces cerevisiae

<400> SEQUENCE: 18

```
atgccgccgc tattcaaggg actgaaacag atggcaaagc caattgccta tgtttcaaga     60
ttttcggcga aacgaccaat tcatataata cttttttctc taatcatatc cgcattcgct    120
tatctatccg tcattcagta ttacttcaat ggttggcaac tagattcaaa tagtgttttt    180
gaaactgctc caaataaaga cttcaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagcgttt ccaaagaaat ttcttctact gatggaacga aatggaggtt aagaagtgac    480
agaaaaagtc ttttcgacgt aaagacgtta gcatattctc tctacgatgt atttttcagaa   540
aatgtaaccc aagcagacaa cttggtgca aattgggtca atgatgcctt caattcattg     600
tacttcgata aggaacgtgt ttctctacca gatttttatta cctcgaatgc ctctgaaaac   660
tttaaagagc aagctattgt tagtgtcacc ccattattat attacaaacc cattaagtcc    720
taccaacgca ttgaggatat ggttcttcta ttgcttcgta atgtcagtgt tgccattcgt    780
gataggttcg tcagtaaatt agttcttttcc gccttagtat gcagtgctgt catcaatgtg   840
tatttattaa atgctgctag aattcatacc agttatactg cagaccaatt ggtgaagact    900
gaagtcacca agaagtctttt tactgctcct gtacaaaagg cttctacacc agttttaacc    960
aataaaacag tcatttctgg atcgaaagtc aaaagtttat catctgcgca atcgagctca   1020
tcaggacctt catcatctag tgaggaagat gattcccgcg atattgaaag cttggataag   1080
aaaatacgtc ctttagaaga attagaagca tcattaagta gtggaaatac aaaacaattg   1140
aagaacaaag aggtcgctgc cttggttatt cacggtaagt taccttttgta cgctttggag  1200
aaaaaattag gtgatactac gagagcggtt gcggtacgta ggaaggctct ttcaattttg   1260
gcagaagctc ctgtattagc atctgatcgt ttaccatata aaaattatga ctacgaccgc   1320
gtatttggcg cttgttgtga aaatgttata ggttacatgc cttgcccgt tggtgttata    1380
```

```
ggcccttgg ttatcgatgg tacatcttat catataccaa tggcaactac agagggttgt    1440
ttggtagctt ctgccatgcg tggctgtaag gcaatcaatg ctggcggtgg tgcaacaact    1500
gttttaacta aggatggtat gacaagaggc ccagtagtcc gtttcccaac tttgaaaaga    1560
tctggtgcct gtaagatatg gttagactca gaagagggac aaaacgcaat taaaaaagct    1620
tttaactcta catcaagatt tgcacgtctg caacatattc aaacttgtct agcaggagat    1680
ttactcttca tgagatttag aacaactact ggtgacgcaa tgggtatgaa tatgatttct    1740
aagggtgtcg aatactcatt aaagcaaatg gtagaagagt atggctggga agatatggag    1800
gttgtctccg tttctggtaa ctactgtacc gacaaaaaac cagctgccat caactggatc    1860
gaaggtcgtg gtaagagtgt cgtcgcagaa gctactattc ctggtgatgt tgtcagaaaa    1920
gtgttaaaaa gtgatgtttc cgcattggtt gagttgaaca ttgctaagaa tttggttgga    1980
tctgcaatgg ctgggtctgt tggtggattt aacgcacgtg cagctaattt agtgacagct    2040
gttttcttgg cattaggaca agatcctgca caaaatgtcg aaagttccaa ctgtataaca    2100
ttgatgaaag aagtggacgg tgatttgaga atttccgtat ccatgccatc catcgaagta    2160
ggtaccatcg gtggtggtac tgttctagaa ccacaaggtg ccatgttgga cttattaggt    2220
gtaagaggcc cacatgctac cgctcctggt accaacgcac gtcaattagc aagaatagtt    2280
gcctgtgccg tcttggcagg tgaattatcc ttatgtgctg ccctagcagc cggccatttg    2340
gttcaaagtc atatgaccca acaggaaa cctgctgaac caacaaaacc taacaatttg    2400
gacgccactg atataaatcg tttgaaagat gggtccgtca cctgcattaa atcctaa      2457
```

<210> SEQ ID NO 19
<211> LENGTH: 2151
<212> TYPE: DNA
<213> ORGANISM: Saccharomyces cerevisiae

<400> SEQUENCE: 19

```
atgccgccgc tattcaaggg actgaaacag atggcaaagc caattgccta tgtttcaaga     60
ttttcggcga aacgaccaat tcatataata cttttttctc taatcatatc cgcattcgct    120
tatctatccg tcattcagta ttacttcaat ggttggcaac tagattcaaa tagtgttttt    180
gaaactgctc caaataaaga cttcaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagcgttt ccaaagaaat ttcttctact gatggaacga atggaggtt aagaagtgac    480 agaaaaagtc ttttcgacgt aaagacgtta gcatattctc tctacgatgt atttcagaa     540 aatgtaaccc aagcagacca taccagttat actgcagacc aattggtgaa gactgaagtc    600
accaagaagt cttttactgc tcctgtacaa aaggcttcta caccagtttt aaccaataaa    660
acagtcattt ctggatcgaa agtcaaaagt ttatcatctg cgcaatcgag ctcatcagga    720
ccttcatcat ctagtgagga agatgattcc cgcgatattg aaagcttgga taagaaaata    780
cgtcctttag aagaattaga agcatcatta agtagtggaa atacaaaaca attgaagaac    840
aaagaggtcg ctgccttggt tattcacggt aagttacctt tgtacgcttt ggagaaaaaa    900
ttaggtgata ctacgagagc ggttgcggta cgtaggaagg ctcttcaatt ttggcagaa     960 gctcctgtat tagcatctga tcgtttacca tataaaaatt atgactacga ccgcgtattt   1020
```

```
ggcgcttgtt gtgaaaatgt tataggttac atgcctttgc ccgttggtgt tataggcccc    1080
ttggttatcg atggtacatc ttatcatata ccaatggcaa ctacagaggg ttgtttggta    1140
gcttctgcca tgcgtggctg taaggcaatc aatgctggcg tggtgcaac aactgtttta    1200 actaaggatg gtatgacaag aggcccagta gtccgtttcc caactttgaa aagatctggt    1260
gcctgtaaga tatggttaga ctcagaagag ggacaaaacg caattaaaaa agcttttaac    1320
tctacatcaa gatttgcacg tctgcaacat attcaaactt gtctagcagg agatttactc    1380
ttcatgagat ttagaacaac tactggtgac gcaatgggta tgaatatgat ttctaagggt    1440
gtcgaatact cattaaagca aatggtagaa gagtatggct gggaagatat ggaggttgtc    1500
tccgtttctg gtaactactg taccgacaaa aaaccagctg ccatcaactg gatcgaaggt    1560
cgtggtaaga gtgtcgtcgc agaagctact attcctggtg atgttgtcag aaaagtgtta    1620
aaaagtgatg tttccgcatt ggttgagttg aacattgcta gaatttggt tggatctgca    1680 atggctgggt ctgttggtgg atttaacgca cgtgcagcta atttagtgac agctgttttc    1740
ttggcattag acaagatcc tgcacaaaat gtcgaaagtt ccaactgtat aacattgatg    1800
aaagaagtgg acggtgattt gagaatttcc gtatccatgc catccatcga agtaggtacc    1860
atcggtggtg gtactgttct agaaccacaa ggtgccatgt ggacttatt aggtgtaaga    1920 ggcccacatg ctaccgctcc tggtaccaac gcacgtcaat tagcaagaat agttgcctgt    1980
gccgtcttgg caggtgaatt atccttatgt gctgccctag cagccggcca tttggttcaa    2040
agtcatatga cccacaacag gaaacctgct gaaccaacaa aacctaacaa tttggacgcc    2100
actgatataa atcgtttgaa agatgggtcc gtcacctgca ttaaatccta a             2151
```

<210> SEQ ID NO 20
<211> LENGTH: 1620
<212> TYPE: DNA
<213> ORGANISM: Saccharomyces cerevisiae

<400> SEQUENCE: 20

```
atgccgccgc tattcaaggg actgaaacat accagttata ctgcagacca attggtgaag      60
actgaagtca ccaagaagtc ttttactgct cctgtacaaa aggcttctac accagtttta     120
accaataaaa cagtcatttc tggatcgaaa gtcaaaagtt tatcatctgc gcaatcgagc     180
tcatcaggac cttcatcatc tagtgaggaa gatgattccc gcgatattga aagcttggat     240
aagaaaatac gtcctttaga gaattagaa gcatcattaa gtagtggaaa tacaaaacaa     300
ttgaagaaca aagaggtcgc tgccttggtt attcacggta agttaccttt gtacgctttg     360
gagaaaaaat taggtgatac tacgagagcg gttgcggtac gtaggaaggc tctttcaatt     420
ttggcagaag ctcctgtatt agcatctgat cgtttaccat ataaaaatta tgactacgac     480
cgcgtatttg gcgcttgttg tgaaaatgtt ataggttaca tgcctttgcc cgttggtgtt     540
ataggccccT tggttatcga tggtacatct tatcatatac caatggcaac tacagagggt     600
tgtttggtag cttctgccat gcgtggctgt aaggcaatca atgctggcgg tggtgcaaca     660
actgttttaa ctaaggatgg tatgacaaga ggcccagtag tccgtttccc aactttgaaa     720
agatctggtg cctgtaagat atggttagac tcagaagagg gacaaaacgc aattaaaaaa     780
gcttttaact ctacatcaag atttgcacgt ctgcaacata ttcaaacttg tctagcagga     840
gatttactct tcatgagatt tagaacaact actggtgacg caatgggtat gaatatgatt     900
tctaagggtg tcgaatactc attaaagcaa atggtagaag agtatggctg ggaagatatg     960
gaggttgtct ccgtttctgg taactactgt accgacaaaa aaccagctgc catcaactgg    1020
```

```
atcgaaggtc gtggtaagag tgtcgtcgca gaagctacta ttcctggtga tgttgtcaga   1080
aaagtgttaa aaagtgatgt ttccgcattg gttgagttga acattgctaa gaatttggtt   1140
ggatctgcaa tggctgggtc tgttggtgga tttaacgcac gtgcagctaa tttagtgaca   1200
gctgttttct tggcattagg acaagatcct gcacaaaatg tcgaaagttc caactgtata   1260
acattgatga agaagtggac ggtgatttg agaatttccg tatccatgcc atccatcgaa   1320
gtaggtacca tcggtggtgg tactgttcta gaaccacaag gtgccatgtt ggacttatta   1380
ggtgtaagag gcccacatgc taccgctcct ggtaccaacg cacgtcaatt agcaagaata   1440
gttgcctgtg ccgtcttggc aggtgaatta tccttatgtg ctgccctagc agccggccat   1500
ttggttcaaa gtcatatgac ccacaacagg aaacctgctg aaccaacaaa acctaacaat   1560
ttggacgcca ctgatataaa tcgtttgaaa gatgggtccg tcacctgcat aaatcctaa    1620
```

<210> SEQ ID NO 21
<211> LENGTH: 1377
<212> TYPE: DNA
<213> ORGANISM: Saccharomyces cerevisiae

<400> SEQUENCE: 21

```
atgccgccgc tattcaaggg actgaaagca tcattaagta gtggaaatac aaaacaattg     60
aagaacaaag aggtcgctgc cttggttatt cacggtaagt tacctttgta cgctttggag    120
aaaaaattag gtgatactac gagagcggtt gcggtacgta ggaaggctct ttcaattttg    180
gcagaagctc ctgtattagc atctgatcgt ttaccatata aaaattatga ctacgaccgc    240
gtatttggcg cttgttgtga aatgttata ggttacatgc ctttgcccgt tggtgttata    300
ggccccttgg ttatcgatgg tacatcttat catataccaa tggcaactac agagggttgt    360
ttggtagctt ctgccatgcg tggctgtaag gcaatcaatg ctggcggtgg tgcaacaact    420
gttttaacta aggatggtat gacaagaggc ccagtagtcc gtttcccaac tttgaaaaga    480
tctggtgcct gtaagatatg gttagactca gaagagggac aaaacgcaat taaaaaagct    540
tttaactcta catcaagatt tgcacgtctg caacatattc aaacttgtct agcaggagat    600
ttactcttca tgagatttag aacaactact ggtgacgcaa tgggtatgaa tatgatttct    660
aagggtgtcg aatactcatt aaagcaaatg gtagaagagt atggctggga agatatggag    720
gttgtctccg tttctggtaa ctactgtacc gacaaaaaac cagctgccat caactggatc    780
gaaggtcgtg gtaagagtgt cgtcgcagaa gctactattc tggtgatgt tgtcagaaaa    840 gtgttaaaaa gtgatgtttc cgcattggtt gagttgaaca ttgctaagaa tttggttgga    900
tctgcaatgg ctgggtctgt tggtggattt aacgcacgtg cagctaattt agtgacagct    960
gttttcttgg cattaggaca agatcctgca caaaatgtcg aaagttccaa ctgtataaca   1020
ttgatgaaag aagtggacgg tgatttgaga atttccgtat ccatgccatc catcgaagta   1080
ggtaccatcg gtggtggtac tgttctagaa ccacaaggtg ccatgttgga cttattaggt   1140
gtaagaggcc cacatgctac cgctcctggt accaacgcac gtcaattagc aagaatagtt   1200
gcctgtgccg tcttggcagg tgaattatcc ttatgtgctg ccctagcagc cggccatttg   1260
gttcaaagtc atatgaccca acaggaaacc tgctgaacaa caaaaaccta acaatttg    1320 gacgccactg atataaatcg tttgaaagat gggtccgtca cctgcattaa atcctaa      1377
```

<210> SEQ ID NO 22
<211> LENGTH: 1302
<212> TYPE: DNA

<213> ORGANISM: Saccharomyces cerevisiae

<400> SEQUENCE: 22

| | | | | | |
|---|---|---|---|---|---|
| atgccgccgc | tattcaaggg | actgaaacct | tgtacgctt | tggagaaaaa | attaggtgat | 60 |
| actacgagag | cggttgcggt | acgtaggaag | gctctttcaa | ttttggcaga | agctcctgta | 120 |
| ttagcatctg | atcgtttacc | atataaaaat | tatgactacg | accgcgtatt | tggcgcttgt | 180 |
| tgtgaaaatg | ttataggtta | catgcctttg | cccgttggtg | ttataggccc | cttggttatc | 240 |
| gatggtacat | cttatcatat | accaatggca | actacagagg | gttgtttggt | agcttctgcc | 300 |
| atgcgtggct | gtaaggcaat | caatgctggc | ggtggtgcaa | caactgtttt | aactaaggat | 360 |
| ggtatgacaa | gaggcccagt | agtccgtttc | ccaactttga | aaagatctgg | tgcctgtaag | 420 |
| atatggttag | actcagaaga | gggacaaaac | gcaattaaaa | aagcttttaa | ctctacatca | 480 |
| agatttgcac | gtctgcaaca | tattcaaact | tgtctagcag | gagatttact | cttcatgaga | 540 |
| tttagaacaa | ctactggtga | cgcaatgggt | atgaatatga | tttctaaggg | tgtcgaatac | 600 |
| tcattaaagc | aaatggtaga | agagtatggc | tgggaagata | tggaggttgt | ctccgtttct | 660 |
| ggtaactact | gtaccgacaa | aaaaccagct | gccatcaact | ggatcgaagg | tcgtggtaag | 720 |
| agtgtcgtcg | cagaagctac | tattcctggt | gatgttgtca | gaaaagtgtt | aaaaagtgat | 780 |
| gtttccgcat | tggttgagtt | gaacattgct | aagaatttgg | ttggatctgc | aatggctggg | 840 |
| tctgttggtg | gatttaacgc | acgtgcagct | aatttagtga | cagctgtttt | cttggcatta | 900 |
| ggacaagatc | ctgcacaaaa | tgtcgaaagt | tccaactgta | taacattgat | gaaagaagtg | 960 |
| gacggtgatt | tgagaatttc | cgtatccatg | ccatccatcg | aagtaggtac | catcggtggt | 1020 |
| ggtactgttc | tagaaccaca | aggtgccatg | ttggacttat | aggtgtaag | aggcccacat | 1080 |
| gctaccgctc | ctggtaccaa | cgcacgtcaa | ttagcaagaa | tagttgcctg | tgccgtcttg | 1140 |
| gcaggtgaat | tatccttatg | tgctgcccta | gcagccggcc | atttggttca | aagtcatatg | 1200 |
| acccacaaca | ggaaacctgc | tgaaccaaca | aaacctaaca | atttggacgc | cactgatata | 1260 |
| aatcgtttga | agatgggtc | cgtcacctgc | attaaatcct | aa | | 1302 |

<210> SEQ ID NO 23
<211> LENGTH: 1203
<212> TYPE: DNA
<213> ORGANISM: Saccharomyces cerevisiae

<400> SEQUENCE: 23

| | | | | | |
|---|---|---|---|---|---|
| atgccgccgc | tattcaaggg | actgaaatct | gatcgtttac | catataaaaa | ttatgactac | 60 |
| gaccgcgtat | ttggcgcttg | ttgtgaaaat | gttataggtt | acatgccttt | gcccgttggt | 120 |
| gttataggcc | ccttggttat | cgatggtaca | tcttatcata | taccaatggc | aactacagag | 180 |
| ggttgtttgg | tagcttctgc | catgcgtggc | tgtaaggcaa | tcaatgctgg | cggtggtgca | 240 |
| acaactgttt | taactaagga | tggtatgaca | agaggcccag | tagtccgttt | cccaactttg | 300 |
| aaaagatctg | gtgcctgtaa | gatatggtta | gactcagaag | agggacaaaa | cgcaattaaa | 360 |
| aaagctttta | actctacatc | aagatttgca | cgtctgcaac | atattcaaac | ttgtctagca | 420 |
| ggagatttac | tcttcatgag | atttagaaca | actactggtg | acgcaatggg | tatgaatatg | 480 |
| atttctaagg | gtgtcgaata | ctcattaaag | caaatggtag | aagagtatgg | ctgggaagat | 540 |
| atggaggttg | tctccgtttc | tggtaactac | tgtaccgaca | aaaaccagc | tgccatcaac | 600 |
| tggatcgaag | gtcgtggtaa | gagtgtcgtc | gcagaagcta | ctattcctgg | tgatgttgtc | 660 |
| agaaaagtgt | taaaaagtga | tgtttccgca | ttggttgagt | tgaacattgc | taagaatttg | 720 |

```
gttggatctg caatggctgg gtctgttggt ggatttaacg cacgtgcagc taatttagtg    780
acagctgttt tcttggcatt aggacaagat cctgcacaaa atgtcgaaag ttccaactgt    840
ataacattga tgaaagaagt ggacggtgat tgagaatttt ccgtatccat gccatccatc    900
gaagtaggta ccatccggtgg tggtactgtt ctagaaccac aaggtgccat gttggactta    960
ttaggtgtaa gaggcccaca tgctaccgct cctggtacca acgcacgtca attagcaaga   1020
atagttgcct gtgccgtctt ggcaggtgaa ttatccttat gtgctgccct agcagccggc   1080
catttggttc aaagtcatat gacccacaac aggaaacctg ctgaaccaac aaaacctaac   1140
aatttggacg ccactgatat aaatcgtttg aaagatgggc cgtcacctg cattaaatcc   1200 taa                                                                 1203
```

<210> SEQ ID NO 24
<211> LENGTH: 975
<212> TYPE: DNA
<213> ORGANISM: Saccharomyces cerevisiae

<400> SEQUENCE: 24

```
atgccgccgc tattcaaggg actgaaaaag gatggtatga caagaggccc agtagtccgt     60
ttcccaactt tgaaaagatc tggtgcctgt aagatatggt tagactcaga agagggacaa    120
aacgcaatta aaaagcttt taactctaca tcaagatttg cacgtctgca acatattcaa    180
acttgtctag caggagattt actcttcatg agatttagaa caactactgg tgacgcaatg    240
ggtatgaata tgatttctaa gggtgtcgaa tactcattaa agcaaatggt agaagagtat    300
ggctgggaag atatggaggt tgtctccgtt tctggtaact actgtaccga caaaaaacca    360
gctgccatca actggatcga aggtcgtggt aagagtgtcg tcgcagaagc tactattcct    420
ggtgatgttg tcagaaaagt gttaaaaagt gatgtttccg cattggttga gttgaacatt    480
gctaagaatt tggttggatc tgcaatggct gggtctgttg gtggattaa cgcacgtgca    540 gctaatttag tgacagctgt tttcttggca ttaggacaag atcctgcaca aaatgtcgaa    600
agttccaact gtataacatt gatgaaagaa gtggacggtg atttgagaat tccgtatcc    660 atgccatcca tcgaagtagg taccatcggt ggtggtactg ttctagaacc acaaggtgcc    720
atgttggact tattaggtgt aagaggccca catgctaccg ctcctggtac caacgcacgt    780
caattagcaa gaatagttgc ctgtgccgtc ttggcaggta attatcctt atgtgctgcc    840 ctagcagccg gccatttggt tcaaagtcat atgacccaca acaggaaacc tgctgaacca    900
acaaaaccta caatttgga cgccactgat ataaatcgtt tgaaagatgg gtccgtcacc    960
tgcattaaat cctaa                                                    975
```

<210> SEQ ID NO 25
<211> LENGTH: 549
<212> TYPE: DNA
<213> ORGANISM: Escherichia coli

<400> SEQUENCE: 25

```
atgcaaacgg aacacgtcat tttattgaat gcacagggag ttcccacggg tacgctggaa     60
aagtatgccg cacacacggc agacacccgc ttacatctcg cgttctccag ttggctgttt    120
aatgccaaag acaattatt agttacccgc cgcgcactga gcaaaaaagc atggcctggc    180
gtgtggacta ctcggtttg tgggcaccca caactgggag aaagcaacga agacgcagtg    240
atccgccgtt gccgttatga gcttggcgtg gaaattacgc ctcctgaatc tatctatcct    300
```

```
gactttcgct accgcgccac cgatccgagt ggcattgtgg aaaatgaagt gtgtccggta      360
tttgccgcac gcaccactag tgcgttacag atcaatgatg atgaagtgat ggattatcaa      420
tggtgtgatt tagcagatgt attacacggt attgatgcca cgccgtgggc gttcagtccg      480
tggatggtga tgcaggcgac aaatcgcgaa gccagaaaac gattatctgc atttacccag      540
cttaaataa                                                             549
```

<210> SEQ ID NO 26
<211> LENGTH: 1332
<212> TYPE: DNA
<213> ORGANISM: Saccharomyces cerevisiae

<400> SEQUENCE: 26

```
atgtcattac cgttcttaac ttctgcaccg ggaaaggtta ttattttggg tgaacactct      60
gctgtgtaca acaagcctgc cgtcgctgct agtgtgtctg cgttgagaac ctacctgcta      120
ataagcgagt catctgcacc agatactatt gaattggact tcccggacat tagctttaat      180
cataagtggt ccatcaatga tttcaatgcc atcaccgagg atcaagtaaa ctcccaaaaa      240
ttggccaagg ctcaacaagc caccgatggc ttgtctcagg aactcgttag tcttttggat      300
ccgttgttag ctcaactatc cgaatccttc cactaccatg cagcgttttg tttcctgtat      360
atgtttgttt gcctatgccc ccatgccaag aatattaagt tttcttttaaa gtctactttta    420 cccatcggtg ctgggttggg ctcaagcgcc tctatttctg tatcactggc cttagctatg      480
gcctacttgg gggggttaat aggatctaat gacttggaaa agctgtcaga aaacgataag      540
catatagtga atcaatgggc cttcataggt gaaaagtgta ttcacggtac cccttcagga      600
atagataacg ctgtggccac ttatggtaat gccctgctat ttgaaaaaga ctcacataat      660
ggaacaataa acacaaacaa tttttaagttc ttagatgatt tcccagccat tccaatgatc      720
ctaacctata ctagaattcc aaggtctaca aaagatcttg ttgctcgcgt tcgtgtgttg      780
gtcaccgaga aatttcctga agttatgaag ccaattctag atgccatggg tgaatgtgcc      840
ctacaaggct tagagatcat gactaagtta agtaaatgta aaggcaccga tgacgaggct      900
gtagaaacta ataatgaact gtatgaacaa ctattggaat tgataagaat aaatcatgga      960
ctgcttgtct caatcggtgt ttctcatcct ggattagaac ttattaaaaa tctgagcgat      1020
gatttgagaa ttggctccac aaaacttacc ggtgctggtg gcggcggttg ctctttgact      1080
ttgttacgaa gagacattac tcaagagcaa attgacagct tcaaaaagaa attgcaagat      1140
gattttagtt acgagacatt tgaaacagac ttgggtggga ctggctgctg tttgttaagc      1200
gcaaaaaatt tgaataaaga tcttaaaatc aaatccctag tattccaatt atttgaaaat      1260
aaaactacca caaagcaaca aattgacgat ctattattgc caggaaacac gaatttacca      1320
tggacttcat aa                                                         1332
```

<210> SEQ ID NO 27
<211> LENGTH: 1197
<212> TYPE: DNA
<213> ORGANISM: Saccharomyces cerevisiae

<400> SEQUENCE: 27

```
atgtctcaga acgtttacat tgtatcgact gccagaaccc caattggttc attccagggt      60
tctctatcct ccaagacagc agtggaattg ggtgctgttg ctttaaaagg cgccttggct      120
aaggttccag aattggatgc atccaaggat tttgacgaaa ttatttttgg taacgttctt      180
tctgccaatt tgggccaagc tccggccaga caagttgctt tggctgccgg tttgagtaat      240
```

```
catatcgttg caagcacagt taacaaggtc tgtgcatccg ctatgaaggc aatcattttg      300
ggtgctcaat ccatcaaatg tggtaatgct gatgttgtcg tagctggtgg ttgtgaatct      360
atgactaacg caccatacta catgccagca gcccgtgcgg gtgccaaatt tggccaaact      420
gttcttgttg atggtgtcga aagagatggg ttgaacgatg cgtacgatgg tctagccatg      480
ggtgtacacg cagaaaagtg tgcccgtgat tgggatatta ctagagaaca acaagacaat      540
tttgccatcg aatcctacca aaaatctcaa aaatctcaaa aggaaggtaa attcgacaat      600
gaaattgtac ctgttaccat taagggattt agaggtaagc ctgatactca agtcacgaag      660
gacgaggaac ctgctagatt acacgttgaa aaattgagat ctgcaaggac tgttttccaa      720
aaagaaaacg gtactgttac tgccgctaac gcttctccaa tcaacgatgg tgctgcagcc      780
gtcatcttgg tttccgaaaa agttttgaag gaaaagaatt tgaagccttt ggctattatc      840
aaaggttggg gtgaggccgc tcatcaacca gctgatttta catgggctcc atctcttgca      900
gttccaaagg ctttgaaaca tgctggcatc gaagacatca attctgttga ttactttgaa      960
ttcaatgaag ccttttcggt tgtcggtttg gtgaacacta agattttgaa gctagaccca     1020
tctaaggtta atgtatatgg tggtgctgtt gctctaggtc acccattggg ttgttctggt     1080
gctagagtgg ttgttacact gctatccatc ttacagcaag aaggaggtaa gatcggtgtt     1140
gccgccattt gtaatggtgg tggtggtgct tcctctattg tcattgaaaa gatatga       1197

<210> SEQ ID NO 28
<211> LENGTH: 1476
<212> TYPE: DNA
<213> ORGANISM: Saccharomyces cerevisiae

<400> SEQUENCE: 28
atgaaactct caactaaact ttgttggtgt ggtattaaag gaagacttag gccgcaaaag       60
caacaacaat tacacaatac aaacttgcaa atgactgaac taaaaaaaca aaagaccgct      120
gaacaaaaaa ccagacctca aaatgtcggt attaaaggta tccaaattta catcccaact      180
caatgtgtca accatctcga gctagagaaa tttgatggcg tttctcaagg taaatacaca      240
attggtctgg gccaaaccaa catgtctttt gtcaatgaca gagaagatat ctactcgatg      300
tccctaactg ttttgtctaa gttgatcaag agttacaaca tcgacaccaa caaaattggt      360
agattagaag tcggtactga aactctgatt gacaagtcca agtctgtcaa gtctgtcttg      420
atgcaattgt ttggtgaaaa cactgacgtc gaaggtattg acacgcttaa tgcctgttac      480
ggtggtacca acgcgttgtt caactctttg aactggattg aatctaacgc atgggatggt      540
agagacgcca ttgtagtttg cggtgatatt gccatctacg ataagggtgc cgcaagacca      600
accggtggtg ccggtactgt tgctatgtgg atcggtcctg atgctccaat tgtatttgac      660
tctgtaagag cttcttacat ggaacacgcc tacgattttt acaagccaga tttcaccagc      720
gaatatcctt acgtcgatgg tcattttca ttaacttgtt acgtcaaggc tcttgatcaa      780
gtttacaaga gttattccaa gaaggctatt tctaaagggt tggttagcga tcccgctggt      840
tcggatgctt tgaacgtttt gaaatatttc gactacaacg ttttccatgt tccaacctgt      900
aaattggtca caaaatcata cggtagatta ctatataacg atttcagagc caatcctcaa      960
ttgttcccag aagttgacgc cgaattagct actcgcgatt atgacgaatc tttaaccgat     1020
aagaacattg aaaaaacttt tgttaatgtt gctaagccat ccacaaaaga gagagttgcc     1080
caatctttga ttgttccaac aaacacaggt aacatgtaca ccgcatctgt ttatgccgcc     1140
```

```
tttgcatctc tattaaacta tgttggatct gacgacttac aaggcaagcg tgttggttta    1200
ttttcttacg gttccggttt agctgcatct ctatattctt gcaaaattgt tggtgacgtc    1260
caacatatta tcaaggaatt agatattact aacaaattag ccaagagaat caccgaaact    1320
ccaaaggatt acgaagctgc catcgaattg agagaaaatg cccatttgaa gaagaacttc    1380
aaacctcaag gttccattga gcatttgcaa agtggtgttt actacttgac caacatcgat    1440
gacaaattta aagatcttac cgatgttaaa aaataa                              1476
```

<210> SEQ ID NO 29
<211> LENGTH: 1356
<212> TYPE: DNA
<213> ORGANISM: Saccharomyces cerevisiae

<400> SEQUENCE: 29

```
atgtcagagt tgagagcctt cagtgcccca gggaaagcgt tactagctgg tggatattta     60
gttttagata caaaatatga agcatttgta gtcggattat cggcaagaat gcatgctgta    120
gcccatcctt acggttcatt gcaagggtct gataagtttg aagtgcgtgt gaaaagtaaa    180
caatttaaag atggggagtg gctgtaccat ataagtccta aaagtggctt cattcctgtt    240
tcgataggcg gatctaagaa ccctttcatt gaaaaagtta tcgctaacgt atttagctac    300
tttaaaccta acatggacga ctactgcaat agaaacttgt tcgttattga tatttctct    360 gatgatgcct accattctca ggaggatagc gttaccgaac atcgtggcaa cagaagattg    420
agttttcatt cgcacagaat tgaagaagtt cccaaaacag ggctgggctc ctcggcaggt    480
ttagtcacag ttttaactac agctttggcc tccttttttg tatcggacct ggaaaataat    540
gtagacaaat atagagaagt tattcataat ttagcacaag ttgctcattg tcaagctcag    600
ggtaaaattg gaagcgggtt tgatgtagcg gcggcagcat atggatctat cagatataga    660
agattcccac ccgcattaat ctctaatttg ccagatattg gaagtgctac ttacggcagt    720
aaactggcgc atttggttga tgaagaagac tggaatatta cgattaaaag taaccatttac    780 ccttcgggat taactttatg gatgggcgat attaagaatg gttcagaaac agtaaaactg    840
gtccagaagg taaaaaattg gtatgattcg catatgccag aaagcttgaa aatatataca    900
gaactcgatc atgcaaattc tagatttatg gatggactat ctaaactaga tcgcttacac    960
gagactcatg acgattacag cgatcagata tttgagtctc ttgagaggaa tgactgtacc   1020
tgtcaaaagt atcctgaaat cacagaagtt agagatgcag ttgccacaat tagacgttcc   1080
tttagaaaaa taactaaaga atctggtgcc gatatcgaac ctcccgtaca aactagctta   1140
ttggatgatt gccagaccct taaaggagtt cttacttgct taatacctgg tgctggtggt   1200
tatgacgcca ttgcagtgat tactaagcaa gatgttgatc ttagggctca aaccgctaat   1260
gacaaaagat tttctaaggt tcaatggctg gatgtaactc aggctgactg gggtgttagg   1320
aaagaaaaag atccggaaac ttatcttgat aaataa                             1356
```

<210> SEQ ID NO 30
<211> LENGTH: 4
<212> TYPE: PRT
<213> ORGANISM: Saccharomyces cerevisiae

<400> SEQUENCE: 30

His Asp Glu Leu
 1

<210> SEQ ID NO 31

```
<211> LENGTH: 4
<212> TYPE: PRT
<213> ORGANISM: Saccharomyces cerevisiae

<400> SEQUENCE: 31

Asp Asp Glu Leu
 1

<210> SEQ ID NO 32
<211> LENGTH: 4
<212> TYPE: PRT
<213> ORGANISM: Saccharomyces cerevisiae

<400> SEQUENCE: 32

Lys Asp Glu Leu
 1

<210> SEQ ID NO 33
<211> LENGTH: 29
<212> TYPE: PRT
<213> ORGANISM: Saccharomyces cerevisiae

<400> SEQUENCE: 33

Met Met Ser Phe Val Ser Leu Leu Leu Val Gly Ile Leu Phe Trp Ala
 1               5                  10                  15

Thr Glu Ala Glu Gln Leu Thr Lys Cys Glu Val Phe Gln
            20                  25

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 34
gccgttgaca gagggtccga gctcggtacc aag                               33

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 35
catactgacc cattgtcaat gggtaataac tgat                              34

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 36
tgtccggtaa atggagac                                                18

<210> SEQ ID NO 37
<211> LENGTH: 18
<212> TYPE: DNA
<213> ORGANISM: Artificial Sequence
<220> FEATURE:
```

<223> OTHER INFORMATION: Description of Artificial Sequence:synthetic
    DNA

<400> SEQUENCE: 37
tgttctcgct gctcgttt                                                18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 38
atgggaaagc tattacaat                                               19

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 39
caaggttgca atggccat                                                18

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 40
caatgtaggg ctatatatg                                               19

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 41
aacttgggga atggcaca                                                18

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:synthetic
    DNA

<400> SEQUENCE: 42
tcacgctctg tgtaaagtgt ata                                          23

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence:synthetic

DNA

<400> SEQUENCE: 43
tgcatctcga gggccgcatc atgtaattag                                          30

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 44
cattagggcc cggccgcaaa ttaaagcctt cg                                       32

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 45
cacggagctc cagttcgagt ttatcattat caa                                      33

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 46
ctctccgcgg tttgtttgtt tatgtgtgtt tattc                                    35

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 47
atggcttcag aaaagaaat tag                                                  23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 48
ctatttgctt ctcttgtaaa ctt                                                 23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence:synthetic
      DNA -continued

<400> SEQUENCE: 49
atggaggcca agatagatga gct                                           23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 50
tcacaattcg gataagtggt cta                                           23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 51
atgccgccgc tattcaaggg act                                           23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 52
ttaggattta atgcaggtga cgg                                           23

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 53
ccaaataaag actccaacac tctattt                                       27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 54
gaattagaag cattattaag tagtgga                                       27

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 55
ggatttaacg cacatgcagc taattta					27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 56
gtctgcttgg gttacatttt ctgaaaa					27

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 57
cataccagtt atactgcaga ccaattg					27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 58
gaatactcat taaagcaaat ggtagaa					27

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 59
aactgcagat gaccgtttac acagcatccg t				31

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 60
cggaattctt attcctttgg tagaccagtc t				31

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 61
tttcagtccc ttgaatagcg gcggcat                27

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 62
cacaaaatca agattgccca gtatgcc                27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 63
agaagatacg gatttctttt ctgcttt                27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 64
aactttggtg caaattgggt caatgat                27

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 65
ttgctcttta aagttttcag aggcatt                27

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 66
gcattattaa gtagtggaaa tacaaaa                27

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 67

```
cctttgtacg ctttggagaa aaaatta                                           27
```

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 68

```
tctgatcgtt taccatataa aaattat                                           27
```

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 69

```
aaggatggta tgacaagagg cccagta                                           27
```

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 70

```
tccccgcgga tggaggccaa gatagat                                           27
```

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 71

```
caactcgagt cacaattcgg ataagtg                                           27
```

<210> SEQ ID NO 72
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 72

```
gctctagagt tcgtcgtgtt tgcttctctt gtaaactt                               38
```

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 73

```
tatctcgagt cacaattcgt catgtaaatt gg                                     32
```

```
<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 74
gcagggaccc caattcggat aagtggtc                                       28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 75
gtagggtccc tggaggccaa gatagatg                                       28

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 76
gcagggaccc tttgcttctc ttgtaaact                                      29

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 77
gtagggtcct cagaaaaaga aattaggag                                      29

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 78
tgtaaaacga cggccagt                                                  18

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 79
taatacgact cactataggg                                                20
```

US 8,759,046 B2

PROCESS FOR PRODUCING PRENYL ALCOHOLS

This application is a continuation of U.S. application Ser. No. 10/450,941, filed 18 Jun. 2003 now abandoned, which is a 371 national phase application of PCT/JP01/11215 filed on 20 Dec. 2001, claiming priority to JP 2000-401701, filed on 28 Dec. 2000, JP 2000-403067, filed 28 Dec. 2000, and JP 2001-282978 filed 18 Sep. 2001, the contents of which are incorporated herein by reference in their entireties.

TECHNICAL FIELD

The present invention relates to methods of producing prenyl alcohols.

BACKGROUND ART

The biosynthesis of terpenoids (isoprenoids) begins with the synthesis of geranyl diphosphate (GPP; $C_{10}$), farnesyl diphosphate (FPP; $C_{15}$) and geranylgeranyl diphosphate (GGPP; $C_{20}$), which are straight-chain prenyl diphosphates, through the sequential condensation reactions of isopentenyl diphosphate (IPP; $C_5$) with an allylic diphosphate substrate (FIG. 1). In FIG. 1, the abbreviations and words in boxes represent enzymes. Specifically, hmgR represents hydroxymethylglutaryl-CoA (HMG-CoA) reductase; GGPS represents GGPP synthase; and FPS represents FPP synthase.

Among prenyl diphosphates, FPP is the most significant biosynthetic intermediate. It is a precursor for the synthesis of tremendous kinds of terpenoids, e.g. steroids including ergosterol (provitamin $D_2$), the side chains of quinone (vitamin K; VK), sesquiterpenes, squalene (SQ), the anchor molecules of farnesylated proteins, dolichols, bactoprenol, and natural rubber.

GGPP is also a biosynthetic intermediate in vivo, and is essential for the biosynthesis of such compounds as phytoene, lycopene, ficaprenol, retinol (vitamin A; VA), β-carotene (provitamin A), phylloquinone (vitamin $K_1$; $VK_1$), tocopherols (vitamin E; VE), the anchor molecules of geranylgeranylated proteins, the side chain of chlorophyll, gibberellins, and the ether lipid of archaea.

It is known that these prenyl diphosphates with up to 20 carbon atoms are condensed into trans forms ((E) forms) and are present as (E,E)-FPP and (E,E,E)-GGPP. Compounds with physiological activities are synthesized from these prenyl diphosphates or prenyl groups with up to 15 or 20 carbon atoms having the all trans (all-E) geometrical isomerism as precursors (K. Ogura and T. Koyama, (1998) *Chemical Reviews*, 98, 1263-1276; IUPAC-IUB Joint Commission on Biochemical Nomenclature (JCBN) Prenol Nomenclature, Recommendations 1986, (http://www.chem.qmw.ac.uk/iupac/misc/prenol.html)). Among prenyl diphosphates with up to 20 or 15 carbon atoms, the only one exception that has the cis ((Z) form) geometrical isomerism is neryl diphosphate ($C_{10}$) known as a precursor for those monoterpenoids as represented by nerol. It has not yet been elucidated whether neryl diphosphate is synthesized through condensation of IPP with dimethylallyl diphosphate (DMAPP; 3,3-dimethylallyl diphosphate) as an allylic diphosphate substrate; or through isomerization of geranyl diphosphate (GPP) that is a trans ((E) form) geometrical isomer with 10 carbon atoms. Those isoprenoids that are synthesized through condensation into cis forms ((Z) forms), e.g. dolichols, bactoprenol (undecaprenol) or natural rubber, are also synthesized from (E,E)-FPP or (E,E,E)-GGPP as an allylic primer substrate (K. Ogura and T. Koyama, (1998) *Chemical Reviews*, 98, 1263-1276; IUPAC-IUB Joint Commission on Biochemical Nomenclature (JCBN) Prenol Nomenclature, Recommendations 1986, (http://www.chem.qmw.ac.uk/iupac/misc/prenol.html)).

(E,E)-Farnesol (FOH; $C_{15}$), which is an alcohol derivative of (E,E)-FPP; (E)-nerolidol (NOH; $C_{15}$), which is an isomer of the tertiary alcohol thereof; (E,E,E)-geranylgeraniol ((E,E,E)-GGOH; $C_{20}$), which is an alcohol derivative of (E,E,E)-GGPP; and the like are known as fragrant substances in essential oils used as the ingredient of perfumes. FOH, NOH and (E,E,E)-GGPP are also important as starting materials for the synthesis of various compounds (including the above-mentioned vitamins) useful as pharmacological agents (FIG. 1).

Although it had been believed that all the biosynthesis of EPP is performed via the mevalonate pathway (a pathway in which IPP is synthesized from acetyl-CoA through mevalonate acid), M. Rohmer et al. elucidated a novel IPP biosynthetic pathway using bacteria at the end of 1980's. This is called the non-mevalonate pathway, DXP (1-deoxy-D-xylulose 5-phosphate) pathway, MEP (2-C-methyl-D-erythritol 4-phosphate) pathway or Rohmer pathway, in which IPP is synthesized from glyceraldehyde-3-phosphate and pyruvate through 1-deoxy-D-xylulose 5-phosphate. Thus, two major pathways, i.e. the mevalonate pathway and the non-mevalonate pathway, are known at present as synthetic pathways for IPP.

FOH and NOH are currently produced by chemical synthesis except for small amounts of them prepared from natural products such as essential oils. GGOH is also produced by chemical synthesis (Japanese Unexamined Patent Publication No. 8-13999). Chemically synthesized FOH, NOH or GOOH generally has the same carbon skeleton, but they are obtained as mixtures containing (E) (trans) double bond and (Z) (cis) double bond geometry. (E,E)-FOH, (E)-NOH or (E,E,E)-GGOH, each of which is (all-E) type, is a compound with the geometrical isomerism synthesized in biosynthetic pathways and is industrially valuable. In order to obtain (E,E)-FOH, (E)-NOH or (E,E,E)-GGOH in a pure form, refining by column chromatography, high precision distillation, etc. is necessary. However, it is difficult to carry out high precision distillation of FOH, a thermolabile allyl alcohol, or its isomer FOH, or GGOH. Also, the refining of these substances by column chromatography is not suitable in industrial practice since it requires large quantities of solvent and column packings as well as complicated operations of analyzing and recovering serially eluting fractions and removing the solvent; thus, this method is complicated and requires high cost. Actually, the (E,E)-FOH and (E,E,E)-GGOH sold as experimental reagents are very expensive. Under circumstances, it is desired to establish a system for synthesizing not mixtures of cis- and trans-((Z)- and (E)-) isomers but pure products of (E,E)-FOH (hereinafter, just referred to as "FOH"), (E)-NOH (hereinafter, just referred to as "NHO") and (E,E,E)-GGOH hereinafter, just referred to as "GGOH") (i.e., the so-called active prenyl alcohols) in large quantities by controlling the generation of (E)- and (Z)-geometrical isomers or by utilizing the characteristics of repeat structures of reaction products.

The substrates for the biosynthesis of FOH, NOH or GGOH are provided via the mevalonate pathway in cells of, for example, *Saccharomyces cerevisiae*, a budding yeast. However, even when HMG-CoA reductase that is believed to be a key enzyme for the biosynthesis was used, it has been only discovered that the use increases the accumulation of squalene, a substance commercially available at a greatly low price than FOH and GGOH (Japanese Unexamined Patent Publication No. 5-192184; Donald et al., (1997) *Appl. Envi-*

*ron. Microbiol.* 63, 3341-3344). Further, it is known that 1.3 mg of FOH per liter of culture broth is accumulated when a squalene synthase gene-deficient clone (ATCC64031) was created by introducing mutations into the squalene synthase gene ERG9 of a particular budding yeast that had acquired sterol intake ability, and cultured (Chambon et al., (1990) *Curr. Genet.* 18, 41-46). The present inventor determined the nucleotide sequence of the squalene synthase gene ERG9 in ATCC64031, and confirmed that this clone has become a squalene synthase gene-deficient clone (erg9 clone) as a result of the introduction of substitution mutations into the coding region of ERG9 and thus acquired the productivity of 1.3 mg/L of FOH. In the coding region of the squalene synthase gene of ATCC64031, the nucleotide at position 745 has been changed from C to T and the nucleotide at position 797 from T to G. As a result, the amino acid residue at position 249 has changed from Gln to termination codon (Q249STOP) and the amino acid residue at position 266 from Ile to Arg (I266R) in the polypeptide encoded by this gene. These changes have led to the expression of a mutant squalene synthase in which the amino acid residue at position 249 and thereafter are deleted, and which has no enzyme activity. However, when ERG9 is made deficient in a conventional strain, the deficiency is lethal to the strain because the strain cannot synthesize ergosterol essential for growth and it has no function to intake sterols from the outside under conventional culture conditions. Thus, an ERG9-deficient clone cannot be obtained; it is impossible to construct an FOH production system. Furthermore, no method of biosynthesis of (E)-NOH (hereinafter, referred to as "NOH") is known. Even if it is possible to provide to a ERG9-deficient clone with a novel character that avoids the lethality, the cultivation of such a clone will require disadvantageous conditions to industrial production, e.g., necessity to add ergosterol to the medium.

With respect to the biosynthesis of GGOH, production of 0.66-3.25 mg per liter of culture broth is achieved by culturing plant cells in Japanese Unexamined Patent Publication No. 9-238692. However, this method needs an expensive plant cell culture medium inappropriate for industrial application and also requires light for culturing cells. Thus, this method is not practical even when compared to the conventional GGOH preparation from natural products such as essential oils. There is known no method of biosynthesis of GGOH suitable for industrialization, e.g. biosynthesis by microorganisms.

DISCLOSURE OF THE INVENTION

It is an object of the present invention to provide a method of producing prenyl alcohols by reducing the amount of squalene synthase gene transcript having translational activity.

As a result of intensive and extensive researches toward the solution of the above problem, the present inventors have developed a prenyl alcohol production system by culturing a mutant cell in which the transcription promoter region of squalene synthase gene has been replaced with a transcription repression type promoter under transcription repression conditions so that an amount of squalene synthase gene transcript having translational activity can be reduced. Further, in order to establish a system to artificially express an IPP biosynthetic pathway-related enzyme gene (represented by HMG-CoA reductase gene), a mutant thereof or a fusion gene thereof in a host, expression shuttle vectors were constructed which comprise a constitutive or inducible transcription promoter and various auxotrophic markers. A gene of interest or a mutant thereof was inserted into the shuttle vector, which was then introduced into the mutant cell of the invention where an amount of squalene synthase gene transcript having translational activity can be reduced. From a culture of the resultant cell, a prenyl alcohol(s) could be obtained, and the above object could be achieved. Thus, the present invention has been completed.

The present invention relates to the following inventions.

(1) A method of producing a prenyl alcohol(s), comprising culturing a mutant cell that has been mutated so that an amount of squalene synthase gene transcript having translational activity can be reduced, and recovering the prenyl alcohol(s) from the resultant culture.

(2) A method of producing a prenyl alcohol(s), comprising preparing a recombinant by introducing a recombinant DNA for expression or a DNA for genomic integration each comprising an IPP biosynthetic pathway-related enzyme gene into a mutant cell that has been mutated so that an amount of squalene synthase gene transcript having translational activity can be reduced, culturing the resultant recombinant, and recovering the prenyl alcohol(s) from the resultant culture.

(3) A method of producing a prenyl alcohol(s), comprising culturing a mutant cell in which the transcription promoter region of squalene synthase gene has been replaced with a transcription repression-type promoter under transcription repression conditions; reducing an amount of squalene synthase gene transcript having translational activity; and recovering the prenyl alcohol(s) from the resultant culture.

(4) A method of producing a prenyl alcohol(s), comprising preparing a recombinant by introducing a recombinant DNA for expression or a DNA for genomic integration each comprising an IPP biosynthetic pathway-related enzyme gene into a mutant cell in which the transcription promoter region of its squalene synthase gene has been replaced with a transcription repression-type promoter so that an amount of squalene synthase gene transcript having translational activity can be reduced, culturing the recombinant under transcription repression conditions; and recovering the prenyl alcohol(s) from the resultant culture.

In the methods described above, the IPP biosynthetic pathway-related enzyme gene includes enzyme genes involved in those reactions where IPP is synthesized from compounds located in the glycolytic pathway or citrate cycle, as well as various prenyl diphosphate synthase genes. The IPP biosynthetic pathway-related enzyme gene includes not only those enzyme genes involved in the mevalonate pathway but also those enzyme genes involved in the so-called non-mevalonate pathway [also called DXP (1-deoxy-D-xylulose 5-phosphate) pathway, MEP (2-C-methyl-D-erythritol 4-phosphate) pathway or Rohmer pathway] that is a novel IPP biosynthetic pathway recently found in prokaryotes and chloroplasts.

In the methods described above, specific examples of the transcription repression type promoter include GAL1 promoter. Specific examples of the transcription repression conditions for GAL1 promoter include the use of a glucose-containing medium. As the IPP biosynthetic pathway-related enzyme gene, any one selected from the group consisting of the following genes (a) through (l) may be given.

(a) farnesyl diphosphate synthase gene
(b) geranylgeranyl diphosphate synthase gene
(c) hydroxymethylglutaryl-CoA reductase gene
(d) isopentenyl diphosphate Δ-isomerase gene
(e) mevalonate kinase gene
(f) acetyl-CoA acetyltransferase gene
(g) hydroxymethylglutaryl-CoA synthase gene
(h) phosphomevalonate kinase gene
(i) diphosphomevalonate decarboxylase gene (j) a mutant gene of any one of the above genes (a) through (i)

(k) a fusion gene composed of a gene selected from the group consisting of the above genes (a) through (i) or a mutant thereof, and another gene or a mutant gene thereof (an artificial sequence may be inserted into the junction site between the two genes)

(l) a gene obtained by introducing an addition, substitution or insertion mutation into any one of the above genes (a) through (k) so that the polypeptide encoded by the resultant gene contains an endoplasmic reticulum signal.

In the junction site of the above-described fusion gene, a nucleotide sequence encoding an artificial amino acid sequence may be inserted freely so that the polypeptides encoded by the two genes before fusion can take conformations that allow them to function appropriately. For example, a sequence 5' GGGTCC 3' encoding Gly Ser may be inserted.

As endoplasmic reticulum signals, His Asp Glu Leu (SEQ ID NO: 30; called "HDEL sequence") or Asp Asp Glu Leu (SEQ ID NO: 31) located at the C-terminal is known in *Saccharomyces cerevisiae*, and Lys Asp Glu Leu (SEQ ID NO: 32) located at the C-terminal is known in eukaryotes in general as a C-terminal signal. It is known that they work as an endoplasmic reticulum retention signal completely equivalent to them in function (B. Lewin, *Genes V*, (1994), Oxford University Press, New York, U.S.A., pp. 279-318; B. Alberts et al., *Molecular Biology of The Cell*, third edition (1994), Garland Publishing. Inc., New York, U.S.A., §12-§13) (hereinafter, these sequences are generically termed "HDEL sequence or the like"). In addition to these endoplasmic reticulum retention signals consisting of the 4 amino acid residues located at the C-terminal, other signal peptides from a part of the domains of ER transition proteins, e.g., the signal peptide $^+H_3N$ Met Met Ser Phe Val Ser Leu Ieu Leu Val Gly Ile Leu Phe Trp Ala Thr Glu Ala Glu Gln Leu Thr Lys Cys Glu Val Phe Gln (SEQ ID NO: 33) located at the N-terminal that functions as a transport signal to ER may also be used (B. Lewin, *Genes V* (1994), Oxford University Press, New York, U.S.A., pp. 279-318; B. Alberts et al., *Molecular Biology of The Cell*, third edition (1994), Garland Publishing. Inc., New York, U.S.A., §12-§13).

A polypeptide in which an endoplasmic reticulum signal has been added, substituted or inserted by introducing an addition, substitution or insertion mutation into its gene may also be regarded as a mutant polypeptide in which 4 amino acid residues are added, substituted or inserted in the corresponding wild type polypeptide. A gene encoding such a mutant polypeptide may also be regarded as a mutant gene in which a nucleotide sequence of about 1-12 nucleotides is added, substituted or inserted in the corresponding wild type gene. Also, a polypeptide encoded by the above-described fusion gene may be regarded as a mutant polypeptide in which more than 300 amino acid residues are added, substituted or inserted in a wild type polypeptide. The fusion gene may also be regarded as a mutant gene in which a nucleotide sequence of about 1000 nucleotides is added, substituted or inserted in a wild type gene. That is, a gene or fusion gene encoding an amino acid sequence in which a signal has been newly created is in itself a mutant gene.

In order to create an HDEL sequence or the like at the C-terminal, insertion of one base that would cause a frame shift resulting in the creation of an HDEL sequence or the like may also be used. It is also possible to replace 2 nucleotides to thereby create an HDEL sequence or the like from the original C-terminal sequence (e.g., HDGI). If an HDEL sequence or the like is present near the C-terminal (e.g., in the case of BTS1), an HDEL sequence or the like can be created at the C-terminal by simply introducing a stop codon. Alternatively, it is possible to newly add 12 nucleotides to the C-terminal to thereby create an HDEL sequence or the like at the C-terminal.

As a host cell to be mutated, yeast, yeast belonging to Ascomycota, yeast belonging to Basidiomycota, or yeast belonging to Fungi Imperfecti may be used, for example. Preferably, yeast belonging to Ascomycota, in particular, budding yeast such as *Saccharomyces cerevisiae, Candida utilis* or *Pichia pastris*; and fission yeast such as *Shizosaccharomyces pombe* may be used. Not only species but also strains are not limited as long as they can produce prenyl alcohol. In the case of *S. cerevisiae*, specific examples of useful strains include A451, YPH499, YPH500, W303-1A and W303-1B. Specific examples of the prenyl alcohol include FOH, NOH and/or GGOH.

In the methods described above, the mutant cell or the recombinant may be cultured under non-transcription repression conditions prior to the cultivation under transcription repression conditions. The cultivation under transcription repression conditions means cultivation in a glucose-containing medium. The cultivation under non-transcription repression conditions means cultivation in a galactose-containing medium.

As the farnesyl diphosphate synthase gene, a gene encoding the amino acid sequence as shown in SEQ ID NO: 2 or 4 may be used. As the geranylgeranyl diphosphate synthase gene, a gene encoding the amino acid sequence as shown in SEQ ID NO: 6 may be used. As the hydroxymethylglutaryl-CoA reductase gene, a gene encoding the amino acid sequence as shown in SEQ ID NO: 8 may be used. As the diphosphomevalonate decarboxylase gene, a gene encoding the amino acid sequence as shown in SEQ ID NO: 10 may be used. As the mutant of hydroxymethylglutaryl-CoA reductase gene, a mutant comprising the nucleotide sequence as shown in any one of SEQ ID NOS: 11, 13 and 15 through 24 may be used.

(5) A mutant cell that has been mutated so that an amount of squalene synthase gene transcript having translational activity can be reduced.

(6) A mutant cell in which the transcription promoter region of its squalene synthase gene has been replaced with a transcription repression-type promoter so that an amount of squalene synthase gene transcript having translational activity can be reduced.

Hereinbelow, the present invention will be described in detail. The present specification encompasses the contents described in the specifications and/or drawings of Japanese Patent Application Nos. 2000-401701, 20004-03067 and 2000-282978 based on which the present application claims priority.

The inventors have attempted to develop a system for producing an active-type prenyl alcohol, in particular, FOH, NOH or GGOH in vivo by using metabolic engineering techniques.

In the present invention, yeast, in particular, a budding yeast *Saccharomyces cerevisiae* was selected as a host cell. In the host cell, a part of the genomic DNA that is believed to be the transcription promoter region of its squalene synthase gene ERG9 was replaced with the transcription promoter of GAL1 gene, which is one of transcription repression type promoters capable of repression with glucose, to thereby prepare strains designated EUG. Thus, a system has been developed which allows accumulation of a prenyl alcohol(s) in culture broth by simply culturing a conventional recombinant host strain (that has no sterol intake ability under aerobic culture conditions) aerobically in a conventional glucose-containing medium without special additives (e.g., YM7 medium, YPD medium, or SD medium).

Generally, FPP is synthesized by the catalytic action of FPP synthase using IPP or DMAPP as a substrate. After the synthesis of FPP, usually, reactions do not proceed toward dephosphorylation to FOH, but proceed toward the synthesis of squalene and various sterols by squalene synthase; the synthesis of GGPP and prenylated proteins by GGPP synthase; the synthesis of medium or long chain prenyl diphosphates (such as hexaprenyl diphosphate, heptaprenyl diphosphate), ubiquinone and prenylated proteins by medium chain prenyl diphosphate synthases such as hexaprenyl diphosphate synthase or heptaprenyl diphosphate; and so on (FIG. 1) (K. Ogura and T. Koyama, (1998) *Chemical Reviews,* 98: 1263-1276). This means that when squalene synthase activity in a cell is lowered by reducing an amount of squalene synthase gene transcript having translational activity, the following can be expected to occur: accumulation of FPP to some extent; accumulation of prenylated proteins and ubiquinone, which are final products of the synthetic pathway using FPP as a substrate; or inhibition of cell growth because the synthesis of ergosterol, an essential component for the growth of the cell, becomes impossible. However, it is completely unpredictable that such reduction of squalene synthase activity makes it possible to construct an FOH production system with high productivity of more than 10 mg/L or more than 100 mg/L. It is also unpredictable that a production system for NOH or GGOH (dephosphorylated product of GGPP) can be obtained by such reduction (FIG. 1). Furthermore, even if IPP synthesis is enhanced by increasing the enzyme activity of an IPP biosynthetic pathway-related enzyme, it is unpredictable whether the enhanced enzyme activity would increase FPP synthesis or GGPP synthesis, and it is totally unpredictable that such enhance enzyme activity would lead to high production of FOH and GGOH (dephosphorylated products) and NOH (an isomer of FOH) (FIG. 1).

The present invention has found that it is possible to allow a cell to produce prenyl alcohols such as FOH, NOH and GGOH that are not explicitly mentioned even in the commonly accepted metabolic pathway map (Gerhard Michael (ed.), *Biochemical Pathways: An Atlas of Biochemistry and Molecular Biology* (1999), John Wiley & Sons, Inc., New York) by mutating the cell so that an amount of squalene synthase gene transcript having translational activity can be reduced and culturing the mutant cell under specific conditions to thereby reduce the transcript. Thus, a biological mass production system for prenyl alcohol has been developed.

The present invention has also developed another biological mass production system for prenyl alcohol by introducing an IPP biosynthetic pathway-related enzyme gene, a mutant thereof or a fusion gene thereof as a transcription unit into the mutant cell of the above-described prenyl alcohol production system of the invention.

1. Preparation of Squalene Synthase Gene Transcript-Mutated Strains

The mutant cell used in the invention comprises the squalene synthase gene of the host cell that has no substitution, insertion or addition in the coding region but has been modified so that the amount of its transcript having translational activity can be reduced. In order to reduce the amount of transcript having translational activity, several approaches may be taken. For example, a method of repressing the transcriptional activity of a gene of interest to thereby reduce the amount of its transcript per se may be used. Alternatively, a method of repressing the translational activity of transcribed mRNA using antisense RNA may be used. Transcriptional activity may be repressed, for example, by replacing the transcription promoter region of the squalene synthase gene of the host with a transcription repression type promoter, or by creating a nucleotide sequence having transcription repressive activity in a region involved in the transcription of the squalene synthase gene. Translational activity may be repressed, for example, by over-expressing a gene from which an antisense RNA against the squalene synthase gene is transcribed. Antisense RNA means an RNA having a nucleotide sequence complementary to the RNA transcribed from a target gene. Antisense RNA reduces the amount of transcript having translational activity in the transcription/translation system in both prokaryotic cells and eukaryotic cells; it has a function as a repressor of gene expression. For example, it is reported that the synthesis of OmpF protein can be repressed by reducing the amount of mRNA from *E. coli* ompF gene with transcriptional activity using antisense RNA [Takeshi Mizuno in *Expression and Control of Genes I (Series: Advances in Molecular Biology*), The Molecular Biology Society of Japan (Eds.), published by Maruzen Co. on Jun. 30, 1989, ISBN4-621-03375-1, Chapter 5 "Control of Bacterial Membrane Protein Synthesis"]. As Mizuno described in this reference, antisense RNAs against certain genes occur in nature, and if a target gene has been decided, it is easy for one of ordinary skill in the art to create an artificial antisense RNA having expression repressive activity by genetic engineering techniques. The artificial antisense RNA technology has been applied to various hosts, including not only the bacterium *E. coli* but also higher organisms, e.g., mammals (mouse), insects (*Drosophila melanogaster*) and angiosperms (tomato) [Mizuno et al., (1984) Proc. Natl. Acad. Sci. U.S.A., 81, 1966-1970; Aiba et al., (1987) *J. Bacteriol,* 169, 3007-3012; Green et al., (1986) *Annu. Rev. Biochem.,* 55, 569-597; Harland et al., (1985) *J. Cell. Biol.,* 101, 1094-1099; Coleman et al., (1984) *Cell,* 37, 429-36; Han et al., (1991) Proc. Natl. Acad. Sci. U.S.A., 88, 4313-4317; Hackett et al., (2000) *Plant Physiol.,* 124, 1079-86)].

As the host cell used in the invention, such a cell may be selected which has been widely used in the fermentation industry from old times, has the mevalonate pathway as an IPP biosynthetic pathway, and can be subjected to various genetic engineering techniques. For example, yeast such as budding yeast may be given. Specific examples of budding yeast include *Saccharomyces cerevisiae*. However, the host is not necessarily limited to yeast such as *S. cerevisiae*. Various other cells may also be used as a host as long as they possess a squalene synthase gene. By reducing an amount of squalene synthase gene transcript having translational activity in the host cell, it is possible to allow the cell to produce various active prenyl alcohols even if any deficiency has not been introduced into the squalene synthase per se by introducing a substitution, insertion or deletion mutation(s) into the coding region of the gene.

In order to reduce the amount of squalene synthase gene transcript having translational activity, a transcription repression type promoter may be used, for example. As a transcription repression type promoter, any transcription promoter may be used as long as it can control transcription under various culture conditions. Specific examples of useful transcription promoters include promoters responsible for the transcription of GAL1, GAL2, GAL7, GAL10, GAL80 and MEL1 whose transcription is repressed in a glucose containing medium; ADH1 and ENO2 whose transcription is repressed under glucose-deprived conditions; PHO5 and PHO81 whose transcription is repressed under high phosphate conditions; and HO gene whose transcription is repressed in phases other than $G_1$ in cell cycle. In addition, a promoter that is responsible for the transcription of a gene whose transcript is detected considerably under specific conditions but detected little under other conditions, such as reported in L. Wodicka et al., (1997) *Nature Biotechnology*, 15, 1359-1367, may also be used as a transcription repression type promoter. For example, (i) promoters responsible for the transcription of such genes as HSP12, INO1, YBR147W and YGR243W whose transcript is not detected in a conventional nutrient medium (rich medium) but detected considerably in minimal medium; or (ii) promoters responsible for the transcription of such genes as YDR046C, GNP1, CHA1 and PTR2 whose transcript is not detected in minimal medium but detected considerably in a conventional nutrient medium, may be enumerated. Further, it is also possible to use a transcription repression type promoter of an organism other than budding yeast. The promoter does not necessarily have transcription repressive activity in the host cell. For example, a transcription promoter may be used which acquires transcription repressive activity only after the introduction of a transcription repression factor gene into the host cell. Further, it is not necessarily required to use a transcription promoter capable of direct repression of transcription (i.e., control of mRNA synthesis) in the host cell, as along as squalene gene transcript having translational activity can be reduced. By deactivating the translational activity of mRNA (the transcript) by antisense RNA technology or the like, it is possible to achieve the same effect as achieved by the use of a transcription repression type promoter, i.e., to allow the host cell to produce prenyl alcohol without modifying the coding region of its squalene synthase gene.

Hereinbelow, a method of replacing the transcription promoter of a squalene synthase gene with transcription repression type promoter will be described using *Saccharomyces cerevisiae* as a hose cell.

First, a gene map around squalene synthase gene ERG9 was obtained from a yeast genome database (*Saccharomyces* Genome Database (SGD); http://genome-www.stanford-.edu./*Saccharomyces*/). Then, PCR primers for amplifying DNA fragments for replacing ERG9 transcription promoter (ERG9p) were designed based on the map (FIG. 2).

Subsequently, pYES2 (FIG. 2C and FIG. 3) were digested with restriction enzymes and blunt-ended with Klenow enzyme, followed by self-ligation to yield pYES2Δ without 2 μori (FIG. 2B). Using pYES2Δ as a template, a DNA fragment comprising a transformant selection marker gene URA3 and a transcription promoter GAL1p was amplified by PCR. A partial DNA sequence of ERG9 gene was ligated to one end of the resultant DNA fragment, and a partial DNA sequence of YHR189W located in the proximity of ERG9 gene was ligated to the other end of this DNA fragment. Thus, a DNA fragment for transformation was prepared (FIG. 2A).

In the present invention, a host for preparing a mutant cell is not particularly limited. Yeast that is important from the viewpoint of industrial application may be used as a host. For example, yeast belonging to Ascomycota, yeast belonging to Basidiomycota, or yeast belonging to Fungi Imperfecti may be used. Preferably, yeast belonging to Ascomycota, in particular, budding yeast such as *Saccharomyces cerevisiae*, *Candida utilis* or *Pichia pastris*; and fission yeast such as *Shizosaccharomyces pombe* may be used. In the case of *S. cerevisiae*, specific examples of useful strains include A451, YPH499, YPH500, W303-1A and W303-1B described below.

A451 (ATCC200589; MATα can1 leu2 trp1 ura3 aro7)

YPH499 (ATCC76625; MATa ura3-52 lys2-801 ade2-101 trp1-Δ63 his3-Δ200 leu2-Δ1; Stratagene)

YPH500 (ATCC76626; MATα ura3-52 lys2-801 ade2-101 trp1-Δ63 his3-Δ200 leu2-Δ1; Stratagene)

W303-1A (ATCC208352; MATa leu2-3 leu2-112 his3-11 ade2-1 ura3-1 trp1-1 can1-100)

W303-1B (ATCC208353; MATα leu2-3 leu2-112 his3-11 ade2-1 ura3-1 trp1-1 can1-100)

The transformation of a host cell with the above DNA fragment may be performed by any of the conventional technique or with a commercial kit. For example, a vector comprising the DNA fragment is introduced into the host yeast using Frozen EZ Yeast Transformation II Kit purchased from Zymo Research (Orange, Calif.).

The DNA fragment thus introduced into the host is integrated into the genome of the host by homologous recombination. As a result, a mutant cell is obtained in which the transcription promoter region of its squalene synthase gene ERG9 is replaced with GAL1 promoter that is a transcription repression type promoter.

The recombinants obtained by replacing ERG9 promoter with GAL1 promoter (a transcription repression type promoter) in order to reduce the amount of squalene synthase gene ERG9 transcript having translational activity were designated EUG (ERG9p::URA3-GAL1p) strains. A451-derived clones are designated EUG1 through EUG10. YPH499-derived clones are designated EUG11 through EUG20. YPH500-derived clones are designated EUG21 through EUG30. W303-1A-derived clones are designated EUG31 through EUG50. W303-1B-derived clones are designated EUG51 through EUG70.

EUG1 through EUG10 (A451; ERG9p::URA3-GAL1p) are A451-derived strains established in the present invention and are capable of reducing the amount of squalene synthase gene ERG9 transcript having translational activity. These strains comprise the polypeptide-coding region of squalene synthase ERG9, a transformant selection marker gene URA3, and a transcription promoter GAL1p located in the ERG9 locus.

EUG11 through EUG20 (YPH499; ERG9p::URA3-GAL1p) are YPH499-derived strains established in the present invention and are capable of reducing the amount of squalene synthase gene ERG9 transcript having translational activity. These strains comprise the polypeptide-coding region of ERG9, the URA3, and the GAL1p located in the ERG9 locus.

EUG21 through EUG30 (YPH500; ERG9p::URA3-GAL1p) are YPH500-derived strains established in the present invention and are capable of reducing the amount of squalene synthase gene ERG9 transcript having translational activity. These stains comprise the polypeptide-coding region of ERG9, the URA3, and the GAL1p located in the ERG9 locus.

EUG31 through EUG50 (W303-1A; ERG9p::URA3-GAL1p) are W303-1A-derived strains established in the present invention and are capable of reducing the amount of squalene synthase gene ERG9 transcript having translational activity. These strains comprise the polypeptide-coding region of ERG9, the URA3, and the GAL1p located in the ERG9 locus.

EUG51 through EUG70 (W303-1B; ERG9p::URA3-GAL1p) are W303-1B-derived strains established in the present invention and are capable of reducing the amount of squalene synthase gene ERG9 transcript having translational activity. These strains comprise the polypeptide-coding region of ERG9, the URA3, and the GAL1p located in the ERG9 locus.

In the present invention, various prenyl alcohols can be obtained by culturing the thus obtained EUG strains in a glucose-containing medium (i.e., transcription repression condition for GAL1p) to thereby reduce an amount of squalene synthase gene transcript having transcriptional activity (cultivation method will be described later). According to the present invention, prenyl alcohols can be obtained without the introduction of a substitution, insertion or deletion mutation(s) into the coding region of a squalene synthase gene as known in ATCC64031, and without the addition of special additives such as ergosterol and surfactants to the medium.

2. Preparation of Recombinant DNAs for Expression or DNA Fragments for Genomic Integration In the present invention, the above-described EUG strains as they may be cultured. Alternatively, these strains may be cultured after further transformation by introducing thereinto a recombinant DNA for expression or a DAN fragment for genomic integration each comprising an IPP biosynthetic pathway-related enzyme gene. The recombinant DNA for expression used in the further transformation of EUG strains can be obtained by ligating or inserting a transcription promoter DNA and a transcription terminator DNA into an EPP biosynthetic pathway-related enzyme gene. It is also possible to prepare in advance a gene expression cassette (transcription unit) comprising an EPP biosynthetic pathway-related enzyme gene to which a transcription promoter and a transcription terminator have been ligated, and to incorporate the cassette into a vector. The ligation or insertion of the promoter and terminator may be performed in any order. However, it is preferable to ligate a promoter upstream of an IPP biosynthetic pathway-related gene and to ligate a terminator downstream of the gene. Alternatively, in the present invention, an IPP biosynthetic pathway-related gene, a transcription promoter and a transcription terminator may be incorporated into an appropriate DNA, e.g. a vector, in this order. If the direction of transcription is properly considered, the incorporation may be performed in any order. An enhancer sequence to enhance the gene expression and various cis elements to control the gene expression may also be incorporated around the transcription unit.

Specific examples of IPP biosynthetic pathway-related genes include the following genes.

(a) farnesyl diphosphate synthase gene (FPP synthase gene)
(b) geranylgeranyl diphosphate synthase gene (GGPP synthase gene)
(c) hydroxymethylglutaryl-CoA reductase gene (HMG-CoA reductase gene)
(d) isopentenyl diphosphate Δ-isomerase gene (IPP Δ-isomerase gene)
(e) mevalonate kinase gene
(f) acetyl-CoA acetyltransferase gene
(g) hydroxymethylglutaryl-CoA synthase gene
(h) phosphomevalonate kinase gene
(i) diphosphomevalonate decarboxylase gene Specific examples of FPP synthase gene include *Saccharomyces cerevisiae*-derived ERG20 (SEQ ID NO: 1), *Escherichia coli*-derived ispA (SEQ ID NO: 3), *Bacillus stearothermophilus*-derived FPP synthase genes (Japanese Unexamined Patent Publication No. 5-219961; U.S. Pat. No. 5,786,192) and *Synechococcus elongatus*-derived FPP synthase gene (C. Ohto et al., (1999) *Plant Mol. Biol.,* 40, 307-321). Specific examples of GGPP synthase gene include *Saccharomyces cerevisiae*-derived BTS1 (SEQ ID NO: 5), *Sulfolobus acidocaldarius*-derived crtE (C. Ohto et al., (1998) *Biosci Biotechnol. Biochem.,* 62, 1243-1246; Japanese Unexamined Patent Publication No. 7-308913; U.S. Pat. No. 5,773,273), *Thermus thermophilus*-derived Tth GGPP synthase gene (C. Ohto et al., (1999) *Biosci. Biotechnol. Biochem.,* 63, 261-270; Japanese Unexamined Patent Publication No. 9-107974, U.S. Pat. No. 6,107,072), and *Synechococcus elongatus*-derived GGPP synthase gene (C. Ohto et al., (1999) *Plant Mol. Biol.,* 40, 307-321). Specific examples of HMG-CoA reductase gene include *Saccharomyces cerevisiae*-derived HMG1 (SEQ ID NO: 7) and HMG2, and *Streptmyces* sp. CL190-derived HMG-CoA reductase gene (S. Takahashi et al., (1999) *J. Bacteriol.,* 181, 1256-1263). Specific examples of IPP Δ-isomerase gene include *Escherichia coli*-derived idi (SEQ ID NO: 25). Further, IPP biosynthetic pathway-related genes having the following nucleotide sequences, respectively, may be enumerated.

Mevalonate kinase gene ERG12 (SEQ ID NO: 26)
Acetyl-CoA acetyltransferase gene ERG10 (SEQ ID NO: 27)
HMG-CoA synthase gene HMGS (ERG13) (SEQ ID NO: 28)
Phosphomevalonate kinase gene ERG8 (SEQ ID NO: 29)
Diphosphomevalonate decarboxylase gene ERG19 (SEQ ID NO: 7)

Depending on the host, its major IPP biosynthetic pathway is the non-mevalonate pathway. Therefore, non-mevalonate pathway-related enzyme genes such as DXP synthase gene, DXP reductoisomerase, MEP cytidyltransferase, CDP-ME kinase gene and MECDP synthase gene (K. Kaneda et al., (2001) *PNAS,* 98, 932-937; T. Kuzuyama et al., (2000) *J. Bacteriol.,* 182, 891-897; T. Kuzuyama et al., (2000) *J. Biol. Chem.,* 275, 19928-19932; S. Takahashi et al., (1998) *PNAS,* 95, 9879-9884) may be used for such a host as an IPP biosynthetic pathway-related gene.

One of ordinary skill in the art can obtain these genes easily by a known method of gene isolation or with a commercial kit for gene isolation.

In the present invention, mutants (sometimes referred to as "mutant type gene(s)") of the above-described IPP biosynthetic pathway-related genes may also be used.

Mutants of the above-described IPP biosynthetic pathway-related genes may be deletion mutants having a deletion of a specific region (e.g., an HMG-CoA reductase gene with a deletion of 2217 nucleotides at the maximum), or mutants having a deletion, addition, substitution or insertion of one or several to ten nucleotides in the nucleotide sequence of a wild type gene or the above-mentioned deletion mutant. Further, about 1000 nucleotides may be added, substituted or inserted. Accordingly, the amino acid sequence encoded by such a mutant may have a mutation(s). Specifically, the amino acid sequence of an IPP biosynthetic pathway-related enzyme (e.g., SEQ ID NO: 2 for FPP synthase; SEQ ID NO: 6 for GGPP synthase; or SEQ ID NO: 8 for wild type HMG-CoA reductase) may have a mutation(s) such as deletion, addition, substitution or insertion of one or several (e.g., one to ten, preferably, one to three) amino acids or more than 300 amino acids. The amino acid sequence of a wild type HMG-CoA reductase (SEQ ED NO: 8) may have a deletion of 739 amino acids at the maximum, and such a deletion mutant type enzyme may further have a mutation(s) such as deletion, addition, substitution or insertion of one or several (e.g., one to ten, preferably, one to three) amino acids. Specific examples of such mutant enzymes include a mutant enzyme FHDEL obtained by adding 4 amino acids to a wild type FPP synthase; mutant enzymes FGG and FGGHDEL obtained by adding more than 300 amino acids to the C-terminal of a wild type FPP synthase; a mutant enzyme GGF obtained by adding more than 300 amino acids to the N-terminal of a wild type FPP synthase; a mutant enzyme GGFHDEL obtained by adding more than 300 amino acids and 4 amino acids to the N-terminal and the C-terminal of a wild type FPP synthase, respectively; mutant enzymes GGF and GGFHDEL obtained by adding more than 300 amino acids to the C-terminal of a wild type GGPP synthase; a mutant enzyme FGG obtained by adding more than 300 amino acids to the N-terminal of a wild type GGPP synthase; and a mutant enzyme FGGHDEL obtained by adding more than 300 amino acids to the N-terminal of a wild type GGPP synthase and deleting 10 amino acids at the C-terminal of the synthase.

Specific examples of mutant genes useful in the invention include a mutant type ERG20 in pRS435FHDEL obtained by adding 12 nucleotides to the 3' end of ERG20; a mutant type ERG20 in pRS435FGG obtained by adding a nucleotide sequence of about 1000 nucleotides encoding BTS1 and Gly Ala to the 3' end of ERG20; a mutant type ERG20 in pRS435FGGHDEL obtained by deleting 30 nucleotides at the 3' end of the preceding mutant type ERG20; a mutant type ERG20 in pRS435GGF obtained by adding a nucleotide sequence of about 1000 nucleotides encoding BTS1 and Gly Ala to the 5' end of ERG20; a mutant type ERG20 in pRS435GGFHDEL obtained by adding a nucleotide sequence of about 1000 nucleotides encoding BTS1 and Gly Ala to the 5' end of ERG20 and adding 12 nucleotides to the 3' end of ERG20; a mutant type BTS1 in pRS435GGHDEL obtained by deleting 30 nucleotides at the 3' end of BTS1; a mutant type BTS1 in pRS435GGF obtained by adding a nucleotide sequence of about 1000 nucleotides encoding ERG20 and Gly Ala to the 3' end of BTS1; a mutant type BTS1 in pRS435GGFHDEL obtained by adding 12 nucleotides to the preceding mutant type BTS1; a mutant type BTS1 in pRS435FGG obtained by adding a nucleotide sequence of about 1000 nucleotides encoding ERG20 and Gly Ala to the 5' end of BTS1; and a mutant type BTS1 in pRS435FGGHDEL obtained by adding a nucleotide sequence of about 1000 nucleotides encoding ERG20 and Gly Ala to the 5' end of BTS1 and deleting 30 nucleotides at the 3' end of BTS1.

In the PCR (polymerase chain reaction) amplification of IPP biosynthetic pathway-related genes, substitution mutations of nucleotides that occur in DNA fragments obtained by amplifying wild-type DNA using a DNA polymerase of low fidelity (such as Taq DNA polymerase) are called "PCR errors". For example, an HMG-CoA reductase gene that has a nucleotide sequence having nucleotide substitutions (which may cause substitution mutations in the encoded polypeptide) attributable to PCR errors when a wild-type HMG-CoA reductase gene (SEQ ID NO: 7) was used as a template may also be used in the present invention. This HMG-CoA reductase gene is designated "HMG1'". An embodiment of nucleotide substitutions resulting from PCR errors when the wild-type HMG-CoA reductase gene (SEQ ID NO: 7) was used as a template is shown in FIG. 4A. HMG1' has the nucleotide sequence as shown in SEQ ID NO: 11, and the amino acid sequence encoded thereby is shown in SEQ ID NO: 12. In FIG. 4A, mutations of nucleotides are expressed in the following order: the relevant nucleotide before substitution (in one letter abbreviation), the position of this nucleotide when the first nucleotide in the initiation codon of the HMG-CoA reductase gene is taken as 1, and the nucleotide after substitution (in one letter abbreviation). The mutations of amino acids contained in the amino acid sequence of the PCR error-type HMG-CoA reductase are expressed in the following order: the relevant amino acid before substitution (in one letter abbreviation), the position of this amino acid in the HMG-CoA reductase, and the amino acid after substitution (in one letter abbreviation). Further, the PCR error-type nucleotide sequence described above may be modified partially by techniques such as site-directed mutagenesis. Such a modified HMG-CoA reductase gene (SEQ ID NO: 14) encoding a modified HMG-CoA reductase (SEQ ID NO: 13) may also be used in the present invention.

As examples of HMG-CoA reductase genes (including PCR error-type) encoding deletion mutants in which predicted transmembrane domains of HMG-CoA reductase gene are deleted, HMG1Δ genes are shown in FIG. 4B that are deletion mutants of the PCR error-type HMG-CoA reductase gene HMG1'. The upper most row represents HMG1' gene without deletion. The portion indicated with thin solid line (-) is the deleted region. Table 1 below shows which region of HMG1' gene (SEQ ID NO: 11) has been deleted for each of the deletion mutants. Deletion mutants of HMG1' are expressed as "HMG1Δxxy" according to the deletion pattern, in which "xx" represents the deletion pattern and "y" represents a working number (any figure). In FIG. 4B, "Δ026" is shown as one example of HMG1Δ02y. (Likewise, examples of other deletion patterns are also shown.) Deletion of 1317 nucleotides is the maximum deletion.

TABLE 1

Embodiment of Deletions

| Designation of Deletion Mutant | Primer 1 | Primer 2 | Plasmid | Deletion of Predicted Transmembrane | Deleted Region | Sequence after Deletion |
|---|---|---|---|---|---|---|
| HMG1 Δ 02y | HMG1 (558-532) | HMG1 (799-825) | pYHMG02X | #2-#3 | 559~798 | SEQ ID NO:15 |
| HMG1 Δ 04y | HMG1 (1191-1165) | HMG1 (1267-1293) | pYHMG04X | #6 | 1192~1266 | SEQ ID NO:16 |
| HMG1 Δ 05y | HMG1 (1380-1354) | HMG1 (1573-1599) | pYHMG05X | #7 | 1381~1572 | SEQ ID NO:17 |
| HMG1 Δ 06y | HMG1 (558-532) | HMG1 (1267-1293) | pYHMG06X | #2-#6 | 559~1266 | SEQ ID NO:18 |
| HMG1 Δ 07y | HMG1 (558-532) | HMG1 (1573-1599) | pYHMG07X | #2-#7 | 559~1572 | SEQ ID NO:19 |
| HMG1 Δ 08y | HMG1 (27-1) | HMG1 (1573-1599) | pYHMG08X | #1-#7 | 27~1572 | SEQ ID NO:20 |
| HMG1 Δ 10y | HMG1 (27-1) | HMG1 (1816-1842) | pYHMG10X | #1-#7 (-605 aa) | 27~1815 | SEQ ID NO:21 |
| HMG1 Δ 11y | HMG1 (27-1) | HMG1 (1891-1917) | pYHMG11X | #1-#7 (-631 aa) | 27~1890 | SEQ ID NO:22 |
| HMG1 Δ 12y | HMG1 (27-1) | HMG1 (1990-2016) | pYHMG12X | #1-#7 (-663 aa) | 27~1989 | SEQ ID NO:23 |
| HMG1 Δ 13y | HMG1 (27-1) | HMG1 (2218-2244) | pYHMG13X | #1-#7 (-739 aa) | 27~2217 | SEQ ID NO:24 |

| Primer Sequence | | |
|---|---|---|
| HMG1 (27-1) | 5' TTT CAG TCC CTT GAA TAG CGG CGG CAT | SEQ ID NO:61 |
| HMG1 (558-532) | 5' GTC TGC TTG GGT TAC ATT TTC TGA AAA | SEQ ID NO:56 |
| HMG1 (799-825) | 5' CAC AAA ATC AAG ATT GCC CAG TAT GCC | SEQ ID NO:62 |

TABLE 1-continued

Embodiment of Deletions

| | | |
|---|---|---|
| HMG1 (1191-1165) | 5' AGA AGA TAC GGA TTT CTT TTC TGC TTT | SEQ ID NO:63 |
| HMG1 (1267-1293) | 5' AAC TTT GGT GCA AAT TGG GTC AAT GAT | SEQ ID NO:64 |
| HMG1 (1380-1354) | 5' TTG CTC TTT AAA GTT TTC AGA GGC ATT | SEQ ID NO:65 |
| HMG1 (1573-1599) | 5' CAT ACC AGT TAT ACT GCA GAC CAA TTG | SEQ ID NO:57 |
| HMG1 (1816-1842) | 5' GCA TTA TTA AGT AGT GGA AAT ACA AAA | SEQ ID NO:66 |
| HMG1 (1891-1917) | 5' CCT TTG TAC GCT TTG GAG AAA AAA TTA | SEQ ID NO:67 |
| HMG1 (1990-2016) | 5' TCT GAT CGT TTA CCA TAT AAA AAT TAT | SEQ ID NO:68 |
| HMG1 (2218-2244) | 5' AAG GAT GGT ATG ACA AGA GGC CCA GTA | SEQ ID NO:69 |

In the present invention, an IPP biosynthetic pathway-related gene or a mutant thereof may be ligated to other gene or a mutant thereof so that a fusion protein is produced. In the present invention, such a gene constructed from two or more genes so that a fusion protein is produced as an expression product is called a "fusion gene". A fusion gene may be regarded as a mutant gene in which about 1000 nucleotides are added to the nucleotide sequence of one of the genes composing the fusion gene. Accordingly, the polypeptide encoded by the fusion gene may also be regarded as a mutant polypeptide in which more than 300 amino acids are added. In order to create a fusion gene, a method may be employed in which one DNA is digested with an appropriate restriction enzyme, followed by ligation to the other DNA predigested with the same restriction enzyme in such a manner that no shift occurs in the reading frames of the amino acid sequences encoded by the DNAs. An artificial nucleotide sequence may be inserted freely into the junction site between the genes composing a fusion gene so that individual translation products of the genes can take conformations that allow them to function appropriately. For example, 5' GGGTCC 3' encoding Gly Ser ("GS" in FIG. 29) may be used for this purpose.

Further, in the present invention, a gene may be prepared and used that encodes a polypeptide modified so that the protein produced by the expression of an IPP biosynthetic pathway-related enzyme gene, a mutant thereof or the above-described fusion gene is directed to the endoplasmic reticulum. As endoplasmic reticulum transition polypeptides, His Asp Glu Leu (SEQ ID NO: 30) or Asp Asp Glu Leu (SEQ ID NO: 31) is known in Saccharomyces cerevisiae as a C-terminal ER retention signal; and Lys Asp Glu Leu (SEQ ID NO: 32) is known as a C-terminal signal in eukaryotes in general; it is known that they work as an ER retention signal completely equivalent to them in function (B. Lewin, Genes V, (1994), Oxford University Press, New York, U.S.A., pp. 279-318; B. Alberts et al., Molecular Biology of The Cell, third edition (1994), Garland Publishing Inc., New York, U.S.A., §12-§13). In addition to these ER retention signals consisting of the 4 amino acid residues at the C-terminal, other signal peptides from a part of the domains of ER transition proteins, e.g., the signal peptide $^+H_3N$ Met Met Ser Phe Val Ser Leu Leu Leu Val Gly Ile Leu Phe Trp Ala Thr Glu Ala Glu Gln Leu Thr Lys Cys Glu Val Phe Gln (SEQ ID NO: 33) located at the N-terminal that functions as a transport signal to ER, may also be used (B. Lewin, Genes V (1994), Oxford University Press, New York, U.S.A., pp. 279-318; B. Alberts et al., Molecular Biology of The Cell, third edition (1994), Garland Publishing Inc., New York, U.S.A., §12-§13). A polypeptide in which an ER signal has been added, substituted or inserted may also be regarded as a mutant polypeptide in which 4 amino acid residues are added, substituted or inserted in the corresponding wild type polypeptide. A gene encoding the mutant polypeptide may also be regarded as a mutant gene in which a nucleotide sequence of about 12 nucleotides is added, substituted or inserted in the corresponding wild type gene.

The DNA used for gene recombination is not particularly limited as long as it may be retained hereditarily in host cells. For example, plasmid DNA, bacteriophage DNA, retrotransposon DNA and artificial chromosomal DNA (YAC: yeast artificial chromosome) may be used for this purpose. With respect to recombinant DNA fragments for genomic integration, replication ability is not necessary; DNA fragments prepared by PCR or chemical synthesis may also be used for this purpose.

Specific examples of useful plasmid DNA include YCp-type E. coli-yeast shuttle vectors such as pRS413, pRS414, pRS415, pRS416, YCp50, pAUR112 or pAUR123; YEp-type E. coli-yeast shuttle vectors such as pYES2 or YEp13; YIp-type E. coli-yeast shuttle vectors such as pRS403, pRS404, pRS405, pRS406, pAUR101 or pAUR135; E. coli-derived plasmids such as ColE plasmids (e.g., pBR322, pBR325, pUC18, pUC19, pUC118, pUC119, pTV118N, pTV119N, pBluescript, pHSG298, pHSG396 or pTrc99A), p15A plasmids (e.g., pACYC177 or pACYC184) and pSC101 plasmids (e.g., pMW118, pMW119, pMW218 or pMW219); and Bacillus subtilis-derived plasmids (e.g., pUB110, pTP5). Specific examples of useful phage DNA include λ phage (Charon4A, Charon21A, EMBL3, EMBL4, λgt10, λgt11, λZAP), φX174, M13mp18 and M13mp19. Specific examples of useful retrotransposon DNA include Ty factor. Specific examples of useful YAC vectors include pYACC2.

When recombinant DNAs are introduced into hosts, selection marker genes are used in many cases. However, marker genes are not necessary if there is an appropriate assay to select recombinants without using such genes.

As the transcription promoter to direct the transcription and expression of an IPP biosynthetic pathway-related enzyme gene, a mutant thereof, a fusion gene thereof, or a gene encoding a polypeptide in which an endoplasmic reticulum signal is added, substituted or inserted in the polypeptide encoded by any one of these genes, a constitutive or inducible promoter may be used. The "constitutive promoter" means a transcription promoter of a gene involved in a major metabolic pathway. Such a promoter has transcriptional activity under any growth conditions. The "inducible promoter" means a promoter whose transcriptional activity is induced only under specific growth conditions.

Any transcription promoter may be used as long as it has activity in hosts such as yeast. For example, GAL1 promoter, GAL10 promoter, TDH3 (GAP) promoter, ADH1 promoter or TEF2 promoter may be used for expression in yeast. For expression in *E. coli*, trp promoter, lac promoter, trc promoter or tac promoter may be used, for example.

Further, cis-elements such as an enhancer, a splicing signal, a poly A addition signal, selectable markers, etc. may be ligated to the recombinant DNA fragment, if desired. Specific examples of useful selectable markers include marker genes such as URA3, LEU2, TRP1, HIS3, ADE2 and LYS2 with non-auxotrophic phenotypes as indicators, and drug resistance genes such as $Amp^r$, $Ter^r$, $Cm^r$, $Km^r$, AUR1-C and can1.

A transcription terminator derived from any gene may be used as long as it has activity in hosts such as yeast. For expression in yeast, ADH1 terminator or CYC1 terminator may be used, for example.

Expression vectors prepared in the present invention as recombinant DNAs for gene transfer may be designated and identified by indicating the name of the relevant gene after the name of the plasmid used. For example, the relation between the designations of expression vectors and their constitution when plasmid pRS434GAP or pRS434GAP is used is shown in Table 2 below. When HMG1 gene is ligated to plasmid pRS434GAP, for example, the resultant expression vector is expressed as "pRS434GAP-HMG1". This method of expression also applies to cases where plasmid pRS434, pRS444, pRS435GAP or pRS445 is used in combination with the above-mentioned promoters.

TABLE 2

| Designation of Expression Vector | Constitution |
| --- | --- |
| pRS435GG or pRS435GAP-BTS1 | Plasmid pRS435GAP to which GGPP synthase gene BTS1 is ligated |
| pRS435F or pRS435GAP-ERG20 | Plasmid pRS435GAP to which FPP synthase gene ERG20 is ligated |
| pRS435GAP-ERG19 | Plasmid pRS435GAP to which diphospho-mevalonate decarboxylase gene ERG19 is ligated |
| pRS434GAP-HMG1 | Plasmid pRS434GAP to which HMG-CoA reductase gene HMG1 is ligated |
| pRS434GAP-HMG1Δ | Plasmid pRS434GAP to which deletion mutant gene HMG1Δ of HMG-CoA reductase gene HMG1 is ligated |
| pRS435GGF | Plasmid pRS435GAP to which a fusion gene where GGPP synthase gene BTS1 and FPP synthase gene ERG20 are ligated in this order is ligated |
| pRS435FGG | Plasmid pRS435GAP to which a fusion gene where FPP synthase gene ERG20 and GGPP synthase gene BTS1 are ligated in this order is ligated |
| pRS435GGHDEL | Plasmid pRS435GG to which a nucleotide sequence encoding HDEL sequence is ligated |
| pRS435FHDEL | Plasmid pRS435F to which a nucleotide sequence encoding HDEL sequence is ligated |
| pRS435FGGHDEL | Plasmid pRS435FGG to which a nucleotide sequence encoding HDEL sequence is ligated |
| pRS435GGFHDEL | Plasmid pRS435GGF to which a nucleotide sequence encoding HDEL sequence is ligated |

3. Preparation of Recombinants

The recombinant of the present invention can be obtained by introducing the recombinant DNA of the present invention into the above-described mutant strain (e.g., EUG strains) in such a manner that various IPP biosynthetic pathway-related genes (including mutants, fusion genes, and genes encoding polypeptides where an ER signal is added, substituted or inserted) can be expressed.

Whether the gene of interest has been transferred into the host cell or not can be confirmed by such methods as PCR (polymerase chain reaction) or Southern blot hybridization. For example, DNA is prepared from the resultant recombinant and subjected to PCR using a pair of primers specific to the transferred DNA. Subsequently, the amplified product is subjected to agarose gel electrophoresis, polyacrylamide gel electrophoresis or capillary electrophoresis, followed by staining with ethidium bromide, SYBR Green solution or the like, or detection of DNA with a UV detector. Thus, by detecting the amplified product as a single band or peak, the transferred DNA can be confirmed. Alternatively, PCR may be performed using primers labeled with a fluorescent dye or the like to detect the amplified product.

4. Production of Prenyl Alcohols

In the present invention, a prenyl alcohol(s) can be obtained by culturing the above-described mutant strain (e.g., EUG strains) and recovering the prenyl alcohol(s) from the resultant culture. Alternatively, a prenyl alcohol(s) can be obtained by preparing a recombinant by transferring into the mutant strain (e.g., EUG strains) an IPP biosynthetic pathway-related gene (including a mutant or fusion gene thereof), culturing the resultant recombinant under transcription repression conditions and recovering the prenyl alcohol(s) from the resultant culture. The term "culture" used herein means any of the following materials: culture supernatant, cultured cells or microorganisms per se, or disrupted products from cultured cells or microorganisms. The mutant strain of the invention (e.g., EUG strains) or the recombinant thereof is cultured by conventional methods used in culturing the host. As the prenyl alcohol, FOH, NOH or GGOH may be enumerated. These prenyl alcohols are accumulated in the culture independently or as a mixture.

As a medium to culture the recombinant obtained from a microorganism as s host, either a complex natural medium or a synthetic medium may be used as long as it contains carbon sources, nitrogen sources and inorganic salts assimilable by the microorganism and is capable of effective cultivation of the recombinant. As carbon sources, sugar sources may be used, for example, and they usually include glucose. These sugar sources are used at 0.1-20% (w/v) in the total, preferably at 1-7% (w/v). The glucose content of the sugar source(s) used is 10-100% (w/w), preferably 50-100% (w/w), and may be selected appropriately depending on the culture conditions (e.g., the type of the host, the type of the recombinant vector introduced, the cultivation period, etc.). Hydrocarbons such as galactose, fructose, sucrose, raffinose, lactose, starch; organic acids such as acetic acid, propionic acid; and alcohols such as ethanol, propanol may also be used together with galactose as carbon sources. In such a case, the mutant strain or recombinant of the invention may be precultured in a galactose-containing medium prior to cultivation in a glucose-containing medium. The galactose content at the time of precultivation may vary depending of various carbon sources contained in the medium. Usually, the galactose content of the sugar source is 50-100% (w/w), preferably 100% (w/w). When EUG strains are used, cultivation in a galactose-containing and non-glucose-containing medium is a non-transcription repression condition for squalene synthase gene ERG9, and cultivation in a glucose-containing medium is a transcription repression condition for squalene synthase gene ERG9. Cultivation of EUG strains in a glucose-containing medium causes a reduction in the amount of squalene synthase gene transcript having translational activity.

As a nitrogen source, ammonia; ammonium salts of inorganic or organic acids such as ammonium chloride, ammonium sulfate, ammonium acetate, ammonium phosphate;

other nitrogen-containing compounds; peptone; meat extract; corn steep liquor, various amino acids, etc. may be used. As an inorganic substance, potassium dihydrogen phosphate, dipotassium hydrogen phosphate, magnesium phosphate, magnesium sulfate, sodium chloride, iron(II) sulfate, manganese sulfate, copper sulfate, calcium carbonate or the like may be used. Usually, the recombinant is cultured under aerobic conditions (e.g., shaking culture or aeration agitation culture) at 26-42° C., preferably at 30° C., for 2-7 days. The adjustment of pH is carried out using an inorganic or organic acid, an alkali solution or the like.

When a recombinant incorporating an expression vector comprising an inducible transcription promoter is cultured, a transcription inducer may be added to the medium if necessary. For example, when GAL1 promoter was used in the vector, galactose may be used as an inducer.

When cultured under the above-described conditions, the mutant stain or recombinant of the invention can produce prenyl alcohols at high yields. For the mass production of prenyl alcohols, a jar fermenter cultivation apparatus or the like may be used.

The prenyl alcohol-producing mutant cells created in the present invention are capable of growing and producing prenyl alcohols at high yields by adjusting the amount of their squalene synthase gene transcript having translational activity without addition of special, essential medium components such as ergosterol required for a squalene synthase gene-deficient strain (erg9 strain; ATCC64031). The production efficiency of prenyl alcohols can be increased further by adding to a conventional medium such substance as terpenoids, oils or surfactants, or by increasing the concentrations of nitrogen sources or carbon sources. Specific examples of these additives include the following substances.

Terpenoids: squalene, tocopherol, IPP, DMAPP
Oils: soybean oil, fish oil, almond oil, olive oil
Surfactants: Tergitol, Triton X-305, Span 85, Adekanol LG109 (Asahi Denka), Adekanol LG294 (Asahi Denka), Adekanol LG295S (Asahi Denka), Adekanol LG297 (Asahi Denka), Adekanol B-3009A (Asahi Denka), Adekapronic L-61 (Asahi Denka)

The concentrations of oils are 0.01% (w/v) or more, preferably 1-3% (w/v). The concentrations of surfactants are 0.005-1% (w/v), preferably 0.05-0.5% (w/v). The concentrations of terpenoids are 0.01% (w/v) or more, preferably 1-3% (w/v).

After the cultivation, the prenyl alcohol of interest is recovered by disrupting microorganisms or cells by, e.g., homogenizer treatment, if the alcohol is produced within the microorganisms or cells. Alternatively, the alcohol may be extracted directly using organic solvents without disrupting the cells. If the prenyl alcohol of the invention is produced outside the microorganisms or cells, the culture broth is used as it is or subjected to centrifugation or the like to remove the microorganisms or cells. Thereafter, the prenyl alcohol of interest is extracted from the culture by, e.g., extraction with an organic solvent. If necessary, the alcohol may be further isolated and purified by various types of chromatography, etc.

In the present invention, yields of prenyl alcohols of individual EUG strains and preferable combinations of EUG strains and vectors with respect to prenyl alcohol production are as illustrated in Table 3 below.

TABLE 3

|  | Mevalonate pathway-related enzyme gene transferred (incl. mutant gene and fusion gene) | Host | FOH Yield (mg/l) 1 | FOH Yield (mg/l) 2 | FOH Yield (mg/l) 3 | NOH Yield (mg/l) 1 | NOH Yield (mg/l) 2 | NOH Yield (mg/l) 3 | GGOH Yield (mg/l) 1 | GGOH Yield (mg/l) 2 | GGOH Yield (mg/l) 3 |
|---|---|---|---|---|---|---|---|---|---|---|---|
| hosts |  | A451 | (0.00) |  |  | (0.00) |  |  | (0.00-0.02) |  |  |
|  |  | YPH499 | (0.00) |  |  | (0.00) |  |  | (0.00) |  |  |
|  |  | YPH500 | (0.00) |  |  | (0.00) |  |  | (0.00) |  |  |
|  |  | W303-1A | (0.00) |  |  | (0.00) |  |  | (0.00) |  |  |
|  |  | W303-1B | (0.00) |  |  | (0.00) |  |  | (0.00) |  |  |
| EUG s |  | EUG5 | 0.05 | 0.05-8.5 | 8.5-57.5 | 0.05 | 0.05-0.43 |  | 0.05 | 0.05-1.65 |  |
|  |  | EUG8 | 0.05 | 0.05-9.1 |  | 0.05 | 0.05-0.06 |  | 0.05 | 0.05-0.17 |  |
|  |  | EUG12 | 0.05 | 0.05-40.6 |  | 0.05 | 0.05-0.36 |  | 0.05 | 0.05-0.10 |  |
|  |  | EUG24 | 0.05 | 0.05-17.9 | 17.9-42.2 | 0.05 | 0.05-1.75 |  | 0.05 | 0.05-1.26 |  |
|  |  | EUG27 | 0.05 | 0.05-18.0 |  | 0.05 |  |  | 0.05 |  |  |
|  |  | EUG36 | 0.05 | 0.05-43 | 43 | 0.05 | 0.05-0.31 |  | 0.05 | 0.05-0.98 |  |
|  |  | EUG64 | 0.05 | 0.05-38 | 38-101.7 | 0.05 | 0.05-0.66 |  | 0.05 | 0.05-2.92 |  |
| HMG1 | HMG1 | EUG5 | 0.05 | 0.05-14.4 | 14.4-67.9 | 0.05 | 0.05-0.48 | 0.48-0.88 | 0.05 | 0.05-2.68 |  |
|  | HMG1 | EUG8 | 0.05 | 0.05-8.1 |  | 0.05 | 0.05-0.07 |  | 0.05 | 0.05-0.16 |  |
|  | HMG1 | EUG12 | 0.05 | 0.05-18.3 | 18.3-21.9 | 0.05 | 0.05-0.62 | 0.62-1.67 | 0.05 | 0.05-2.05 |  |
|  | HMG1 | EUG24 | 0.05 | 0.05-8.1 | 8.1-23.7 | 0.05 | 0.05-0.46 |  | 0.05 | 0.05-0.94 |  |
|  | HMG1 | EUG27 | 0.05 | 0.05-13.6 |  | 0.05 | 0.05-0.42 |  | 0.05 | 0.05-2.05 |  |
|  | HMG1 | EUG36 | 0.05 | 0.05-2.9 | 2.9-17.8 | 0.05 | 0.05-0.31 |  | 0.05 | 0.05-0.97 |  |
|  | HMG1 | EUG64 | 0.05 | 0.05-12.3 | 12.3-42.8 | 0.05 | 0.05-0.38 |  | 0.05 | 0.05-1.58 |  |
| HMG1 Δ | HMG Δ026 | EUG5 | 0.05 | 0.05-3.2 |  | 0.05 | 0.05-0.07 |  | 0.05 | 0.05-0.09 |  |
|  | HMG Δ044 | EUG5 | 0.05 | 0.05-8.7 |  | 0.05 | 0.05-0.07 |  | 0.05 | 0.05-0.09 |  |
|  | HMG Δ056 | EUG5 | 0.05 | 0.05-8.7 |  | 0.05 | 0.05-0.07 |  | 0.05 | 0.05-0.11 |  |
|  | HMG Δ062 | EUG5 | 0.05 | 0.05-5.6 |  | 0.05 | 0.05-0.06 |  | 0.05 | 0.05-0.13 |  |
|  | HMG Δ076 | EUG5 | 0.05 | 0.05-8.1 |  | 0.05 | 0.05-0.07 |  | 0.05 | 0.05-0.15 |  |
|  | HMG Δ081 | EUG5 | 0.05 | 0.05-9.8 |  | 0.05 | 0.05-0.10 |  | 0.05 | 0.05-0.14 |  |
|  | HMG Δ100 | EUG5 | 0.05 | 0.05-6.6 |  | 0.05 | 0.05-0.11 |  | 0.05 | 0.05-0.18 |  |
|  | HMG Δ112 | EUG5 | 0.05 | 0.05-12.1 |  | 0.05 | 0.05-0.10 |  | 0.05 | 0.05-0.34 |  |
|  | HMG Δ122 | EUG5 | 0.05 | 0.05-8.2 |  | 0.05 | 0.05-0.08 |  | 0.05 | 0.05-0.13 |  |
|  | HMG Δ133 | EUG5 | 0.05 | 0.05-6.3 |  | 0.05 | 0.05-0.08 |  | 0.05 | 0.05-0.71 |  |
|  | HMG Δ026 | EUG12 | 0.05 | 0.05-13.8 |  | 0.05 | 0.05-0.38 |  | 0.05 | 0.05-0.63 |  |
|  | HMG Δ044 | EUG12 | 0.05 | 0.05-10.7 |  | 0.05 | 0.05-0.28 |  | 0.05 | 0.05-0.44 |  |
|  | HMG Δ056 | EUG12 | 0.05 | 0.05-9.7 |  | 0.05 | 0.05-0.22 |  | 0.05 | 0.05-0.40 |  |
|  | HMG Δ062 | EUG12 | 0.05 | 0.05-10.7 |  | 0.05 | 0.05-0.25 |  | 0.05 | 0.05-0.45 |  |
|  | HMG Δ076 | EUG12 | 0.05 | 0.05-14.4 |  | 0.05 | 0.05-0.34 |  | 0.05 | 0.05-0.55 |  |

TABLE 3-continued

| | Mevalonate pathway-related enzyme gene transferred (incl. mutant gene and fusion gene) | Host | FOH Yield (mg/l) 1 | FOH Yield (mg/l) 2 | FOH Yield (mg/l) 3 | NOH Yield (mg/l) 1 | NOH Yield (mg/l) 2 | NOH Yield (mg/l) 3 | GGOH Yield (mg/l) 1 | GGOH Yield (mg/l) 2 | GGOH Yield (mg/l) 3 |
|---|---|---|---|---|---|---|---|---|---|---|---|
| | HMG Δ081 | EUG12 | 0.05 | 0.05-13.5 | | 0.05 | 0.05-0.33 | | 0.05 | 0.05-0.49 | |
| | HMG Δ100 | EUG12 | 0.05 | 0.05-12.4 | | 0.05 | 0.05-0.33 | | 0.05 | 0.05-0.44 | |
| | HMG Δ112 | EUG12 | 0.05 | 0.05-13.1 | | 0.05 | 0.05-0.33 | | 0.05 | 0.05-0.53 | |
| | HMG Δ122 | EUG12 | 0.05 | 0.05-13.6 | | 0.05 | 0.05-0.37 | | 0.05 | 0.05-0.50 | |
| | HMG Δ133 | EUG12 | 0.05 | 0.05-12.0 | | 0.05 | 0.05-0.27 | | 0.05 | 0.05-0.44 | |
| BTS1 | BTS1 | EUG8 | 0.05 | 0.05-3.9 | | | | | 0.05 | 0.05-1.42 | |
| | BTS1 | EUG12 | 0.05 | 0.05-10.6 | | 0.05 | 0.05-0.65 | | 0.05 | 0.05-6.4 | |
| | BTS1 | EUG27 | 0.05 | 0.05-7.0 | | 0.05 | 0.05-0.67 | | 0.05 | 0.05-4.4 | |
| | BTS1-HDEL | EUG5 | 0.05 | 0.05-5.2 | | 0.05 | 0.05-0.10 | | 0.05 | 0.05-0.40 | |
| | BTS1-HDEL | EUG12 | 0.05 | 0.05-9.7 | | 0.05 | 0.05-0.44 | | 0.05 | 0.05-0.73 | |
| ERG20 | ERG20 | EUG8 | 0.05 | 0.05-1.5 | | — | | | — | | |
| | ERG20 | EUG12 | 0.05 | 0.05-10.6 | | 0.05 | 0.05-0.90 | | 0.05 | 0.05-6.6 | |
| | ERG20 | EUG27 | 0.05 | 0.05-3.47 | | 0.05 | 0.05-0.38 | | 0.05 | 0.05-1.37 | |
| | ERG20-HDEL | EUG5 | 0.05 | 0.05-6.8 | | 0.05 | 0.05-0.10 | | 0.05 | 0.05-0.17 | |
| | ERG20-HDEL | EUG12 | 0.05 | 0.05-11.0 | | 0.05 | 0.05-0.62 | | 0.05 | 0.05-0.09 | |
| GGF fusion | BTS1-ERG20 | EUG5 | 0.05 | 0.05-22.6 | 22.6-28.9 | 0.05 | 0.05-0.68 | 0.68-0.75 | 0.05 | 0.05-7.3 | 7.3-10.1 |
| | BTS1-ERG20 | EUG12 | 0.05 | 0.05-7.8 | 4.0-10.5 | 0.05 | 0.05-0.60 | 0.60-0.77 | 0.05 | 0.05-5.4 | 1.6-7.0 |
| | BTS1-ERG20-HDEL | EUG5 | 0.05 | 0.05-25.3 | 7.4-25.3 | 0.05 | 0.05-0.64 | 0.43-0.64 | 0.05 | 0.05-7.0 | 7.0-17.6 |
| | BTS1-ERG20-HDEL | EUG12 | 0.05 | 0.05-5.0 | 5.0-12.6 | 0.05 | 0.05-0.42 | 0.42-0.92 | 0.05 | 0.05-5.6 | 5.6-8.0 |
| FGG fusion | ERG20-BTS1 | EUG5 | 0.05 | 0.05-2.6 | | 0.05 | 0.05-0.09 | | 0.05 | 0.05-2.43 | |
| | ERG20-BTS1 | EUG12 | 0.05 | 0.05-8.3 | | 0.05 | 0.05-0.49 | | 0.05 | 0.05-4.8 | |
| | ERG20-BTS1-HDEL | EUG5 | 0.05 | 0.05-4.2 | | 0.05 | 0.05-0.16 | | 0.05 | 0.05-0.79 | |
| | ERG20-BTS1-HDEL | EUG12 | 0.05 | 0.05-8.5 | | 0.05 | 0.05-0.41 | | 0.05 | 0.05-2.4 | |
| HMG1&BTS1 | HMG1&BTS1 | EUG5 | 0.05 | 0.05-11.0 | 11.0-55.7 | 0.05 | 0.05-0.43 | | 0.05 | 0.05-2.8 | 2.8-19.8 |
| | HMG1&BTS1 | EUG24 | 0.05 | 0.05-2.4 | 2.4-13.1 | 0.05 | 0.05-0.19 | | 0.05 | 0.05-1.1 | 1.1-4.8 |
| | HMG1&BTS1 | EUG36 | 0.05 | 0.05-4.2 | 4.2-16.9 | 0.05 | 0.05-0.31 | | 0.05 | 0.05-2.2 | 2.2-26.9 |
| | HMG1&BTS1 | EUG64 | 0.05 | 0.05-3.5 | 3.5-17.4 | 0.05 | 0.05-0.38 | | 0.05 | 0.05-1.1 | 1.1-62.7 |
| ERG19 | ERG19 | EUG5 | 0.05 | 0.05-8.9 | | 0.05 | 0.05-0.08 | | 0.05 | 0.10 | |
| | ERG19 | EUG12 | 0.05 | 0.05-9.6 | | 0.05 | 0.05-0.29 | | 0.05 | 0.05-0.13 | |
| | ERG19 | EUG24 | 0.05 | 0.05-11.4 | | 0.05 | 0.05-0.34 | | 0.05 | 0.05-0.13 | |

In the columns of FOH, NOH and GGOH yields, columns marked with "1" show the lower limit; columns marked with "2" show preferable range, and columns marked with "3" show more preferable range.
Mark "—" means no data.

(i) A451-derived EUG5 or EUG8 produced 8.5-9.1 mg/L of FOH when cultured in YM7 medium (a glucose-containing medium), and produced 57.5 mg/L of FOH, 0.43 mg/L of NOH and 1.65 mg/L of GGOH when cultured in YPD07rich medium containing sugar sources and nitrogen sources at high concentrations and oils added thereto. YPH499-derived EUG12 produced 7.4-40.6 mg/L of FOH when cultured in YM7 medium. YPH500-derived EUG24 or EUG27 produced 4.9-18.0 mg/L of FOH when cultured in YM7 medium, and produced 42.2 mg/L of FOH, 1.75 mg/L of NOH and 1.26 mg/L of GGOH when cultured in YPD07rich medium. When W303-1A-derived EUG36 and W303-1B-derived EUG64 were cultured in the same manner in YPD07rich medium, they produced 43 mg/L and 101.7 mg/L of FOH, respectively. Each of EUG strains was precultured in a galactose-containing medium, and then cultured in a glucose-containing medium, i.e., under transcription repression conditions.

(ii) When a plasmid comprising HMG-CoA reductase gene HMG1 downstream of TDH3 (GAP) promoter was prepared and introduced into EUG strains, FOH accumulation increased further in the resultant recombinant strains. In some strains, GGOH accumulation was also increased. The recombinant from EUG5 produced 67.9 mg/L of FOH and 2.68 mg/L of GGOH. Increase in GGOH accumulation was also observed in recombinants from EUG12 and EUG27; both recombinants produced 2.05 mg/L of GGOH at the maximum.

(iii) When HMGΔxyy genes, which are deletion mutants of HMG1' that is a substitution mutation-type mutant of HMG1, were transferred into EUG5, the resultant recombinants cultured in YM7 medium exhibited FOH yields higher than 8.5 mg/L achieved before the HMGΔxyy transfer. The maximum yield was 12.1 mg/L of FOH when HMGΔ122 was transferred.

(iv) When a plasmid comprising GGPP synthase gene BTS1 downstream of TDH3 (GAP) promoter was prepared and introduced into EUG stains, FOH and GGOH were produced. The recombinant from EUG5 exhibited an FOH yield of 11.0 mg/L, which was higher than 8.5 mg/L achieved before the BTS1 transfer in YM7 medium. The recombinant from EUG12 produced 1.6 mg/L of GGOH in YM7 medium; and the recombinant from EUG27 produced 1.5 mg/L of GGOH in YM7 medium. When cultured in YPD07rich medium, the recombinant from EUG5 produced 19.8 mg/L of GGOH; the recombinant from EUG36 produced 26.9 mg/L of GGOH; and the recombinant from EUG64 produced 62.7 mg/L of GGOH. When a mutant type BTS1 gene encoding a mutant type GGPP synthase having an ER signal HDEL at the C-terminal was transferred, FOH productivity increased from 2.6 mg/L (the yield when wild type BTS1 was transferred) to 9.7 mg/L in the recombinant from EUG12.

(v) While ERG20-transferred YPH499 strain produced little prenyl alcohol (0.05 mg/L or less), ERG20-transferred EUG12 produced 4.5 mg/L of FOH and also exhibited a good result in GGOH production (6.6 mg/L). The transfer of a mutant type ERG20 encoding a mutant polypeptide to which HDEL is added was sometimes effective in NOH production; the recombinant from EUG12 produced 0.62 mg/L of NOH.

(vi) While the transfer of BTS1-ERG20 fusion gene or this fusion gene engineered so that one of its ends encodes HDEL sequence into A451 resulted in GGOH production of only about 0.26 mg/L, the same gene-transferred EUG5 produced 6.5-6.6 mg/L of GGOH in YM7 medium.

(vii) When ERG20-BTS1 fusion gene or this fusion gene engineered so that one of its ends encodes HDEL sequence was transferred into EUG5, the resultant recombinant also produced 0.79-2.43 mg/L of GGOH as in (vi) above.

(viii) When ERG19 was transferred into EUG strains, it appeared that FOH production was not considerably improved in any of the resultant recombinants. However, when FOH yields per $OD_{600}$ value of the culture broth were compared, FOH production efficiency were improved two- to several-fold in recombinants prepared from YPH strain-derived EUG12 and EUG24.

BRIEF DESCRIPTION OF THE DRAWINGS

FIG. 6C presents graphs showing the prenyl alcohol production of EUG27.

FIG. 10A presents graphs showing the prenyl alcohol production of W303-1A-derived EUG strains.

FIG. 12C presents graphs showing the prenyl alcohol production of EUG8 cultured in media with varied initial sugar concentration/composition.

FIG. 14A presents graphs showing the prenyl alcohol production of FUG27 cultured in media with varied initial sugar concentration/composition.

FIG. 15C presents graphs showing the production of FOH by EUG8, EUG12 and EUG27 cultured in media with varied initial sugar concentration/composition.

FIG. 34A presents graphs showing GGOH yields of pRS435GGF- or pRS435GGFHDEL-introduced EUG5 cultured in a medium with the indicated initial sugar composition for 2 days.

BEST MODE FOR CARRYING OUT THE INVENTION

Hereinbelow, the present invention will be described in more detail with reference to the following Examples. However, the technical scope of the invention is not limited to these Examples.

The Examples encompass the following contents.

(1) Mutant strains (EUG strains) are prepared by replacing the transcription promoter for the squalene synthase gene in their genome with GAL1 promoter (a transcription repression type promoter), and used as prenyl alcohol-producing microorganisms. The resultant EUG strains are cultured under transcription repression conditions (i.e., in a glucose-containing medium), followed by determination of the yields of prenyl alcohols. [Examples 1-2]

(2) Expression vectors pRS435GAP and so forth are prepared based on pRS vectors (Stratagene), pYES vectors (Invitrogen) or genomic DNA from *E. coli*, for transferring genes into EUG strains. [Example 3]

(3) Cloning of IPP Biosynthetic Pathway-Related Genes

As genes to be transferred into the above EUG strains, HMG-CoA reductase gene, diphosphomevalonate decarboxylase gene, FPP synthase gene, GGPP synthase gene, and mutants thereof are cloned, followed by preparation of expression plasmids. [Examples 4-6 and 8]

(4) Recombinants into which the genes cloned in (3) above were transferred are cultured under transcription repression conditions (i.e., in a glucose-containing medium), followed by determination of the yields of prenyl alcohols. [Examples 7-8]

(5) EUG strains are cultured in media with varied glucose concentration or media to which sugar sources, nitrogen sources and oil additives were added, to thereby examine conditions suitable for prenyl alcohol production. [Examples 9-10]

Example 1

Preparation of EUG Strains

Figure 1:
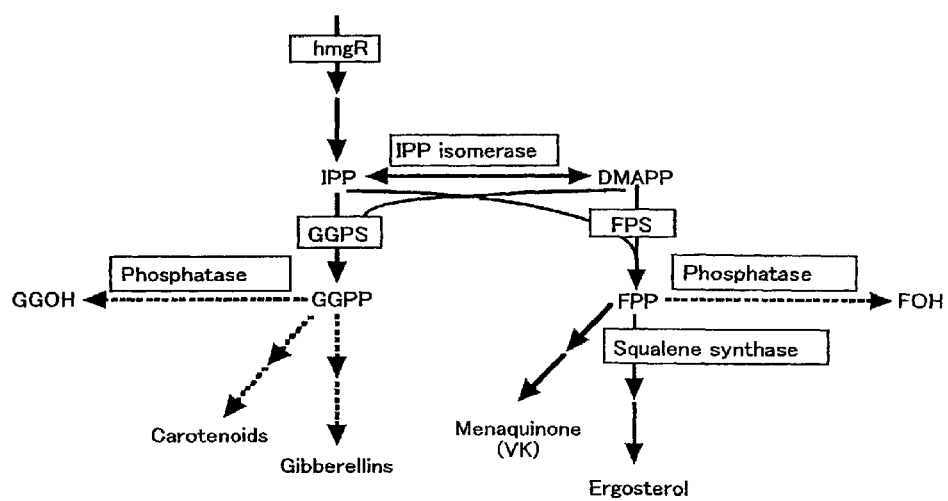
FIG. 1 is a diagram showing a metabolic pathway of IPP biosynthetic pathway-related enzymes.
Figure 2A:
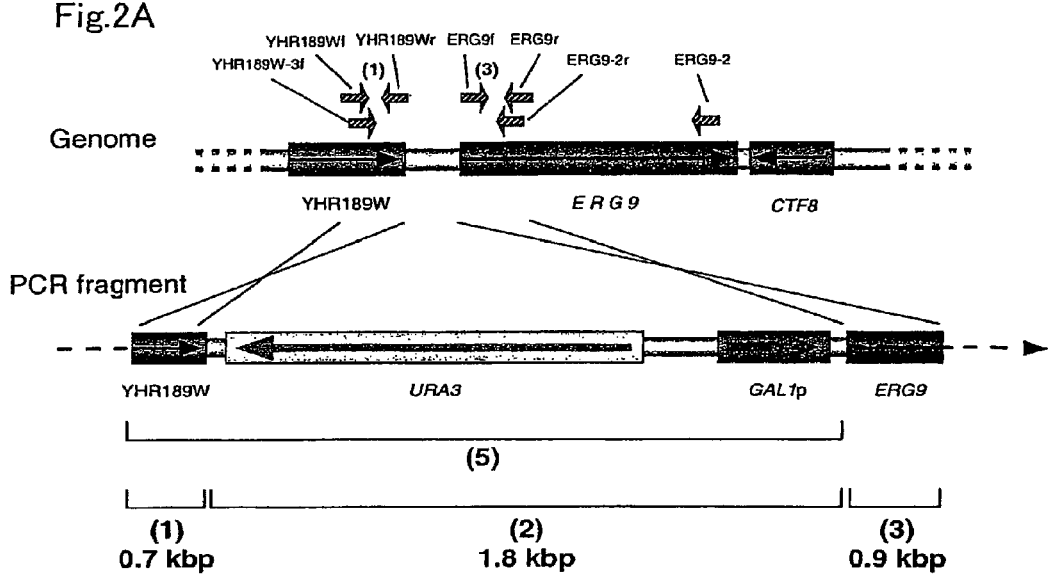
FIG. 2 presents a physical map around the ERG9 locus and diagrams showing the construction of DNA fragments for replacing the ERG9 promoter region.
Figure 2B:
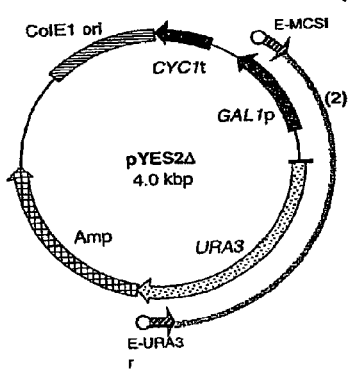
Figure 2C:
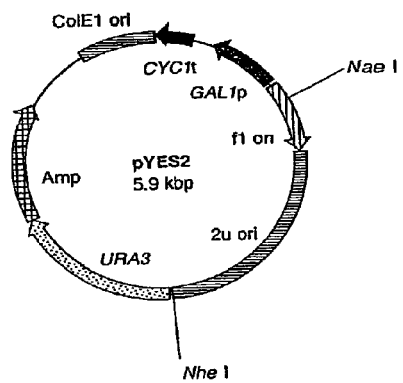

A gene map around squalene synthase gene ERG9 was obtained from SGD. Based on this map, PCR primer DNAs for amplifying DNA fragments for replacing ERG9 transcription promoter (ERG9p) were designed (FIG. 2). On the other hand, a 1.8 kbp DNA fragment (FIG. 2A, (2)) comprising a transformant selection marker gene URA3 and a transcription promoter GAL1p was prepared by PCR amplification using, as a template, pYES2Δ (FIG. 2B) obtained by digesting pYES2 (FIG. 2C) with NaeI and NheI, blunt-ending with Klenow enzyme and deleting 2μ ori by self-ligation.

The primers used in the PCR are as follows.

```
E-MCSf:
                                         (SEQ ID NO: 34)
5'-GCC GTT GAC AGA GGG TCC GAG CTC GGT ACC AAG-3'

E-URA3r:
                                         (SEQ ID NO: 35)
5'-CAT ACT GAC CCA TTG TCA ATG GGT AAT AAC TGA
T-3'
```

In each of the above primers, an Eam1105I recognition site (the underlined portion) was added so that a 0.7 kbp DNA fragment comprising a downstream portion of the open reading frame YHR189W in the genome of *S. cerevisiae* and a 0.9 kbp DNA fragment comprising an upstream portion of ERG9 can be carried out T/A ligation. The YHR189W fragment (i) was prepared by PCR using the following primers YHR189Wf and YHR189Wr, and YPH499 genomic DNA as a template. The ERG9 fragment (ii) was prepared by PCR using the following primers ERG9f and ERG9r, and YPH499 genomic DNA as a template. YPH499 genomic DNA was prepared with a yeast genomic DNA preparation kit "Dr. GenTLE™" (Takara).

```
YHR189Wf:
5'-TGT CCG GTA AAT GGA GAC-3'     (SEQ ID NO: 36)

YHR189Wr:
5'-TGT TCT CGC TGC TCG TTT-3'     (SEQ ID NO: 37)

ERG9f:
5'-ATG GGA AAG CTA TTA CAA T-3'   (SEQ ID NO: 38)

ERG9r:
5'-CAA GGT TGC AAT GGC CAT-3'     (SEQ ID NO: 39)
```

The 1.8 kbp DNA fragment was digested with Eam1105I and then ligated to the 0.7 kbp DNA fragment. With the resultant fragment as a template, 2nd PCR was carried out using the above-described primers YHR189Wf and E-MCSf. The amplified 2.5 kbp DNA fragment (FIG. 2A, (5)) was digested with Eam11051 and then ligated to the 0.9 kbp fragment. With the resultant fragment as a template, 3rd PCR was carried out using the following primers YHR189W-3f and ERG9-2r. As a result, a 3.4 kbp DNA fragment was amplified. This was used as a DNA fragment for transformation.

```
YHR189W-3f:
5'-CAA TGT AGG GCT ATA TAT G-3'   (SEQ ID NO: 40)

ERG9-2r:
5'-AAC TTG GGG AAT GGC ACA-3'     (SEQ ID NO: 41)
```

The DNA fragment for transformation was introduced into yeast strains using Frozen EZ Yeast Transformation II kit purchased from Zymo Research (Orange, Calif.). As host strains for the DNA transfer, A451, YPH499, YPH500, W303-1A and W303-1B were used.

The resultant recombinants were cultured on an agar medium called SGR-U medium that had been obtained by adding CSM-URA (purchased from BIO 101, Vista, Calif.) and adenine sulfate (final concentration 40 mg/L) to SGR medium [a variation of SD (synthetic dextrose) medium where the glucose component is replaced with galactose and raffinose] at 30° C. Colonies grown on the medium were spread on the same medium again, cultured and then subjected to single colony isolation.

The resultant recombinants were designated EUG (ERG9p::URA3-GAL1p) strains. Of these, clones derived from A451 were designated EUG1 through EUG10; clones derived from YPH499 were designated EUG11 through EUG20; clones derived from YPH500 were designated EUG21 through EUG30; clones derived from W303-1A were designated EUG31 through EUG50; and clones derived from W303-1B were designated EUG51 through EUG70.

Figure 5:
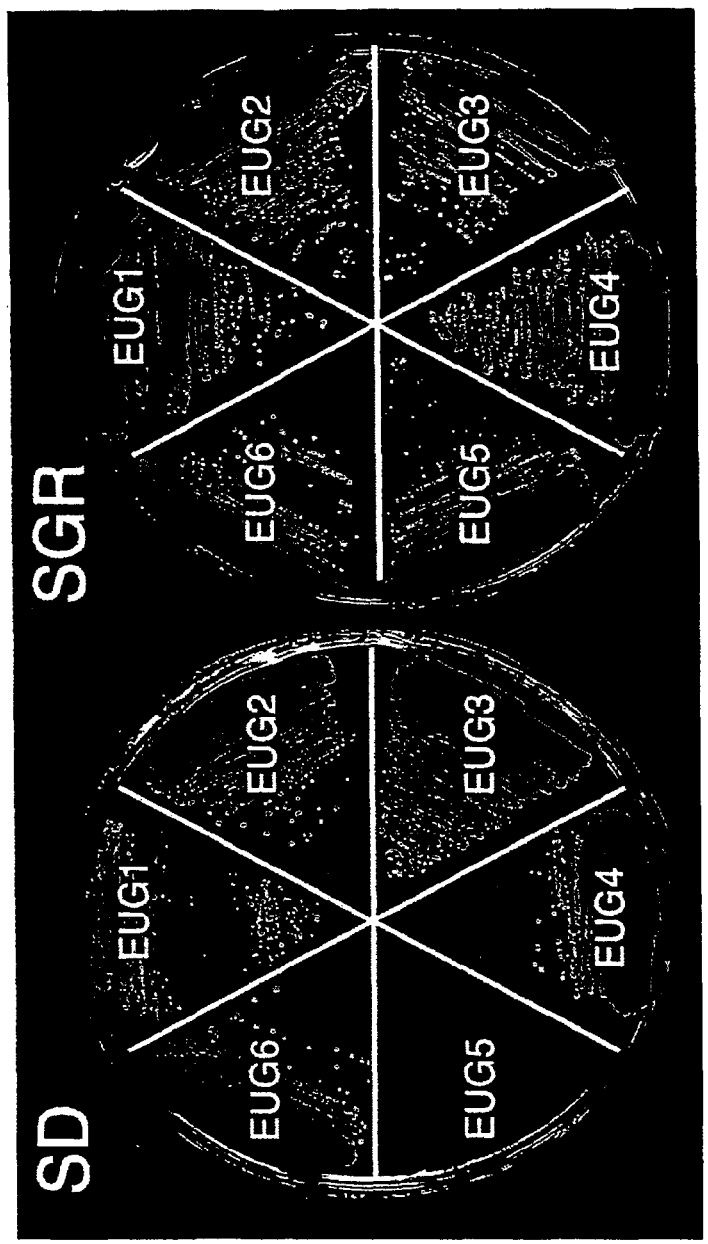
FIG. 5 is a photograph showing the colony formation of EUG strains on agar plate medium.

These clones were cultured on SD medium to select those clones that exhibit a decrease in growth rate as a result of reduction in the amount of squalene synthase gene transcript having translational activity due to glucose repression. As a result, EUG8 from A451, EUG12 from YPH499 and EUG27 from YPH500 were obtained. Representative examples of states of growth on SD-U agar medium and SGR-U agar medium are shown in FIG. 5. A clone could be obtained (in FIG. 5, EUG5 among EUG1 through EUG6) that grew normally on SGR-U plate (FIG. 5, right panel) but exhibited a decrease in growth rate on SD-U plate (FIG. 5, left panel titled "SD") as a result of reduction in the amount of squalene synthase gene transcript having translational activity caused by the repression of transcription of the squalene synthase gene under the control of GAL1 promoter due to glucose repression.

Among those recombinants that exhibited a decrease in growth rate as a result of reduction of the amount of squalene synthase gene transcript having translational activity, EUG8, EUG12 and EUG27 were selected, followed by preparation of genomic DNA using Dr. GenTLE™. Then, PCR was carried out using the genomic DNA as a template and primers YHR189Wf and ERG9-2 (5'-TCA CGC TCT GTG TAA AGT GTA TA-3' (SEQ ID NO: 42)), and the size of the amplified DNA fragment was examined by agarose gel electrophoresis. The results confirmed that the 1.8 kbp PCR fragment comprising URA3 and GAL1p is integrated into the squalene synthase gene locus in the genome of each strain.

Example 2

Production of Prenyl Alcohols by Individual EUG Strains (1) Determination of Prenyl Alcohol Yields: Part I
(1-1) Cultivation EUG8, EUG12 and EUG27 were precultured in SGR-U medium, and 0.3 ml of each preculture broth was added to 30 ml of YM7 medium, YME medium or YM7 (Gal) medium. Then, each strain was cultured under reciprocal shaking at 130 rpm in a 300 ml Erlenmeyer flask at 30° C. YM7 medium refers to YM medium whose pH is adjusted to 7 with NaOH. YME medium refers to YM7 medium to which 50 mg/L of ergosterol is added. Specifically, this medium is prepared by adding 1/1000 volume of an ergosterol stock solution in ethanol-Tergitol (50 mg/ml) to YM7 medium. YM7 (Gal) medium refers to YM7 medium where its glucose component is replaced with galactose.

A 2.5 ml sample of the culture broth was taken out on day 1, 2, 3, 4, 7, 8 and 9 of the cultivation and subjected to determination of prenyl alcohol yields. Briefly, 2.5 ml of methanol was added to each sample and mixed. About 5 ml of pentane was added to this mixture, agitated vigorously and then left stationary. The resultant pentane layer was transferred into a fresh glass tube, which was then placed in a draft. Pentane was evaporated therein to condense the solute components. Subsequently, prenyl alcohols were identified and quantitatively determined by gas chromatography/mass spectrometry (GC/MS). At that time, the degree of cell growth was also examined by diluting 50 μl of each culture broth 30-fold with water and measuring the absorbance at 600 nm.

(1-2) GC/MS Analysis

The fraction extracted with pentane was separated, identified and quantitatively determined with HP6890/5973 GC/MS system (Hewlett-Packard, Wilmington, Del.). The column used was HP-5MS (0.25 mm×30 m; film thickness 0.25 μm). Analytical conditions were as described below. The same conditions were used for all the GC/MS analyses in this specification.

Inlet temperature: 250° C.
Detector temperature: 260° C.
[MS Zone Temperatures]
   MS Quad: 150° C.
   MS Source: 230° C.
   Mass scan range: 35-200
[Injection Parameters]
   Automated injection mode
   Sample volume: 2 μl
   Methanol washing: 3 times; hexane washing: twice
   Split ratio: 1/20
   Carrier gas: helium 1.0 ml/min
Solvent retardation: 2 min
[Oven Heating Conditions]
   115° C. for 90 sec
   Heating up to 250° C. at 70° C./min and retaining for 2 min
   Heating up to 300° C. at 70° C./min and retaining for 7 min
Internal standard: 0.01 μl of 1-undecanol in ethanol
Reliable standards:
   (all-E)-Nerolidol (Eisai)
   (all-E)-Farnesol (Sigma)
   (all-E)-Geranylgeraniol (Eisai)
   Squalene (Tokyo Kasei Kogyo)

(2) Determination of Prenyl Alcohol Yields: Part II

Those EUG strains that exhibited a decrease in growth rate in SD medium were cultured in 1-5 ml of YM7 medium at 30° C. under reciprocal shaking at 130 rpm. A sample (0.8-2.5 ml) of the culture broth was taken out on day 1, 2, 3, 4 and 7 of the cultivation, followed by determination of the amounts of prenyl alcohols in the same manner as described in (1) above.

(3) Changes in Prenyl Alcohol Yields Depending on Sugar Composition

The glucose (Glc) component in YM7 medium was varied as indicated in Table 4 below, and EUG strains were cultured therein for 2 days at 30° C. under reciprocal shaking at 130 rpm. Subsequently, 5% (w/v) Glc was added to the YM7 medium to prepare YM Glc medium and 5% (w/v) galactose (Gal) was added to the YM7 medium to prepare YM Gal medium, as shown in Table 5, and the strains were cultured further up to day 7. With respect to YMrich medium, the total sugar concentration in YM7 was set at 6% (w/v) from the start of the cultivation, and the sugar composition therein was as shown in Table 4. The relationships between medium composition and cultivation period may be summarized as shown in Table 5. A 2.5 ml sample of the culture broth was taken out on day 2, 4 and 7 of the cultivation, followed by determination of the prenyl alcohol yields in the same manner as described in (1) above.

TABLE 4

| No. | Glucose (%) | Galactose (%) |
|---|---|---|
| 1 | 100 | 0 |
| 2 | 75 | 25 |
| 3 | 50 | 50 |
| 4 | 20 | 80 |
| 5 | 10 | 90 |
| 6 | 5 | 95 |
| 7 | 1 | 99 |
| 8 | 0 | 100 |

TABLE 5

| Medium | Day 0 | Day 2 | Day 4 | Day 7 |
|---|---|---|---|---|
| YM Glc | 1% | 6% (5% Glc added) | 6% | 6% |
| YM Gal | 1% | 6% (5% Gal added) | 6% | 6% |
| YM rich | 6% | 6% | 6% | 6% |
| No. | xxx-1 | xxx-2 | xxx-3 | xxx-4 |

(4) Results and Considerations (4-1) Penyl Alcohol Production by EUG Strains

Figure 6A:
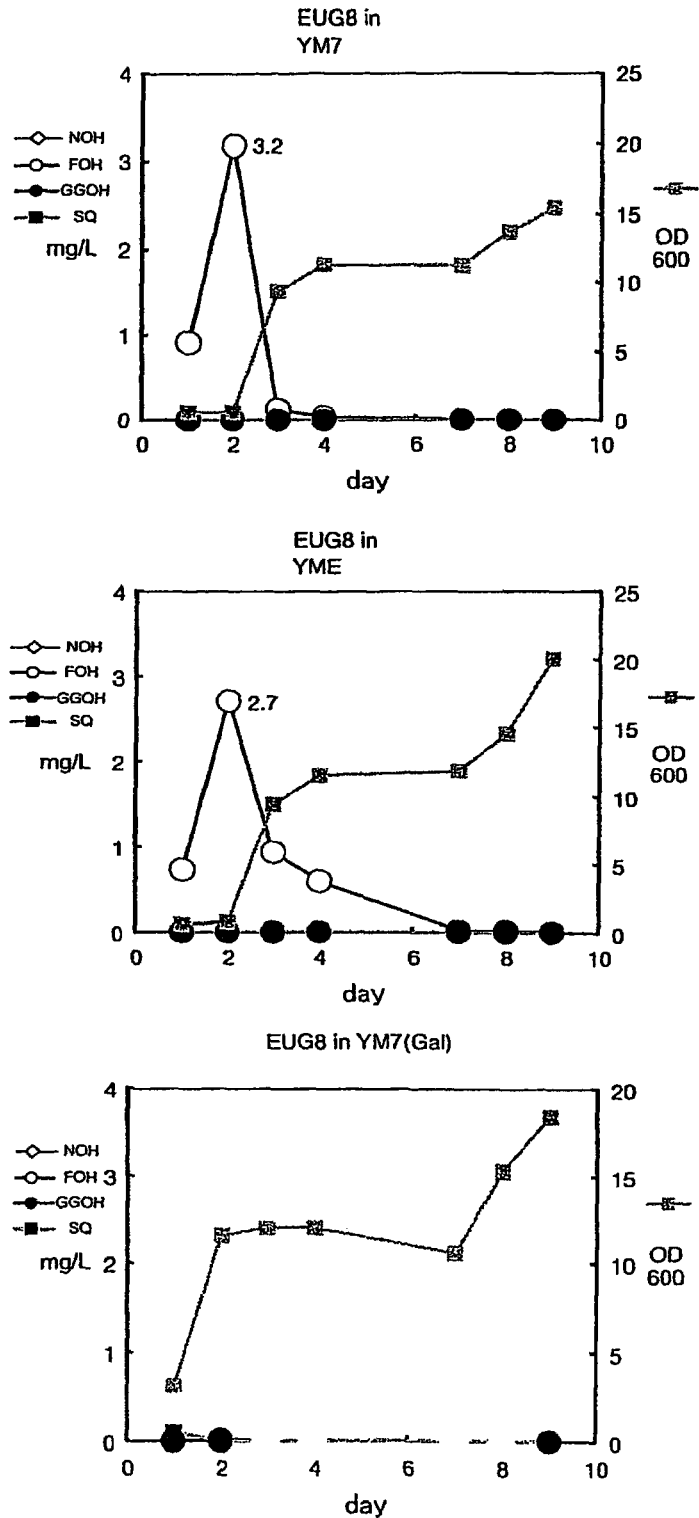
FIG. 6A presents graphs showing the prenyl alcohol production of EUG8.
Figure 6B:
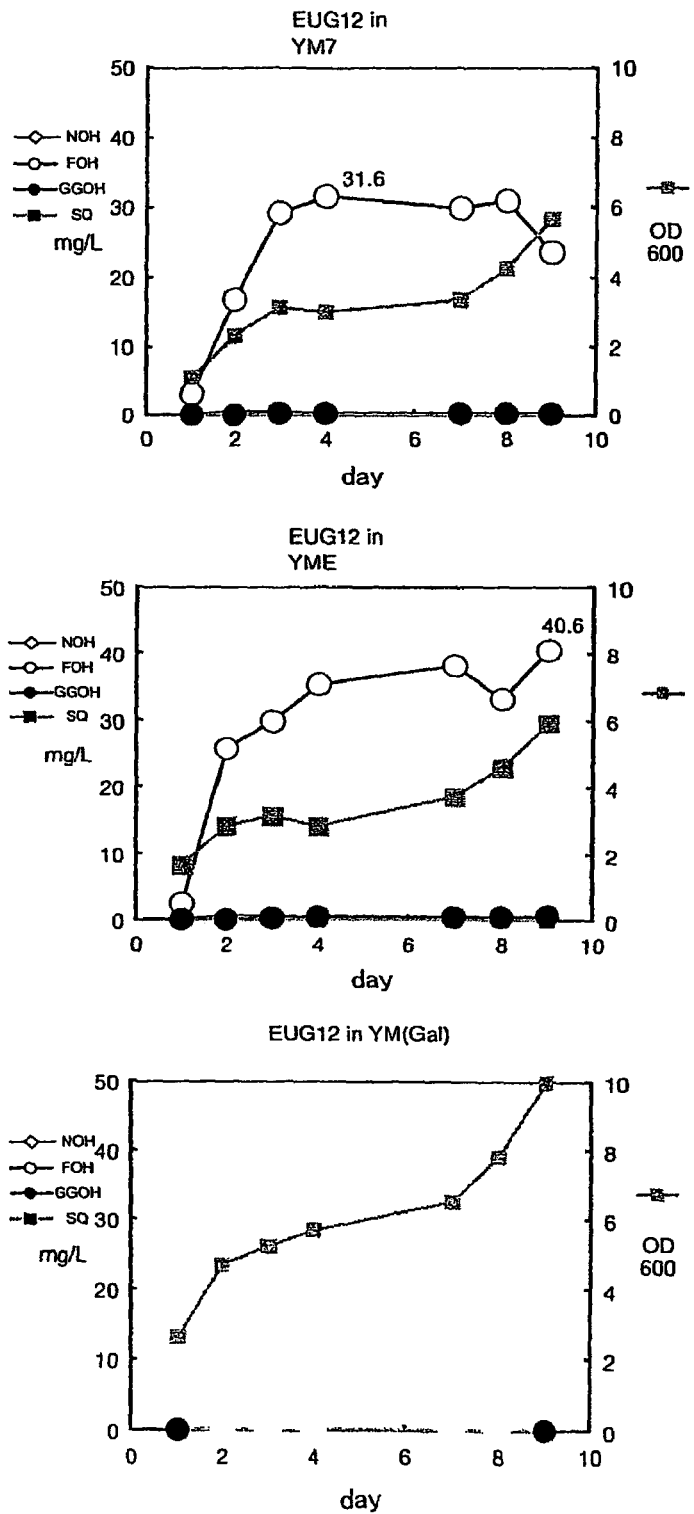
FIG. 6B presents graphs showing the prenyl alcohol production of EUG12.

A451-, YPH499- and YPH500-derived EUG strains that exhibited a decrease in growth rate in a glucose-containing medium and had GAL1p completely integrated into the genome were selected (EUG8, EUG12 and EUG27 were selected from respective strains), and their prenyl alcohol yields were determined. The results are shown in FIG. 6A-C. When they were cultured in YM7 or YME medium both containing Glc as a carbon source, FOH-producing systems were obtained. When cultured in YME medium containing ergosterol, EUG12 and EUG27 exhibited a tendency of increase in FOH concentration. They accumulated 40.6 mg/L and 18.0 mg/L of FOH at the maximum, respectively. A451-derived EUG8, YPH499-derived EUG12 and YPH500-derived EUG27 are different in production profile, and it is believed that YPH-derived strains are more suitable for prenyl alcohol production. Thus, a yeast clone was developed that can produce about 30 mg/L of FOH when cultured for only 4 days in the common medium YM7 (see EUG12 in FIG. 6) without addition of ergosterol (Erg) essential for the growth of conventional ERG9-defficient strains (erg9 strain: ATCC64031).

Figure 7:
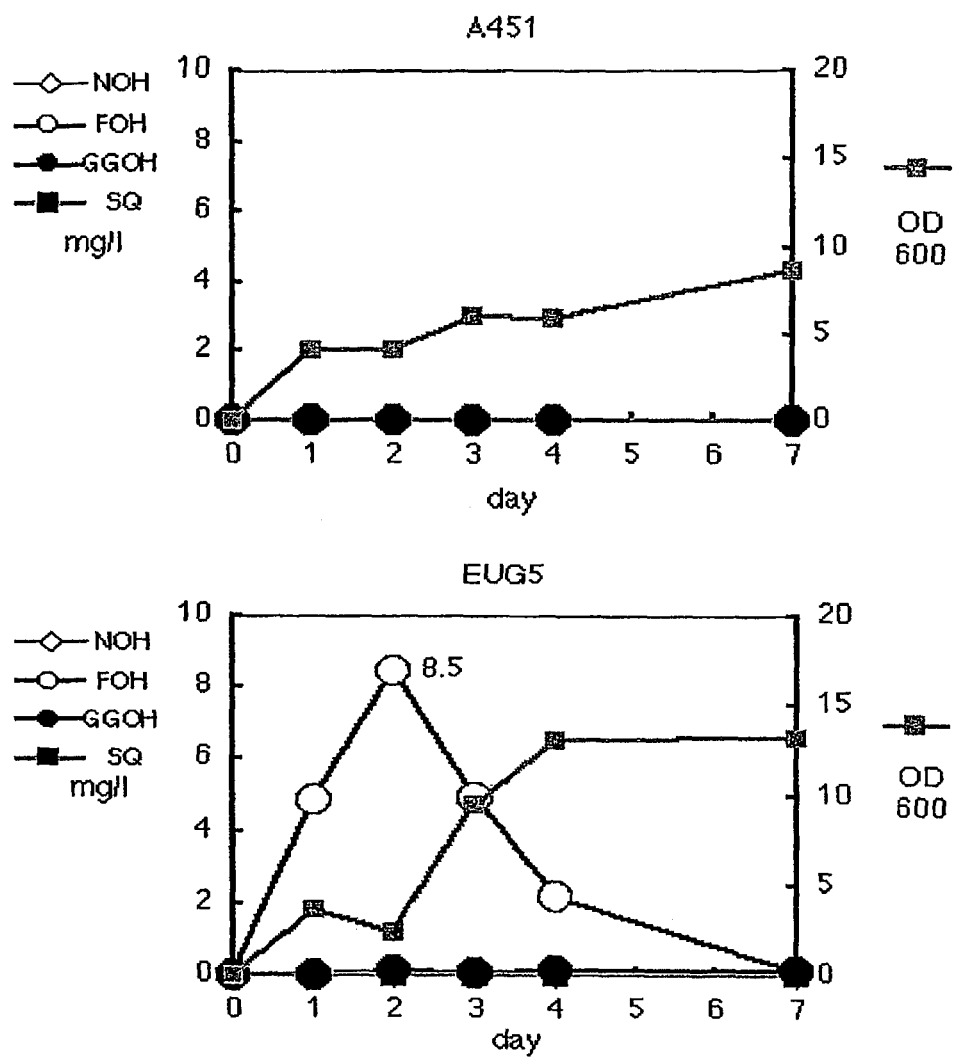
FIG. 7 presents graphs showing the prenyl alcohol production of EUG5 which is an A451-derived EUG strain.
Figure 8:
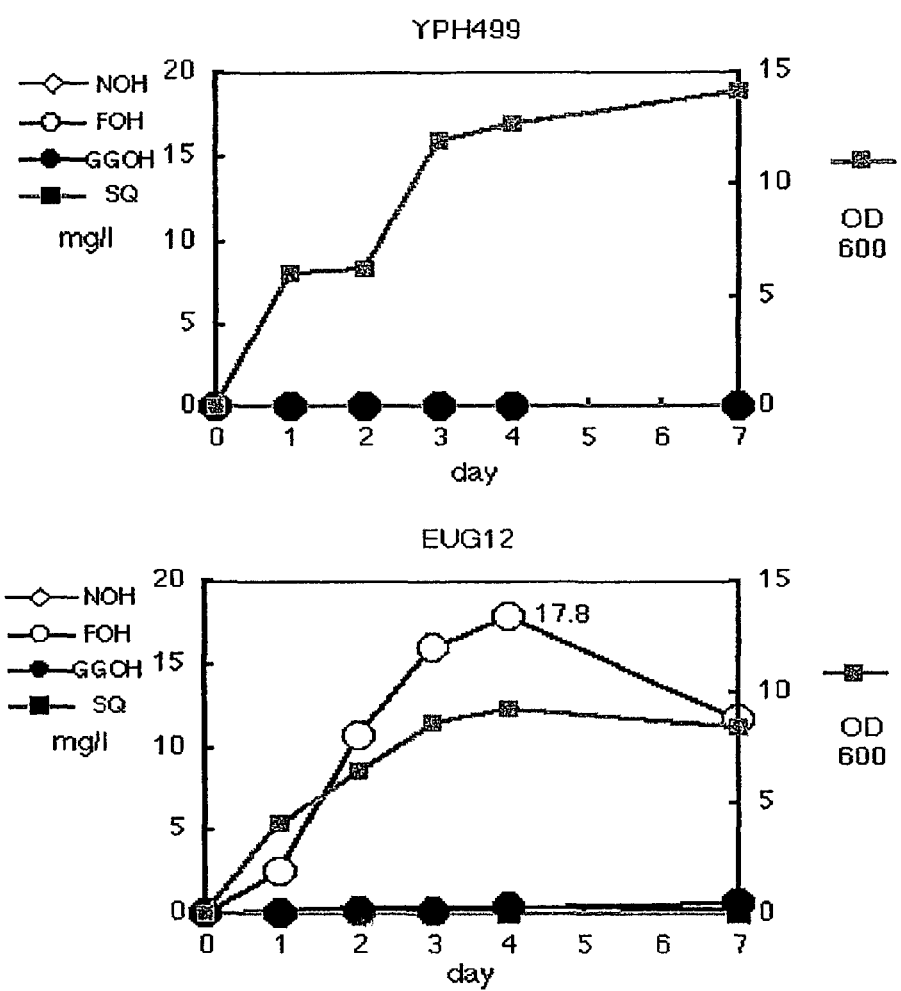
FIG. 8 presents graphs showing the prenyl alcohol production of EUG12 which is a YPH499-derived EUG strain.
Figure 9:
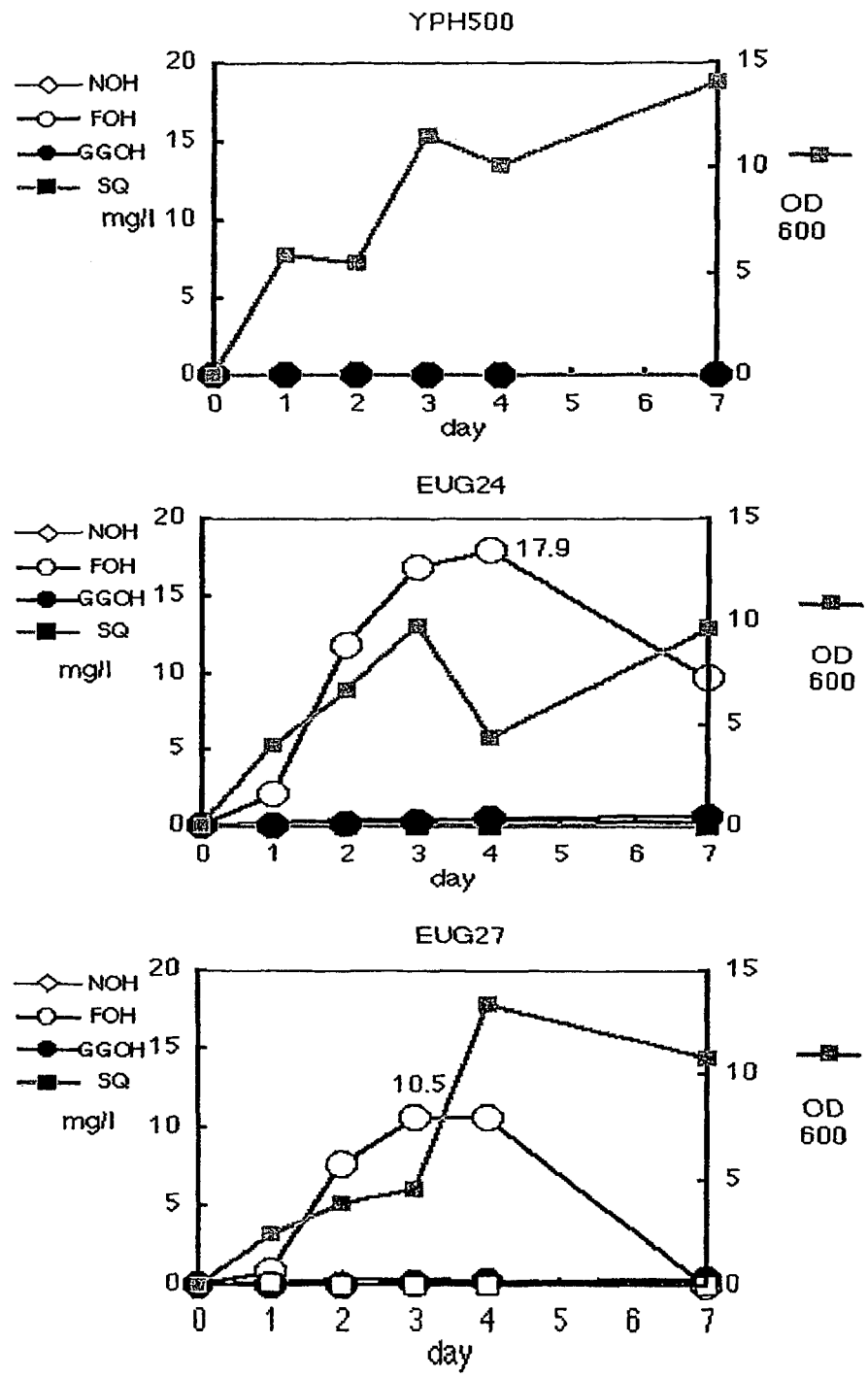
FIG. 9 presents graphs showing the prenyl alcohol production of EUG24 and EUG27 which are YPH50-derived EUG strains.
Figure 10B:
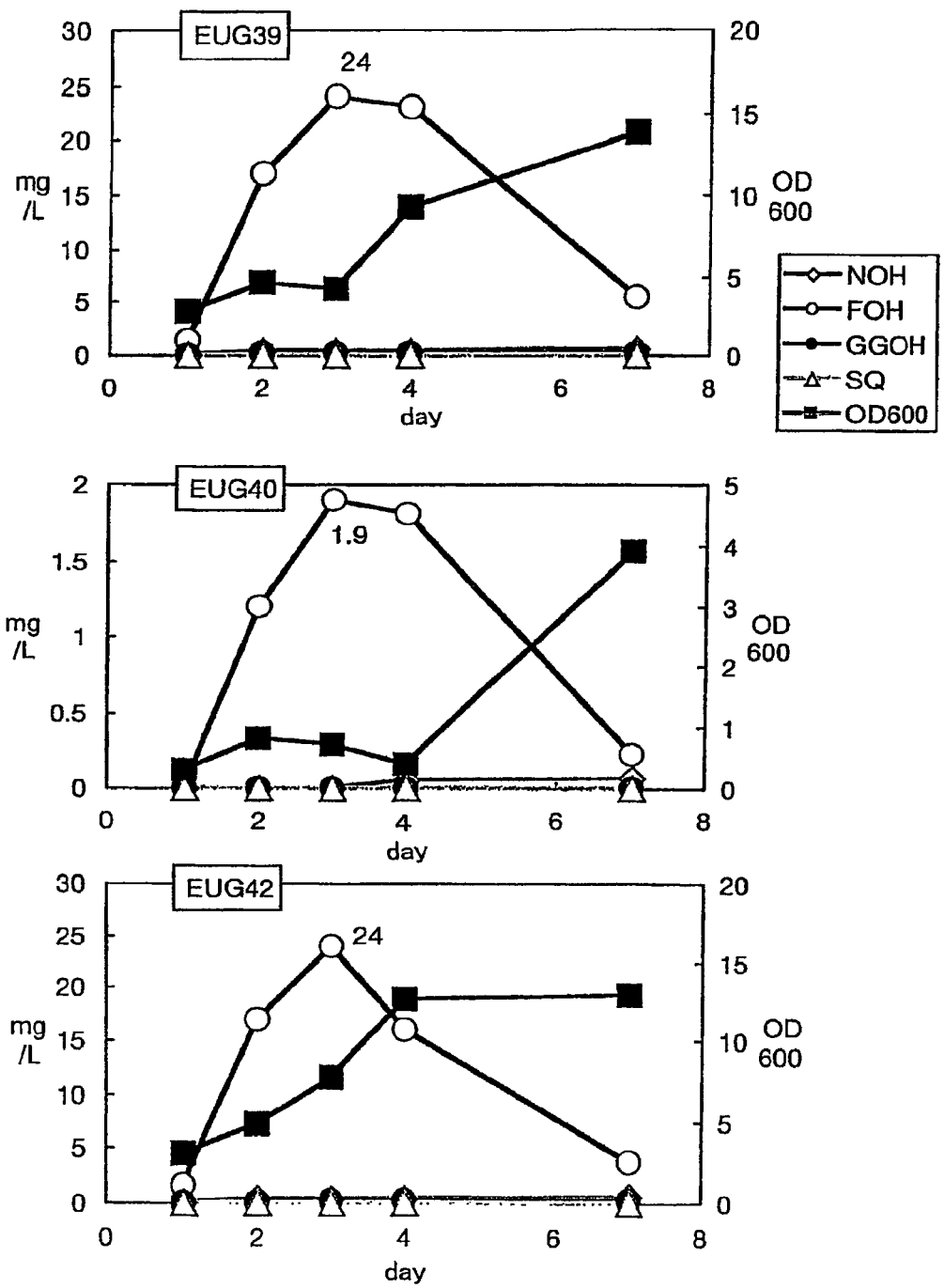
FIG. 10B presents graphs showing the prenyl alcohol production of W303-1A-derived EUG strains.
Figure 10C:
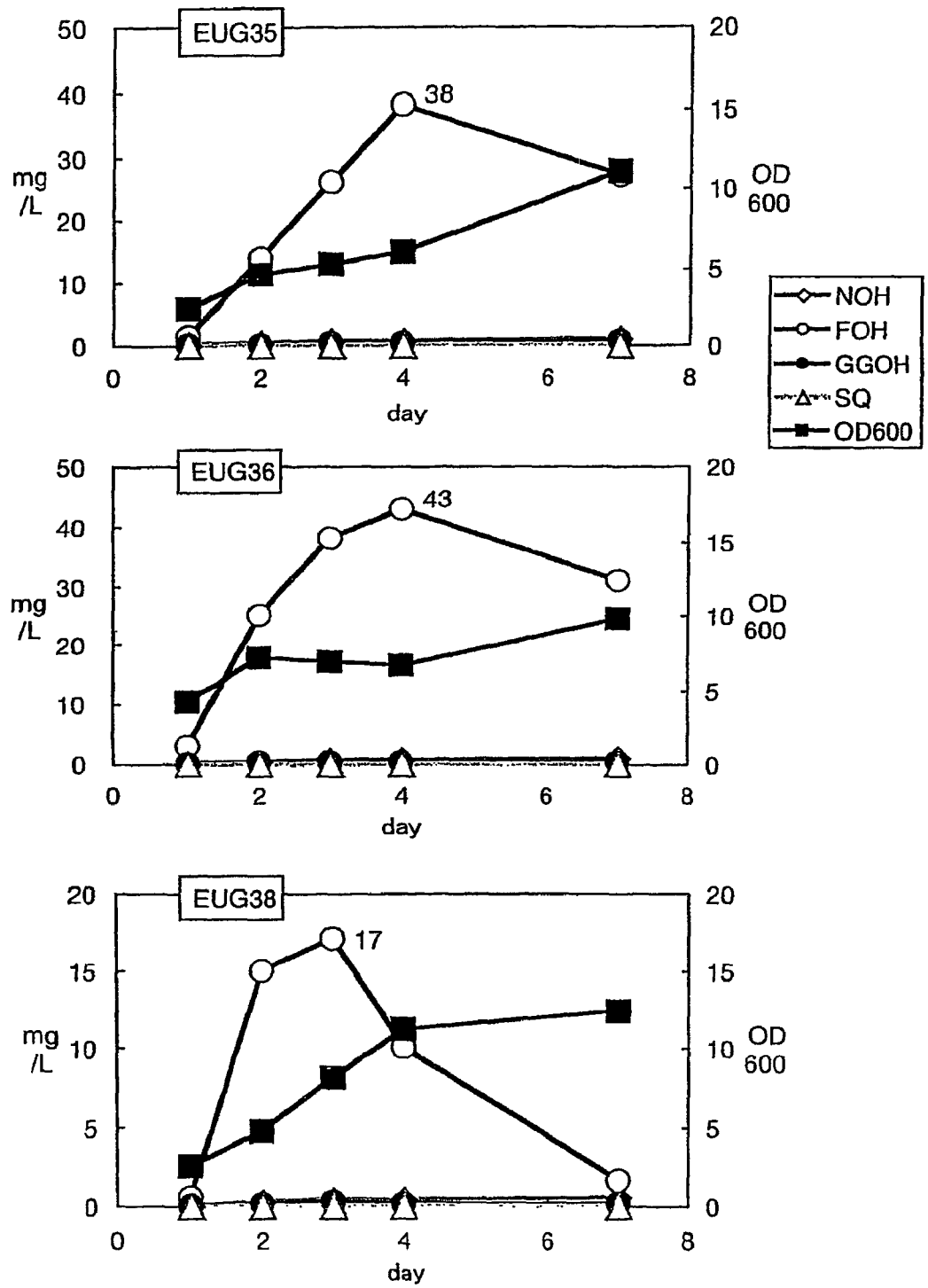
FIG. 10C presents graphs showing the prenyl alcohol production of W303-1A-derived EUG strains.
Figure 10D:
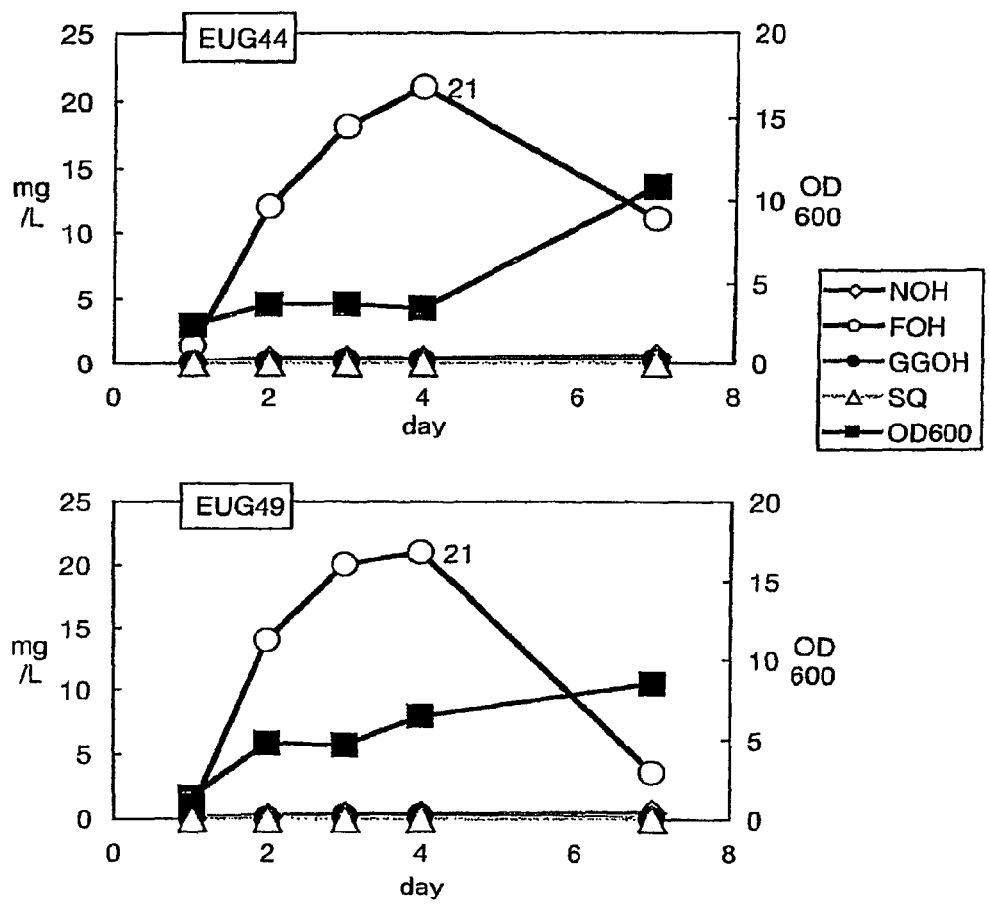
FIG. 10D presents graphs showing the prenyl alcohol production of W303-1A-derived EUG strains.
Figure 11A:
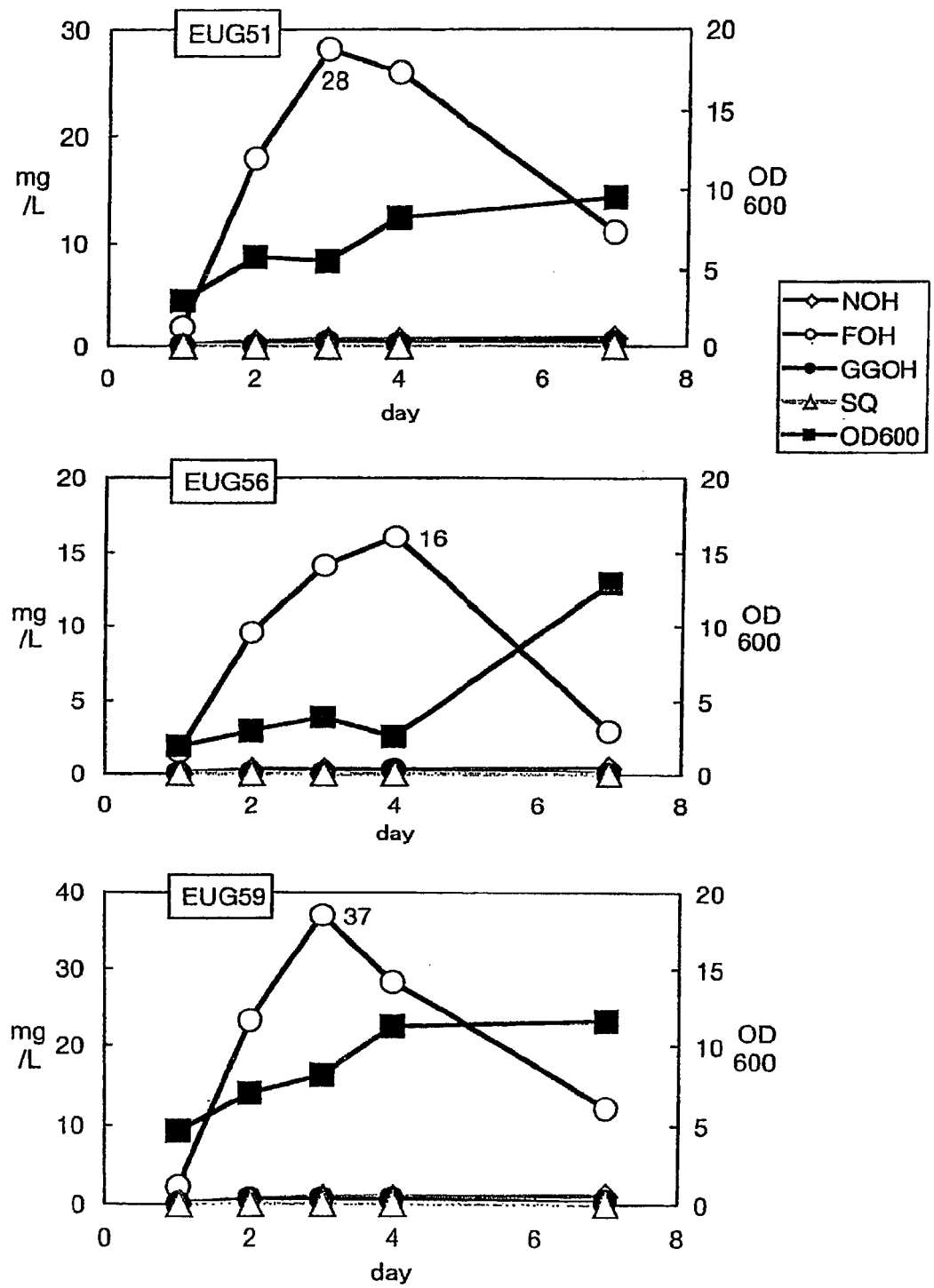
FIG. 11A presents graphs showing the prenyl alcohol production of W303-1B-derived EUG strains.
Figure 11B:
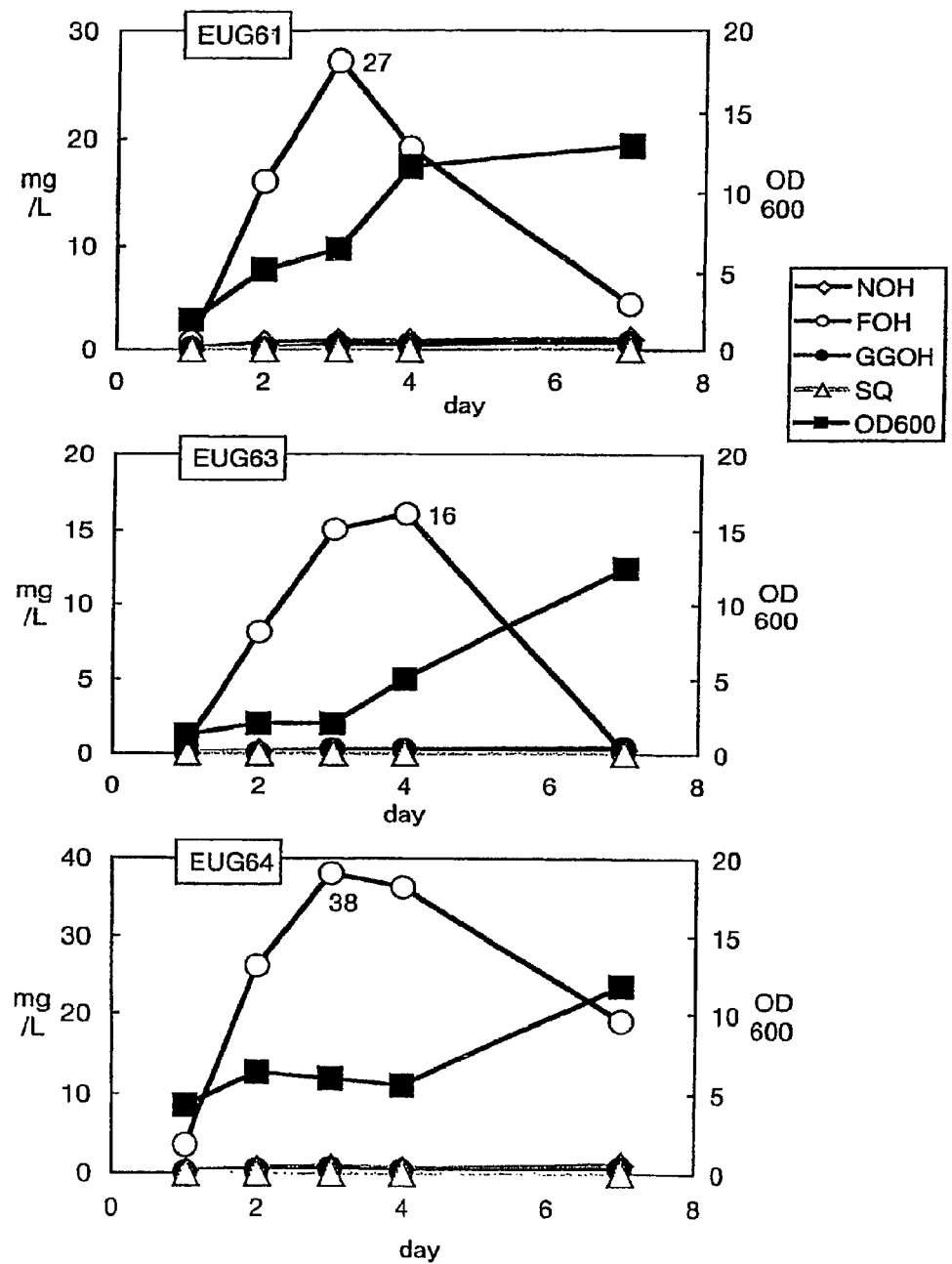
FIG. 11B presents graphs showing the prenyl alcohol production of W303-1B-derived EUG strains.
Figure 12A:
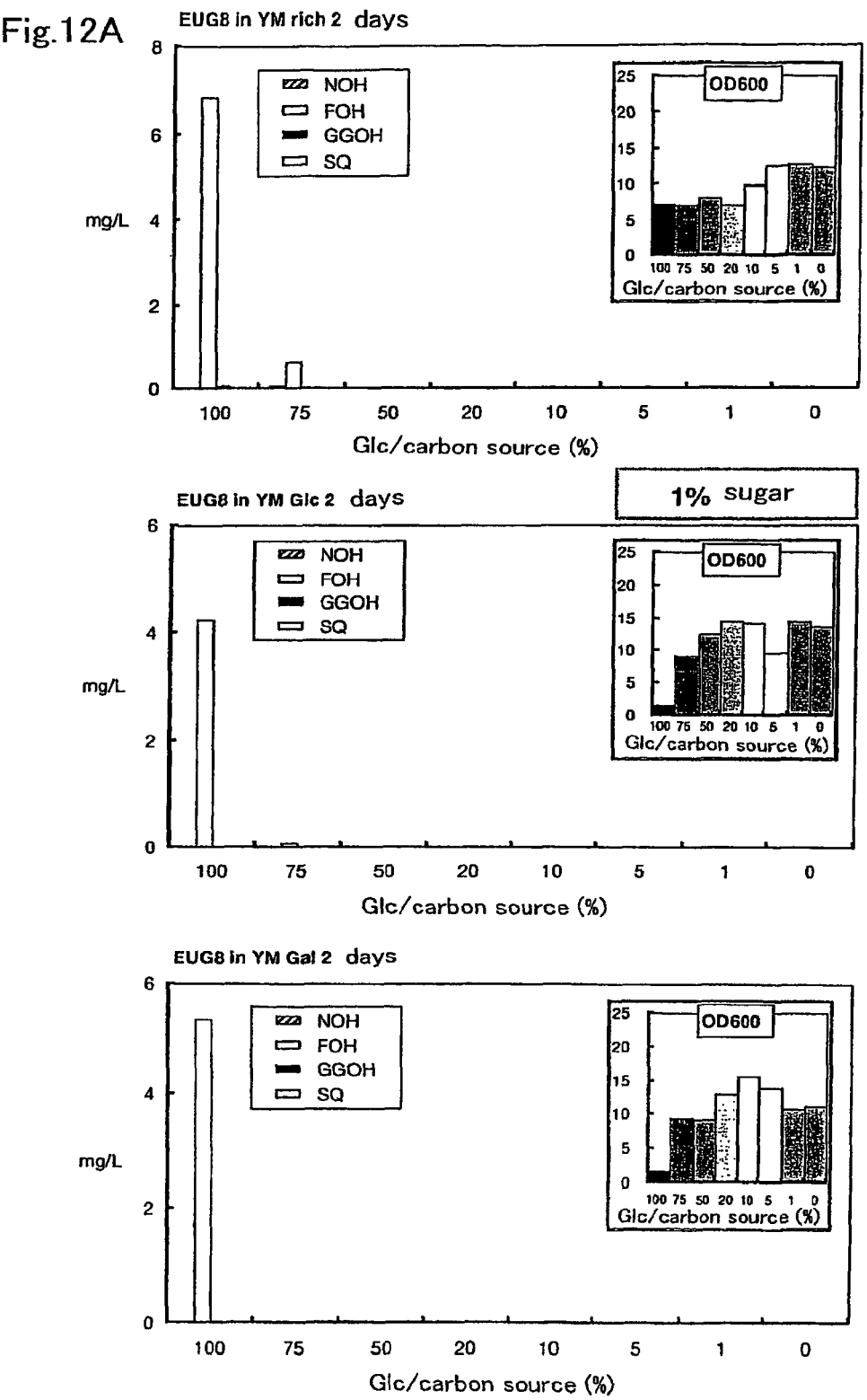
FIG. 12A presents graphs showing the prenyl alcohol production of EUG8 cultured in media with varied initial sugar concentration/composition.
Figure 12B:
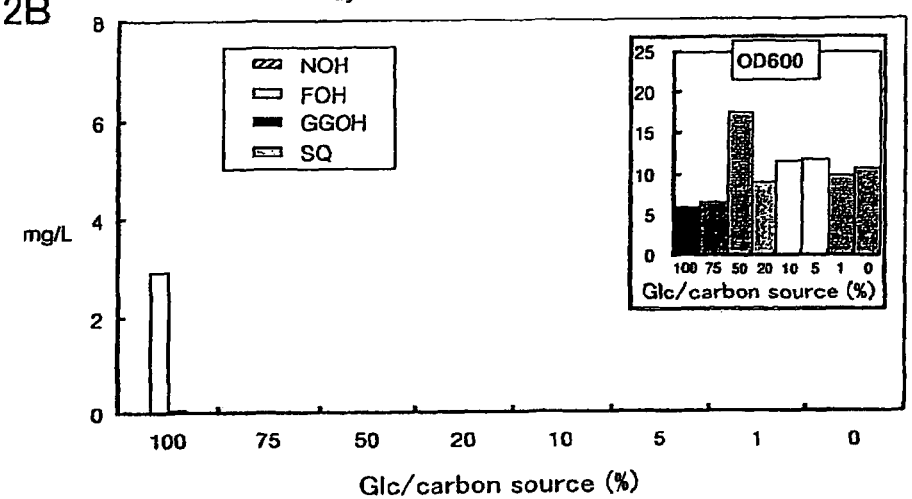
FIG. 12B presents graphs showing the prenyl alcohol production of EUG8 cultured in media with varied initial sugar concentration/composition.
Figure 12B:
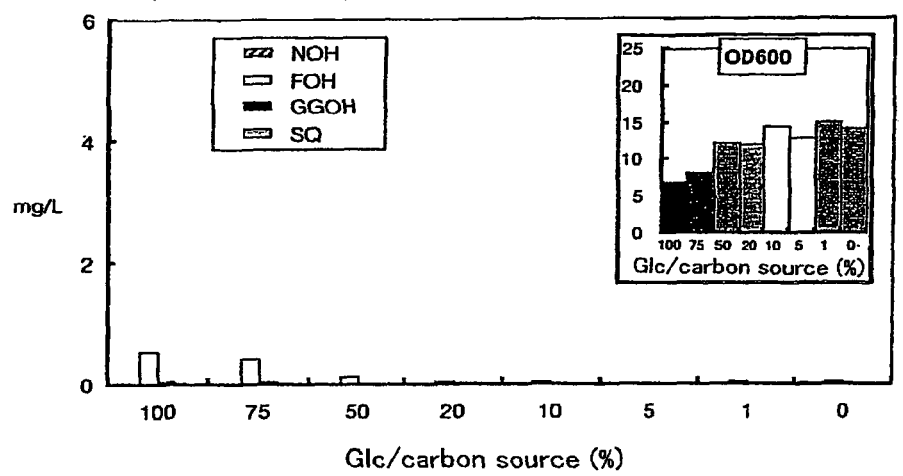
Figure 12B:
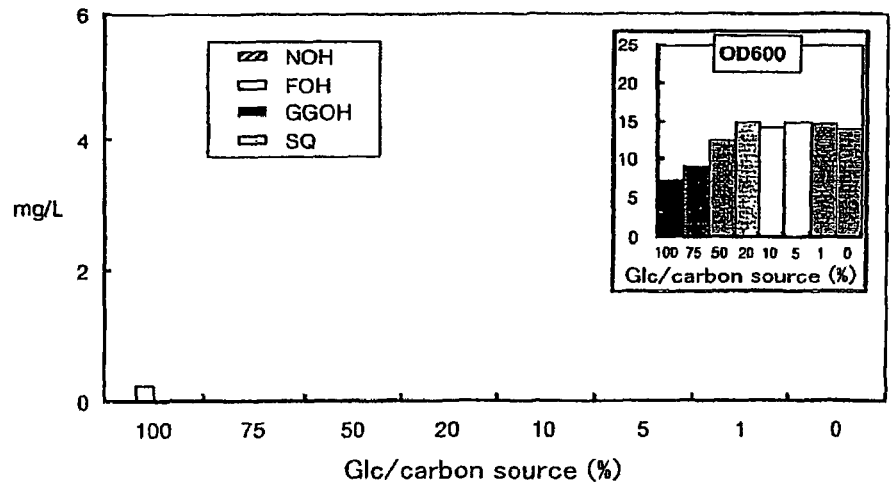
Figure 13A:
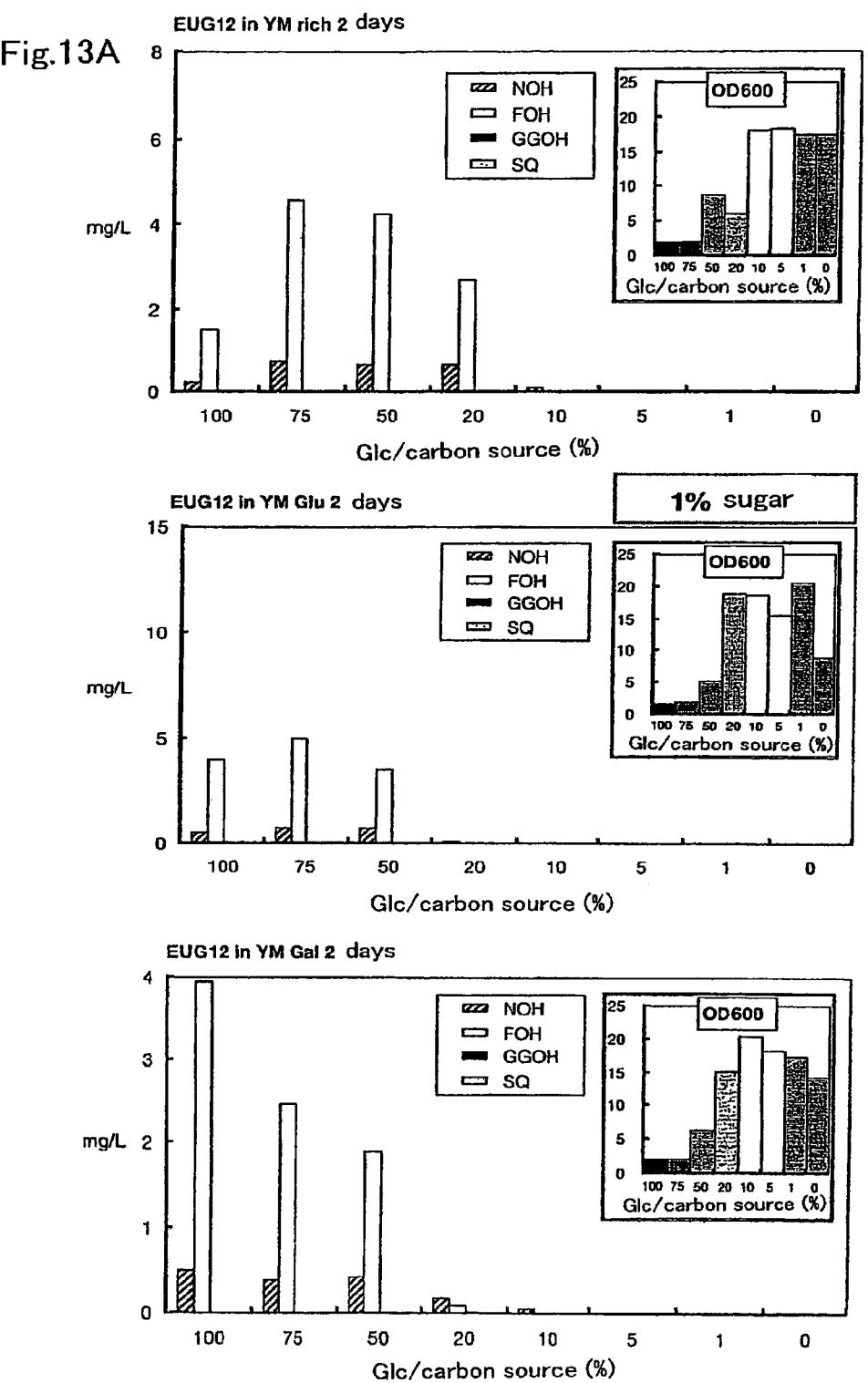
FIG. 13A presents graphs showing the prenyl alcohol production of EUG12 cultured in media with varied initial sugar concentration/composition.
Figure 13B:
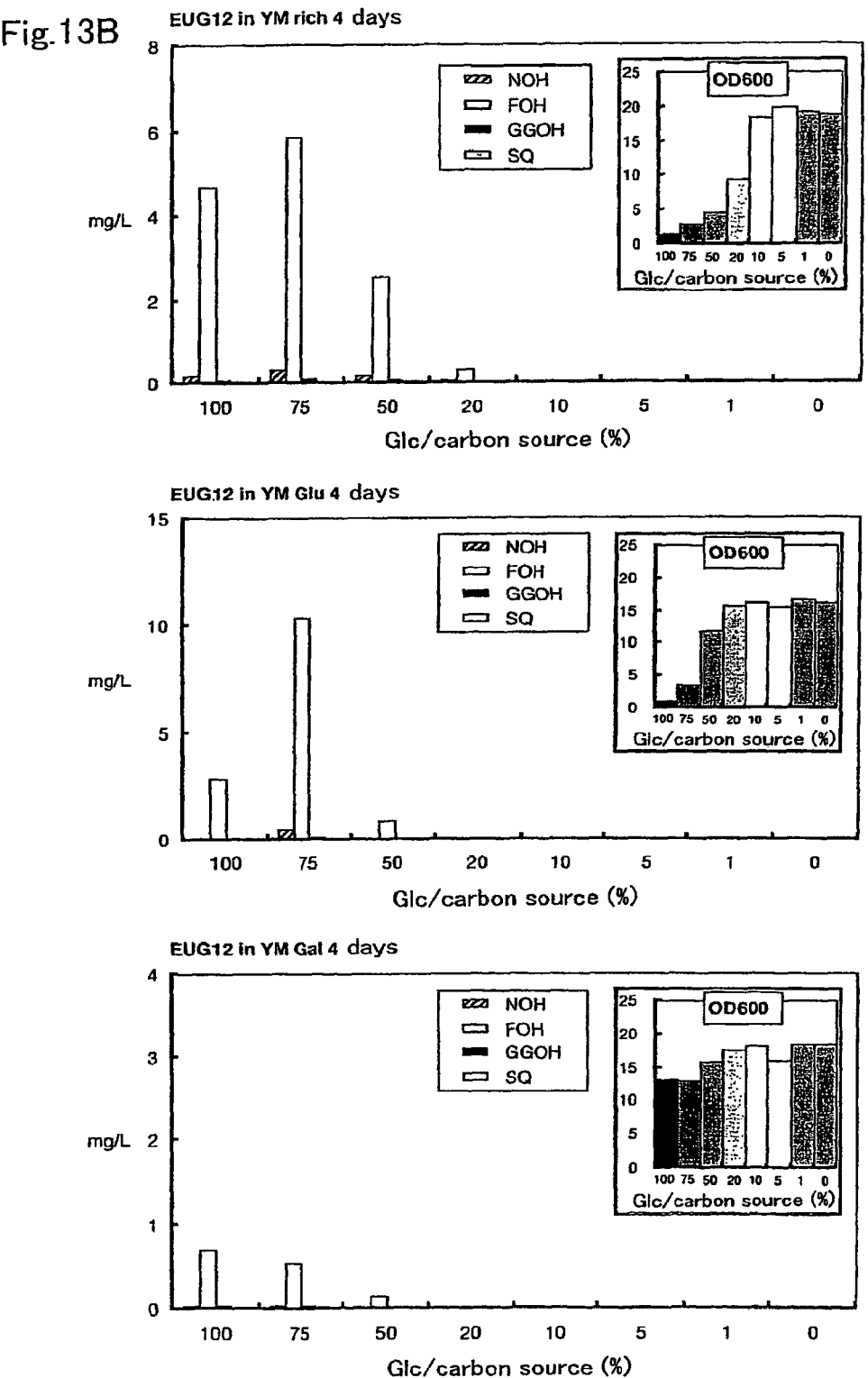
FIG. 13B presents graphs showing the prenyl alcohol production of EUG12 cultured in media with varied initial sugar concentration/composition.
Figure 13C:
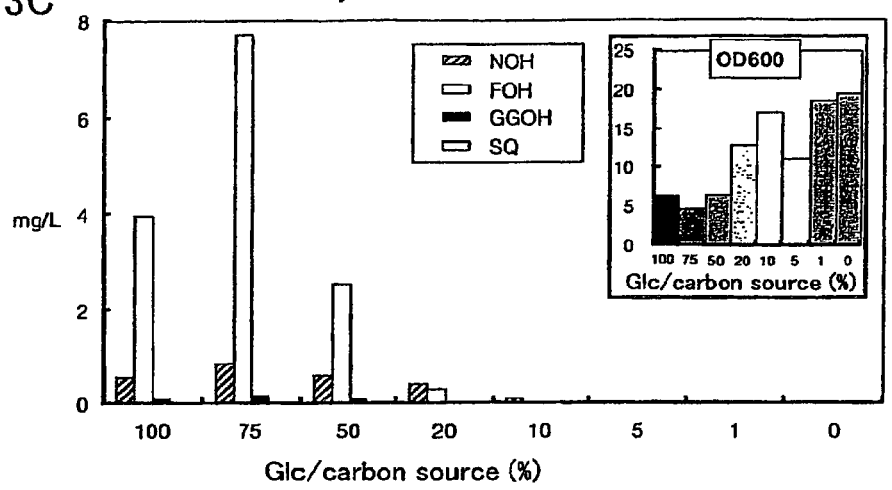
FIG. 13C presents graphs showing the prenyl alcohol production of EUG12 cultured in media with varied initial sugar concentration/composition.
Figure 13C:
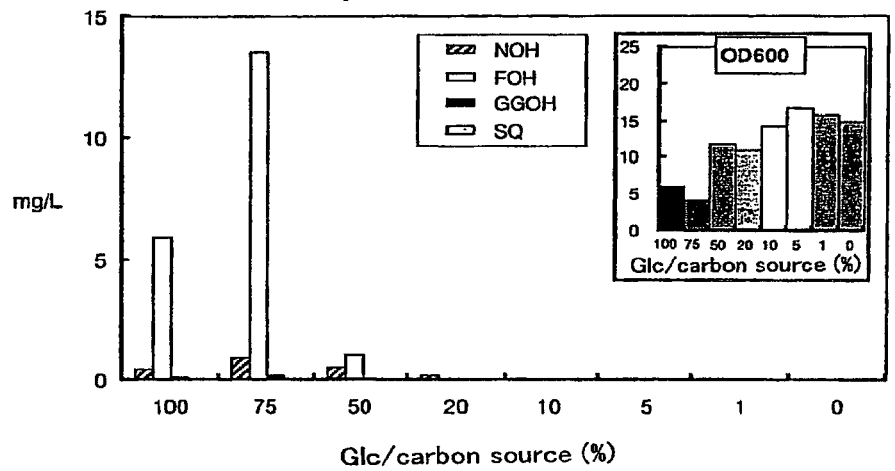
Figure 13C:
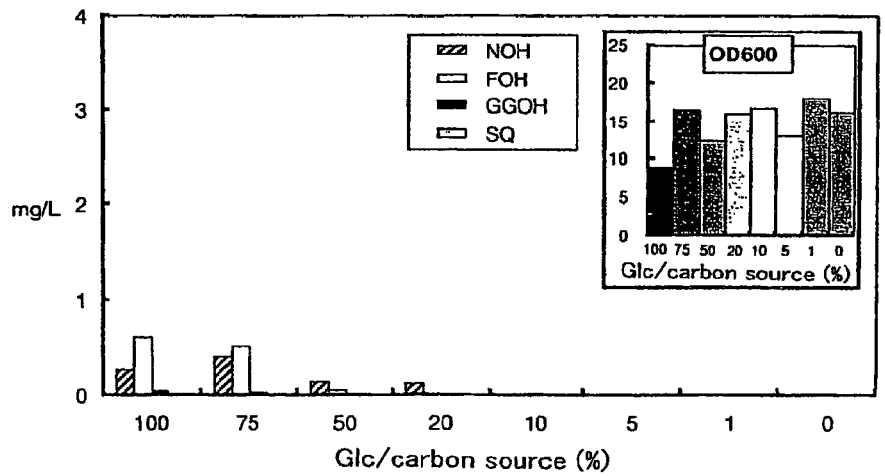

Subsequently, out of EUG1 through EUG70, those clones that exhibited a decrease in growth rate in SD medium were cultured and their prenyl alcohol yields were compared (FIGS. 7-11). With respect to the production of FOH, EUG5 exhibited a higher yield (8.5 mg/L) among A451-derived strains (FIG. 7); EUG12 exhibited a higher yield (17.8 mg/L) among YPH499-derived stains (FIG. 8); and EUG24 and EUG27 exhibited higher yields (17.9 mg/L and 10.5 mg/L, respectively) among other strains (FIG. 9). Among W303-1A-derived clones (FIG. 10A-D) and W303-1B-derived clones (FIG. 11A-B), the strains indicated in the respective Figures exhibited higher yields than other strains.

W303-1A-derived clones:

EUG31 (16 mg/L), EUG33 (41 mg/L), EUG35 (38 mg/L), EUG36 (43 mg/L), EUG38 (17 mg/L), EUG39 (24 mg/L), EUG42 (24 mg/L), EUG44 (21 mg/L), EUG49 (21 mg/L)

W303-1B-derived clones:
EUG51 (28 mg/L), EUG56 (16 mg/L), EUG59 (37 mg/L), EUG61 (27 mg/L), EUG63 (16 mg/L), EUG64 (38 mg/L)

(4-2) Difference in Productivity Depending on Changes in Glucose Concentration

Figure 14B:
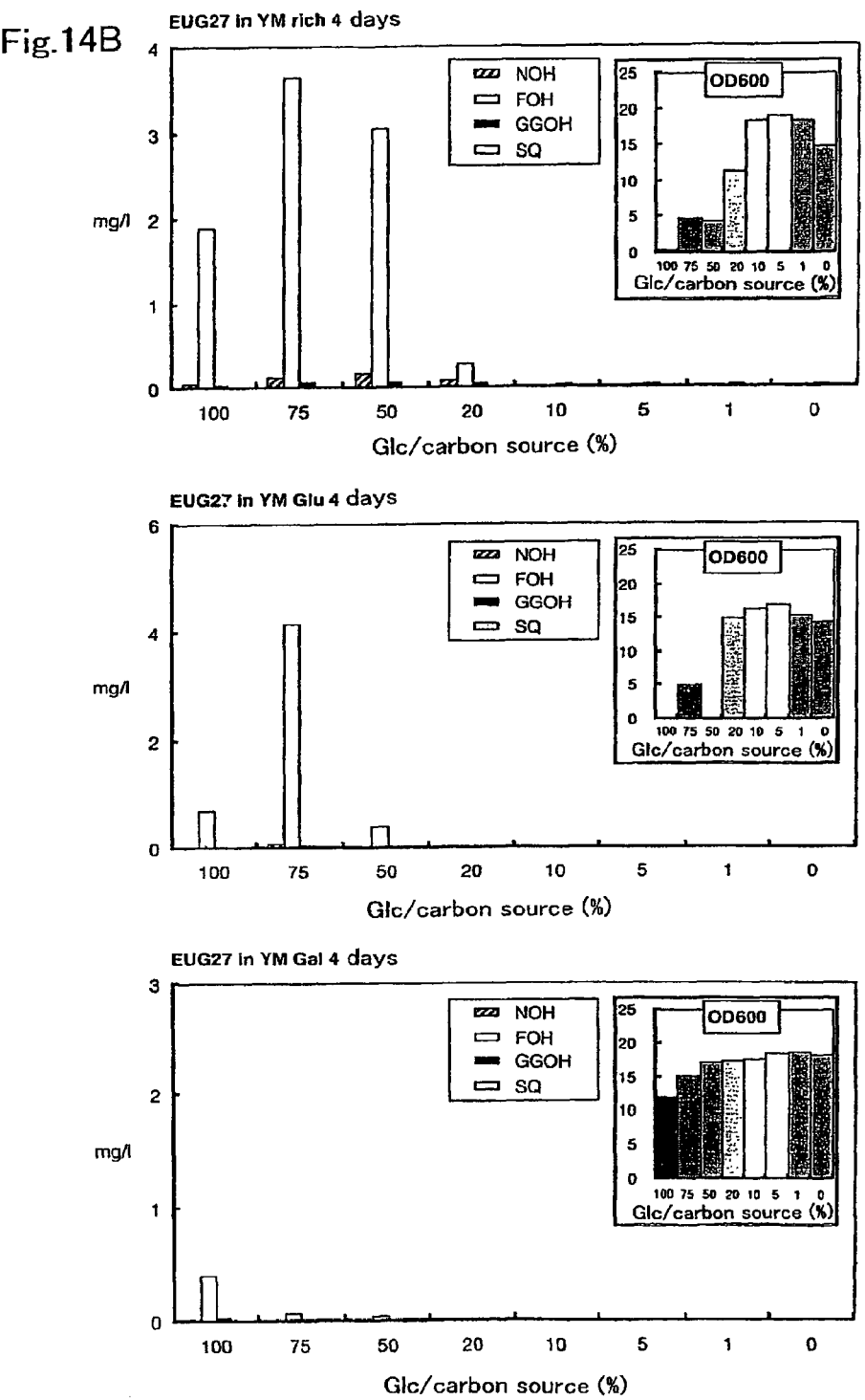
FIG. 14B presents graphs showing the prenyl alcohol production of EUG27 cultured in media with varied initial sugar concentration/composition.
Figure 14C:
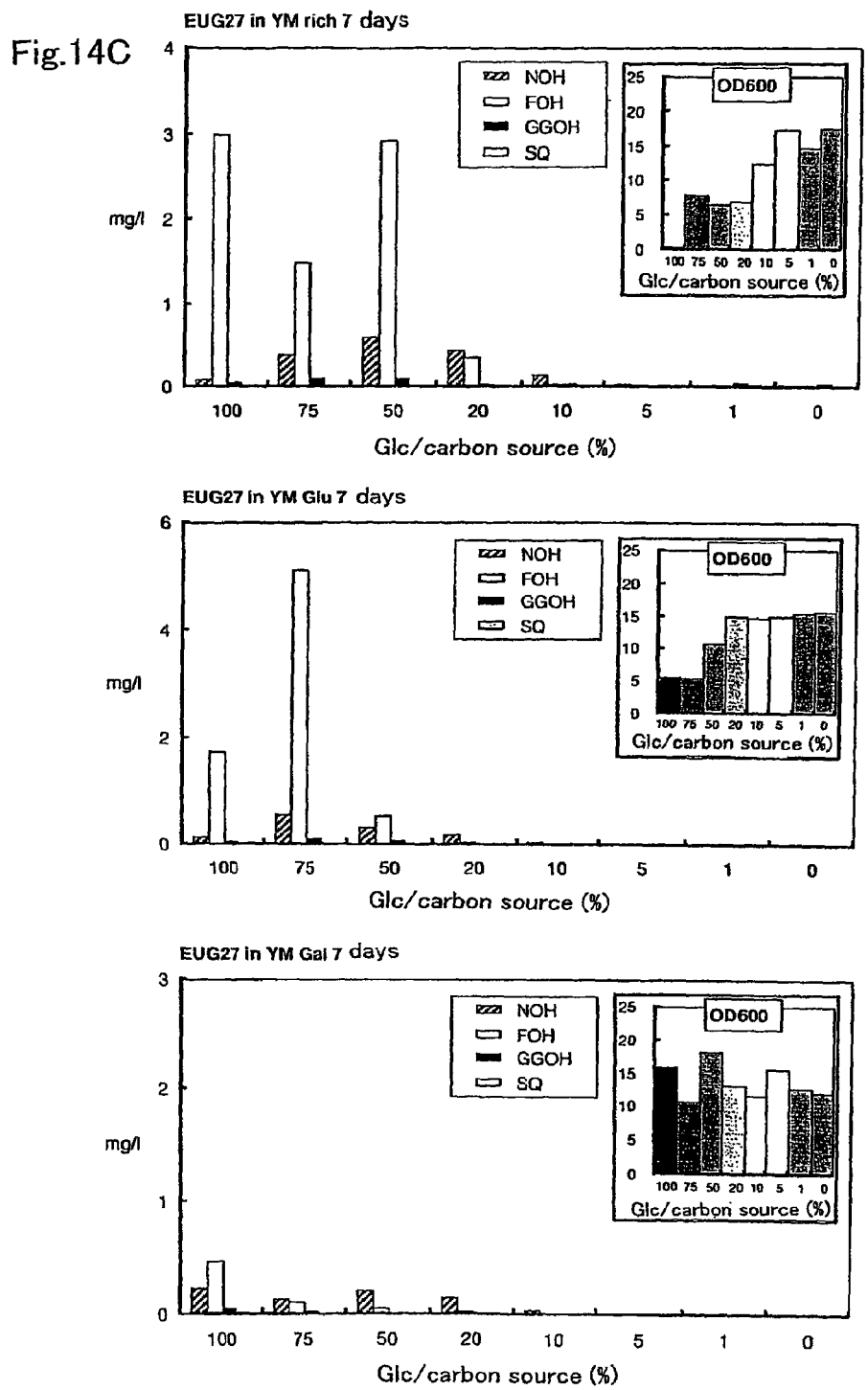
FIG. 14C presents graphs showing the prenyl alcohol production of EUG27 cultured in media with varied initial sugar concentration/composition.
Figure 15A:
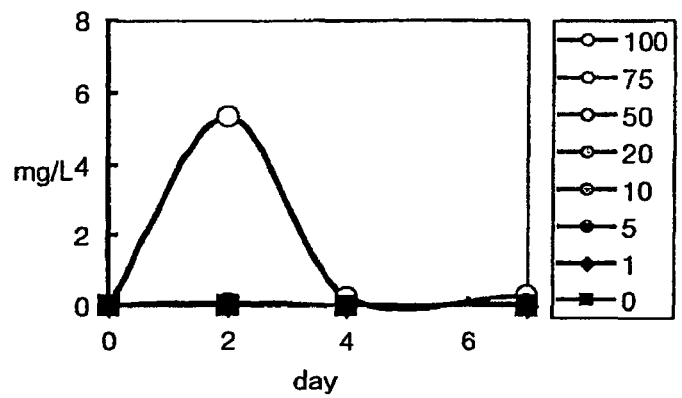
FIG. 15A presents graphs showing the production of FOH by EUG8, EUG12 and EUG27 cultured in media with varied initial sugar concentration/composition.
Figure 15A:
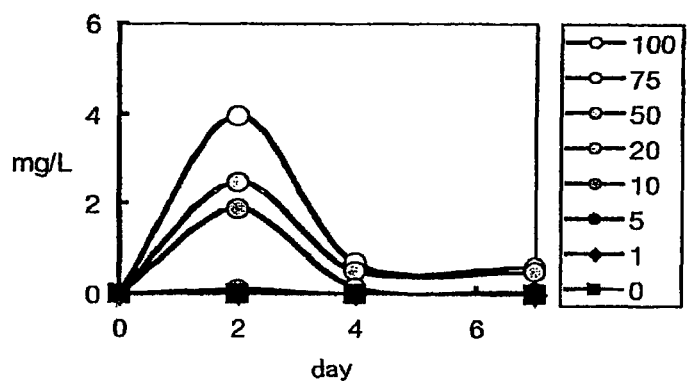
Figure 15A:
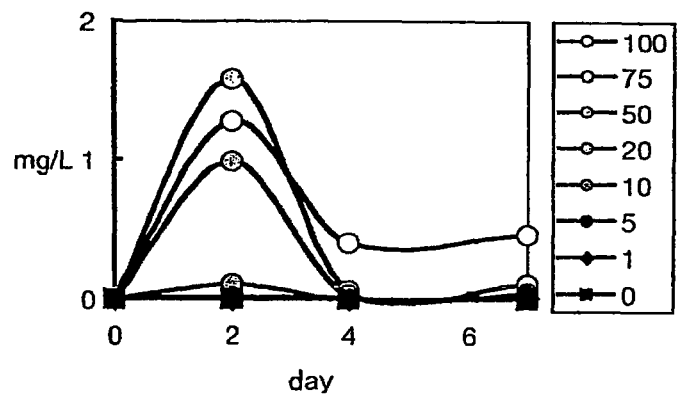
Figure 15B:
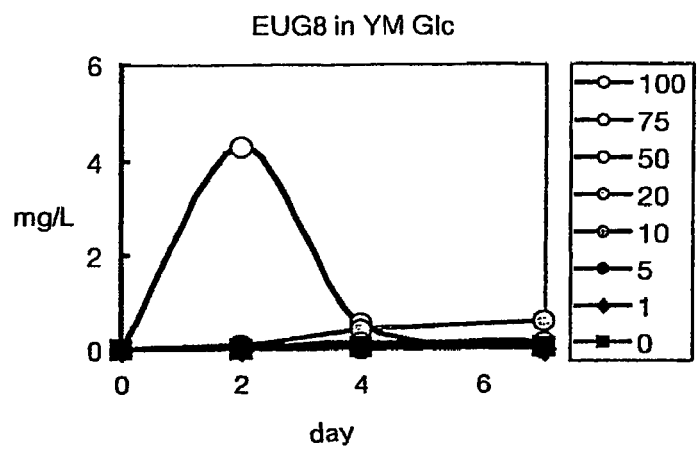
FIG. 15B presents graphs showing the production of FOH by EUG8, EUG 12 and EUG27 cultured in media with varied initial sugar concentration/composition.
Figure 15B:
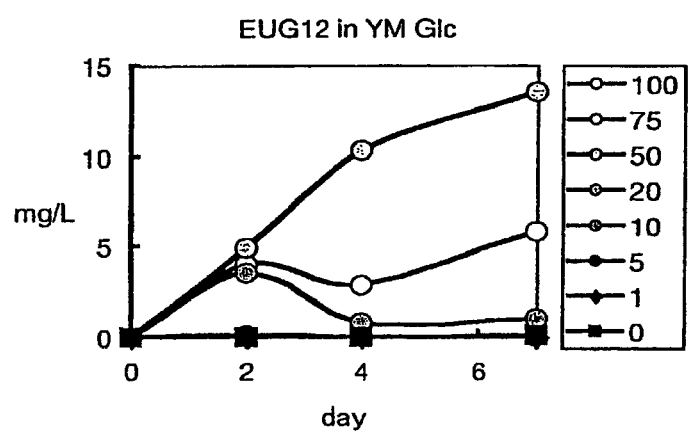
Figure 15B:
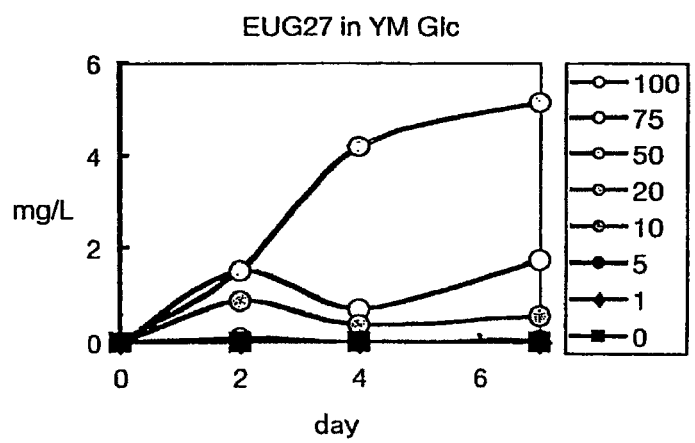
Figure 16A:
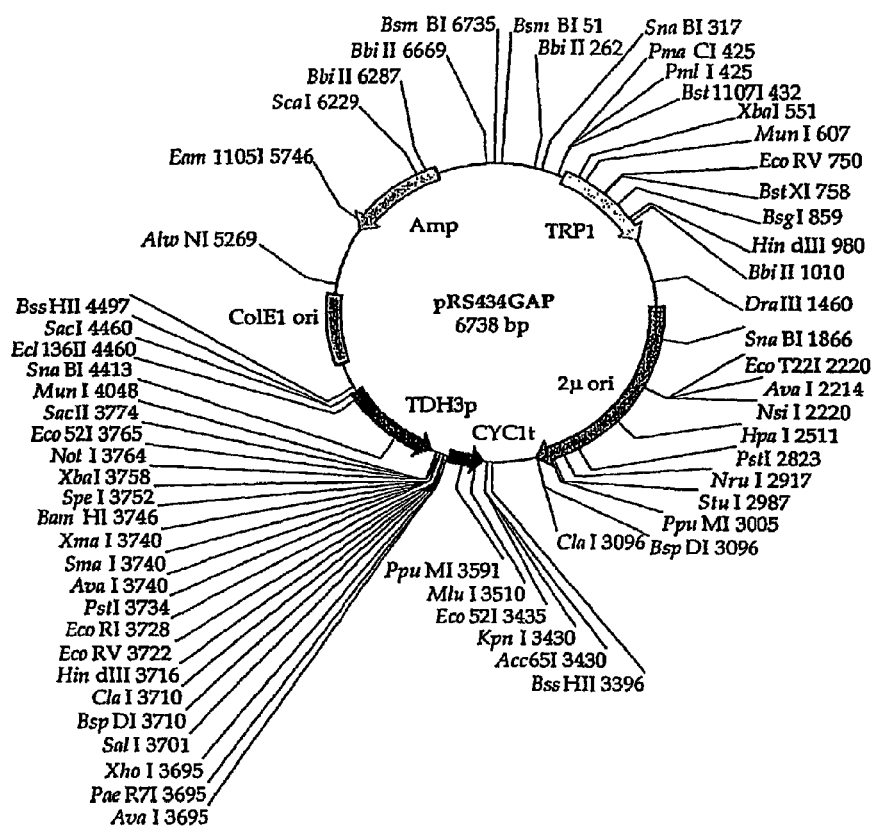
FIG. 16A is a diagram showing plasmid pRS434GAP.
Figure 16B:
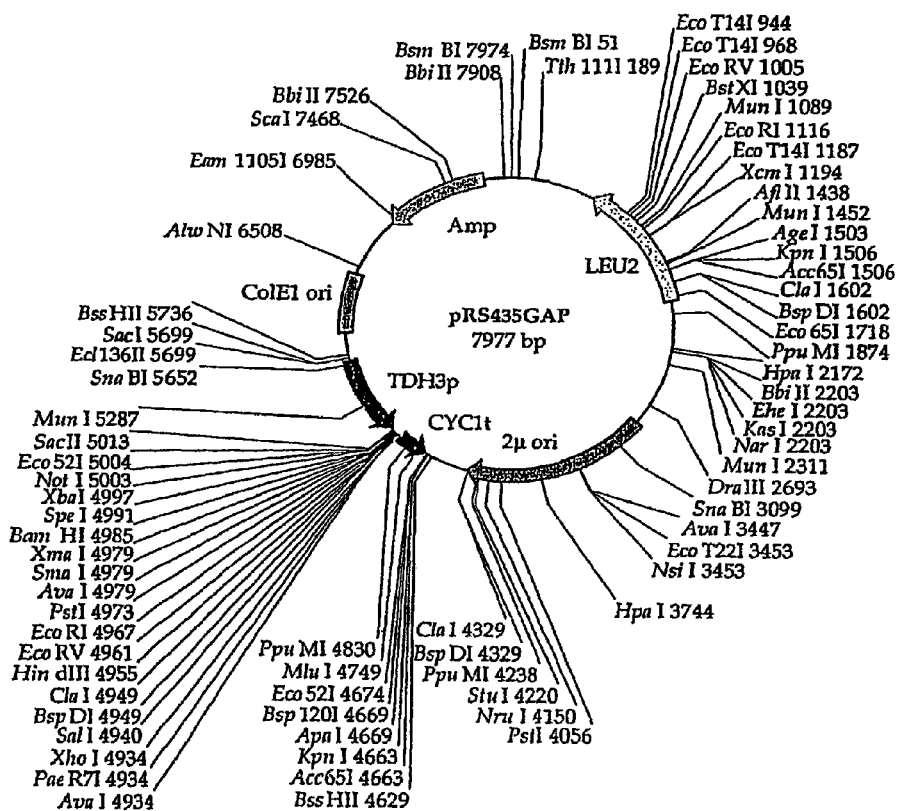
FIG. 16B is a diagram showing plasmid pRS435GAP.
Figure 16C:
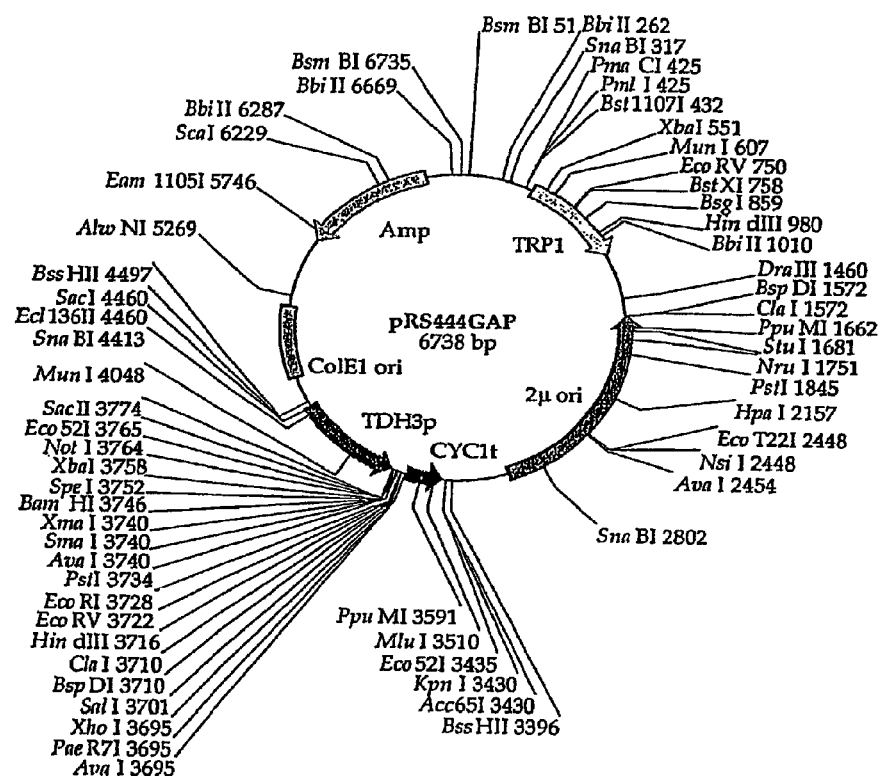
FIG. 16C is a diagram showing plasmid pRS444GAP.
Figure 16D:
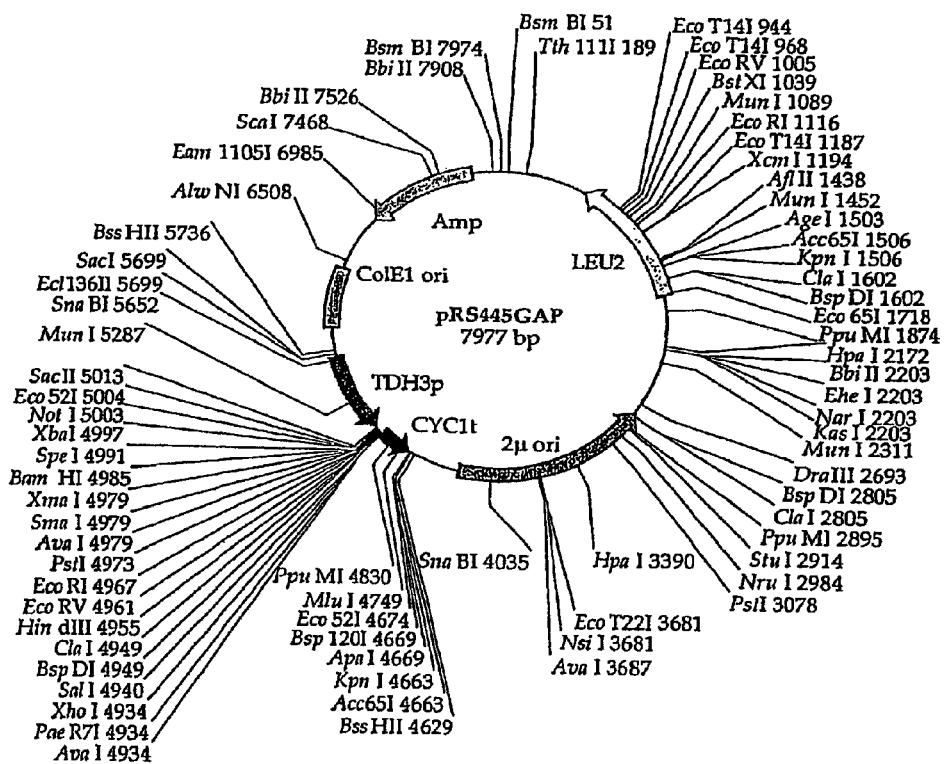
FIG. 16D is a diagram showing plasmid pRS445GAP.

FIGS. 12 to 14 show the yields of prenyl alcohols when EUG8, EUG12 and EUG27 were cultured under varied Glc and Gal concentrations. Although FOH was the only product in most cases, it can be seen that production profile is different between A451-derived EUG8 (FIG. 12A-C) and YPH-derived EUG12 (FIG. 13A-C) and EUG27 (FIG. 14A-C). EUG8 exhibited the highest yield when the sugar composition in the initial medium was 100% Glc under any of the conditions used. On the other hand, EUG12 and EUG27 exhibited good yields when the sugar composition in the initial medium was 75% Glc. Further, EUG12 and EUG27 in FOH well under such conditions that the sugar composition in the initial medium was 75% Glc (in 1% (w/v) total sugar) and that Glc was added further to the medium on day 2 to make the final sugar concentration 5% (w/v). It is believed that the transcription of ERG9 minimum to cell growth was carried out under the condition of 75% Glc in the sugar composition of the initial medium, leading to an appropriate balance between cell growth and FOH. When strains were cultured in YM Gal medium, a decrease in FOH production is observed on day 4 and thereafter. It is believed that such a decrease occurs because FOH in the medium is assimilated as the intracellular synthesis of Erg is activated as a result of the promotion of ERG9 transcription by the addition of Gal. The results of FOH production summarized in FIG. 15A-C would help understanding of the difference in production profile between A451-derived EUG8 and YPH-derived EUG12 and EUG27. Under the "conditions that the sugar composition in the initial medium was 75% Glc (1% (w/v) sugar) and that Glc was added further to the medium on day 2 to make the final sugar concentration 5% (w/v)", there is almost no change in $OD_{600}$ values. However, FOH yield increased from day 2 to day 4, and from day 4 to day 7 under such conditions. Accordingly, it is believed that these cells were in a physiological state where FOH is produced without cell division. If such cells can be fixed, it will be possible to develop an efficient system for FOH production.

By the development of EUG strains described in this Example, it is possible to reduce the amount of squalene synthase gene transcript having translational activity. Different from squalene synthase genedeficient strains (such as ATCC64031) obtained by introducing mutations such as substitution, insertion or deletion into the coding region of the gene, EUG strains are capable of producing FOH (an active prenyl alcohol) through fermentation in a common medium such as YM7 without introduction of special mechanisms to complement the lethality because of the squalene synthase deficiency (e.g., addition of sterol intake ability or Erg addition). Thus, it is possible to create a system for FOH production using EUG strains. Further, since EUG strains were created from conventional hosts for recombination, they can be genetically modified further easily (unlike strains such as ATCC64031) and are applicable to the development of strains with still higher productivity.

Example 3

Construction of Expression Vectors (1) *E. coli-S. cerevisiae* Shuttle Vectors

Plasmids pRS404 and pRS405 were purchased from Stratagene. Plasmid pYES2 (FIG. 3) was purchased from Invitrogen (Carlsbad, Calif.).

(2) Genomic DNA

Genomic DNA was prepared from *S. cerevisiae* YPH499 according to the protocol attached to Dr. GenTLE™, a genomic DNA preparation kit for yeast purchased from Takara.

Plasmid DNA from *E. coli* was prepared with Wizard PureFection Plasmid DNA Purification System purchased from Promega (Madison, Wis.).

(3) Insertion of CYC1t Fragment into pRS Vectors

CYC1t (CYC1 transcription terminator) fragment was prepared by PCR. The following oligo-DNAs, XhoI-Tcyc1FW and ApaI-Tcyc1RV, were used as PCR primers. As a template, pYES2 was used.

```
XhoI-Tcyc1FW:
                                        (SEQ ID NO: 43)
5'-TGC ATC TCG AGG GCC GCA TCA TGT AAT TAG-3'

ApaI-Tcyc1RV:
                                        (SEQ ID NO: 44)
5'-CAT TAG GGC CCG GCC GCA AAT TAA AGC CTT CG-3'
```

Briefly, 50 µl of a reaction solution containing 0.1 µg of pYES2, 50 pmol of each primer DNA, 1× Pfu buffer containing $MgSO_4$ (Promega, Madison, Wis.), 10 nmol dNTPs, 1.5 units of Pfu DNA polymerase (Promega) and 1 µl of Perfect Match polymerase enhancer (Stratagene) was prepared. Following an initial denaturation of 2 min at 95° C., PCR was carried out for 30 cycles each consisting of denaturation of 45 sec at 95° C., annealing of 30 sec at 60° C., and extension of 1 min at 72° C. A final extension of 5 min at 72° C. was done. After completion of the reaction, the solution was stored at 4° C. The amplified two DNA fragments were digested with XhoI and ApaI, and subjected to agarose gel electrophoresis to purity a 260 bp DNA fragment, which was designated CYC1t-XA.

CYC1t-XA was inserted into the XhoI-ApaI site of pRS404 and pRS405 to thereby obtain pRS404Tcyc and pRS405Tcyc, respectively.

(4) Preparation of a Transcription Promoter

A DNA fragment comprising a transcription promoter was prepared by PCR using yeast genomic DNA as a template. The DNA primers used are as follows.

```
SacI-Ptdh3FW:
                                        (SEQ ID NO: 45)
5'-CAC GGA GCT CCA GTT CGA GTT TAT CAT TAT CAA-3'

SacII-Ptdh3RV:
                                        (SEQ ID NO: 46)
5'-CTC TCC GCG GTT TGT TTG TTT ATG TGT GTT TAT
TC-3'
```

As a reaction solution, a 100 µl solution containing 0.46 µg of yeast genomic DNA, 100 pmol of each primer DNA, 1×ExTaq buffer (Takara), 20 nmol dNTPs, 0.5 U of ExTaq DNA polymerase (Takara) and 1 µl of Perfect Match polymerase enhancer was prepared. Following an initial denaturation of 2 min at 95° C., PCR was carried out for 30 cycles each consisting of 45 sec at 95° C., 1 min at 60° C. and 2 min at 72° C. A final extension of 4 min at 72° C. was done. After completion of the reaction, the solution was stored at 4° C. The amplified DNA was digested with SacI and SacII, and subjected to agarose gel electrophoresis to purify a 0.7 kbp fragment. Thus, TDH3p was obtained.

(5) Preparation of 2μ DNA Replication Origin Site pYES2, which is a YEp vector, was digested with SspI and NheI. The resultant 1.5 kbp fragment containing 2μ DNA replication origin (2μ ori) was purified by agarose gel electrophoresis and then blunt-ended. This DNA fragment was designated 2μ OriSN.

(6) Preparation of YEp Expression Vectors

2μ OriSN was inserted into the NaeI site of pRS404Tcyc and pRS405Tcyc pretreated with BAP (bacterial alkaline phosphatase: Takara). The resultant plasmids were transformed into *E. coli* SURE2, and then plasmid DNA was prepared. The plasmid DNA was digested with DraIII EcoRI, HpaI or PstI; and PvuII, followed by agarose gel electrophoresis to examine the insertion and the direction of 2μ ori. The resultant pRS404Tcyc and pRS405Tcyc into which 2μ ori had been inserted in the same direction as in pYES2 were designated pRS434Tcyc2μOri and pRS435Tcyc2μOri, respectively. The resultant pRS404Tcyc and pRS405Tcyc into which 2μ ori had been inserted in the opposite direction to that in pYES2 were designated pRS444Tcyc2μOri and pRS445Tcyc2μOri, respectively.

The transcription promoter-containing fragment, i.e., TDH3p (GAPp), was inserted into the SacI-SacII site of the above-described four plasmids pRS434Tcyc2μOri, pRS435Tcyc2μOri, pRS444Tcyc2μOri and pRS445Tcyc2μOri to clone the DNA. As a result, the following plasmids were obtained: (i) pRS434GAP from pRS434Tcyc2μOri; (ii) pRS435GAP from pRS435Tcyc2μOri; (iii) pRS444GAP from pRS444Tcyc2μOri; and (iv) pRS445GAP from pRS445Tcyc2μOri (FIG. 16A-D).

(7) Introduction of YEp Expression Vectors into Yeast

Approximately 40 ng of each YEp expression vector was introduced into YPH499 using Frozen-EZ Yeast Transformation II kit (Zyrno Research, Orange, Calif.). (The procedures followed the protocol attached to the kit.) Then, colonies growing on SD-W agar plate (DOB+CMS-Trp; BIO101, Vista, Calif.) were examined. Since 1000 or more Try non-requiring colonies were observed, it was confirmed that the DNA replication site of each of the YEp expression vectors prepared functions and that each vector is retained normally in the recombinant as a plasmid.

Example 4

Cloning of IPP Biosynthetic Pathway-Related Enzyme Genes

In the cloning of genes from yeast cDNA, an *S. cerevisiae* DBY746-derived cDNA library "Quick-Clone cDNA" purchased from Clontech (Palo Alto, Calif.) was used.

(1) Cloning of Farnesyl Diphosphate Synthase Gene

*S. cerevisiae*-Derived FPP Synthase Gene ERG20:

A DNA fragment of approximately 0.9 kbp encoding *S. cerevisiae* FPP synthase gene ERG20 (SEQ ID NO: 1) was amplified by PCR (polymerase chain reaction) using the above cDNA as a template. The PCR primers used are as follows.

```
Primer 1 (SCFPS1):
                               (SEQ ID NO: 47)
5'-ATG GCT TCA GAA AAA GAA ATT AG-3'

Primer 2 (SCFPS2):
                               (SEQ ID NO: 48)
5'-CTA TTT GCT TCT CTT GTA AAC TT-3'
```

| | |
|---|---|
| 10x ExTaq buffer (Takara) | 5 μl |
| 2.5 mM dNTP mix | 4 μl |
| 5 U/μl ExTaq (Takara) | 1 μl |
| 10 pmol Primer 1 | |
| 10 pmol Primer 2 | |
| 0.5 ng cDNA | |

To give a 50 μl solution in total

The PCR was carried out in the reaction solution described above for 30 cycles each consisting of 45 sec at 94° C., 1 min at 55° C. and 2 min at 72° C. Unless otherwise indicated, PCR reactions in the following Examples were carried out under similar conditions.

The amplified fragment was purified by agarose gel electrophoresis and then cloned into pT7Blue-T (Novagen, Madison, Wis.) by T/A ligation. It was found that ERG20 was inserted in the same direction as lacZ in pT7Blue-T. The nucleotide sequence of the cloned fragment was determined and compared to the corresponding nucleotide sequence registered in SGD. As a result, no PCR errors were found in nucleotide positions 1-300 and 610-1059. The amino acid sequence encoded by ERG20 is shown in SEQ ID NO: 2.

The plasmid DNA prepared was designated pT7ERG20.

(2) Cloning of Geranylgeranyl Diphosphate Synthase Gene

*S. cerevisiae*-derived GGPP synthase gene BTS1 (SEQ ID NO: 3) was cloned as described below.

Based on information about the *S. cerevisiae*-derived GGPP synthase gene registered at the GenBank (http://www.ncbi.nlm.nih.gov/Genbanmcindex.htm/) (Accession No. (A.N.): U31632) (Y. Jiang, et al., *J. Biol. Chem.* 270 (37), 21793-21799 (1995)), a pair of primers matching the N-terminal and C-terminal of the protein encoded by the gene were designed. Using these primers and a yeast cDNA library (Clontech; No. CL7220-1) as a template, PCR was carried out.

```
N-terminal primer:
                               (SEQ ID NO: 49)
5'-ATG GAG GCC AAG ATA GAT GAG CT-3'

C-terminal primer:
                               (SEQ ID NO: 50)
5'-TCA CAA TTC GGA TAA GTG GTC TA-3'
```

The PCR was performed using Perfect Match Polymerase Enhancer for 30 cycles each consisting of denaturation of 45 sec at 94° C., annealing of 1 min at 55° C. and extension of 2 min at 72° C.

A fragment of interest (approx. 1.0 kbp) was confirmed. This fragment (BTS1) was cloned into pT7Blue T vector capable of TA cloning, followed by sequencing of the entire region of BTS1. The results revealed that the nucleotide sequence of this gene was completely identical with the corresponding nucleotide sequence registered at the GenBank. Thus, it was confirmed that this gene is the *S. cerevisiae*-derived GGPP synthase gene. The amino acid sequence encoded by BTS1 is shown in SEQ ID NO: 4.

(3) Cloning of HMG-CoA Reductase Gene

The cloning of *S. cerevisiae*-derived HMG1 gene was carried out as described below.

Based on information about *S. cerevisiae*-derived HMG1 gene (A.N.: M22002) (M. E. Basson, et al., *Mol. Cell Biol.* 8, 3797-3808 (1988): SEQ ID NO: 5) registered at the GenBank, a pair of primers were designed which match the N-terminal and the C-terminal of the protein encoded by this gene. Using these primers and the yeast cDNA library (Clontech) as a template, PCR was carried out.

```
N-terminal primer:
                                    (SEQ ID NO: 51)
5'-ATG CCG CCG CTA TTC AAG GGA CT-3'

C-terminal primer:
                                    (SEQ ID NO: 52)
5'-TTA GGA TTT AAT GCA GGT GAC GG-3'
```

The PCR was carried out using Perfect Match Polymerase Enhancer for 30 cycles each consisting of denaturation of 45 sec at 94° C., annealing of 1 min at 55° C. and extension of 2 min at 72° C.

Figures 4A, 4B:
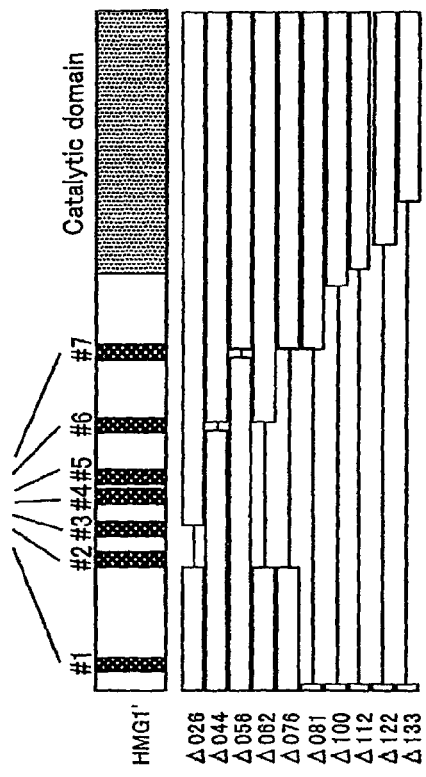
FIG. 4A shows patterns of substitution mutations.
FIG. 4B shows the construction of deletion mutants of HMG1'.

A fragment of interest (3.2 kbp) was confirmed. This fragment (HMG1) was cloned into pT7Blue T vector capable of TA cloning to thereby obtain pT7HMG1. The nucleotide sequence of the thus cloned HMG1 was determined. As a result, the nucleotide sequence as shown in SEQ ID NO: 5 and the amino acid sequence as shown in SEQ ID NO: 6 were confirmed. The thus determined nucleotide sequence was partially different from the corresponding nucleotide sequence registered at the GenBank due to PCR errors (FIG. 4A). This PCR error-containing, mutant type HMG-CoA reductase gene is designated HMG1'.

(4) Correction of PCR Errors in HMG-CoA Reductase Gene

PCR errors were corrected by subcloning the HMG1 fragment from pT7HMG1 and correcting those mutations resulting from PCR errors in the HMG1 coding region that would cause amino acid substitutions.

Briefly, the HMG1' fragment was subcloned from plasmid pT7HMG1 comprising HMG1', a PCR error type mutant of HMG-CoA reductase. Then, the amino acid substitutions resulting from the PCR errors in the coding region of HMG1 were corrected by site-directed mutagenesis to thereby prepare pALHMG106. The details of this preparation are as described below.

Plasmid pT7HMG1 was used as cloned HMG1. As a vector for introducing site-directed mutations, pALTER-1 (Promega) was purchased.

Site-directed mutagenesis was carried out according to the procedures described in "Protocols and Application Guide, 3rd edition, 1996 Promega, ISBN 1-882274-57-1" published by Promega. As oligos for introducing mutations, the following three oligos were synthesized chemically.

```
HMG1 (190-216):
5'-CCAAATAAAGACTCCAACACTCTATTT-3'    (SEQ ID NO: 53)

HMG1 (1807-1833):
5'-GAATTAGAAGCATTATTAAGTAGTGGA-3'    (SEQ ID NO: 54)

HMG1 (2713-2739):
5'-GGATTTAACGCACATGCAGCTAATTTA-3'    (SEQ ID NO: 55)
```

First, pT7HMG1 was digested with SmaI, ApaLI and SalI, followed by preparation of a 3.2 kbp HMG1 fragment by agarose gel electrophoresis. This fragment was inserted into the SmaI-SalI site of pALTER-1 to prepare pALHMG1. After denaturation of this plasmid with alkali, the above-described oligos for introducing mutations, Amp repair oligo (Promega) as repair oligos, and Tet knockout oligo (Promega) as knockout oligos were annealed thereto. The resultant plasmid was introduced into *E. Coli* ES1301 (Promega). Transformants retaining those plasmids into which site-directed mutations had been introduced were selected and cultured with 125 µg/ml of ampicillin to prepare plasmid DNA. The nucleotide sequence of the resultant plasmid DNA was examined with primers having the sequences as shown below. The results revealed that all the sequences corresponding to HMG1 (190-216), HMG1 (1807-1833) and HMG1 (2713-2739) were corrected so that they had the sequences of these oligonucleotides (SEQ ID NO: 13). The amino acid sequence encoded by the corrected nucleotide sequence (SEQ ID NO: 14) was consistent with the amino acid sequence encoded by HMG1' (SEQ ID NO: 12) (silent mutations).

```
HMG1 (558-532):
5'-GTCTGCTTGGGTTACATTTTCTGAAAA-3'    (SEQ ID NO: 56)

HMG1 (1573-1599):
5'-CATACCAGTTATACTGCAGACCAATTG-3'    (SEQ ID NO: 57)

HMG1 (2458-2484):
5'-GAATACTCATTAAAGCAAATGGTAGAA-3'    (SEQ ID NO: 58)
```

Figure 17:
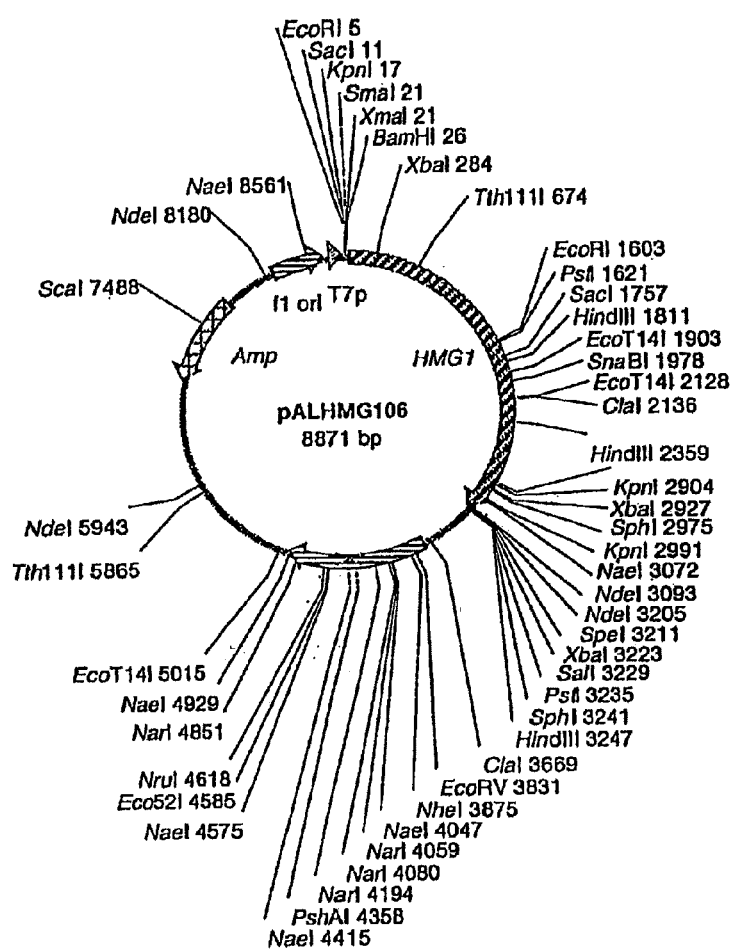
FIG. 17 is a physical map of plasmid pALHMG106.

The plasmid where the sequence of the HMG1 coding region had been corrected was designated pALHMG106 (FIG. 17).

(5) Cloning of Diphosphomevalonate Decarboxylase Gene

A fragment of approx. 1.2 kbp encoding *S. cerevisiae*-derived diphosphomevalonate decarboxylase gene ERG19 (MVD1) (SEQ ID NO: 7) was amplified by PCR using cDNA as a template. The PCR primers used are as follows.

```
Primer 1 (SCU-1):
                                    (SEQ ID NO: 59)
5'-AAC TGC AGA TGA CCG TTT ACA CAG CAT CCG T-3'

Primer 2 (SCU-2):
                                    (SEQ ID NO: 60)
5'-CGG AAT TCT TAT TCC TTT GGT AGA CCA GTC T-3'

(Restriction enzyme recognition sites are under-
lined.)
```

The PCR fragment was digested with PstI and EcoRI, purified by agarose gel electrophoresis, and cloned into the PstI-EcoRI site of pT7Blue. By these procedures, ERG19 (MVD1) was inserted into pT7Blue in the direction opposite to that of lacZ in this plasmid. The nucleotide sequence of the cloned fragment was determined and compared to the corresponding sequence registered in SGD. As a result, no PCR error was found. The amino acid sequence encoded by ERG19 is shown in SEQ ID NO: 8.

The plasmid DNA prepared was designated pT7ERG19.

Example 5

Cloning of Mutant Genes

Figure 3:
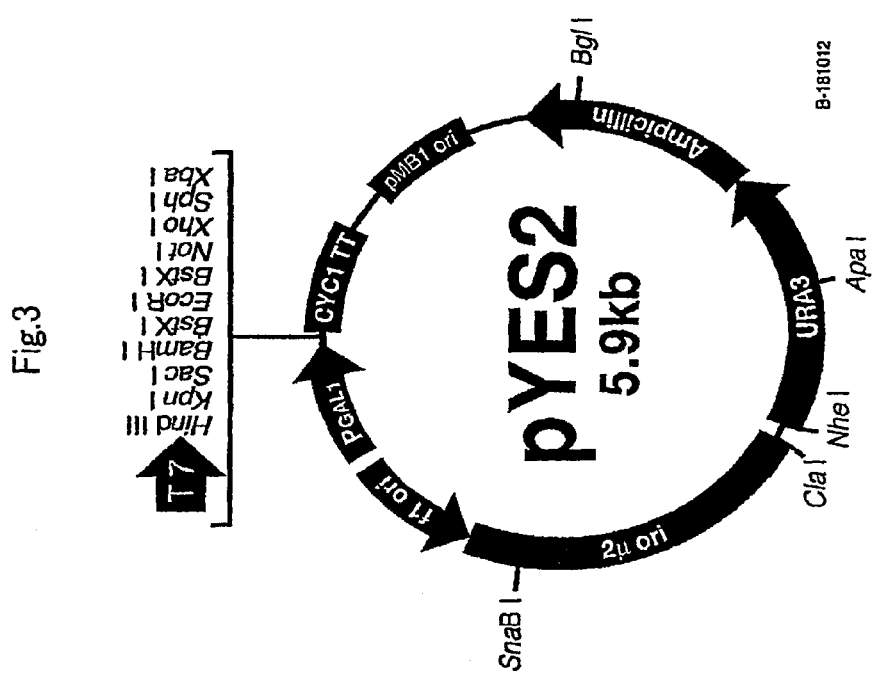
FIG. 3 is a physical map of an expression shuttle vector pYES2.

Cloning of Deletion Mutants of HMG-CoA Reductase Gene:

pT7HMG1 prepared in (3) in Example 4 was digested with BamHI, SalI and ScaI to obtain the HMG1' gene having PCR errors. This gene was introduced into the BamHI-XhoI site of pYES2 (Invitrogen, Carlsbad, Calif.) to thereby obtain a recombinant vector pYES-HMG1. The nucleotide sequence within the vector was confirmed to be the nucleotide sequence of SEQ ID NO: 9. pYES is a shuttle vector for expression in yeast having the ori of yeast 2 μm DNA as a replication origin and GAL1 promoter inducible by galactose (FIG. 3).

In order to prepare deletion mutants of HMG-CoA reductase gene having deletion of regions corresponding to transmembrane domains, PCR was carried out using the vector pYES-HMG1 prepared above as a template to thereby generate DNA fragments in which a part of the HMG1 coding region is deleted. The resultant fragment was blunt-ended with Klenow enzyme, circularized by self-ligation, and transformed into E. coli JM109. Then, plasmid DNA was prepared. Synthetic DNA sequences used as primers and their combinations are shown in Table 1.

For each of the plasmid DNA obtained, it was confirmed with 373A DNA sequencer (Perlin Elmer, Foster City, Calif.) that there was no shift in the reading frame of amino acids between the upstream and downstream of the deleted region in HMG1, and that there was no amino acid substitution resulting from PCR errors around the junction site. As a result, the following plasmids were obtained which have no amino acid substitution resulting from PCR errors around the junction site and in which a part of the gene could be deleted without any shift in the reading frame. Deletion mutants of HMG1 gene are expressed as, e.g., "Δ02y" according to the deletion pattern (where y represents a working number that may be any figure), and a pYES2 vector comprising Δ02y is expressed as, e.g., pYHMG026. (This expression method is also applied to other deletion mutants.)

HMG1Δ026: SEQ ID NO: 15
HMG1Δ044: SEQ ID NO: 16
HMG1Δ056: SEQ ID NO: 17
HMG1Δ062: SEQ ID NO: 18
HMG1Δ076: SEQ ID NO: 19
HMG1Δ081: SEQ ID NO: 20
HMG1Δ100: SEQ ID NO: 21
HMG1Δ112: SEQ ID NO: 22
HMG1Δ122: SEQ ID NO: 23
HMG1Δ133: SEQ ID NO: 24
Plasmids: pYHMG026, pYHMG027, pYHMG044, pYHMG045, pYHMG059, pYHMG062, pYHMG063, pYHMG065, pYHMG076, pYHMG081, pYHMG083, pYHMG085, pYHMG094, pYHMG100, pYHMG106, pYHMG107, pYHMG108, pYHMG109, pYHMG112, pYHMG122, pYHMG123, pYHMG125, pYHMG133 and pYHMG134

Example 6

Subcloning of Genes

In this Example, pRS vectors prepared in Example 3 were used that are E. coli-S. cerevisiae YEp shuttle vectors having a constitutive promoter.
(1) Subcloning of FPP Synthase Gene
S. cerevisiae-Derived FPP Synthase Gene ERG20:
pT7ER20 described in (1) in Example 4 was digested with XbaI and BamHI, and subjected to agarose gel electrophoresis to thereby purify a 1.1 kbp fragment of ERG20. This fragment was inserted into the XbaI-BamHI site of pRS435GAP and pRS445GAP to obtain pRS435GAP-ERG20 and pRS445GAP-ERG20, respectively.
(2) Subcloning of GGPP Synthase Gene or Mutants Thereof
S. cerevisiae-Derived GGPP Synthase Gene BTS1:
The pT7Blue T vector described in (2) in Example 4 was digested with BamHI and SalI to obtain BTS1 fragment, which was then introduced into the BamHI-XhoI site of pYES2 (Invitrogen). The resultant recombinant vector was designated pYESGGPS.

pYESGGPS was digested with BamHI and MluI, and subjected to agarose gel electrophoresis to purify a 1.3 kbp fragment. This fragment was inserted into the BamHI-MluI site of pRS435GAP and pRS445GAP to obtain pRS435GAP-BTS1 and pRS445GAP-BTS1, respectively.
(3) Subcloning of HMG-CoA Reductase Gene or Mutants Thereof
pALHMG106 (FIG. 17) described in (4) in Example 4 was digested with SmaI and SalI, and subjected to agarose gel electrophoresis to purify a 3.2 kbp fragment encoding the PCR error-corrected HMG1 gene. This fragment was inserted into the SmaI-SalI site of pRS434GAP and pRS444GAP. Physical maps of the HMG1-subcloned plasmids were examined by restriction enzyme mapping using XhoI, SpeI, NaeI and SphI, and by confirming the nucleotide sequences of the border regions of the inserted 3.2 kbp HMG1 gene. Then, those plasmids created exactly as designed were selected and designated pRS434GAP-HMG1 and pRS444GAP-HMG1, respectively.

Deletion mutants of HMG-CoA reductase gene were obtained from pYES2 plasmids incorporating deletion mutants of HMG1 (see Example 5) and cloned into pRS434GAP in the same manner as described in the preceding paragraph.
(4) Subcloning of Diphosphomevalonate Decarboxylase Gene
pT7ERG19 described in (5) in Example 4 was digested with BamHI and SalI, and subjected to agarose gel electrophoresis to purify an ERG19 fragment (BamHI-SalI 1.5 kbp). This fragment was inserted into the BamHI-SalI site of pRS435GAP and pRS445GAP. The ERG19-subcloned plasmids were examined by XbaI recognition site mapping, followed by selection of those plasmids created exactly as designed. Selected plasmids were designated pRS435GAP-ERG19 and pRS445GAP-ERG19, respectively.

Example 7

Prenyl Alcohol Production by Gene-Transferred EUG Strains (1) Strains Used
EUG5, EUG8, EUG12, EUG24, EUG27, EUG36 and EUG64 were used.
(2) Expression Plasmids
As diphosphomevalonate decarboxylase gene (ERG19) expression plasmid, pRS445GAP-ERG19 was used.
As HMG-CoA reductase gene (HMG1) expression plasmid, pRS434GAP-HMG1 and pRS444GAP-HMG1 were used. As deletion mutant type HMG1 expression plasmid, pRS434GAP-HMG026, pRS434GAP-HMG044, pRS434GAP-HMG056, pRS434GAP-HMG062, pRS434GAP-HMG076, pRS434GAP-HMG081, pRS434GAP-HMG100, pRS434GAP-HMG112, pRS434GAP-HMG122 and pRS434GAP-HMG133 were used. The numbers following "HMG" in these designations indicate deletion patterns (FIG. 4B). The deletion domains were deleted by PCR using the primer DNAs shown in Table 1.

As FPP synthase gene (ERG20) expression plasmid, pRS435GAP-ERG20 and pRS445GAP-ERG20 were used.
As GGPP synthase gene (BTS1) expression plasmid, pRS435GAP-BTS1 and pRS445GAP-BTS1 were used.
(3) Transformation
Transformation of the above-mentioned yeast strains was carried out using Frozen EZ yeast transformation II kit purchased from Zymo Research (Orange, Calif.) II kit. Transformants were grown on selection medium agar plates that are based on SGR medium and have appropriate auxotrophy as an indicator. For cloning, cultivation on selection medium agar plates was carried out twice.

(4) Cultivation

Transformants prepared were precultured in SGR selection medium. Then, 0.01-0.05 ml of each preculture broth was added to 1-5 ml of YM7, and cultured in a test tube 18 mm in diameter at 30° C. under reciprocal shaking at 130 rpm.

(5) Determination of Prenyl Alcohol Yields

An equal volume of methanol was added to the resultant culture broth and mixed. Approximately 2 volumes of pentane was added to this mixture, agitated vigorously and then left stationary. The resultant pentane layer was transferred into a fresh glass tube, which was then placed in a draft. Pentane was evaporated therein to condense the solute components. Subsequently, prenyl alcohols were identified and quantitatively determined by GC/MS. At that time, the degree of cell growth was also examined by diluting 50 μl of the culture broth 30-fold with water and measuring the absorbance at 600 nm. The yields of prenyl alcohols were determined with PH6890/5973 GC/MS system in the same manner as described in (1-2) in Example 2.

Figure 18A:
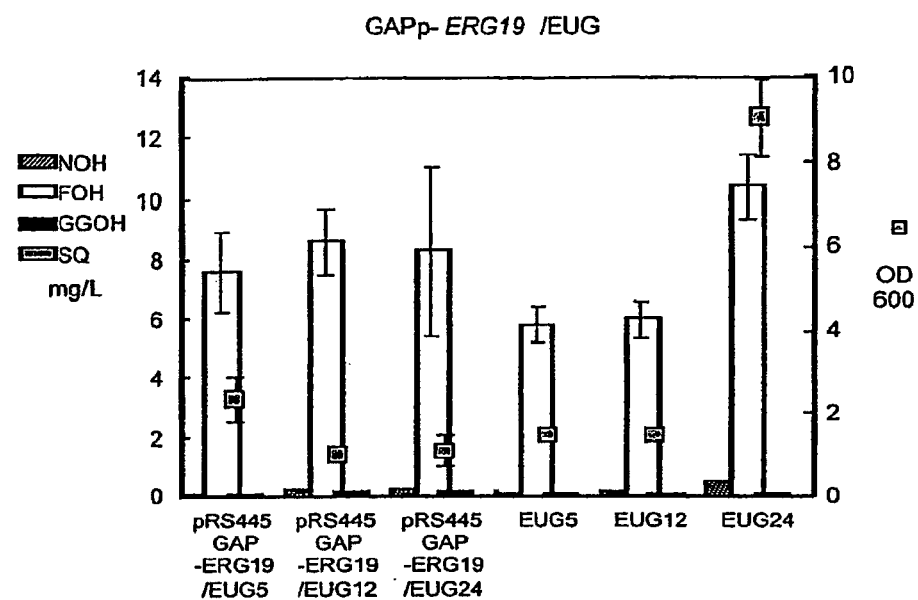
FIG. 18A is a graph showing the prenyl alcohol production of EUG strains into which ERG19 expression plasmid has been introduced.
Figure 18B:
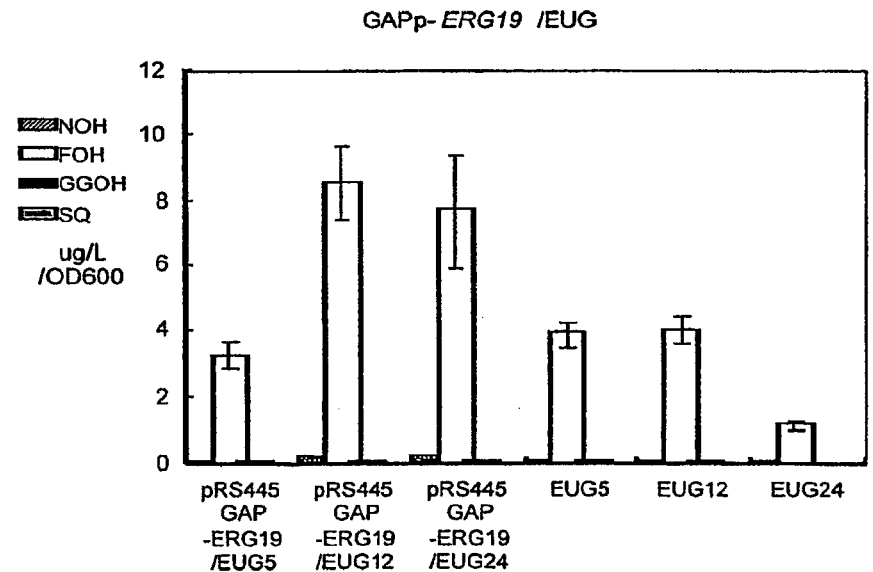
FIG. 18B is a graph showing the prenyl alcohol production of EUG strains into which ERG19 expression plasmid has been introduced.

(6) Results and Considerations (6-1) Prenyl Alcohol Production by ERG19 Expression Strains First, diphosphomevalonate decarboxylase gene ERG19 expression plasmid was introduced into EUG strains. pRS445GAP-ERG19 was introduced into A451-derived EUG5, YPH499-derived EUG12 and YPH500-derived EUG24, followed by determination of the yields of prenyl alcohols (FIG. 18A). Although it appears that FOH production is not significantly improved in any of the recombinant strains tested, FOH production efficiency is increased 2- to several-fold in the recombinants created from YPH-derived EUG12 and EUG24 when their FOH yields per $OD_{600}$ value of the culture broth are compared (FIG. 18B). Thus, it was demonstrated that, if a mutant cell of the invention capable of reducing an amount of squalene synthase gene transcript having translational activity without complete or partial deletion of its squalene synthase gene is used as a host, it can produce FOH efficiently by enhancement of ERG19 expression even in such environments where the number of cells is small.

(6-2) Prenyl Alcohol Production by HMG1 or HMG1Δ Expression Strains

Figure 19A:
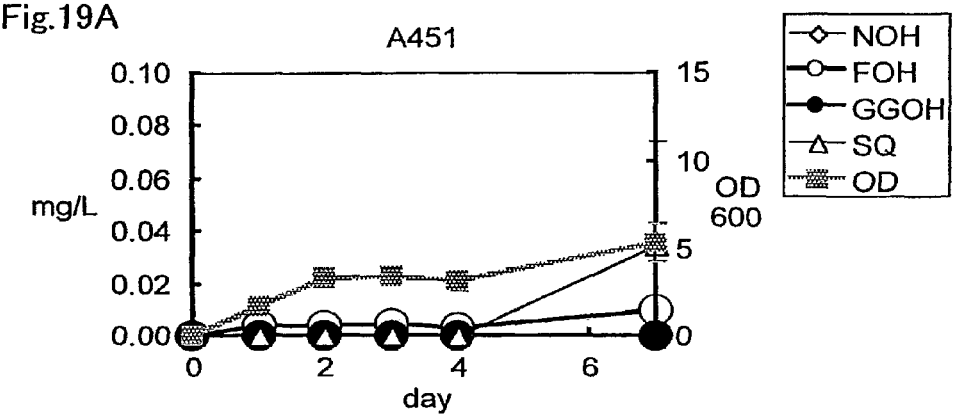
FIG. 19A is a graph showing the prenyl alcohol production of A451.
Figure 19B:
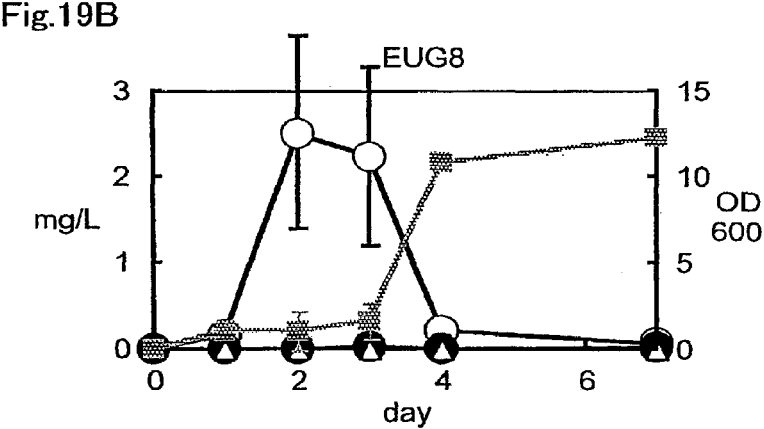
FIG. 19B is a graph showing the prenyl alcohol production of EUG8.
Figure 20A:
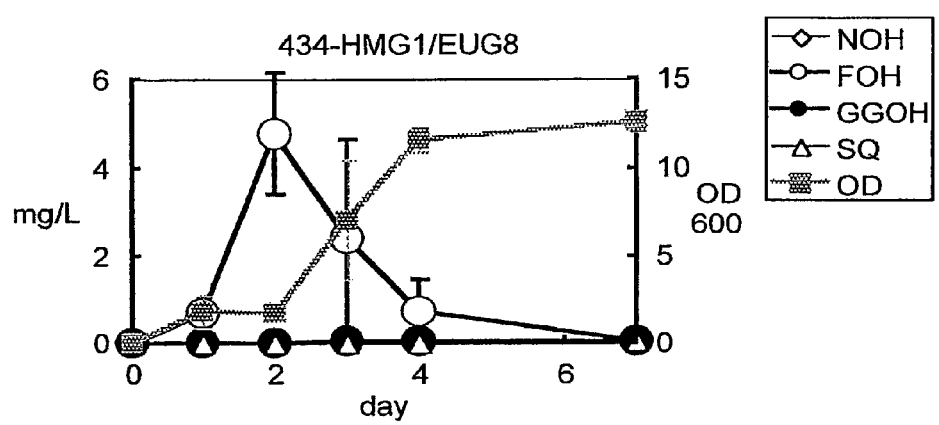
FIG. 20A is a graph showing the prenyl alcohol production of EUG8 when pRS434GAP-HMG1 has been introduced thereinto.
Figure 20B:
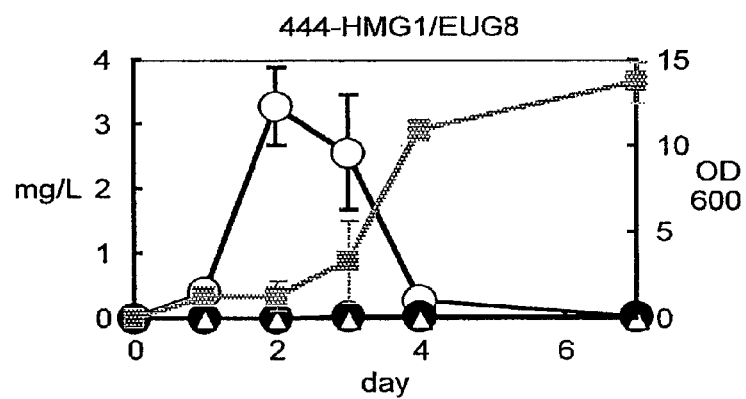
FIG. 20B is a graph showing the prenyl alcohol production of EUG8 when rpRS444GAP-HMG1 has been introduced thereinto.

First, the prenyl alcohol yields of each 5 colonies of A451 and A451-derived EUG8 are shown in FIG. 19A and FIG. 19B, respectively. EUG8, the host, produced 2.5 mg/L of FOH on the average (3.3 mg/L at the maximum) when cultured for 2 days. Each 5 colonies of pRS434GAP-HMG1/EUG8 (FIG. 20A) and pRS444GAP-HMG1/EUG8 (FIG. 20B) were cultured, and mean values of their prenyl alcohol yields and standard deviations were recorded in graphs. They produced FOH at 4.8 mg/L on the average (6.7 mg/L at the maximum) and at 3.5 mg/L on the average (4.0 mg/L at the maximum) when cultured for 2 days, respectively. It was found that when EUG8 is used as a host, the improvement effect on prenyl alcohol productivity by the expression of HMG1 gene is more excellent than when A451 is used as a host.

Figure 21:
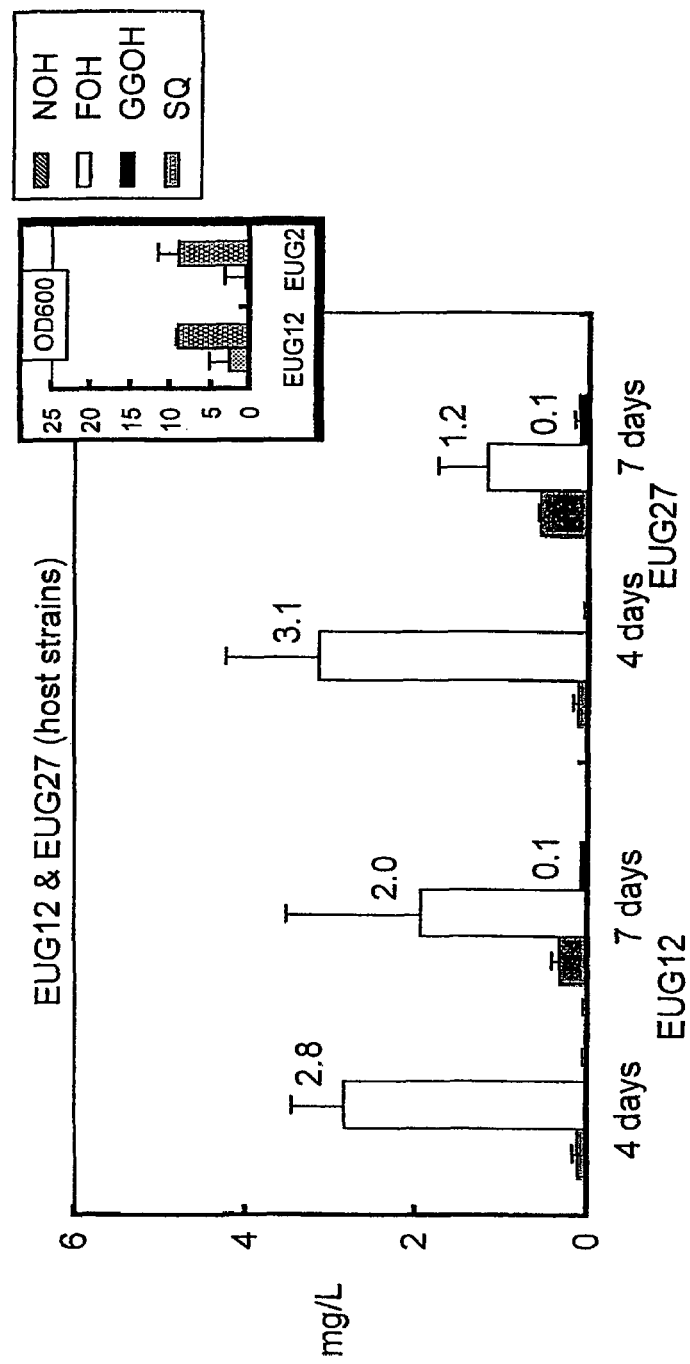
FIG. 21 is a graph showing the prenyl alcohol production of EUG12 and EUG27.
Figure 22A:
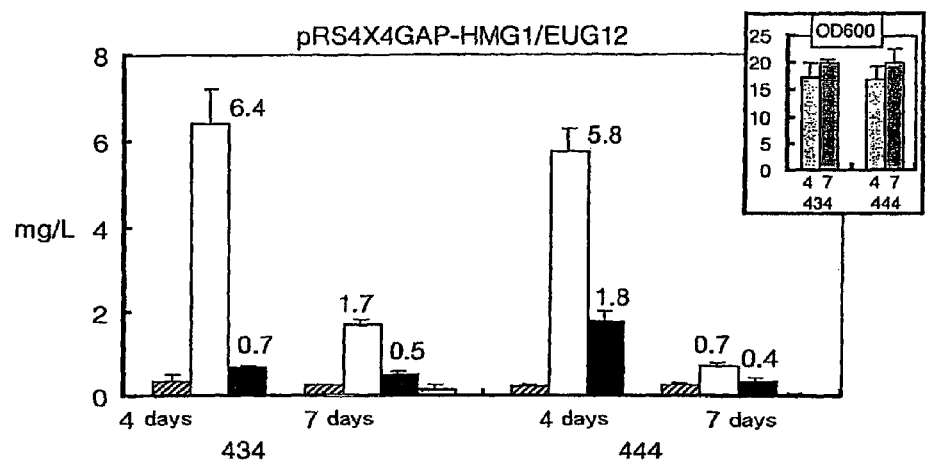
FIG. 22A is a graph showing the prenyl alcohol production of EUG12 when pRS434GGAP-HMG1 or pRS444GAP-HMG1 has been introduced thereinto.
Figure 22B:
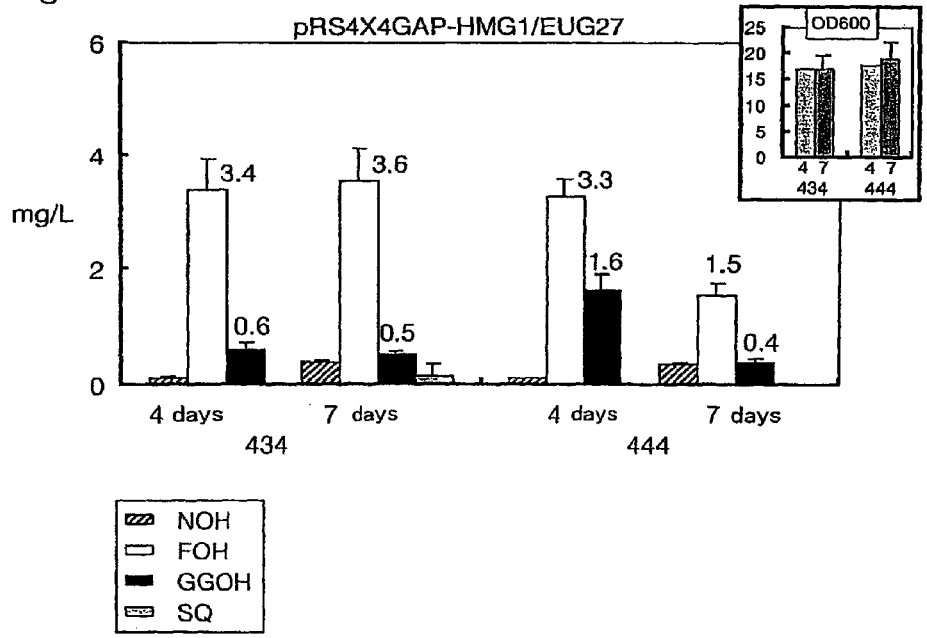
FIG. 22B is a graph showing the prenyl alcohol production of EUG27 when pRS434GGAP-HMG1 or pRS444GAP-HMG1 has been introduced thereinto.

Subsequently, the effect of enhancement of HMG1 gene expression upon YPH499-derived EUG12 and YPH500-derived EUG27 was examined. As already reported in Japanese Unexamined Patent Publication 5-192184 and by Donald et al., (1997) *Appl. Environ. Microbiol.* 63, 3341-3344, HMG1-transferred YPH499 or YPH500 only shows an increase in SQ production but produces little prenyl alcohols. These facts were confirmed by preliminary experiments. Each 5 colonies of EUG12 and EUG27 were cultured in liquid medium, and the prenyl alcohol accumulation was determined on day 4 and day 7 of the cultivation. The results are shown in FIG. 21. The major product was FOH; NOH (which is an isomer of FOH) was produced in small amounts and GGOH was produced little. When HMG1 expression plasmid (pRS434GAP-HMG1 or pRS444GAP-HMG1) was introduced into EUG12 and EUG27, the results shown in FIG. 22 were obtained. It was remarkable that the number of cells increased as a result of partial complementarion of the erg9 phenotype by the enhancement of HMG1 expression. With respect to FOH production, the yield increased almost 2-fold in recombinants from EUG12 (FIG. 22A), whereas the yield remained on the same level in recombinants from EUG27 was used (FIG. 22B). On the other hand, GGOH production was improved in both recombinants; 2.05 mg/L of GGOH was accumulated in both of them at the maximum. With respect to GGOH production, pRS444GAP-HMG1-transferred recombinants exhibited higher effect. Thus, it was demonstrated that HMG1 gene is effective not only on FOH production but also on GGOH production when EUG12 or EUG27 is used as a host. However, the tendency that production decreases when cultured for 7 days is characteristic to EUG strains.

Figures 23A, 23B:
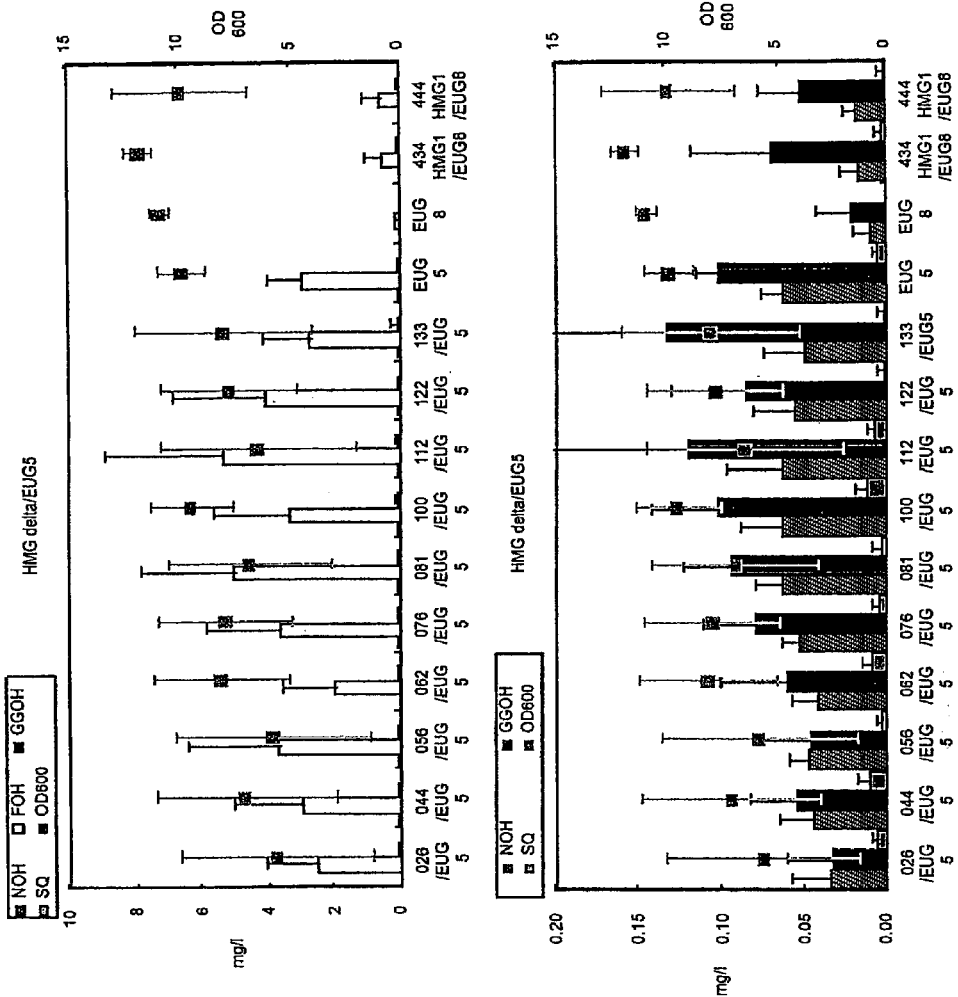
FIG. 23A is a graph showing prenyl alcohol yields of EUG5 when plasmids for expressing deletion mutants of HMG1 gene have been introduced thereinto.
FIG. 23B is a graph showing prenyl alcohol yields of EUG5 when plasmids for expressing deletion mutants of HMG1 gene have been introduced thereinto.
Figure 24A:
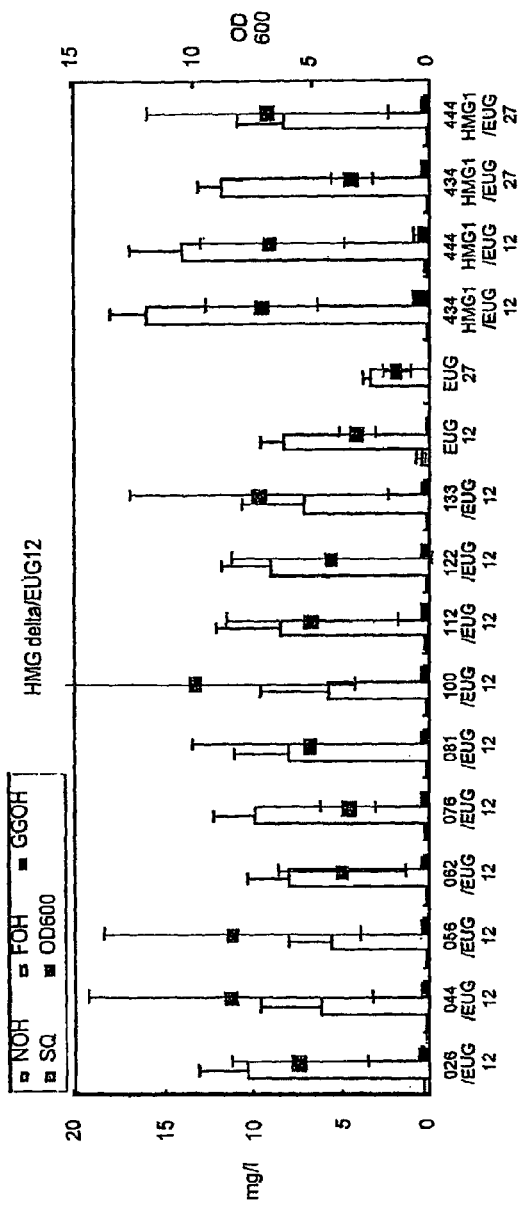
FIG. 24A is a graph showing prenyl alcohol yields of EUG12 when plasmids for expressing deletion mutants of HMG1 gene have been introduced thereinto.
Figure 24B:
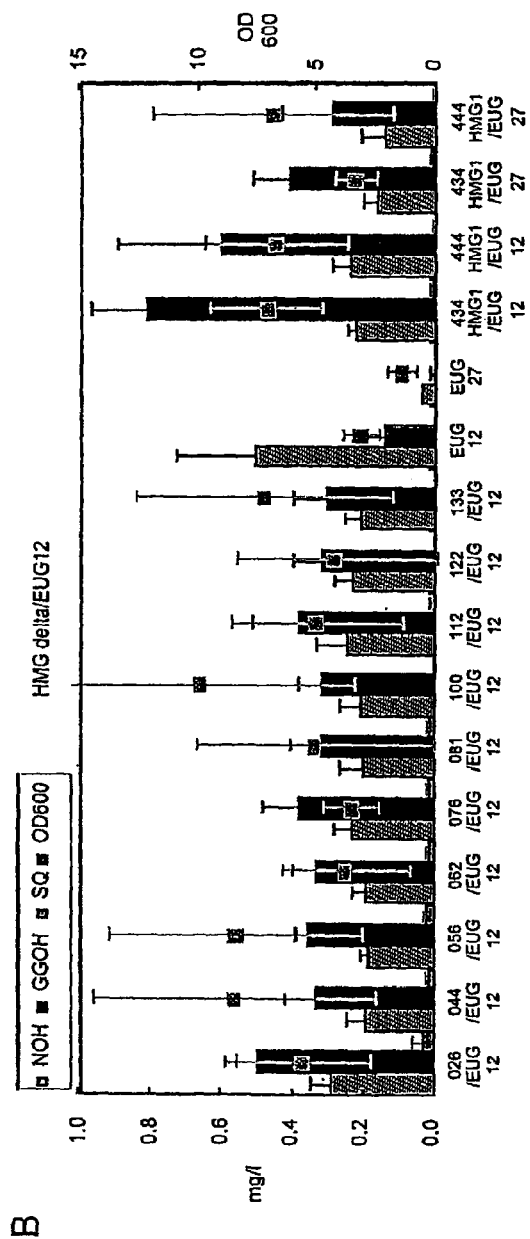
FIG. 24B is a graph showing prenyl alcohol yields of EUG12 when plasmids for expressing deletion mutants of HMG1 gene have been introduced thereinto.

FIGS. 23-24 show the results of expression of individual deletion mutants of HMG1 in EUG5 and EUG12. When EUG5 was used, improvement of productivity as a result of the expression enhancement of those deletion mutants was not so remarkable. When EUG12 was used, the expression of those deletion mutants was effective in improving GGOH productivity, though their effects were smaller than the full-length HMG1 (FIG. 24B).

(6-3) Prenyl Alcohol Production by ERG20 Expression Strains

Figure 25A:
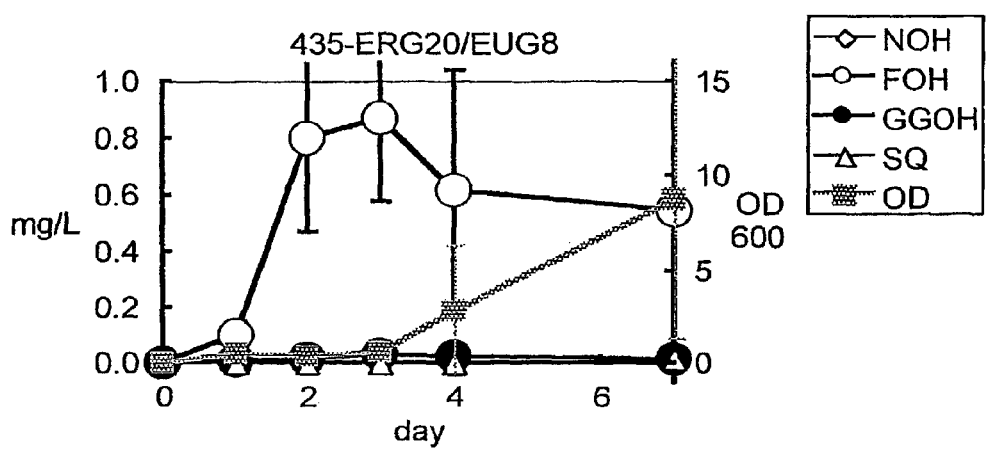
FIG. 25A is a graph showing prenyl alcohol yields of EUG8 when ERG20 gene expression plasmid has been introduced thereinto.
Figure 25B:
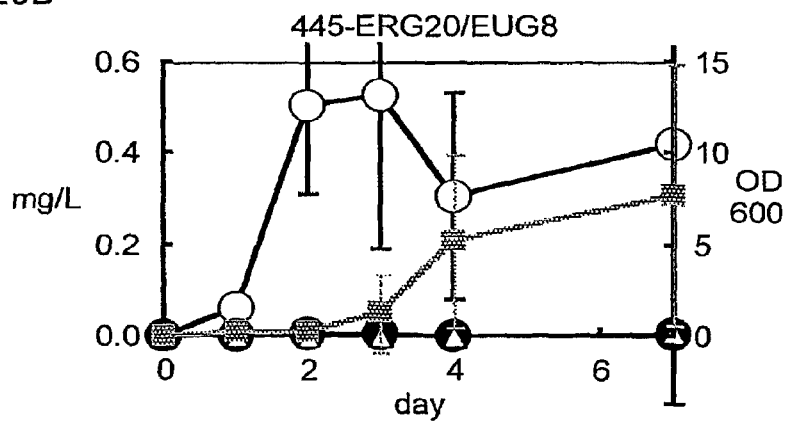
FIG. 25B is a graph showing prenyl alcohol yields of EUG8 when ERG20 gene expression plasmid has been introduced thereinto.

When each 5 colonies of pRS435GAP-ERG20/EUG8 (FIG. 25A) and pRS445GAP-ERG20/EUG8 (FIG. 25B) were cultured, the average FOH yields were 0.9 mg/L and 0.5 mg/L, respectively, and the maximum yield was 1.5 mg/L.

Figure 26A:
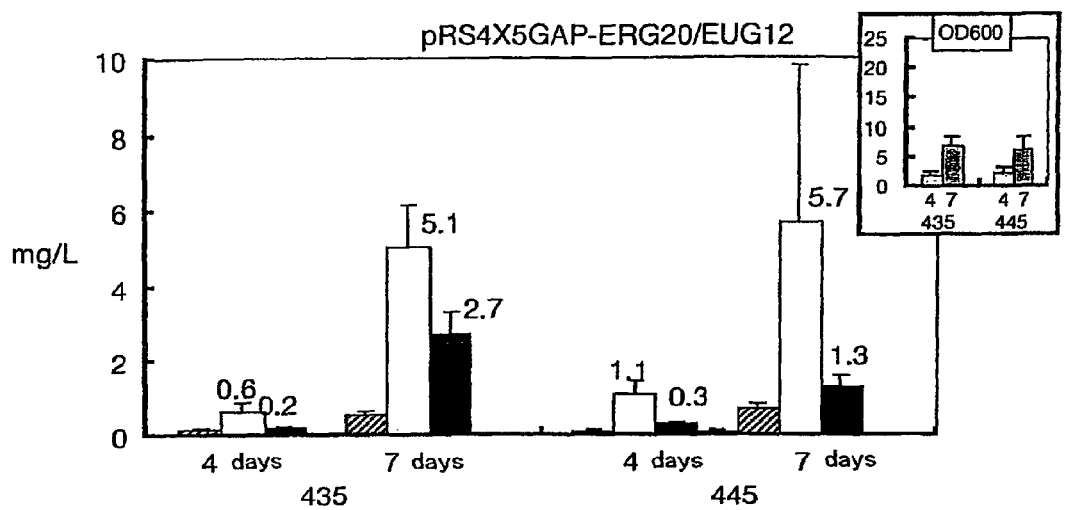
FIG. 26A is a graph showing prenyl alcohol yields of EUG12 when ERG20 gene expression plasmid has been introduced thereinto.
Figure 26B:
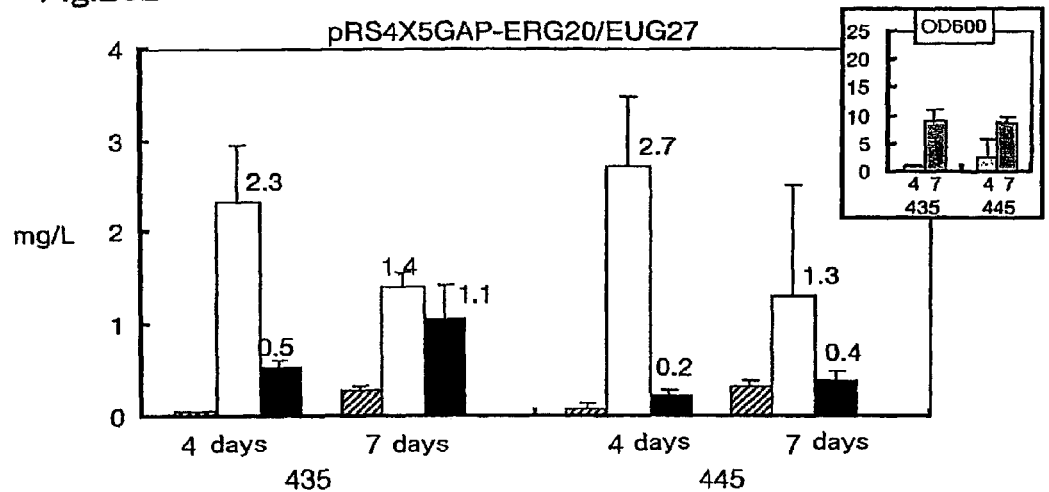
FIG. 26B is a graph showing prenyl alcohol yields of EUG27 when ERG20 gene expression plasmid has been introduced thereinto.

Subsequently, the effect of the expression enhancement of ERG20 upon YPH499-derived EUG12 and YPH500-derived EUG27 was examined. Each 5 colonies of these EUG strains into which pRS435GAP-ERG20 or pRS445GAP-ERG20 had been introduced were cultured. Then, mean values of their prenyl alcohol yields and standard deviations were recorded in graphs. The effect of ERG20 expression on prenyl alcohol production was as follows. When pRS435GAP-ERG20 was introduced into EUG12 and EUG27, recombinants produced GGOH at 2.7 mg/L on the average (3.6 mg/L at the maximum) and 1.1 mg/L on the average (1.37 mg/L at the maximum), respectively, when cultured for 7 days (FIG. 26A, B). Since ERG20 encodes an FPP synthase gene, this fact that the expression enhancement of ERG20 led to production of GGOH suggests that, actually, GGPP synthase uses not DMAPP but FPP as a homoallylic primer substrate and that GGPP production ability was increased as a result of increased intracellular FPP synthesis activity caused by the ERG20 expression enhancement. Thus, it was demonstrated that ERG20 is effective in GGOH production in EUG strains.

(6-4) Prenyl Alcohol Production by BTS1 Expression Strains

Figure 27A:
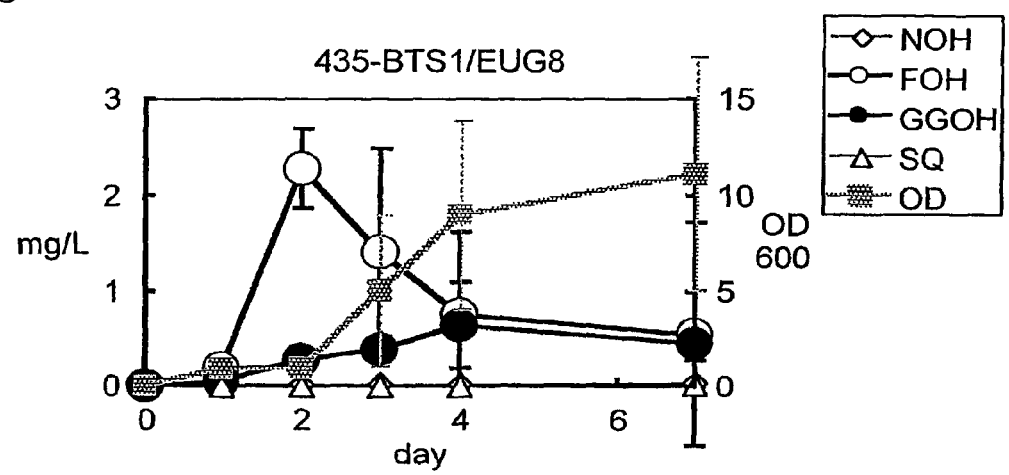
FIG. 27A is a graph showing prenyl alcohol yields of EUG8 when BTS1 gene expression plasmid pRS435GAP-BTS1 has been introduced thereinto.
Figure 27B:
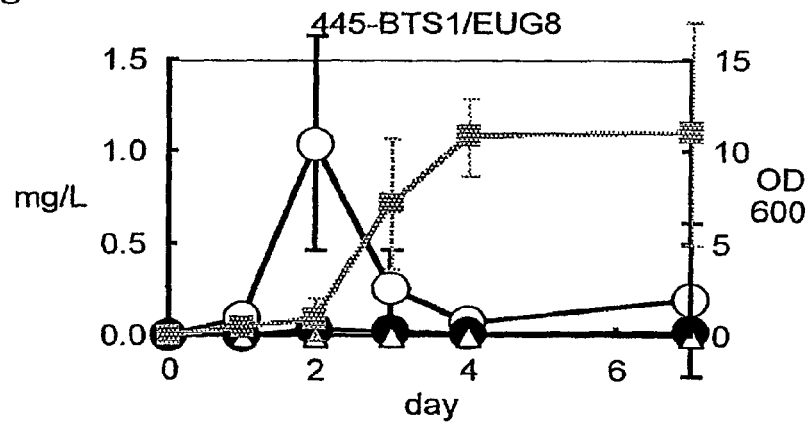
FIG. 27B is a graph showing prenyl alcohol yields of EUG8 when BTS1 gene expression plasmid pRS445GAP-BTS1 has been introduced thereinto.

Each 5 colonies of pRS435GAP-BTS1/EUG8 (FIG. 27A) and pRS445GAP-BTS1/EUG8 (FIG. 27B) were cultured. Then, mean values of their prenyl alcohol yields and standard deviations were recorded in graphs. The effect of BTS1 expression on prenyl alcohol production was as follows. When pRS435GAP-BTS1 was introduced, GGOH productivity was improved to about 0.5 mg/L on the average (the maximum yield was 1.42 mg/L). From the results of preliminary experiments, it was already found that even the introduction of pRS435GAP-BTS1 into A451 leads to GGOH productivity of about 0.1-0.3 mg/L. Now, it was found that the introduction of the same plasmid is also effective on GGOH production when EUG8 is used as a host.

Figure 28A:
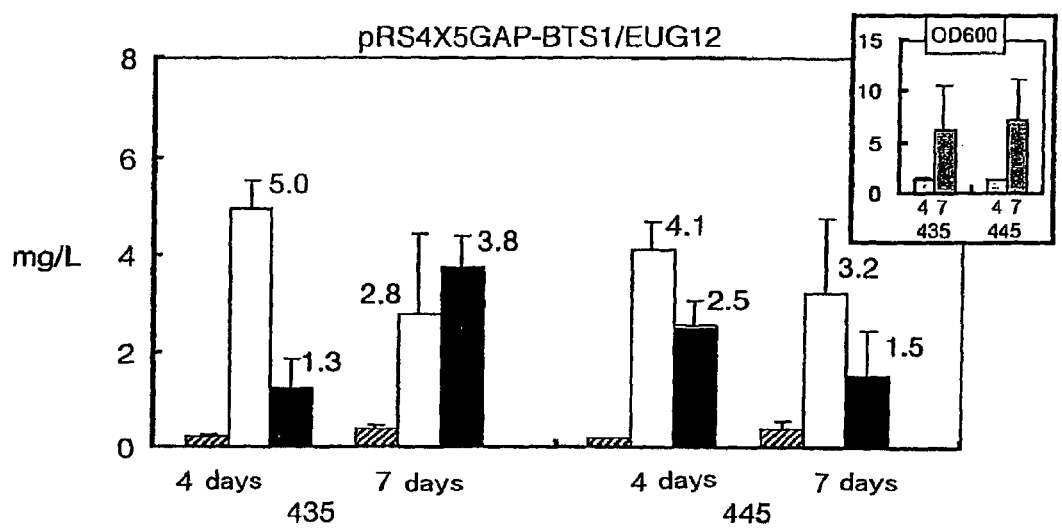
FIG. 28A is a graph showing prenyl alcohol yields of EUG12 when BTS1 gene expression plasmid has been introduced thereinto.
Figure 28B:
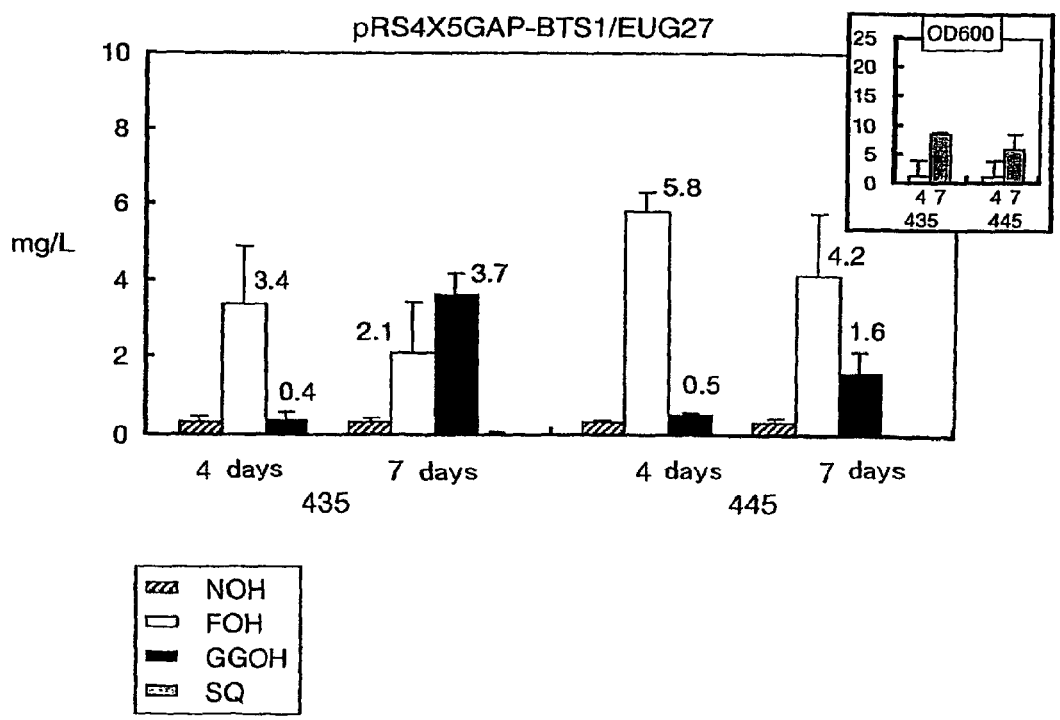
FIG. 28B is a graph showing prenyl alcohol yields of EUG27 when BTS1 gene expression plasmid has been introduced thereinto.

Subsequently, the effect of the expression enhancement of BTS1 upon YPH499-derived EUG12 and YPH500-derived EUG27 was examined. Each 5 colonies of these EUG strains into which pRS435GAP-BTS1 or pRS445GAP-BTS1 had been introduced were cultured. Then, mean values of their prenyl alcohol yields and standard deviations were graphed. The effect of BTS1 expression on prenyl alcohol production was as follows. When pRS435GAP-BTS1 was introduced, GGOH productivity of about 3.7-3.8 mg/L on the average was observed when recombinants were cultured for 7 days (maximum yields were 4.2 mg/L and 4.4 mg/L, respectively) (FIG. 28A, B). From the results of preliminary experiments, it was already found that even the introduction of pRS435GAP-BTS1 into YPH499 and YPH500 leads to GGOH productivity of about 0.1-0.2 mg/L. Now, it was found that the introduction of the same plasmid into EUG12 and EUG27 is more effective on GGOH production than the introduction into conventional hosts for recombination.

From the results so far described, it is understood that (i) mutating a cell so that an amount of squalene synthase gene transcript having translational activity can be reduced, to thereby prepare a mutant cell of the invention (e.g., EUG strains) without deleting its squalene synthase gene completely or partially; (ii) preparing a recombinant by introducing into the above mutant cell a recombinant DNA for expression or a DNA for genomic integration comprising an IPP biosynthetic pathway-related enzyme (e.g., HMG1, ERG20 or GTS1); and (iii) culturing the recombinant can lead to construction of a system capable of producing prenyl alcohol as a result of reduction in the amount of the squalene synthase gene transcript having translational activity.

Example 8

Prenyl Alcohol Production by Fusion Gene-Transferred EUG Strains

An unexpected result was obtained in Example 7 that the introduction of FPP synthase gene into EUG strains improves GGOH productivity. This suggests that the GGPP synthase encoded by *S. cerevisiae* BTS1 prefers FPP to DMAPP as a primer substrate. Therefore, it was believed that enforcement of FPP synthesis ability is also required for further enforcing the ability to synthesize GGPP (a precursor of GGOH) from IPP.

In view of this, fusion genes composed of BTS1 and ERG20 were created in this Example.

In this Example, it was attempted to express the fusion gene in *S. cerevisiae* cells and to ascertain whether GGOH productivity improves or not. Further, it was also attempted to create mutants of BTS1, ERG20 and their fusion genes in which a nucleotide sequence encoding an ER signal is located at the 3' end and to examine the effect of introduction of these mutants upon prenyl alcohol production.
(1) Preparation of Plasmid DNA for Fusion Gene Transfer A series of PCR reactions were carried out using pYESG-GPS, which is a pYES2 plasmid incorporating GGPP synthase gene BTS1, and pT7ER20, which is a pT7 plasmid incorporating FPP synthase gene ERG20, as a template. The PCR primers used are as follows.

SacI1-BTS1:
(SEQ ID NO: 70)
5'-TGG CCG CGG ATG GAG GCC AAG ATA GAT-3'

BTS1-XhoI:
(SEQ ID NO: 71)
5'-CAA CTC GAG TCA CAA TTC GGA TAA GTG-3'

ERG20HDEL-XbaI:
(SEQ ID NO: 72)
5'-GCT CTA GAG TTC GTC GTG TTT GCT TCT CTT GTA AAC TT-3'

BTS1HDEL-XhoI:
(SEQ ID NO: 73)
5'-TAT CTC GAG TCA CAA TTC GTC ATG TAA ATT GG-3'

BTSI-109I
(SEQ ID NO: 74)
5'-GCA GGG ACC CCA ATT CGG ATA AGT GGT C-3'

109I-BTS1:
(SEQ ID NO: 75)
5'-GTA GGG TCC CTG GAG GCC AAG ATA GAT G-3'

ERG20-109I:
(SEQ ID NO: 76)
5'-GCA GGG ACC CTT TGC TTC TCT TGT AAA CT-3'

109I-ERG20:
(SEQ ID NO: 77)
5'-GTA GGG TCC TCA GAA AAA GAA ATT AGG AG-3'

-21:
(SEQ ID NO: 78)
5'-TGT AAA ACG ACG GCC AGT-3'

T7:
(SEQ ID NO: 79)
5'-TAA TAC GAC TCA CTA TAG GG-3'

The nucleotides from position 3 to position 8 of ERG20HDEL-XbaI and the nucleotides from position 4 to position 9 of BTS1 HDEL-XhoI (both 6 nucleotides are underlined) represent the SacII, XhoI or XbaI recognition site for vector ligation. The nucleotide from position 4 to position 10 of BTS1-109I, 109I-BTS1, ERG20-109I and 109I-ERG20 (individual 7 nucleotides are underlined) represent the EcoO109I recognition site for fusion gene preparation.

The PCR was carried out in the following reaction solution.

1x KOD-Plus buffer (Toyobo)
0.2 mM dNTPs
0.25 mM MgSO$_4$
15 pmol Primer 1
15 pmol Primer 2
0.01-0.1 μg Template DNA
1 unit KOD-Plus DNA polymerase (Toyobo)

Total: 50 μl

KOD-Plus contains 1.6 μg/μl of KOD antibody. Following an initial denaturation of 2 min at 94° C., the PCR was carried out for 30 cycles each consisting of 15 sec at 94° C., 30 sec for 55° C. and 1 min at 68° C. Then, the solution was retained at 68° C. for 2 min.

Figure 29:
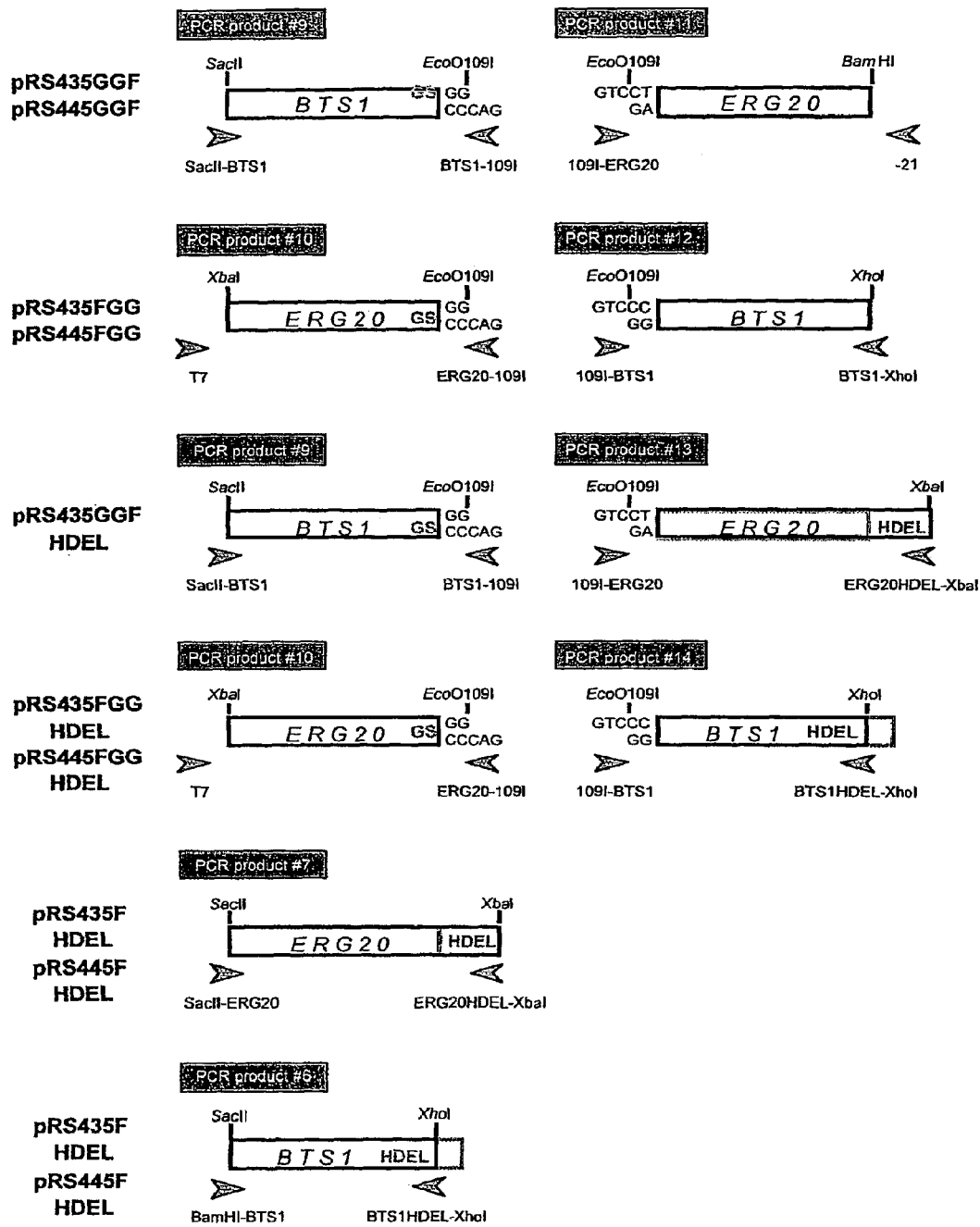
FIG. 29 shows primers used in the preparation of BTS1-ERG20 fusion genes and genes encoding polypeptide having an ER signal at the C-terminal, as well as the locations and directions of such primers.

1st PCR reactions were carried out using the combinations of a template and a pair of primers (Primer 1, Primer 2) as indicated in Table 6 and FIG. 29. The designations of PCR products are also shown in Table 6 and FIG. 29. In FIG. 29, the final designations of plasmids are shown in the leftmost column. The sequences written in gray letters represent amino acids. Of these amino acids, GS was introduced into the binding sequence of the fusion gene, and HDEL was located at the 3' end of the fusion gene by insertion or deletion mutation. Each arrowhead indicates the location and direction of each primer used in the PCR.

TABLE 6

| Template | primer 1 | primer 2 | PCR Product |
|---|---|---|---|
| pT7ERG20 | SacII-BTS1 | BTS1HDEL-XhoI | #6 |
| pYESGGPS | SacII-ERG20 | ERG20HDEL-XbaI | #7 |
| pYESGGPS | SacII-BTS1 | BTS1-109I | #9 |
| PT7ERG20 | T7 | ERG20-109I | #10 |
| PT7ERG20 | 109I-ERG20 | -21 | #11 |
| pYESGGPS | 109-BTS1 | BTS1-XhoI | #12 |
| PT7ERG20 | 109I-ERG20 | ERG20HDEL-XbaI | #13 |
| pYESGGPS | 109I-BTS1 | BTS1HDEL-XhoI | #14 |

PCR products #9, #10, #11, #12, #13 and #14 were digested with the restriction enzyme Eco1019I. Then, #9 and #11, #10 and #12, #9 and #13, and #10 and #14 were ligated to each other individually. Using the resultant ligation solutions as a template, 2nd PCR reactions were carried out under the same conditions as in the 1st PCR. As primers, the combinations of SacII-BTS1 and -21, T7 and BTS1-XhoI, SacII-BTS1 and ERG20HDEL-XbaI, and T7 and BTS1HDEL-XhoI were used, respectively. As a result, 2nd PCR products #9-#11, #10-#12, #9-#13 and #10-#14 were obtained.

The product #9-#11 was digested with SacII and BamHI, and inserted into the SacII-BamHI site of pRS435GAP and pRS445GAP to obtain pRS435GGF and pRS445GGF, respectively.

The product #10-#12 was digested with XbaI and XhoI, and inserted into the XbaI-XhoI site of pRS435GAP and pRS445GAP to obtain pRS435FGG and pRS445FGG, respectively.

The product #9-#13 was digested with SacII and XbaI, and inserted into the SacII-XbaI site of pRS435GAP to obtain pRS435GGFHDEL.

The product #10-#14 was digested with XbaI and XhoI, and inserted into the XbaI-XhoI site of pRS435GAP and pRS445GAP to obtain pRS435FGGHDEL and pRS445FGGHDEL, respectively.

The product #7 was digested with SacII and XbaI, and inserted into the SacII-XbaI site of pRS435GAP and pRS445GAP to obtain pRS435FHDEL and pRS445FHDEL, respectively.

The product #6 was digested with BamHI and XhoI, and inserted into the BamHI-XhoI site of pRS435GAP and pRS445GAP to obtain pRS435GGHDEL and pRS445GGHDEL, respectively.

It was confirmed by DNA sequencing that each of the resultant plasmid DNAs has the exact nucleotide sequence as designed. BTS1-ERG20 fusion gene was designated GGF; ERG20-BTS1 fusion gene was designated FGG; a gene recombined so that a sequence encoding HDEL is located at the 3' end of GGF was designated GGFHDEL; a gene recombined so that a sequence encoding HDEL is located at the 3' end of FGG was designated FGGHDEL; and a gene recombined so that a sequence encoding HDEL is located at the 3' end of BTS1 was designated GGHHDEL.

As plasmids for expressing non-fusion genes BTS1 and ERG20 separately, pRS435GAP-BTS1 (called pRS435GG), pRS445GAP-BTS1 (called pRS445GG), pRS435GAP-ERG20 (called pRS435F) and pRS445GAP-ERG20 (called pRS445F) were used. As plasmids for expressing HMG1, pRS434TEF-HMG1 and pRS434GAP-HMG1 were used.

(2) Preparation of Recombinants

Recombinants were prepared by introducing the plasmid prepared above into the host using Frozen EZ yeast transformation kit (Zymo Research, Orange, Calif.). As the host, EUS5 and EUG12 were used. As controls, A451 and YPH499 were used.

(3) Determination of Prenyl Alcohol Yields

A451 and YPH499 were inoculated into SD medium. EUG strains and recombinants created therefrom were inoculated into SGR medium. All of them were cultured at 30° C. to prepare preculture broth. Ten or 25 µl of the preculture broth was added to 1.0 or 2.5 ml of YM7+ade medium (YM, pH 7, 40 µg/ml adenine sulfate) or YMO7 medium [YM7+ade, 1% (w/v) soybean oil, 0.1% (w/v) Adekanol LG-109 (Asalai Denka Kogyo, Tokyo, Japan)] and cultured at 30° C. for 4 days or 7 days under reciprocal shaking at 130 rpm.

After completion of the cultivation, an equal volume of methanol was added to the culture broth and mixed. Approximately 2 volumes of pentane was added to this mixture, agitated vigorously and then left stationary. The resultant pentane layer was transferred into a fresh glass tube, which was then placed in a draft. Pentane was evaporated therein to condense the solute components. Subsequently, prenyl alcohols were identified and quantitatively determined by GC/MS using undecanol as an internal standard for quantitative determination. At that time, the degree of cell growth was also examined by diluting 20 µl of the culture broth 30-fold with water and measuring the absorbance at 600 nm.

The yields of prenyl alcohols were determined with PH6890/5973 GC/MS system in the same manner as described in (1-2) in Example 2.

(4) Results and Considerations

Figure 30:
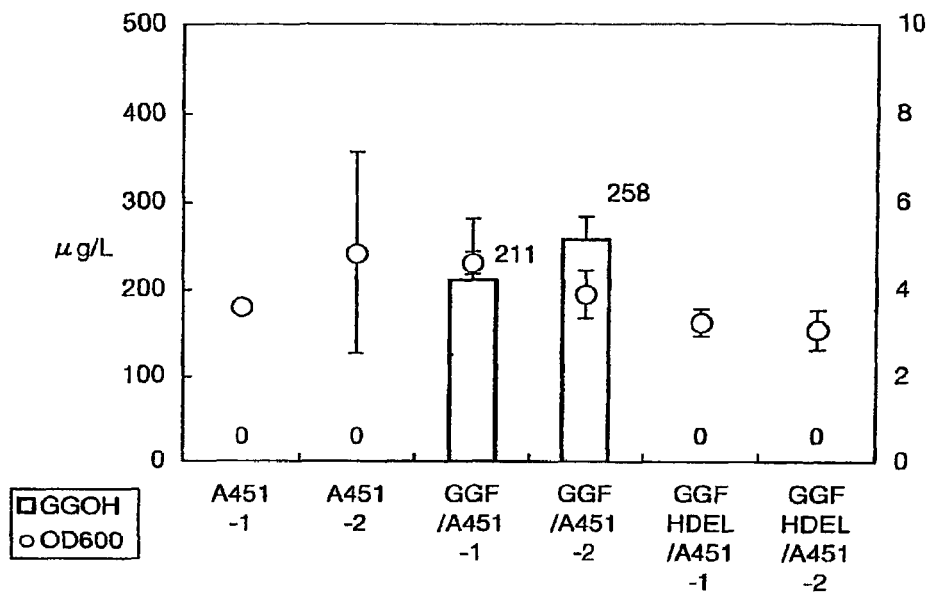
FIG. 30 shows the results of determination of GGOH yields in YM7 medium when A451 or EUG5 was used as a host.
Figure 30:
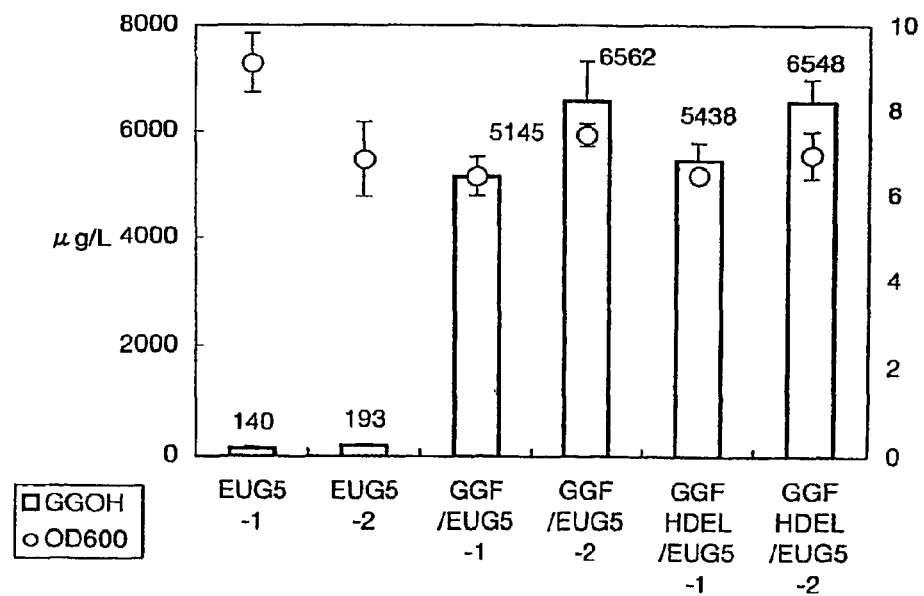
Figure 31:
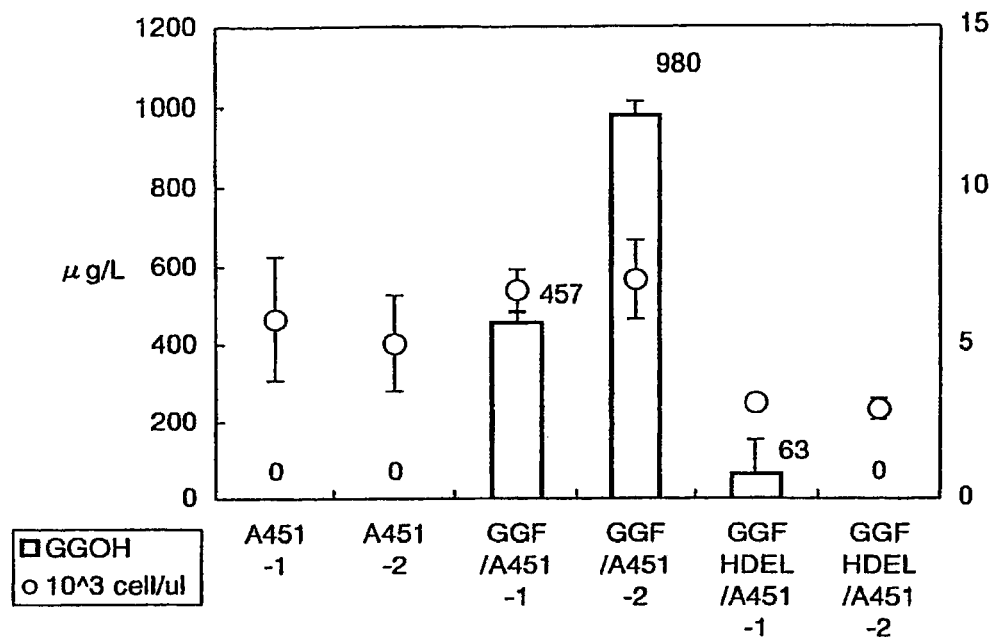
FIG. 31 shows the results of determination of GGOH yields in YMO7 medium when A451 or EUG5 was used as a host.
Figure 31:
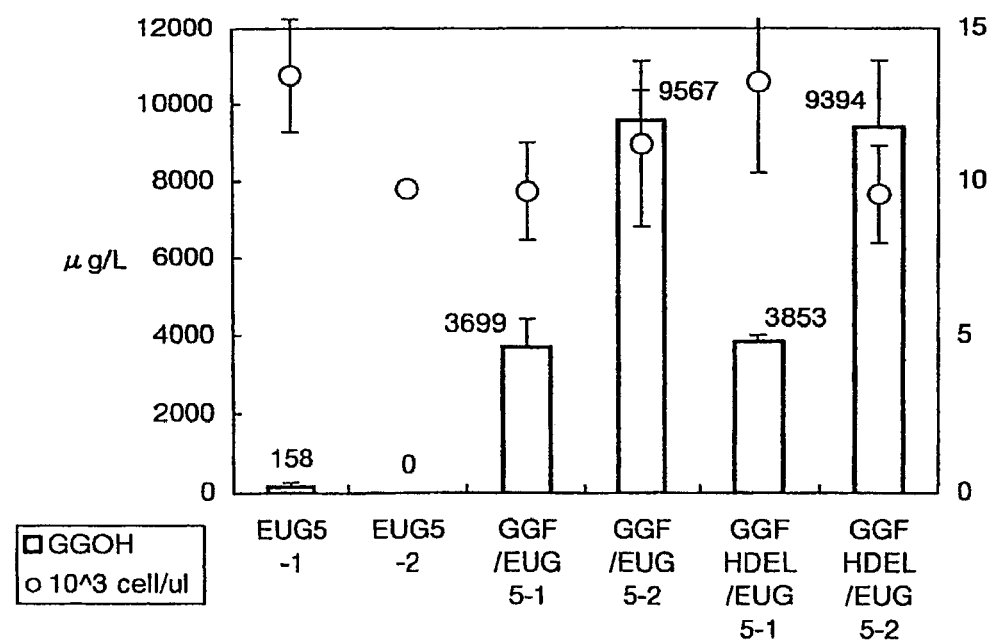
Figure 32:
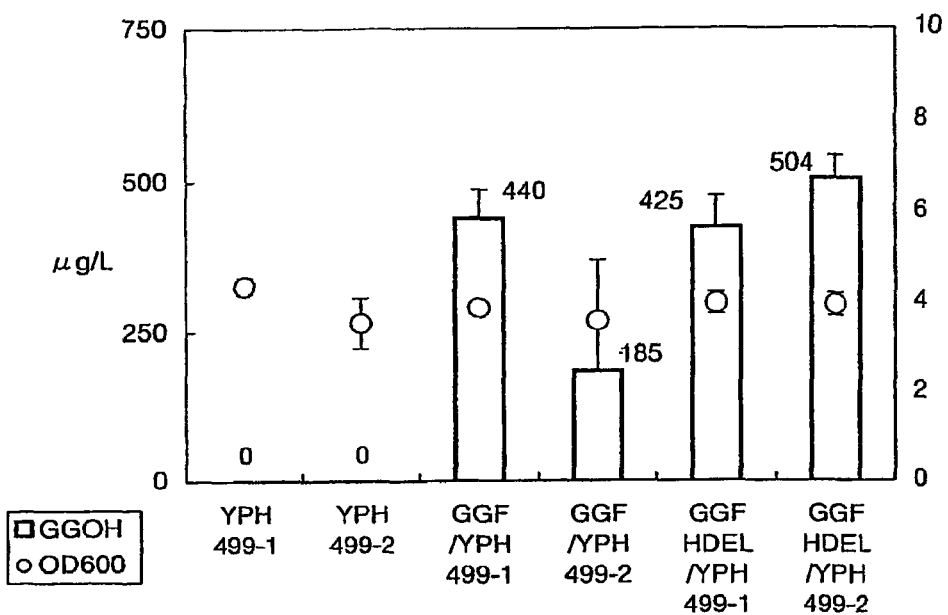
FIG. 32 shows the results of determination of GGOH yields in YM7 medium when YPH499 or EUG12 was used as a host.
Figure 32:
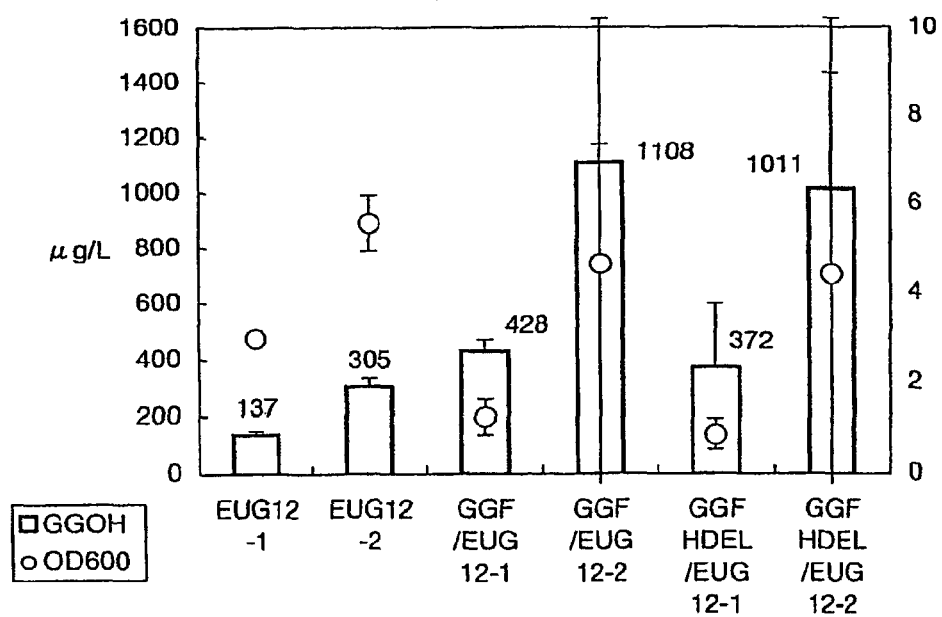
Figure 33:
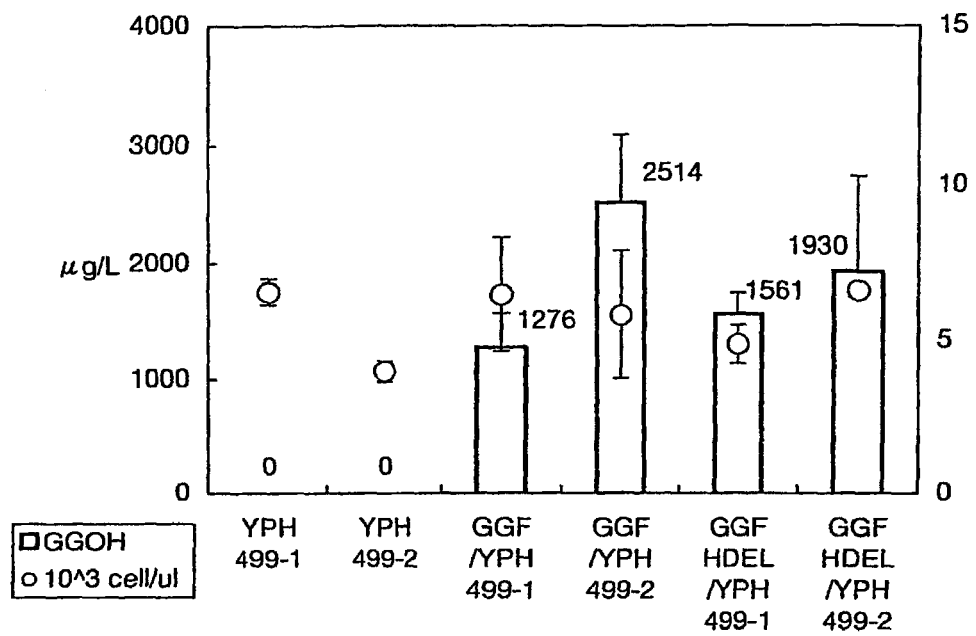
FIG. 33 shows the results of determination of GGOH yields in MYO7 medium when YPH499 or EUG12 was used as a host.
Figure 33:
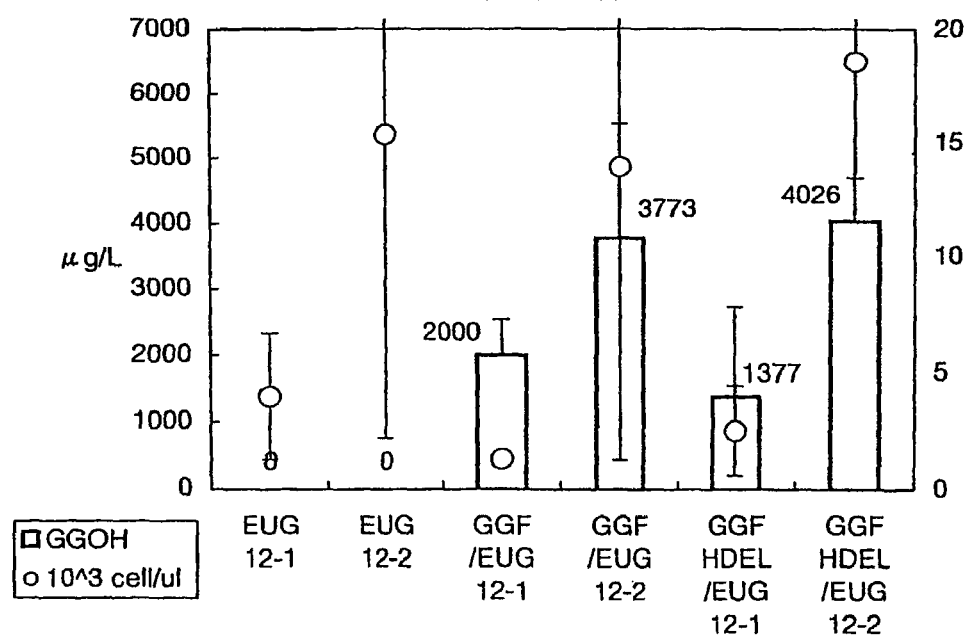

Each of the recombinants prepared was cultured in YM7 medium and YMO7 medium for 4 to 7 days, followed by determination of prenyl alcohol yields. The results obtained using A451-derived EUG strains as hosts are shown in FIGS. 30 and 31. The results obtained using YPH499-derived EUG strains as hosts are shown in FIGS. 32 and 33. In FIGS. 30 and 31, "GGFHDEL" represents pRS435GGFHDEL. "−1" represents the yield when cells were cultured for 4 days, and "−2" represents the yield when cells were cultured for 7 days. Since cells are suspended in soybean oil in YMO7 medium, the amount of cells is expressed as the number of cells. "10^3 cell/µl" represents a value obtained by dividing the number of cells per microliter by 1000.

pRS435GGF/A451 produced 0.26 mg/L of GGOH on the average (0.28 mg/L at the maximum) when cultured for 7 days in YM7 medium (FIG. 30; upper panel; GGF/A451-2), and produced 0.98 mg/L on the average (1.0 mg/L at the maximum) when cultured for 7 days in YMO7 medium (FIG. 31; upper panel; GGF/A451-2).

On the other hand, when EUG5 was used as the host, pRS435GGF-transferred recombinants produced 6.6 mg/L of GGOH on the average (maximum: 7.3 mg/L) when cultured for 7 days in YM7 medium (FIG. 30; lower panel; GGF/EUG5-2), and produced 9.6 mg/L of GGOH on the average (maximum: 10.1 mg/L) when cultured for 7 days in YMO7 medium (FIG. 31; lower panel; GGF/EUG5-2).

pRS435GGF-transferred YPH499 produced 0.19 mg/L of GGOH on the average (0.37 mg/L at the maximum) when cultured for 7 days in YM7 medium (FIG. 32; upper panel; GGF/YPH499-2), and produced 2.5 mg/L on the average (2.9 mg/L at the maximum) in YMO7 medium (FIG. 33; upper panel; GGF/YPH499-2). On the other hand, when YPH499-derived EUG12 was used as the host, the pRS435GGF- or pRS435GGFHDEL-transferred clones produced 3.7-4.0 mg/L of GGOH on the average (5.4-5.8 mg/L at the maximum) when cultured for 7 days in YM0 medium (FIG. 33; lower panel; GGF/EUG12-2 and GGFHDEL/UG12-2). Thus, it was demonstrated that recombinants prepared from the mutant cell of the invention (such as EUG5 or EUG12) have higher GGOH productivity than those recombinants prepared from conventional hosts for recombination (such as YPH499 or A451). As described earlier, the mutant cell of the invention is engineered so that an amount of squalene synthase gene transcript having translational activity can be reduced without total or partial deletion of the squalene synthase gene.

Example 9

Prenyl Alcohol Production by Gene-Transferred EUG in Media with Various Glucose-Galactose Compositions (1) Introduction of Vectors into Hosts and Their Cultivation In this Example, how the prenyl alcohol production by budding yeast will change when Glc-Gal sugar composition is varied is examined. In addition, the effect of the expression of BTS1-ERG20 fusion genes upon prenyl alcohol production is also examined.

Vectors were introduced into yeast hosts using Frozen EZ yeast transformation II kit purchased from Zymo Research (Orange, Calif.). As BTS1-ERG20 fusion gene-expression plasmids, pRS435GGF and pRS435GGFHDEL were used. As hosts, EUG5 and EUG12 were used. As control hosts, A451 and YPH499 were used.

Each of the recombinants obtained was precultured in SGR selection medium. Then, 0.01-0.05 ml of the preculture broth was added to 1-5 ml of the YM7 medium described below and cultured in a test tube 18 mm in diameter at 30° C. under reciprocal shaking at 130 rpm. Five types of YM7 medium having the following sugar components (Glc-Gal composition ratios), respectively, were prepared in advance: 0% Glc-100% Gal, 20% Glc-80% Gal, 50% Glc-50% Gal, 75% Glc-25% Gal, and 100% Glc-0% Gal. First, cells were cultured in these media at 30° C. under reciprocal shaking at 130 rpm. Two days after the start of cultivation, Glc was added further to each medium to give a final concentration of 5% (w/v). Cells were cultured further up to day 7.

(2) Results and Considerations (2-1) GGOH Production by EUG5

Figure 34B:
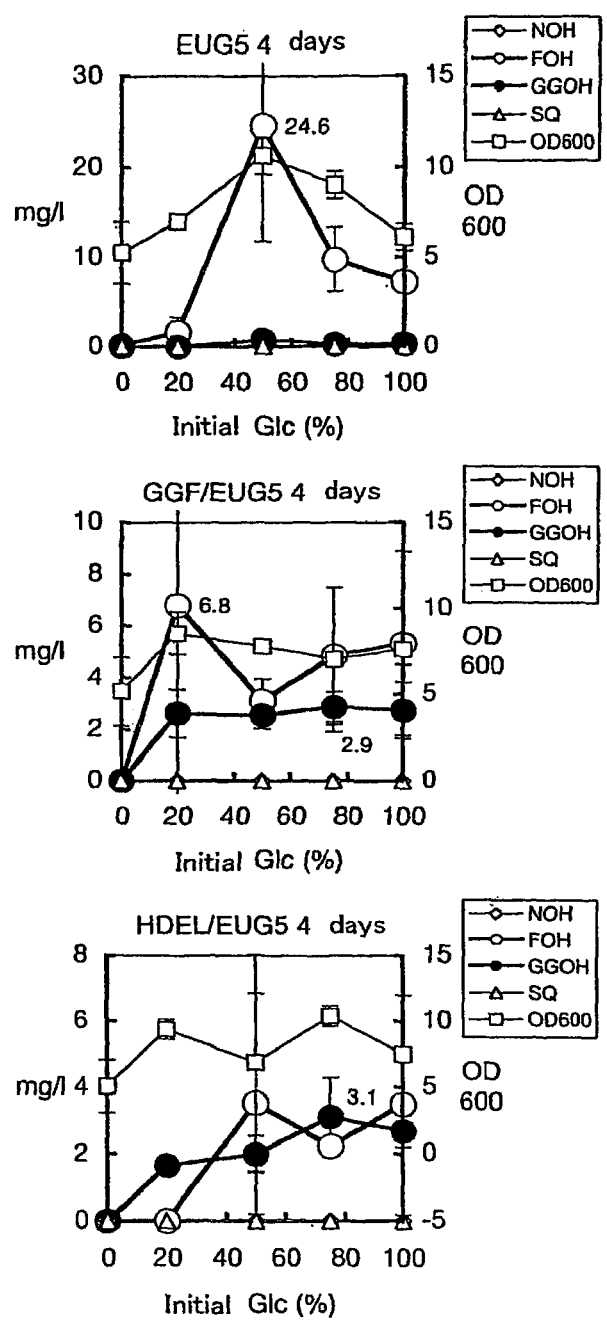
FIG. 34B presents graphs showing GGOH yields of pRS435GGF- or pRS435GGFHDEL-introduced EUG5 cultured in a medium with the indicated initial sugar composition for 4 days.
Figure 34C:
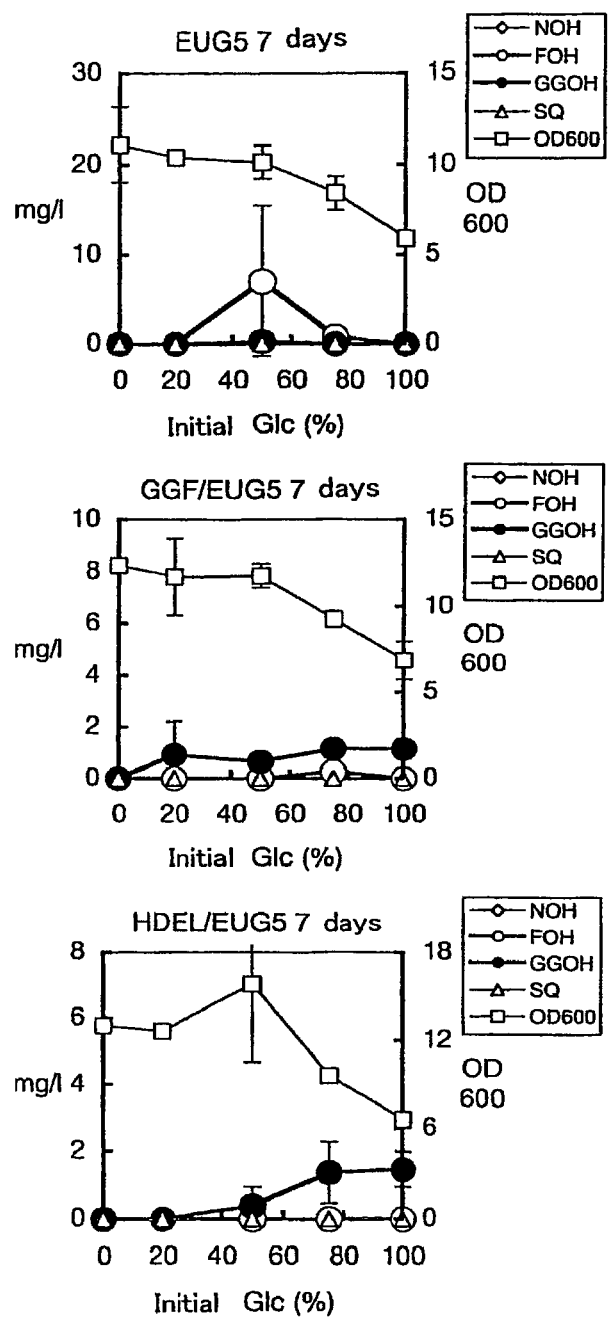
FIG. 34C presents graphs showing GGOH yields of pRS435GGF- or pRS435GGFHDEL-introduced EUG5 cultured in a medium with the indicated initial sugar composition for 7 days.

FIG. 34 shows the results of GGOH production when pRS435GGF or pRS435GGFHDEL was transferred into EUG5. In both pRS435GGF-transferred clone (expressed as "GGF/EUG5" in FIG. 34) and pRS435GGFHDEL-transferred clone (expressed as "HDEL/DUG5" in FIG. 34), good results were obtained after 2-4 days cultivation when the initial Glc was 20-80%.

(2-2) GGOH Production by EUG12

Figure 35A:
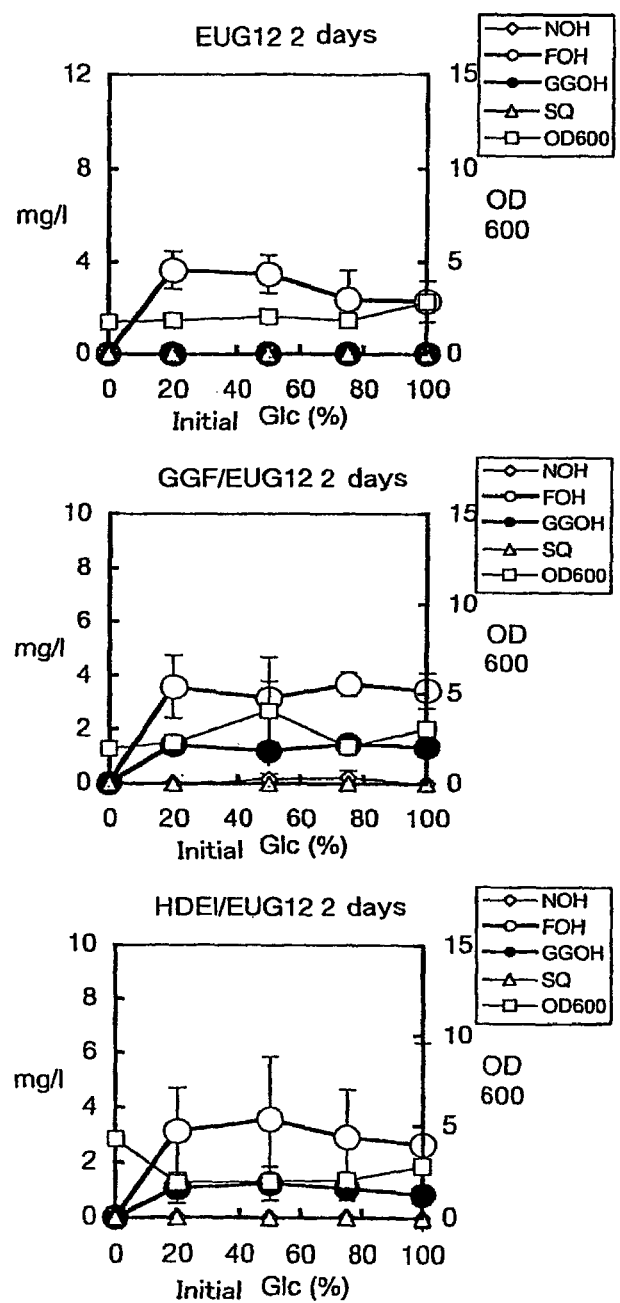
FIG. 35A presents graphs showing GGOH yields of pRS435GGF- or pRS435GGFHDEL-introduced EUG12 cultured in a medium with the indicated initial sugar composition for 2 days.
Figure 35B:
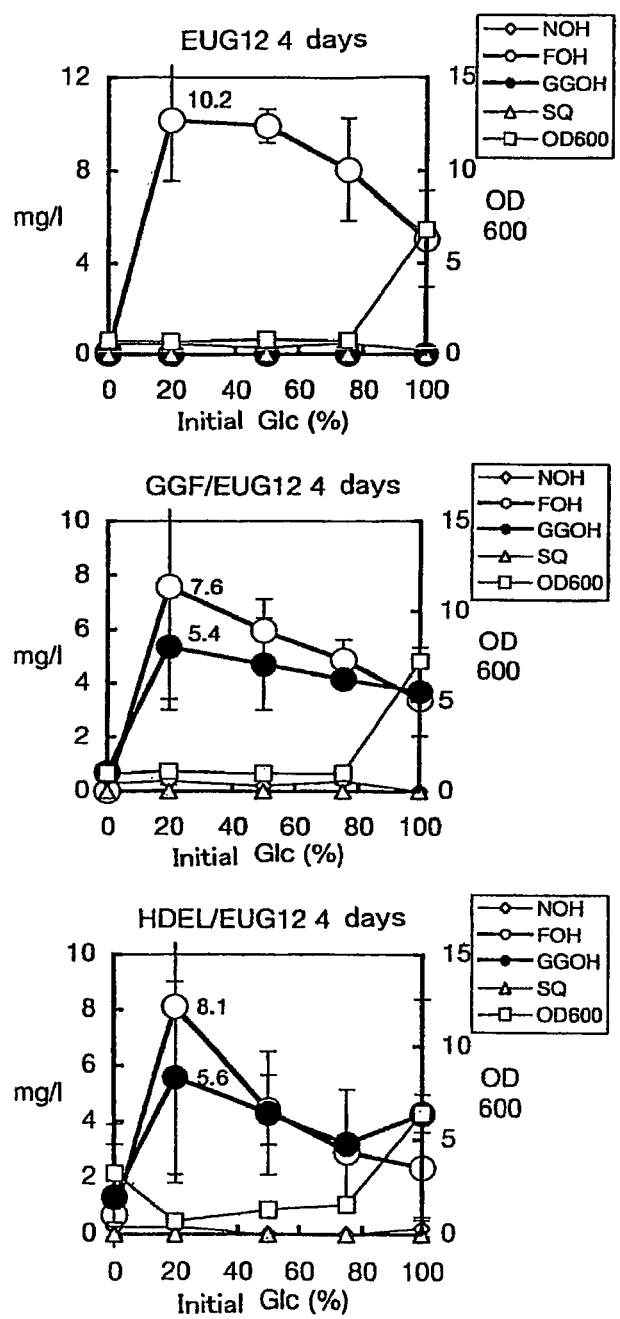
FIG. 35B presents graphs showing GGOH yields of pRS435GGF- or pRS435GGFHDEL-introduced EUG12 cultured in a medium with the indicated initial sugar composition for 4 days.
Figure 35C:
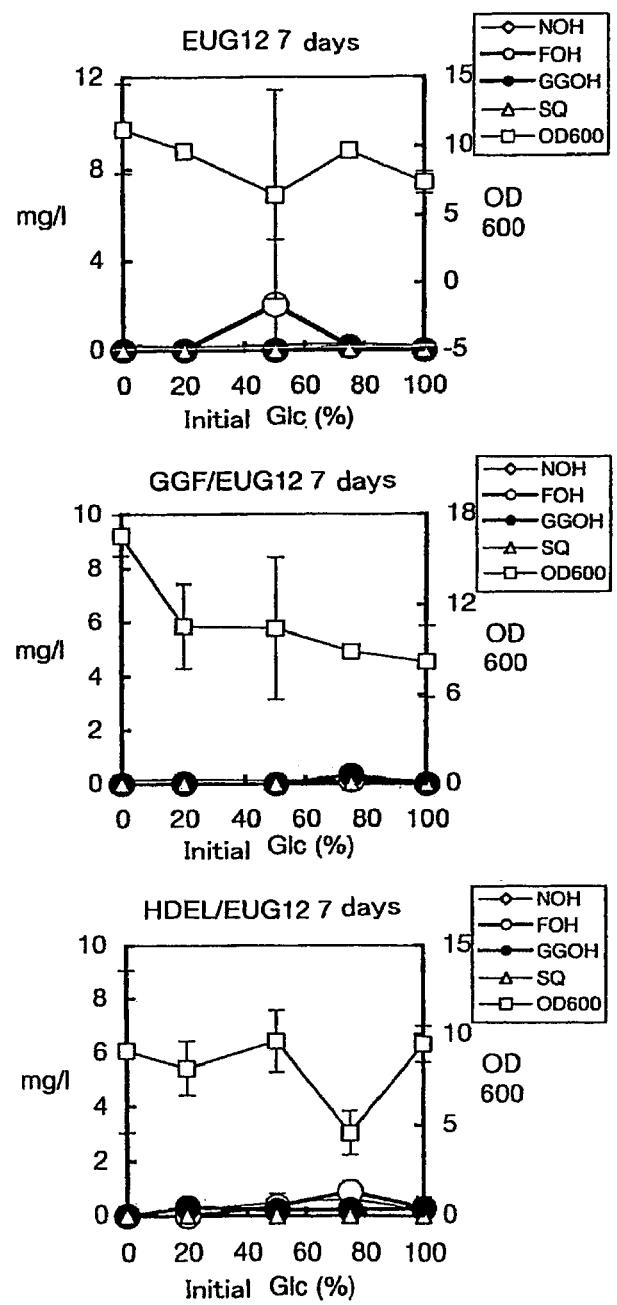
FIG. 35C presents graphs showing GGOH yields of pRS435GGF- or pRS435GGFHDEL-introduced EUG12 cultured in a medium with the indicated initial sugar composition for 7 days.

FIG. 35A-C shows the results of GGOH production when pRS435GGF or pRS435GGFHDEL was transferred into EUG12. When the initial Glc was 20%, both of the recombinants exhibited high prenyl alcohol productivity. When the initial Glc was 20%, pRS435GGF/EUG12 (expressed as "GGF/EUG12" in FIG. 35) and pRS435GGFHDEL/EUG12 (expressed as "HDEL/EUG12" in FIG. 35) produced FOH at 7.6 mg/L on the average (10.5 mg/L at the maximum) and at 8.1 mg/L on the average (12.6 mg/L at the maximum), respectively, when cultured for 4 days, even when the amounts of their cells corresponded to $OD_{600}=1.1$ and 0.70, respectively (data not shown). On the other hand, average GGOH yields of these recombinants were 5.4 mg/L (7.0 mg/L at the maximum) and 5.6 mg/L (8.0 mg/L at the maximum), respectively. It is believed that these production results are very efficient as productivity per cell.

Example 10

Prenyl Alcohol Yields in YPD07rich Medium (1) Cultivation and Determination of Prenyl Alcohol Yields EUG5, EUG24, EUG36 and EUG64 prepared in Example 1; recombinants prepared by introducing pRS434-GAP-HMG1 into these EUG strains; and recombinants prepared by further introducing pRS435GG into each of the resultant recombinants were cultured in YPD07rich medium [YPD, 1% (v/v) soybean oil, 0.1% (v/v) Adekanol LG-109, 5% (w/v) Glc (final concentration 7% (w/v) Glc), pH 7] at 30° C. under reciprocal shaking at 130 rpm. Then, prenyl alcohol yields were determined in the same manner as described in Example 2.

(2) Results and Considerations

FIG. 36A-D shows the amounts of prenyl alcohols accumulated in the culture broth and the absorbance of the broth at 600 nm ($OD_{600}$) arranged in graphs. By culturing the cells in YPD07rich medium containing nitrogen sources and sugar sources at higher concentrations than YM medium, prenyl alcohols of still higher concentrations could be produced.

Figure 36A:
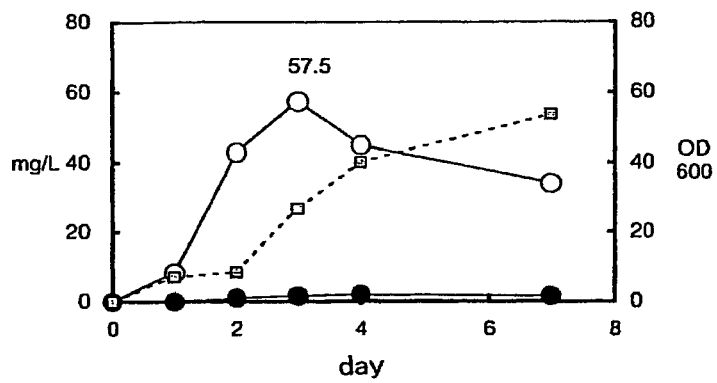
FIG. 36A presents graphs showing the time course of prenyl alcohol yields and $OD_{600}$ values when EUG5 and recombinants derived therefrom were cultured in YPDO7rich medium.
Figure 36A:
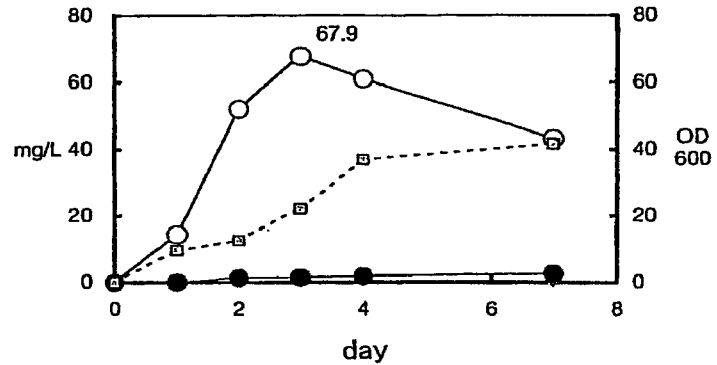
Figure 36A:
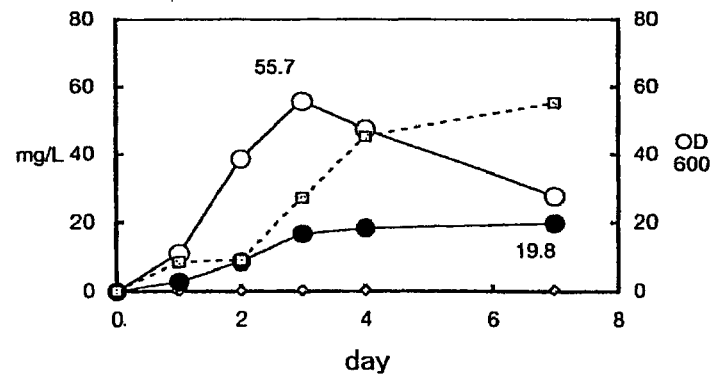
Figure 36B:
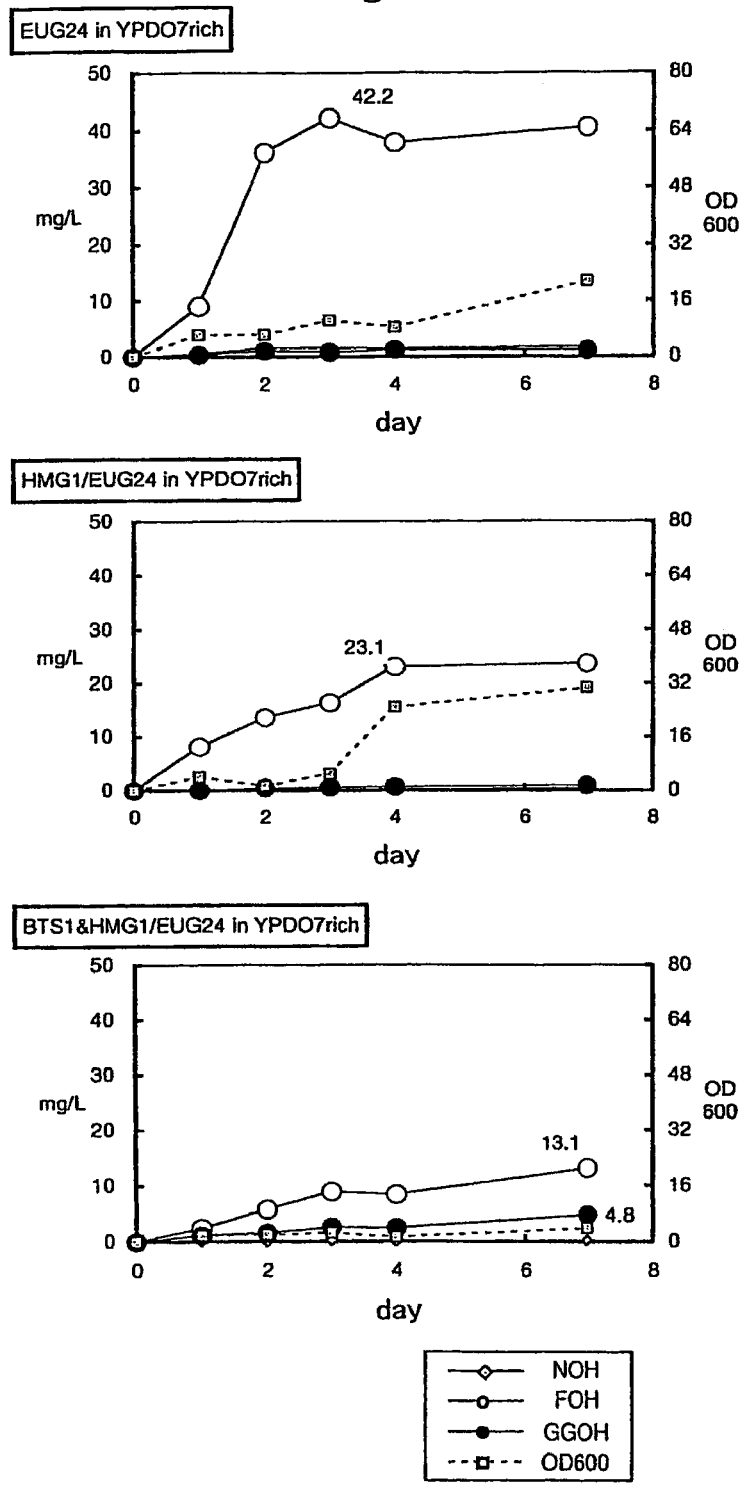
FIG. 36B presents graphs showing the time course of prenyl alcohol yields and $OD_{600}$ values when EUG24 and recombinants derived therefrom were cultured in YPDO7rich medium.
Figure 36C:
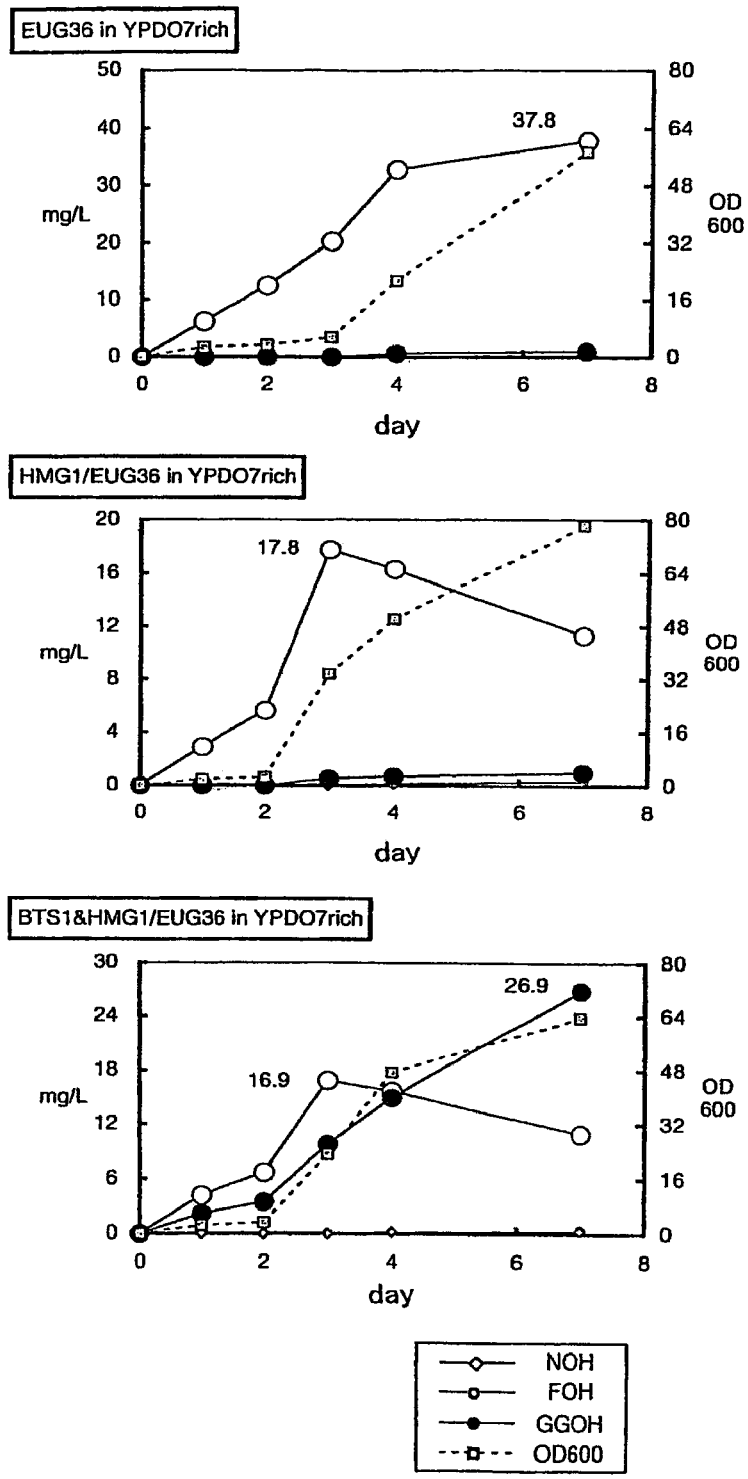
FIG. 36C presents graphs showing the time course of prenyl alcohol yields and $OD_{600}$ values when EUG36 and recombinants derived therefrom were cultured in YPDO7rich medium.
Figure 36D:
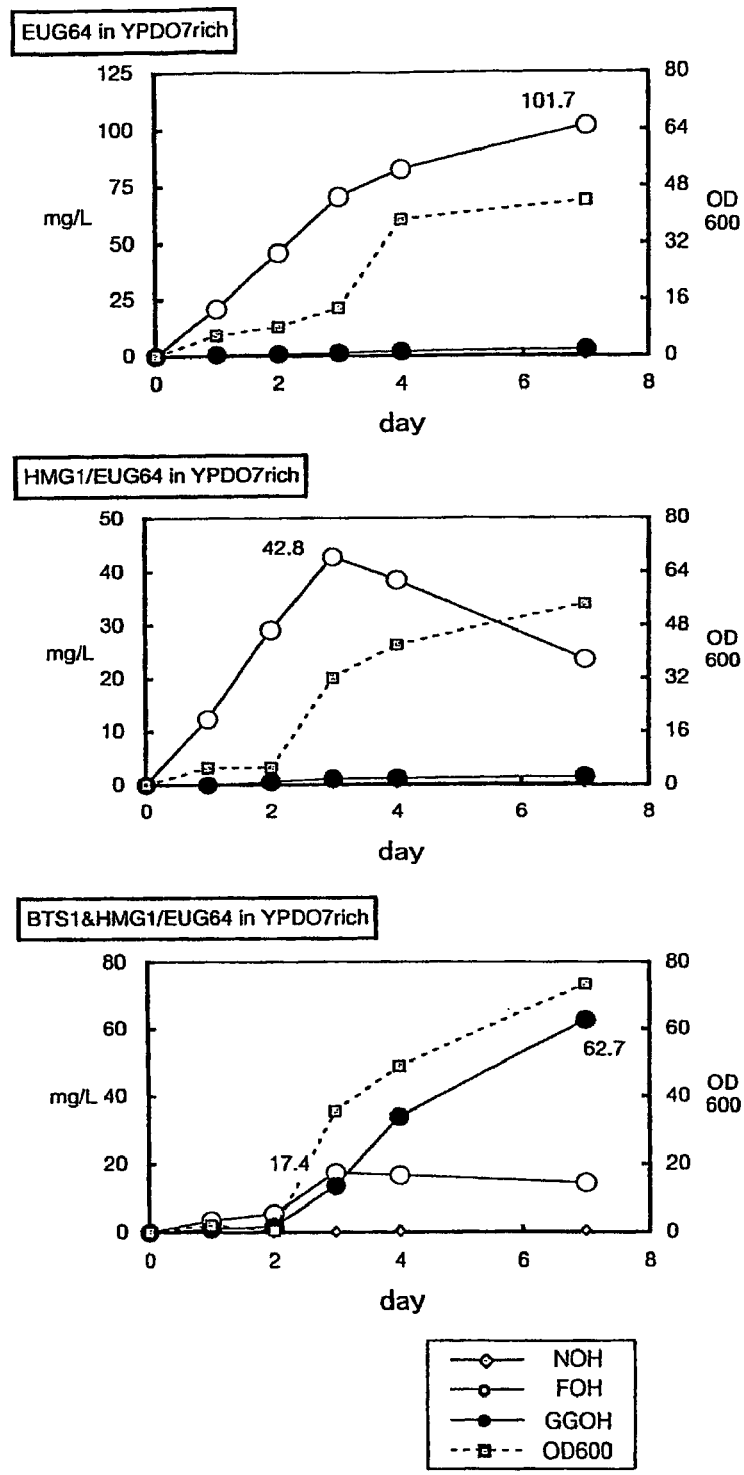
FIG. 36D presents graphs showing the time course of prenyl alcohol yields and $OD_{600}$ values when EUG64 and recombinants derived therefrom were cultured in YPDO7rich medium.

When EUG5 was cultured in YPDO7rich medium for 3 days, this strain produced 57.5 mg/L of FOH and 1.70 mg/L of GGOH (FIG. 36A, "EUG5 in YPDO7rich"). FUG24 produced 42.2 mg/L and 0.87 mg/L, respectively, when cultured for 3 days (FIG. 36B, "EUG24 in YPDO7rich"). FUG36 produced 37.8 mg/L and 0.98 mg/L, respectively, when cultured for 7 days (FIG. 36C, "EUG36 in YPDO7rich"). FUG64 produced 101.7 mg/L and 2.92 mg/L, respectively, when cultured for 7 days (FIG. 36D, "EUG64 in YPDO7rich"). Thus, it has become clear that a system capable of producing 0.1 g or more prenyl alcohols per liter of culture broth can be constructed by using the mutant cell of the invention (e.g. EUG64) as a host, preparing a recombinant by introducing into the mutant cell a recombinant DNA for expression or a DNA for genomic integration comprising an IPP biosynthetic pathway-related gene, and culturing the recombinant, and reducing an amount of squalene synthase gene transcript having transcriptional activity. The system, unlike simple squalene synthase gene-deficient strains such as *S. cerevisiae* ATCC64031, does not require addition of sterols to the medium caused by ergosterol requirement.

With respect to HMG1-transferred recombinants, the recombinant from EUG5 produced 67.9 mg/L of FOH when cultured for 3 days (FIG. 36A, "HMG1/EUG5 in YPDO7rich"), but the FOH productivity of other recombinants was not improved compared to the productivity of their host strains.

When BTS1 was further introduced into HMG1-transferred EUG5, the recombinant exhibited high production of GGOH while retaining the FOH production of the host. The recombinant produced 16.7 mg/L of GGOH when cultured for 3 days, and 19.8 mg/L of GGOH when cultured for 7 days (FIG. 36A, "BTS1&HMG1/EUG5 in YPDO7rich"). Remarkably, the recombinant created from EUG64 produced 62.7 mg/L of GGOH when cultured for 7 days. This means that when a recombinant is prepared by introducing into the mutant cell of the invention (e.g., EUG64) a recombinant DNA for expression or a DNA for genomic integration each comprising an IPP biosynthetic pathway-related gene and then cultured, a system can be constructed which is capable of producing such prenyl alcohols (e.g., GGOH) that are not detected in the culture broth of simple squalene synthase gene-deficient strains such as *S. cerevisiae* ATCC64031, at a high level exceeding 0.06 g per liter of the culture broth as a result of reduction of the squalene synthase gene transcript having translational activity.

All publications, patents and patent applications cited herein are incorporated herein by reference in their entirety.

INDUSTRIAL APPLICABILITY

According to the present invention, there are provided methods of producing various prenyl alcohols having geometrical isomerisms of naturally occurring prenyl alcohols.

Since active prenyl alcohols having geometrical isomerisms of naturally occurring prenyl alcohols can be obtained in large quantities according to the invention, they are applicable to industrial production of huge varieties of isoprenoid/terpenoid compounds important in vivo, and also applicable as basic systems to find out novel physiological activities of active prenyl alcohols. Thus, the methods of the invention are useful.

SEQUENCE LISTING FREE TEXT

SEQ ID NOS: 34-79: synthetic DNA

What is claimed is:

1. A method of producing a prenyl alcohol(s) selected from the group consisting of farnesol, nerolidol and geranylgeraniol, comprising the steps of:
    culturing a mutant cell into which a fusion gene of farnesyl diphosphate synthase gene and geranylgeranyl diphosphate synthase gene has been introduced to produce a fusion protein having both farnesyl diphosphate synthase activity and geranylgeranyl diphosphate synthase activity;
    wherein the mutant cell is derived from a mutant strain of *Saccharomyces cerevisiae*, and wherein the mutant strain is prepared by replacing a transcription promoter of a squalene synthase gene with a transcription repression type promoter; and
    recovering the prenyl alcohol(s) selected from the group consisting of farnesol, nerolidol and geranylgeraniol from the resultant culture;
    wherein the farnesol diphosphate (FPP) synthase gene encodes a polypeptide having the amino acid sequence set forth in SEQ ID NO:2 or 4 or a polypeptide having FPP synthase activity and an amino acid sequence derived from the amino acid sequence set forth in SEQ ID NO:2 or 4 by deletion, substitution, or addition of from one to ten amino acids; and
    wherein the geranylgeranyl diphosphate (GGPP) synthase gene encoding a polypeptide having the amino acid sequence set forth in SEQ ID NO:6 or a polypeptide having GGPP synthase activity and an amino acid sequence derived from the amino acid sequence set forth in SEQ ID NO:6 by deletion, substitution, or addition of from one to ten amino acids.

2. The method according to claim 1, wherein the mutant cell comprises hydroxymethylglutaryl-CoA reductase gene that has been further introduced thereinto; and
    wherein the hydroxymethylglutaryl-CoA (HMG-CoA) reductase gene encodes a polypeptide having the amino acid sequence set forth in SEQ ID NO:8 or a polypeptide having HMG-CoA reductase activity and an amino acid sequence derived from the amino acid sequence set forth in SEQ ID NO:8 by deletion, substitution, or addition of from one to ten amino acids.

3. The method according to claim 1, wherein the fusion gene comprises an artificial nucleotide sequence between farnesyl diphosphate synthase gene and geranylgeranyl diphosphate synthase gene.

4. The method according to claim 3, wherein the artificial nucleotide sequence encodes ER retention signal.

5. The method according to claim 1, wherein the farnesyl diphosphate synthase gene is SEQ ID NO: 1.

6. The method according to claim 1, wherein the farnesyl diphosphate synthase gene is SEQ ID NO: 3.

7. The method according to claim 1, wherein the geranylgeranyl diphosphate synthase gene is SEQ ID NO: 5.

* * * * *

UNITED STATES PATENT AND TRADEMARK OFFICE
CERTIFICATE OF CORRECTION

PATENT NO. : 8,759,046 B2  
APPLICATION NO. : 12/060434  
DATED : June 24, 2014  
INVENTOR(S) : Chikara Ohto et al.

Page 1 of 1

It is certified that error appears in the above-identified patent and that said Letters Patent is hereby corrected as shown below:

In the Specification

At column 12, line 53, change "(SEQ ED NO: 8)" to -- (SEQ ID NO: 8) --.

At column 15, line 61, change "Gin" to -- Gln --.

At column 23, line 48, change "YPH50-derived EUG" to -- YPH500-derived EUG --.

At column 24, line 14, change "FUG27" to -- EUG27 --.

At column 30, line 28, change "(4-1) Penyl Alcohol" to -- (4-1) Prenyl Alcohol --.

At column 45, line 51, change "HDEL/DUG5" to -- HDEL/EUG5 --.

At column 46, line 29, change "FUG24" to -- EUG24 --.

At column 46, line 31, change "FUG36" to -- EUG36 --.

At column 46, line 34, change "FUG64" to -- EUG64 --.

Signed and Sealed this  
Fourteenth Day of April, 2015

Michelle K. Lee  
*Director of the United States Patent and Trademark Office*